US009840702B2

(12) United States Patent
Collingwood et al.

(10) Patent No.: US 9,840,702 B2
(45) Date of Patent: Dec. 12, 2017

(54) CRISPR-BASED COMPOSITIONS AND METHODS OF USE

(71) Applicant: INTEGRATED DNA TECHNOLOGIES, INC., Skokie, IL (US)

(72) Inventors: Michael Allen Collingwood, North Liberty, IA (US); Ashley Mae Jacobi, Tiffin, IA (US); Garrett Richard Rettig, Coralville, IA (US); Mollie Sue Schubert, Cedar Rapids, IA (US); Mark Aaron Behlke, Coralville, IA (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 0 days.

(21) Appl. No.: 14/975,709

(22) Filed: Dec. 18, 2015

(65) Prior Publication Data
US 2016/0177304 A1 Jun. 23, 2016

Related U.S. Application Data

(60) Provisional application No. 62/239,546, filed on Oct. 9, 2015, provisional application No. 62/093,588, filed on Dec. 18, 2014.

(51) Int. Cl.
*C12N 15/11* (2006.01)

(52) U.S. Cl.
CPC ........ *C12N 15/111* (2013.01); *C12N 2310/10* (2013.01); *C12N 2310/20* (2017.05); *C12N 2310/315* (2013.01); *C12N 2310/317* (2013.01); *C12N 2310/321* (2013.01); *C12N 2310/322* (2013.01); *C12N 2310/3231* (2013.01); *C12N 2310/346* (2013.01); *C12N 2310/531* (2013.01); *C12N 2320/51* (2013.01); *C12N 2320/53* (2013.01)

(58) Field of Classification Search
None
See application file for complete search history.

(56) References Cited

U.S. PATENT DOCUMENTS

| | | | |
|---|---|---|---|
| 5,672,695 A | 9/1997 | Eckstein et al. | |
| 6,248,878 B1 | 6/2001 | Matulic-Adamic et al. | |
| 8,697,359 B1 * | 4/2014 | Zhang | C12N 15/85 424/94.1 |
| 2014/0273232 A1 | 9/2014 | Zhang et al. | |
| 2014/0295557 A1 | 10/2014 | Joung et al. | |
| 2015/0059010 A1 | 2/2015 | Cigan et al. | |
| 2015/0073041 A1 * | 3/2015 | Saltzman | A61K 31/7088 514/44 A |
| 2016/0024524 A1 | 1/2016 | Joung et al. | |
| 2016/0289675 A1 | 10/2016 | Ryan et al. | |

FOREIGN PATENT DOCUMENTS

| | | |
|---|---|---|
| WO | 2014065596 A1 | 5/2014 |
| WO | 2014124226 A1 | 8/2014 |
| WO | 2014144592 A2 | 9/2014 |
| WO | 2016080097 A1 | 5/2016 |
| WO | 2016089433 A1 | 6/2016 |
| WO | 2016164356 | 10/2016 |

OTHER PUBLICATIONS

Behlke, Mark A., "Chemical Modification of siRNAs for In Vivo Use," Oligonucleotides 18(4):305-320 (2008).
Briner et al., "Guide RNA Functional Modules Direct Cas9 Activity and Orthogonality," Mol Cell. 56(2):333-339 (2014).
Eder et al., "Substrate Specificity and Kinetics of Degradation of Antisense Oligonucleotides by a 3' Exonuclease in Plasma," Antisense Res and Develop, 1(2):141-151 (1991).
Fu et al., "IMproving CRISPR-Cas nuclease specificity using truncated guide RNAs," Nature Biotechnol. 32(3):279-284 (2014).
Jinek et al., "Structures of Cas9 Endonucleases Reveal RNA-Mediated Conformational Activation," Science 343(6176):1247997-1247997 (2014).
Kurreck, "Antisense technologies Improvement through novel chemical modifications," Eur. J. Biochem. 270:1628-1644 (2003).
Lennox et al., "Chemical modification and design of anti-miRNA oligonucleotides," Gene Therapy 18:1111-1120 (2011).
Lennox et al., "Improved Performance of Anti-miRNA Oligonucleotides Using a Novel Non-Nucleotide Modifier," Molecular Therapy—Nucleic Acids 2:e117 (2013).
Nishimasu et al., "Crystal Structure of Cas9 in Complex with Guide RNA and Target DNA," Cell 156(5):935-949 (2014).
O'Connell, et al., "Programmable RNA recognition and cleavage by CRISPR/Cas9," Nature 516(7530):263-266 (2014).
Sahin, et al., "mRNA-based therapeutics-developing a new class of drugs," Nat Rev Drug Discov 13(10):759-780 (2014).
Xu, et al., "Cas9-Based Tools for Targeted Genome Editing and Transcriptional Control," Appl Environ Microbiol 80(5):1544-1552 (2014).
Aida, et al., "Cloning-free CRISPR/Cas system facilitates functional cassette knock-in in mice," Genome Biology (2015)16:87, 11 pages, plus additional file 1, 46 pages.
Cencic et al., "Protospacer Adjacent Motif (PAM)-Distal Sequences Engage CRISPR Cas9 DNA Target Cleavage", PLOS One 9(10):e109213 (2014).
Hendel et al., "Chemically modified guide RNAs enhance CRISPR-Cas genome editing in human primary cells", Nat. Biotech. 33(9):985 (2015).

(Continued)

*Primary Examiner* — Addison D Ault
(74) *Attorney, Agent, or Firm* — Klintworth & Rozenblat IP LLP

(57) ABSTRACT

This invention pertains to modified compositions for use in CRISPR systems, and their methods of use. In particular, length-modified and chemically-modified forms of crRNA and tracrRNA are described for use as a reconstituted guide RNA for interaction with Cas9 of CRIPSR systems. The resultant length-modified and chemically-modified forms of crRNA and tracrRNA are economical to produce and can be tailored to have unique properties relevant to their biochemical and biological activity in the context of the CRIPSR Cas9 endonuclease system.

1 Claim, 13 Drawing Sheets

(56) References Cited

OTHER PUBLICATIONS

Jinek et al., "A Programmable Dual-RNA-Guided DNA Endonuclease in Adaptive Bacterial Immunity", Science 337:816-821 (2012).

Jinek et al., Supplementary Materials for "A Programmable Dual-RNA-Guided DNA Endonuclease in Adaptive Bacterial Immunity", Science 337 (2012).

Rahdar et al., "Synthetic CRISPR RNA-Cas9-guided genome editing in human cells," Proc. Natl. Acad. Sci. (pub. Nov. 16, 2015).

International Search Report and Written Opinion for PCT/US2015/066942 dated Aug. 25, 2016, 25 pages.

Behlke, M.A., "Chemical Modification of siRNAs for In Vivo Use" Oligonucleotides (2008) 18:305-320.

Briner, A.E. et al., "Guide RNA Functional Modules Direct Cas9 Activity and Orthogonality." Molecular Cell (2014) 56:333-339.

Eder, P.S. et al., "Substrate Specificity and Kinetics of Degradation of Antisense Oligonucleotides by a 3' Exonuclease in Plasma." Antisense Research and Development (1991) 1:141-151.

Gasiunas, G. et al., "Cas9-crRNA ribonucleoprotein complex mediates specific DNA cleavage for adaptive immunity in bacteria." Proc Natl Acad Sci USA (2012) 109(39):E2579-86.

Jinek, M. et al., "A Programmable Dual-RNA-Guided DNA Endonuclease in Adaptive Bacterial Immunity." Science (2012) 337(6096):816-21.

Jinek, M. et al., "Structures of Cas9 Endonucleases Reveal RNA-Mediated Conformational Activation." Science (2014) 343:1215-26.

Kurreck, J., "Antisense technologies Improvement through novel chemical modifications." Eur. J. Biochem. (2003) 270:1628-1644.

Lennox, K.A. et al., "Chemical modification and design of anti-miRNA oligonucleotides." Gene Therapy (2011) 18:1111-1120.

Nishimasu, H. et al., "Crystal Structure of Cas9 in Complex with Guide RNA and Target DNA." Cell (2014) 156 (5):935-949.

O'Connell, M.R. et al., "Programmable RNA recognition and cleavage by CRISPR/Cas9." Nature (2014) 516:263-278.

Sahin, U. et al., "mRNA-based therapeutics—developing a new class of drugs." Nat Rev Drug Discov (2014) 13:759-780.

Xu, T. et al., "Cas9-Based Tools for Targeted Genome Editing and Transcriptional Control." Applied Environmental Microbiology (2014) 80(6):1544-1552.

\* cited by examiner cuuauauccaacacuucguggunuaga--gcuaugcuguuuug (SEQ ID NO.:46)
||||||||||||||||||||||||    ||||||||||||
c-ggaauaaauugaacgauacgauacgaaaacuuaccaaggung u |
a | guccguuaucaacuug
       |||| a
       |||| a
       agccaggugaaa
       g |||||||
       ucgguugcuuuuuuuu (SEQ ID NO.:18)

FIG. 1

```
cuuauuccaacacuuguggunuaga--gcuag
         |||||||||||||  ||||| a
         |||||||||||||  ||||| a
       c-ggaaaaauugaacgaua
       u|  |||
       a|  |||
       guccguuaucaacuug
                ||||| a
                ||||| a
              agccacggugaaa
              g|||||||
           ucggugcuuu  (SEQ ID NO.:428)
```

FIG. 2

| SEQ ID No. | tracrRNA Sequence (5'-3') | Cleavage (%) |
|---|---|---|
| 18 | GUUGGAACCAUUCAAAACAGCAUAGCAAGUUAAAAUAAGGCUAGUCCGUUAUCAACUUGAAAAAGUGGCACCGAGUCGGUGCUUUUUU | 38 |
| 30 | CAAAACAGCAUAGCAAGUUAAAAUAAGGCUAGUCCGUUAUCAACUUGAAAAAGUGGCACCGAGUCGGUGCUUUU | 26 |
| 31 | AACAGCAUAGCAAGUUAAAAUAAGGCUAGUCCGUUAUCAACUUGAAAAAGUGGCACCGAGUCGGUGCUUU | 32 |
| 2 | AGCAUAGCAAGUUAAAAUAAGGCUAGUCCGUUAUCAACUUGAAAAAGUGGCACCGAGUCGGUGCUUU | 57 |
| 32 | AGCAUAGCAAGUUAAAAUAAGGCUAGUCCGUUAUCAACUUGAAAAAGUGGCACCGAGUCGGUGCU | 47 |
| 33 | CAUAGCAAGUUAAAAUAAGGCUAGUCCGUUAUCAACUUGAAAAAGUGGCACCGAGUCGGUGCU | 27 |
| 34 | AGCAUAGCAAGUUAAAAUA         GUUAUCAACUUGAAAAAGUGGCACCGAGUCGGUGCU | 0 |
| 35 | AGCAUAGCAAGUUAAAAUA                AACUUGAAAAAGUGGCACCGAGUCGGUGCU | 0 |
| 36 | AGCAUAGCAAGUUAAAAUAAGGCUAGUCCGUUAUCAACUUGAAAAAGUGGCACCGAGUCGGUGC | 53 |
| 37 | AGCAUAGCAAGUUAAAAUAAGGCUAGUCCGUUAUCAACUUGAAAAAGUGGCACCGAGUCGGUG | 56 |
| 38 | AGCAUAGCAAGUUAAAAUAAGGCUAGUCCGUUAUCAACUUGAAAAAGUGGCACCGAGUCGGU | 56 |
| 39 | AGCAUAGCAAGUUAAAAUAAGGCUAGUCCGUUAUCAACUUGAAAAAGUGGCACCGAGUCGG | 53 |
| 40 | AGCAUAGCAAGUUAAAAUAAGGCUAGUCCGUUAUCAACUUGAAAAAGUG      CCGAGUCGG | 5 |
| 41 | AGCAUAGCAAGUUAAAAUAAGGCUAGUCC         AACUUGAAAAAGUGGCACCGAGUCGGUGCU | 0 |
| 42 | AGCAUAGCAAGUUAAAAUAAGGCUAGUCC              AACUUGAAAAAGUGGCACCGAGUCGG | 0 |
| 43 | AGCAUAGCAAGUUAAAAUAAGGCUAGUCC              AACUUGAAAAAGUG      CCGAGUCGG | 0 |
| 44 | AGCAUAGCAAGUUAAAAUAAGGCUAGUCCGUUAUCAACUUGAAAAAGUG | 0 |
| 45 | AGCAUAGCAAGUUAAAAUAAGGCUAGUCCGUUAUCA               GCACCGAGUCGGUGCU | 0 |
| 427 | AGCAUAGCAAGUUAAAAUAAGGCUAGUCCGU CAACUUGAAAAAGUGGCACCGAGUCGGUGCUUU | 4 |

FIG. 3

| SEQ ID No. | crRNA and tracrRNA Sequences 5'-3' | Length |
|---|---|---|
| 46 | CUUAUAUCCAACAUUCGUGGUUUUAGAGCUAUGCUGUUUUG | 42 base crRNA |
| 47 | CUUAUAUCCAACACUUCGUGGUUUUAGAGCUAUGCUGUU | 39 base crRNA |
| 48 | CUUAUAUCCAACACUUCGUGGUUUUAGAGCUAUGCU | 36 base crRNA |
| 49 | CUUAUAUCCAACAUUCGUGGUUUUAGAGCUAUG | 34 base crRNA |
| 18 | GUUGGAACCAUUCAAAACAGCAUAGCAAGUUAAAAUAAGGCUAGUCCGUUAUCAACUUGAAAAAGUGGCACCGAGUCGGUGCUUUUUUU | 89 base tracrRNA |
| 50 | CAAAACAGCAUAGCAAGUUAAAAUAAGGCUAGUCCGUUAUCAACUUGAAAAAGUGGCACCGAGUCGGUGCUUUU | 74 base tracrRNA |
| 51 | AACAGCAUAGCAAGUUAAAAUAAGGCUAGUCCGUUAUCAACUUGAAAAAGUGGCACCGAGUCGGUGCUUUU | 70 base tracrRNA |
| 2 | AGCAUAGCAAGUUAAAAUAAGGCUAGUCCGUUAUCAACUUGAAAAAGUGGCACCGAGUCGGUGCUUU | 67 base tracrRNA |
| 52 | AGCAUAGCAAGUUAAAAUAAGGCUAGUCCGUUAUCAACUUGAAAAAGUGGCACCGAGUCGGUGCU | 65 base tracrRNA |
| 53 | CAUAGCAAGUUAAAAUAAGGCUAGUCCGUUAUCAACUUGAAAAAGUGGCACCGAGUCGGUGCU | 63 base tracrRNA |

FIG. 4

```
cuuauauccaacacuucguggguuuaga--gcuaugcu  (SEQ ID NO.:48)
         ||||||||||||||||||||    ||||||||
         c-ggaauaaaauugaacgauacga
         u|||
         a|||
         guccguuauccaacuug
                      ||||| a
                      ||||| a
                      agccacggugaaa
                      g|||||||
                      ucgggugcuuu  (SEQ ID NO.: 2)
```

FIG. 5

```
c*u*u*auauccaacacuucguggtuuuaga--gcuau*g*c*u (SEQ ID NO.: 178)
       ||||||| |||||||   ||| ||| |||
     c-ggaauaaauugaACGAUA C*G*A
     u|||
     a|||
     ggucguuaucaacUUG
                ||||A
                ||||A
                AGCCACGGUGAAA
              G|||||||
              UCGGUGCU*u*u (SEQ ID NO.: 100)
```

FIG. 8

C*U*U*AUAUCCAACAC uuCGuGGuuuUAGA--GC

| 20 base protospacer guide Target-specific domain | 16 base universal tracrRNA-binding domain | Modification Pattern # |
|---|---|---|
| n n n nnnnnnnnnnnnnnnnn | guuuuagagcuau g c u | 1 (SEQ ID NO.:429) |
| n*n*n*nnnnnnnnnnnnnnnnn | guuuuagagcuau*g*c*u | 2 (SEQ ID NO.:430) |
| n*n*n*<u>n</u>nnnnnnnnnnnnnnnn | guuuuagagcuau*g*c*u | 3 (SEQ ID NO.:431) |
| n*n*<u>n</u>*<u>n</u>nnnnnnnnnnnnnnnn | guuuuagagcuau*g*<u>c</u>*u | 4 (SEQ ID NO.:432) |
| n*<u>n</u>*<u>n</u>*<u>nnnnnnnnn</u>nnnnnnnn | guuuuagagcuau*g*<u>c</u>*u | 5 (SEQ ID NO.:433) |
| n*<u>n</u>*<u>n</u>*<u>nnnnnnnnnnnn</u>nnnnn | guuuuagagcuau*g*<u>c</u>*u | 6 (SEQ ID NO.:434) |
| n*<u>n</u>*<u>n</u>*<u>nnnnnnnnnnnnnnn</u>nn | guuuuagagcuau*g*<u>c</u>*u | 7 (SEQ ID NO.:435) |
| n*<u>n</u>*<u>n</u>*<u>nnnnnnnnnnnnnnnnn</u> | guuuuagagcuau*g*<u>c</u>*u | 8 (SEQ ID NO.:436) |
| n*<u>n</u>*<u>n</u>*<u>nnnnnnnnnnnnnnnnn</u> | <u>guuuuagagcuau</u>*g*<u>c</u>*u | 9 (SEQ ID NO.:437) |
| C3-n n n nnnnnnnnnnnnnnnnn | guuuuagagcuau g c u-C3 | 10 (SEQ ID NO.:438) |
| ZEN-n n n nnnnnnnnnnnnnnnnn | guuuuagagcuau g c u-ZEN | 11 (SEQ ID NO.:439) |

FIG. 10

```
N*N*N*NNNNNNnnnnnnnnGuuuUAGA--GCUAU*G*C*U (SEQ ID NO:434)
            ||||||| ||||| ||| |||
        c-ggaauaaauuGAACGAUA  C*G*A
        u|  |||
        a|  |||
         ggucguuAUCCACUUG
                ||||  A
                ||||  A
              AGCCACGGUGAAA
              G |||||||
              UCGGUGCU*U*U (SEQ ID NO:134)
```

FIG. 12

SEQUENCE LISTING

```
<160> NUMBER OF SEQ ID NOS: 451

<210> SEQ ID NO 1
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uuauauccaa cacuucgugg uuuuagagcu augcu                                 35

<210> SEQ ID NO 2
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
agcauagcaa guuaaaauaa ggcuaguccg uuaucaacuu gaaaaagugg caccgagucg      60
gugcuuu                                                               67

<210> SEQ ID NO 3
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(89)
<223> OTHER INFORMATION: 2'-O-methyl nucleotide

<400> SEQUENCE: 3
guuggaacca uucaaaacag cauagcaagu uaaaauaagg cuaguccguu aucaacuuga      60
aaaaguggca ccgagucggu gcuuuuuu                                        89

<210> SEQ ID NO 4
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(67)
<223> OTHER INFORMATION: 2'-O-methyl nucleotide
```

-continued

```
<400> SEQUENCE: 4
agcauagcaa guuaaaauaa ggcuaguccg uuaucaacuu gaaaaagugg caccgagucg    60
gugcuuu                                                              67

<210> SEQ ID NO 5
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uuauauccaa cacuucgugg uuuuagagcu augcuguuuu g                        41

<210> SEQ ID NO 6
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(89)
<223> OTHER INFORMATION: 2'-O-methyl nucleotide

<400> SEQUENCE: 6
guuggaacca uucaaaacag cauagcaagu uaaaauaagg cuaguccguu aucaacuuga    60
aaaaguggca ccgagucggu gcuuuuuuu                                      89

<210> SEQ ID NO 7
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(41)
<223> OTHER INFORMATION: 2'-O-methyl nucleotide

<400> SEQUENCE: 7
uuauauccaa cacuucgugg uuuuagagcu augcuguuuu g                        41

<210> SEQ ID NO 8
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(41)
<223> OTHER INFORMATION: 2'-O-methyl nucleotide

<400> SEQUENCE: 8
uuauauccaa cacuucgugg uuuuagagcu augcuguuuu g                        41

<210> SEQ ID NO 9
<211> LENGTH: 35
<212> TYPE: RNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (1)..(35)
<223> OTHER INFORMATION: 2'-O-methyl nucleotide

<400> SEQUENCE: 9
uuauauccaa cacuucgugg uuuuagagcu augcu                               35

<210> SEQ ID NO 10
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(35)
<223> OTHER INFORMATION: 2'-O-methyl nucleotide

<400> SEQUENCE: 10
uuauauccaa cacuucgugg uuuuagagcu augcu                               35

<210> SEQ ID NO 11
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(67)
<223> OTHER INFORMATION: 2'-O-methyl nucleotide

<400> SEQUENCE: 11
agcauagcaa guuaaaauaa ggcuaguccg uuaucaacuu gaaaaagugg caccgagucg    60
gugcuuu                                                              67

<210> SEQ ID NO 12
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2'-O-methyl nucleotide
<220> FEATURE:
<221> NAME/KEY: modified_base
<222> LOCATION: (21)..(24)
<223> OTHER INFORMATION: 2'-O-methyl nucleotide
<220> FEATURE:
<221> NAME/KEY: modified_base
<222> LOCATION: (28)..(28)
<223> OTHER INFORMATION: 2'-O-methyl nucleotide
<220> FEATURE:
<221> NAME/KEY: modified_base
<222> LOCATION: (39)..(67)
<223> OTHER INFORMATION: 2'-O-methyl nucleotide

<400> SEQUENCE: 12
agcauagcaa guuaaaauaa ggcuaguccg uuaucaacuu gaaaaagugg caccgagucg    60
```

```
gugcuuu                                                              67

<210> SEQ ID NO 13
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide

<400> SEQUENCE: 13
agcauagcaa guuaaaauaa ggcuaguccg uuaucaacuu gaaaaagugg caccgagucg    60
gugcuuu                                                              67

<210> SEQ ID NO 14
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(35)
<223> OTHER INFORMATION: 2'-O-methyl nucleotide

<400> SEQUENCE: 14
uuauauccaa cacuucgugg uuuuagagcu augcu                               35

<210> SEQ ID NO 15
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(12)
<223> OTHER INFORMATION: 2'-O-methyl nucleotide

<400> SEQUENCE: 15
uuauauccaa cacuucgugg uuuuagagcu augcu                               35

<210> SEQ ID NO 16
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(12)
<223> OTHER INFORMATION: 2'-O-methyl nucleotide
<220> FEATURE:
<221> NAME/KEY: modified_base
<222> LOCATION: (25)..(35)
<223> OTHER INFORMATION: 2'-O-methyl nucleotide

<400> SEQUENCE: 16
uuauauccaa cacuucgugg uuuuagagcu augcu                               35
```

```
<210> SEQ ID NO 17
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: 2'-O-methyl nucleotide
<220> FEATURE:
<221> NAME/KEY: modified_base
<222> LOCATION: (41)..(41)
<223> OTHER INFORMATION: 2'-O-methyl nucleotide
<220> FEATURE:
<221> NAME/KEY: modified_base
<222> LOCATION: (43)..(43)
<223> OTHER INFORMATION: 2'-O-methyl nucleotide
<220> FEATURE:
<221> NAME/KEY: modified_base
<222> LOCATION: (45)..(45)
<223> OTHER INFORMATION: 2'-O-methyl nucleotide
<220> FEATURE:
<221> NAME/KEY: modified_base
<222> LOCATION: (47)..(47)
<223> OTHER INFORMATION: 2'-O-methyl nucleotide
<220> FEATURE:
<221> NAME/KEY: modified_base
<222> LOCATION: (49)..(49)
<223> OTHER INFORMATION: 2'-O-methyl nucleotide
<220> FEATURE:
<221> NAME/KEY: modified_base
<222> LOCATION: (51)..(51)
<223> OTHER INFORMATION: 2'-O-methyl nucleotide
<220> FEATURE:
<221> NAME/KEY: modified_base
<222> LOCATION: (53)..(53)
<223> OTHER INFORMATION: 2'-O-methyl nucleotide
<220> FEATURE:
<221> NAME/KEY: modified_base
<222> LOCATION: (55)..(55)
<223> OTHER INFORMATION: 2'-O-methyl nucleotide
<220> FEATURE:
<221> NAME/KEY: modified_base
<222> LOCATION: (57)..(57)
<223> OTHER INFORMATION: 2'-O-methyl nucleotide
<220> FEATURE:
<221> NAME/KEY: modified_base
<222> LOCATION: (59)..(59)
<223> OTHER INFORMATION: 2'-O-methyl nucleotide
<220> FEATURE:
<221> NAME/KEY: modified_base
<222> LOCATION: (61)..(61)
<223> OTHER INFORMATION: 2'-O-methyl nucleotide
<220> FEATURE:
<221> NAME/KEY: modified_base
<222> LOCATION: (63)..(63)
<223> OTHER INFORMATION: 2'-O-methyl nucleotide
<220> FEATURE:
<221> NAME/KEY: modified_base
<222> LOCATION: (65)..(65)
<223> OTHER INFORMATION: 2'-O-methyl nucleotide
<220> FEATURE:
<221> NAME/KEY: modified_base
<222> LOCATION: (67)..(67)
<223> OTHER INFORMATION: 2'-O-methyl nucleotide

<400> SEQUENCE: 17
agcauagcaa guuaaaauaa ggcuaguccg uuaucaacuu gaaaaagugg caccgagucg      60
gugcuuu                                                               67

<210> SEQ ID NO 18
<211> LENGTH: 89
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
guuggaacca uucaaaacag cauagcaagu uaaaauaagg cuaguccguu aucaacuuga    60
aaaaguggca ccgagucggu gcuuuuuu                                      89

<210> SEQ ID NO 19
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (57)..(89)
<223> OTHER INFORMATION: 2'-O-methyl nucleotide

<400> SEQUENCE: 19
guuggaacca uucaaaacag cauagcaagu uaaaauaagg cuaguccguu aucaacuuga    60
aaaaguggca ccgagucggu gcuuuuuu                                      89

<210> SEQ ID NO 20
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (57)..(57)
<223> OTHER INFORMATION: 2'-O-methyl nucleotide
<220> FEATURE:
<221> NAME/KEY: modified_base
<222> LOCATION: (59)..(59)
<223> OTHER INFORMATION: 2'-O-methyl nucleotide
<220> FEATURE:
<221> NAME/KEY: modified_base
<222> LOCATION: (61)..(61)
<223> OTHER INFORMATION: 2'-O-methyl nucleotide
<220> FEATURE:
<221> NAME/KEY: modified_base
<222> LOCATION: (63)..(63)
<223> OTHER INFORMATION: 2'-O-methyl nucleotide
<220> FEATURE:
<221> NAME/KEY: modified_base
<222> LOCATION: (65)..(65)
<223> OTHER INFORMATION: 2'-O-methyl nucleotide
<220> FEATURE:
<221> NAME/KEY: modified_base
<222> LOCATION: (67)..(67)
<223> OTHER INFORMATION: 2'-O-methyl nucleotide
<220> FEATURE:
<221> NAME/KEY: modified_base
<222> LOCATION: (69)..(69)
<223> OTHER INFORMATION: 2'-O-methyl nucleotide
<220> FEATURE:
<221> NAME/KEY: modified_base
<222> LOCATION: (71)..(71)
<223> OTHER INFORMATION: 2'-O-methyl nucleotide
<220> FEATURE:
<221> NAME/KEY: modified_base
<222> LOCATION: (73)..(73)
<223> OTHER INFORMATION: 2'-O-methyl nucleotide
<220> FEATURE:
<221> NAME/KEY: modified_base
<222> LOCATION: (75)..(75)
<223> OTHER INFORMATION: 2'-O-methyl nucleotide
```

```
<220> FEATURE:
<221> NAME/KEY: modified_base
<222> LOCATION: (77)..(77)
<223> OTHER INFORMATION: 2'-O-methyl nucleotide
<220> FEATURE:
<221> NAME/KEY: modified_base
<222> LOCATION: (79)..(79)
<223> OTHER INFORMATION: 2'-O-methyl nucleotide
<220> FEATURE:
<221> NAME/KEY: modified_base
<222> LOCATION: (81)..(81)
<223> OTHER INFORMATION: 2'-O-methyl nucleotide
<220> FEATURE:
<221> NAME/KEY: modified_base
<222> LOCATION: (83)..(83)
<223> OTHER INFORMATION: 2'-O-methyl nucleotide
<220> FEATURE:
<221> NAME/KEY: modified_base
<222> LOCATION: (85)..(85)
<223> OTHER INFORMATION: 2'-O-methyl nucleotide
<220> FEATURE:
<221> NAME/KEY: modified_base
<222> LOCATION: (87)..(87)
<223> OTHER INFORMATION: 2'-O-methyl nucleotide
<220> FEATURE:
<221> NAME/KEY: modified_base
<222> LOCATION: (89)..(89)
<223> OTHER INFORMATION: 2'-O-methyl nucleotide

<400> SEQUENCE: 20
guuggaacca uucaaaacag cauagcaagu uaaaauaagg cuaguccguu aucaacuuga      60
aaaaguggca ccgagucggu gcuuuuuuu                                       89

<210> SEQ ID NO 21
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: 2'-O-methyl nucleotide
<220> FEATURE:
<221> NAME/KEY: modified_base
<222> LOCATION: (34)..(34)
<223> OTHER INFORMATION: 2'-O-methyl nucleotide
<220> FEATURE:
<221> NAME/KEY: modified_base
<222> LOCATION: (39)..(42)
<223> OTHER INFORMATION: 2'-O-methyl nucleotide
<220> FEATURE:
<221> NAME/KEY: modified_base
<222> LOCATION: (46)..(46)
<223> OTHER INFORMATION: 2'-O-methyl nucleotide
<220> FEATURE:
<221> NAME/KEY: modified_base
<222> LOCATION: (56)..(89)
<223> OTHER INFORMATION: 2'-O-methyl nucleotide

<400> SEQUENCE: 21
guuggaacca uucaaaacag cauagcaagu uaaaauaagg cuaguccguu aucaacuuga      60
aaaaguggca ccgagucggu gcuuuuuuu                                       89

<210> SEQ ID NO 22
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(19)
<223> OTHER INFORMATION: 2'-O-methyl nucleotide

<400> SEQUENCE: 22
uuauauccaa cacuucgugg uuuuagagcu augcu                               35

<210> SEQ ID NO 23
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-fluoro nucleotide
<220> FEATURE:
<221> NAME/KEY: modified_base
<222> LOCATION: (3)..(3)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2'-fluoro nucleotide
<220> FEATURE:
<221> NAME/KEY: modified_base
<222> LOCATION: (5)..(5)
<223> OTHER INFORMATION: 2'-O-methyl nucleotide
<220> FEATURE:
<221> NAME/KEY: modified_base
<222> LOCATION: (6)..(8)
<223> OTHER INFORMATION: 2'-fluoro nucleotide
<220> FEATURE:
<221> NAME/KEY: modified_base
<222> LOCATION: (9)..(10)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2'-fluoro nucleotide
<220> FEATURE:
<221> NAME/KEY: modified_base
<222> LOCATION: (12)..(12)
<223> OTHER INFORMATION: 2'-O-methyl nucleotide
<220> FEATURE:
<221> NAME/KEY: modified_base
<222> LOCATION: (13)..(16)
<223> OTHER INFORMATION: 2'-fluoro nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2'-fluoro nucleotide
<220> FEATURE:
<221> NAME/KEY: modified_base
<222> LOCATION: (19)..(20)
<223> OTHER INFORMATION: 2'-O-methyl nucleotide
<220> FEATURE:
<221> NAME/KEY: modified_base
<222> LOCATION: (21)..(24)
<223> OTHER INFORMATION: 2'-fluoro nucleotide
<220> FEATURE:
<221> NAME/KEY: modified_base
<222> LOCATION: (25)..(28)
<223> OTHER INFORMATION: 2'-O-methyl nucleotide
<220> FEATURE:
<221> NAME/KEY: modified_base
<222> LOCATION: (29)..(30)
<223> OTHER INFORMATION: 2'-fluoro nucleotide
<220> FEATURE:
<221> NAME/KEY: modified_base
<222> LOCATION: (31)..(31)
```

```
<223> OTHER INFORMATION: 2'-O-methyl nucleotide
<220> FEATURE:
<221> NAME/KEY: modified_base
<222> LOCATION: (32)..(32)
<223> OTHER INFORMATION: 2'-fluoro nucleotide
<220> FEATURE:
<221> NAME/KEY: modified_base
<222> LOCATION: (33)..(33)
<223> OTHER INFORMATION: 2'-O-methyl nucleotide
<220> FEATURE:
<221> NAME/KEY: modified_base
<222> LOCATION: (34)..(35)
<223> OTHER INFORMATION: 2'-fluoro nucleotide

<400> SEQUENCE: 23
uuauauccaa cacuucgugg uuuuagagcu augcu                          35

<210> SEQ ID NO 24
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(35)
<223> OTHER INFORMATION: 2'-fluoro nucleotide

<400> SEQUENCE: 24
uuauauccaa cacuucgugg uuuuagagcu augcu                          35

<210> SEQ ID NO 25
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(19)
<223> OTHER INFORMATION: 2'-O-methyl nucleotide

<400> SEQUENCE: 25
uuauauccaa cacuucgugg uuuuagagcu augcuguuuu g                   41

<210> SEQ ID NO 26
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(12)
<223> OTHER INFORMATION: 2'-O-methyl nucleotide
<220> FEATURE:
<221> NAME/KEY: modified_base
<222> LOCATION: (25)..(40)
<223> OTHER INFORMATION: 2'-O-methyl nucleotide

<400> SEQUENCE: 26
uuauauccaa cacuucgugg uuuuagagcu augcuguuuu g                   41

<210> SEQ ID NO 27
<211> LENGTH: 938
<212> TYPE: DNA
<213> ORGANISM: Homo sapiens
```

<400> SEQUENCE: 27

```
gaatgttgtg ataaaaggtg atgctcacct ctcccacacc cttttatagt ttagggattg    60
tatttccaag gtttctagac tgagagccct tttcatcttt gctcattgac actctgtacc   120
cattaatcct ccttattagc tccccttcaa tggacacatg ggtagtcagg gtgcaggtct   180
cagaactgtc cttcaggttc caggtgatca accaagtgcc ttgtctgtag tgtcaactca   240
ttgctgcccc ttcctagtaa tccccataat ttagctctcc atttcatagt ctttccttgg   300
gtgtgttaaa agtgaccatg gtacactcag cacggatgaa atgaaacagt gtttagaaac   360
gtcagtcttc tcttttgtaa tgccctgtag tctctctgta tgttatatgt cacattttgt   420
aattaacagc ttgctggtga aaaggacccc acgaagtgtt ggatataagc cagactgtaa   480
gtgaattact tttttgtca atcatttaac catctttaac ctaaaagagt tttatgtgaa   540
atggcttata attgcttaga gaatatttgt agagaggcac atttgccagt attagattta   600
aaagtgatgt tttctttatc taaatgatga attatgattc tttttagttg ttggatttga   660
aattccagac aagtttgttg taggatatgc ccttgactat aatgaatact tcagggattt   720
gaatgtaagt aattgcttct ttttctcact cattttccaa aacacgcata aaaatttagg   780
aaagagaatt gttttctcct tccagcacct cataatttga acagactgat ggttcccatt   840
agtcacataa agctgtagtc tagtacagac gtccttagaa ctggaacctg gccaggctag   900
ggtgacactt cttgttggct gaaatagttg aacagctt                           938
```

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
aagaatgttg tgataaaagg tgatgct                                        27
```

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
acacatccat gggacttctg cctc                                           24
```

<210> SEQ ID NO 30
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30

```
caaaacagca uagcaaguua aaauaaggcu aguccguuau caacuugaaa aaguggcacc    60
gagucggugc uuuu                                                      74
```

<210> SEQ ID NO 31
<211> LENGTH: 70
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 31
aacagcauag caaguuaaaa uaaggcuagu ccguuaucaa cuugaaaaag uggcaccgag      60
ucggugcuuu                                                            70

<210> SEQ ID NO 32
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
agcauagcaa guuaaaauaa ggcuaguccg uuaucaacuu gaaaagugg caccgagucg       60 gugcu                                                                 65

<210> SEQ ID NO 33
<211> LENGTH: 63
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
cauagcaagu uaaauaagg cuaguccguu aucaacuuga aaaguggca ccgagucggu       60 gcu                                                                   63

<210> SEQ ID NO 34
<211> LENGTH: 55
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
agcauagcaa guuaaaauag uuaucaacuu gaaaagugg caccgagucg gugcu           55

<210> SEQ ID NO 35
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
agcauagcaa guuaaaauaa acuugaaaaa guggcaccga gucggugcu                 49

<210> SEQ ID NO 36
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
agcauagcaa guuaaaauaa ggcuaguccg uuaucaacuu gaaaagugg caccgagucg      60
```

```
gugc                                                              64

<210> SEQ ID NO 37
<211> LENGTH: 63
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
agcauagcaa guuaaaauaa ggcuaguccg uuaucaacuu gaaaaagugg caccgagucg    60
gug                                                               63

<210> SEQ ID NO 38
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
agcauagcaa guuaaaauaa ggcuaguccg uuaucaacuu gaaaaagugg caccgagucg    60
gu                                                                62

<210> SEQ ID NO 39
<211> LENGTH: 61
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
agcauagcaa guuaaaauaa ggcuaguccg uuaucaacuu gaaaaagugg caccgagucg    60
g                                                                 61

<210> SEQ ID NO 40
<211> LENGTH: 58
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
agcauagcaa guuaaaauaa ggcuaguccg uuaucaacuu gaaaaagugc cgagucgg      58

<210> SEQ ID NO 41
<211> LENGTH: 59
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
agcauagcaa guuaaaauaa ggcuagucca acuugaaaaa guggcaccga gucggugcu     59

<210> SEQ ID NO 42
<211> LENGTH: 55
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 42
agcauagcaa guuaaaauaa ggcuagucca acuugaaaaa guggcaccga gucgg    55

<210> SEQ ID NO 43
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
agcauagcaa guuaaaauaa ggcuagucca acuugaaaaa gugccgaguc gg    52

<210> SEQ ID NO 44
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
agcauagcaa guuaaaauaa ggcuaguccg uuaucaacuu gaaaagug    49

<210> SEQ ID NO 45
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
agcauagcaa guuaaaauaa ggcuaguccg uuaucagcac cgagucggug cu    52

<210> SEQ ID NO 46
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
cuuauaucca acacuucgug guuuuagagc uaugcuguuu ug    42

<210> SEQ ID NO 47
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
cuuauaucca acacuucgug guuuuagagc uaugcuguu    39

<210> SEQ ID NO 48
<211> LENGTH: 36
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 48
cuuauaucca acacuucgug guuuuagagc uaugcu                                    36

<210> SEQ ID NO 49
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
cuuauaucca acacuucgug guuuuagagc uaug                                      34

<210> SEQ ID NO 50
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
caaaacagca uagcaaguua aaauaaggcu aguccguuau caacuugaaa aaguggcacc          60
gagucggugc uuuu                                                            74

<210> SEQ ID NO 51
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
aacagcauag caaguuaaaa uaaggcuagu ccguuaucaa cuugaaaaag uggcaccgag          60
ucggugcuuu                                                                 70

<210> SEQ ID NO 52
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
agcauagcaa guuaaaauaa ggcuaguccg uuaucaacuu gaaaaagugg caccgagucg          60
gugcu                                                                      65

<210> SEQ ID NO 53
<211> LENGTH: 63
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
cauagcaagu uaaaauaagg cuaguccguu aucaacuuga aaaguggca ccgagucggu           60 gcu                                                                        63
```

<210> SEQ ID NO 54
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
uauauccaac acuucgugguu uuuagagcua ugcu                              34

<210> SEQ ID NO 55
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
auauccaaca cuucgugguu uuagagcuau gcu                                33

<210> SEQ ID NO 56
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
aauuaugggg auuacuagga guuuuagagc uaugcu                             36

<210> SEQ ID NO 57
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57 auuauggga uuacuaggag uuuuagagcu augcu                               35

<210> SEQ ID NO 58
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58 uuaugggau uacuaggagu uuuagagcua ugcu                                34

<210> SEQ ID NO 59
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59 uaugggauu acuaggaguu uuagagcuau gcu                                 33

```
<210> SEQ ID NO 60
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
auuucacaua aaacucuuuu guuuuagagc uaugcu                                    36

<210> SEQ ID NO 61
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
uuucacauaa aacucuuuug uuuuagagcu augcu                                     35

<210> SEQ ID NO 62
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
uucacauaaa acucuuuugu uuuagagcua ugcu                                      34

<210> SEQ ID NO 63
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ucacauaaaa cucuuuuguu uuagagcuau gcu                                       33

<210> SEQ ID NO 64
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
uccauuucau agucuuuccu guuuuagagc uaugcu                                    36

<210> SEQ ID NO 65
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
ccauuucaua gucuuuccug uuuuagagcu augcu                                     35
```

```
<210> SEQ ID NO 66
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
cauuucauag ucuuuccugu uuagagcua ugcu                                    34

<210> SEQ ID NO 67
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
auuucauagu cuuccuguu uuagagcuau gcu                                     33

<210> SEQ ID NO 68
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
uccauuucau agucuuuccu guuuuagagc uaugcuguuu ug                          42

<210> SEQ ID NO 69
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uuuuguaauu aacagcuugc guuuuagagc uaugcu                                 36

<210> SEQ ID NO 70
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
uuuuguaauu aacagcuugc guuuuagagc uaugcuguuu ug                          42

<210> SEQ ID NO 71
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
cuuagagaau auuuguagag guuuuagagc uaugcu                                 36

<210> SEQ ID NO 72
```

<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 72
cuuagagaau auuuguagag guuuuagagc uaugcuguuu ug        42

<210> SEQ ID NO 73
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 73
uugacuauaa ugaauacuuc guuuuagagc uaugcu        36

<210> SEQ ID NO 74
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 74
uugacuauaa ugaauacuuc guuuuagagc uaugcuguuu ug        42

<210> SEQ ID NO 75
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 75
caaaacacgc auaaaaauuu guuuuagagc uaugcu        36

<210> SEQ ID NO 76
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 76
caaaacacgc auaaaaauuu guuuuagagc uaugcuguuu ug        42

<210> SEQ ID NO 77
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 77
aauuaugggg auuacuagga guuuuagagc uaugcuguuu ug        42

<210> SEQ ID NO 78
<211> LENGTH: 36

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
ggucacuuuu aacacaccca guuuuagagc uaugcu                                36

<210> SEQ ID NO 79
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
ggucacuuuu aacacaccca guuuuagagc uaugcuguuu ug                         42

<210> SEQ ID NO 80
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
ggcuuauauc caacacuucg guuuuagagc uaugcu                                36

<210> SEQ ID NO 81
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
ggcuuauauc caacacuucg guuuuagagc uaugcuguuu ug                         42

<210> SEQ ID NO 82
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
auuucacaua aaacucuuuu guuuuagagc uaugcuguuu ug                         42

<210> SEQ ID NO 83
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
ucaaauuaug aggugcugga guuuuagagc uaugcu                                36

<210> SEQ ID NO 84
<211> LENGTH: 42
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 84
ucaaauuaug aggugcugga guuuuagagc uaugcuguuu ug                    42

<210> SEQ ID NO 85
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
uacagcuuua ugugacuaau guuuuagagc uaugcu                          36

<210> SEQ ID NO 86
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
uacagcuuua ugugacuaau guuuuagagc uaugcuguuu ug                    42

<210> SEQ ID NO 87
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: 2'-O-methyl nucleotide

<400> SEQUENCE: 87
agcauagcaa guuaaaauaa ggcuaguccg uuaucaacuu gaaaaagugg caccgagucg    60
gugcuuu                                                             67

<210> SEQ ID NO 88
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (65)..(67)
<223> OTHER INFORMATION: 2'-O-methyl nucleotide

<400> SEQUENCE: 88
agcauagcaa guuaaaauaa ggcuaguccg uuaucaacuu gaaaaagugg caccgagucg    60
gugcuuu                                                             67

<210> SEQ ID NO 89
<211> LENGTH: 67
<212> TYPE: RNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: 2'-O-methyl nucleotide
<220> FEATURE:
<221> NAME/KEY: modified_base
<222> LOCATION: (65)..(67)
<223> OTHER INFORMATION: 2'-O-methyl nucleotide

<400> SEQUENCE: 89
agcauagcaa guuaaaauaa ggcuaguccg uuaucaacuu gaaaagugg caccgagucg    60 gugcuuu                                                              67

<210> SEQ ID NO 90
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: 2'-O-methyl nucleotide

<400> SEQUENCE: 90
agcauagcaa guuaaaauaa ggcuaguccg uuaucaacuu gaaaagugg caccgagucg    60 gugcu                                                                65

<210> SEQ ID NO 91
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (59)..(64)
<223> OTHER INFORMATION: 2'-O-methyl nucleotide

<400> SEQUENCE: 91
agcauagcaa guuaaaauaa ggcuaguccg uuaucaacuu gaaaagugg caccgagucg    60 gugcu                                                                65

<210> SEQ ID NO 92
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)..(54)
<223> OTHER INFORMATION: 2'-O-methyl nucleotide

<400> SEQUENCE: 92
agcauagcaa guuaaaauaa ggcuaguccg uuaucaacuu gaaaagugg caccgagucg    60 gugcu                                                                65

<210> SEQ ID NO 93
<211> LENGTH: 65
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(40)
<223> OTHER INFORMATION: 2'-O-methyl nucleotide
<220> FEATURE:
<221> NAME/KEY: modified_base
<222> LOCATION: (45)..(54)
<223> OTHER INFORMATION: 2'-O-methyl nucleotide

<400> SEQUENCE: 93
agcauagcaa guuaaaauaa ggcuaguccg uuaucaacuu gaaaaagugg caccgagucg     60
gugcu                                                                65

<210> SEQ ID NO 94
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(40)
<223> OTHER INFORMATION: 2'-O-methyl nucleotide
<220> FEATURE:
<221> NAME/KEY: modified_base
<222> LOCATION: (45)..(54)
<223> OTHER INFORMATION: 2'-O-methyl nucleotide
<220> FEATURE:
<221> NAME/KEY: modified_base
<222> LOCATION: (59)..(64)
<223> OTHER INFORMATION: 2'-O-methyl nucleotide

<400> SEQUENCE: 94
agcauagcaa guuaaaauaa ggcuaguccg uuaucaacuu gaaaaagugg caccgagucg     60
gugcu                                                                65

<210> SEQ ID NO 95
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (38)..(40)
<223> OTHER INFORMATION: 2'-O-methyl nucleotide
<220> FEATURE:
<221> NAME/KEY: modified_base
<222> LOCATION: (45)..(54)
<223> OTHER INFORMATION: 2'-O-methyl nucleotide
<220> FEATURE:
<221> NAME/KEY: modified_base
<222> LOCATION: (59)..(64)
<223> OTHER INFORMATION: 2'-O-methyl nucleotide

<400> SEQUENCE: 95
agcauagcaa guuaaaauaa ggcuaguccg uuaucaacuu gaaaaagugg caccgagucg     60
gugcu                                                                65

<210> SEQ ID NO 96
<211> LENGTH: 65
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(44)
<223> OTHER INFORMATION: 2'-O-methyl nucleotide
<220> FEATURE:
<221> NAME/KEY: modified_base
<222> LOCATION: (55)..(58)
<223> OTHER INFORMATION: 2'-O-methyl nucleotide

<400> SEQUENCE: 96
agcauagcaa guuaaaauaa ggcuaguccg uuaucaacuu gaaaaagugg caccgagucg    60
gugcu                                                               65

<210> SEQ ID NO 97
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<223> OTHER INFORMATION: 3' C3 spacer

<400> SEQUENCE: 97
agcauagcaa guuaaaauaa ggcuaguccg uuaucaacuu gaaaaagugg caccgagucg    60
gugcuuu                                                             67

<210> SEQ ID NO 98
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: misc_feature
<222> LOCATION: (65)..(67)
<223> OTHER INFORMATION: Phosphorothioate linkage

<400> SEQUENCE: 98
agcauagcaa guuaaaauaa ggcuaguccg uuaucaacuu gaaaaagugg caccgagucg    60
gugcuuu                                                             67

<210> SEQ ID NO 99
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (38)..(67)
```

```
<223> OTHER INFORMATION: 2'-O-methyl nucleotide
<220> FEATURE:
<223> OTHER INFORMATION: 3' C3 spacer

<400> SEQUENCE: 99
agcauagcaa guuaaaauaa ggcuaguccg uuaucaacuu gaaaagugg caccgagucg    60 gugcuuu                                                              67

<210> SEQ ID NO 100
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 100
agcauagcaa guuaaaauaa ggcuaguccg uuaucaacuu gaaaagugg caccgagucg    60 gugcuuu                                                              67

<210> SEQ ID NO 101
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: misc_feature
<222> LOCATION: (64)..(67)
<223> OTHER INFORMATION: Phosphorothioate linkage

<400> SEQUENCE: 101
agcauagcaa guuaaaauaa ggcuaguccg uuaucaacuu gaaaagugg caccgagucg    60 gugcuuu                                                              67

<210> SEQ ID NO 102
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (65)..(67)
```

<223> OTHER INFORMATION: 2'-O-methyl nucleotide

<400> SEQUENCE: 102
agcauagcaa guuaaaauaa ggcuaguccg uuaucaacuu gaaaagugg caccgagucg    60 gugcuuu    67

<210> SEQ ID NO 103
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (64)..(67)
<223> OTHER INFORMATION: Phosphorothioate linkage
<220> FEATURE:
<221> NAME/KEY: modified_base
<222> LOCATION: (65)..(67)
<223> OTHER INFORMATION: 2'-O-methyl nucleotide

<400> SEQUENCE: 103
agcauagcaa guuaaaauaa ggcuaguccg uuaucaacuu gaaaagugg caccgagucg    60 gugcuuu    67

<210> SEQ ID NO 104
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' ZEN modifier

<400> SEQUENCE: 104
agcauagcaa guuaaaauaa ggcuaguccg uuaucaacuu gaaaagugg caccgagucg    60 gugcuuu    67

<210> SEQ ID NO 105
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 105
agcauagcaa guuaaaauaa ggcuaguccg uuaucaacuu gaaaagugg caccgagucg    60 gugcuuu    67

<210> SEQ ID NO 106
<211> LENGTH: 62
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (38)..(62)
<223> OTHER INFORMATION: 2'-O-methyl nucleotide
<220> FEATURE:
<221> NAME/KEY: misc_feature
<222> LOCATION: (60)..(62)
<223> OTHER INFORMATION: Phosphorothioate linkage

<400> SEQUENCE: 106
agcauagcaa guuaaaauaa ggcuaguccg uuaucaacuu gaaaaagugg caccgagucg    60
gu                                                                  62

<210> SEQ ID NO 107
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (31)..(62)
<223> OTHER INFORMATION: 2'-O-methyl nucleotide
<220> FEATURE:
<221> NAME/KEY: misc_feature
<222> LOCATION: (60)..(62)
<223> OTHER INFORMATION: Phosphorothioate linkage

<400> SEQUENCE: 107
agcauagcaa guuaaaauaa ggcuaguccg uuaucaacuu gaaaaagugg caccgagucg    60
gugcuuu                                                             67

<210> SEQ ID NO 108
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(20)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
```

```
<221> NAME/KEY: misc_feature
<222> LOCATION: (65)..(67)
<223> OTHER INFORMATION: Phosphorothioate linkage

<400> SEQUENCE: 108
agcauagcaa guuaaaauaa ggcuaguccg uuaucaacuu gaaaaagugg caccgagucg    60
gugcuuu                                                              67

<210> SEQ ID NO 109
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (15)..(20)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 109
agcauagcaa guuaaaauaa ggcuaguccg uuaucaacuu gaaaaagugg caccgagucg    60
gugcuuu                                                              67

<210> SEQ ID NO 110
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (37)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 110
agcauagcaa guuaaaauaa ggcuaguccg uuaucaacuu gaaaaagugg caccgagucg    60
gugcuuu                                                              67

<210> SEQ ID NO 111
<211> LENGTH: 67
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (36)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 111
agcauagcaa guuaaaauaa ggcuaguccg uuaucaacuu gaaaaagugg caccgagucg    60
gugcuuu                                                             67

<210> SEQ ID NO 112
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (35)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 112
agcauagcaa guuaaaauaa ggcuaguccg uuaucaacuu gaaaaagugg caccgagucg    60
gugcuuu                                                             67

<210> SEQ ID NO 113
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (34)..(67)
<223> OTHER INFORMATION: 2'-O-methyl nucleotide
```

```
<220> FEATURE:
<221> NAME/KEY: misc_feature
<222> LOCATION: (65)..(67)
<223> OTHER INFORMATION: Phosphorothioate linkage

<400> SEQUENCE: 113
agcauagcaa guuaaaauaa ggcuaguccg uuaucaacuu gaaaaagugg caccgagucg    60
gugcuuu                                                             67

<210> SEQ ID NO 114
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 114
agcauagcaa guuaaaauaa ggcuaguccg uuaucaacuu gaaaaagugg caccgagucg    60
gugcuuu                                                             67

<210> SEQ ID NO 115
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (32)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 115
agcauagcaa guuaaaauaa ggcuaguccg uuaucaacuu gaaaaagugg caccgagucg    60
gugcuuu                                                             67

<210> SEQ ID NO 116
<211> LENGTH: 67
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 116
agcauagcaa guuaaaauaa ggcuaguccg uuaucaacuu gaaaaagugg caccgagucg      60
gugcuuu                                                               67

<210> SEQ ID NO 117
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 117
agcauagcaa guuaaaauaa ggcuaguccg uuaucaacuu gaaaaagugg caccgagucg      60
gugcuuu                                                               67

<210> SEQ ID NO 118
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
```

<223> OTHER INFORMATION: Phosphorothioate linkage

<400> SEQUENCE: 118
agcauagcaa guuaaaauaa ggcuaguccg uuaucaacuu gaaaaagugg caccgagucg    60
gugcuuu    67

<210> SEQ ID NO 119
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 119
agcauagcaa guuaaaauaa ggcuaguccg uuaucaacuu gaaaaagugg caccgagucg    60
gugcuuu    67

<210> SEQ ID NO 120
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 120
agcauagcaa guuaaaauaa ggcuaguccg uuaucaacuu gaaaaagugg caccgagucg    60
gugcuuu    67

<210> SEQ ID NO 121
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (14)..(20)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 121
agcauagcaa guuaaaauaa ggcuaguccg uuaucaacuu gaaaagugg caccgagucg    60 gugcuuu                                                              67

<210> SEQ ID NO 122
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (13)..(20)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 122
agcauagcaa guuaaaauaa ggcuaguccg uuaucaacuu gaaaagugg caccgagucg    60 gugcuuu                                                              67

<210> SEQ ID NO 123
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
```

```
<222> LOCATION: (12)..(20)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 123
agcauagcaa guuaaaauaa ggcuaguccg uuaucaacuu gaaaaagugg caccgagucg      60
gugcuuu                                                                67

<210> SEQ ID NO 124
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (11)..(20)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 124
agcauagcaa guuaaaauaa ggcuaguccg uuaucaacuu gaaaaagugg caccgagucg      60
gugcuuu                                                                67

<210> SEQ ID NO 125
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(20)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 125
```

```
agcauagcaa guuaaaauaa ggcuaguccg uuaucaacuu gaaaaagugg caccgagucg    60
gugcuuu                                                               67
```

<210> SEQ ID NO 126
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (21)..(23)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 126

```
agcauagcaa guuaaaauaa ggcuaguccg uuaucaacuu gaaaaagugg caccgagucg    60
gugcuuu                                                               67
```

<210> SEQ ID NO 127
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (26)..(29)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 127

```
agcauagcaa guuaaaauaa ggcuaguccg uuaucaacuu gaaaaagugg caccgagucg    60
gugcuuu                                                               67
```

<210> SEQ ID NO 128
<211> LENGTH: 67
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (21)..(29)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 128
agcauagcaa guuaaaauaa ggcuaguccg uuaucaacuu gaaaaagugg caccgagucg      60
gugcuuu                                                                67

<210> SEQ ID NO 129
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(2)
<223> OTHER INFORMATION: LNA nucleotide
<220> FEATURE:
<221> NAME/KEY: misc_feature
<222> LOCATION: (65)..(67)
<223> OTHER INFORMATION: Phosphorothioate linkage
<220> FEATURE:
<221> NAME/KEY: modified_base
<222> LOCATION: (66)..(67)
<223> OTHER INFORMATION: LNA nucleotide

<400> SEQUENCE: 129
agcauagcaa guuaaaauaa ggcuaguccg uuaucaacuu gaaaaagugg caccgagucg      60
gugcutt                                                                67

<210> SEQ ID NO 130
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' C3 spacer
<220> FEATURE:
<221> NAME/KEY: modified_base
```

```
<222> LOCATION: (1)..(9)
<223> OTHER INFORMATION: 2'-O-methyl nucleotide
<220> FEATURE:
<221> NAME/KEY: modified_base
<222> LOCATION: (38)..(67)
<223> OTHER INFORMATION: 2'-O-methyl nucleotide
<220> FEATURE:
<221> NAME/KEY: modified_base
<222> LOCATION: (68)..(68)
<223> OTHER INFORMATION: Inverted-dT

<400> SEQUENCE: 130
agcauagcaa guuaaaauaa ggcuaguccg uuaucaacuu gaaaaagugg caccgagucg    60
gugcuuut                                                             68

<210> SEQ ID NO 131
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (38)..(62)
<223> OTHER INFORMATION: 2'-O-methyl nucleotide
<220> FEATURE:
<223> OTHER INFORMATION: 3' C3 spacer

<400> SEQUENCE: 131
agcauagcaa guuaaaauaa ggcuaguccg uuaucaacuu gaaaaagugg caccgagucg    60
gu                                                                   62

<210> SEQ ID NO 132
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' C3 spacer
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: modified_base
<222> LOCATION: (38)..(62)
<223> OTHER INFORMATION: 2'-O-methyl nucleotide
<220> FEATURE:
<221> NAME/KEY: modified_base
<222> LOCATION: (63)..(63)
<223> OTHER INFORMATION: Inverted-dT

<400> SEQUENCE: 132
agcauagcaa guuaaaauaa ggcuaguccg uuaucaacuu gaaaaagugg caccgagucg    60
gut                                                                  63

<210> SEQ ID NO 133
<211> LENGTH: 67
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: misc_feature
<222> LOCATION: (9)..(38)
<223> OTHER INFORMATION: Phosphorothioate linkage
<220> FEATURE:
<221> NAME/KEY: modified_base
<222> LOCATION: (38)..(67)
<223> OTHER INFORMATION: 2'-O-methyl nucleotide

<400> SEQUENCE: 133
agcauagcaa guuaaaauaa ggcuaguccg uuaucaacuu gaaaaagugg caccgagucg    60
gugcuuu                                                             67

<210> SEQ ID NO 134
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 134
agcauagcaa guuaaaauaa ggcuaguccg uuaucaacuu gaaaaagugg caccgagucg    60
gugcuuu                                                             67

<210> SEQ ID NO 135
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (32)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage
```

-continued

<400> SEQUENCE: 135
agcauagcaa guuaaaauaa ggcuaguccg uuaucaacuu gaaaaagugg caccgagucg    60
gugcuuu                                                             67

<210> SEQ ID NO 136
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (33)..(62)
<223> OTHER INFORMATION: 2'-O-methyl nucleotide
<220> FEATURE:
<221> NAME/KEY: misc_feature
<222> LOCATION: (60)..(62)
<223> OTHER INFORMATION: Phosphorothioate linkage

<400> SEQUENCE: 136
agcauagcaa guuaaaauaa ggcuaguccg uuaucaacuu gaaaaagugg caccgagucg    60
gu                                                                  62

<210> SEQ ID NO 137
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (32)..(62)
<223> OTHER INFORMATION: 2'-O-methyl nucleotide
<220> FEATURE:
<221> NAME/KEY: misc_feature
<222> LOCATION: (60)..(62)
<223> OTHER INFORMATION: Phosphorothioate linkage

<400> SEQUENCE: 137
agcauagcaa guuaaaauaa ggcuaguccg uuaucaacuu gaaaaagugg caccgagucg    60
gu                                                                  62

<210> SEQ ID NO 138
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 138
agcauagcaa gttaaaataa ggctagtccg ttaucaacuu gaaaaagugg caccgagucg    60
gugcuuu                                                              67

<210> SEQ ID NO 139
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 139
agcauagcaa gttaaaataa ggcuaguccg uuaucaacuu gaaaaagugg caccgagucg    60
gugcuuu                                                              67

<210> SEQ ID NO 140
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 140
agcauagcaa guuaaaauaa ggctagtccg ttaucaacuu gaaaaagugg caccgagucg    60
gugcuuu    67

<210> SEQ ID NO 141
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (12)..(32)
<223> OTHER INFORMATION: 2'-fluoro nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 141
agcauagcaa guuaaaauaa ggcuaguccg uuaucaacuu gaaaaagugg caccgagucg    60
gugcuuu    67

<210> SEQ ID NO 142
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (12)..(21)
<223> OTHER INFORMATION: 2'-fluoro nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 142
agcauagcaa guuaaaauaa ggcuaguccg uuaucaacuu gaaaaagugg caccgagucg    60
gugcuuu                                                             67

<210> SEQ ID NO 143
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (22)..(32)
<223> OTHER INFORMATION: 2'-fluoro nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 143
agcauagcaa guuaaaauaa ggcuaguccg uuaucaacuu gaaaaagugg caccgagucg    60
gugcuuu                                                             67

<210> SEQ ID NO 144
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 144
agcauagcaa guuaaaauaa ggcuaguccg uuaucaacuu gaaaaagugg caccgagucg    60
gugcuuu                                                             67

<210> SEQ ID NO 145
<211> LENGTH: 67
<212> TYPE: RNA
<213> ORGANISM: Artificial Sequence -continued

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 145
agcauagcaa guuaaaauaa ggcuaguccg uuaucaacuu gaaaagugg caccgagucg     60 gugcuuu                                                              67

<210> SEQ ID NO 146
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (15)..(15)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 146
agcauagcaa guuaaaauaa ggcuaguccg uuaucaacuu gaaaagugg caccgagucg     60 gugcuuu                                                              67

<210> SEQ ID NO 147
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
```

<222> LOCATION: (1)..(11)
<223> OTHER INFORMATION: 2'-O-methyl nucleotide
<220> FEATURE:
<221> NAME/KEY: modified_base
<222> LOCATION: (16)..(16)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 147
agcauagcaa guuaaaauaa ggcuaguccg uuaucaacuu gaaaaagugg caccgagucg    60
gugcuuu                                                              67

<210> SEQ ID NO 148
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (17)..(17)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 148
agcauagcaa guuaaaauaa ggcuaguccg uuaucaacuu gaaaaagugg caccgagucg    60
gugcuuu                                                              67

<210> SEQ ID NO 149
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2'-O-methyl nucleotide
<220> FEATURE:
<221> NAME/KEY: modified_base
<222> LOCATION: (33)..(67)

<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 149
agcauagcaa guuaaaauaa ggcuaguccg uuaucaacuu gaaaaagugg caccgagucg    60
gugcuuu                                                               67

<210> SEQ ID NO 150
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (19)..(19)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 150
agcauagcaa guuaaaauaa ggcuaguccg uuaucaacuu gaaaaagugg caccgagucg    60
gugcuuu                                                               67

<210> SEQ ID NO 151
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 151
agcauagcaa guuaaaauaa ggcuaguccg uuaucaacuu gaaaaagugg caccgagucg    60
gugcuuu                                                              67

<210> SEQ ID NO 152
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (21)..(21)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 152
agcauagcaa guuaaaauaa ggcuaguccg uuaucaacuu gaaaagugg caccgagucg      60 gugcuuu                                                              67

<210> SEQ ID NO 153
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (22)..(22)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 153
agcauagcaa guuaaaauaa ggcuaguccg uuaucaacuu gaaaagugg caccgagucg      60 gugcuuu                                                              67

<210> SEQ ID NO 154
<211> LENGTH: 67
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (23)..(23)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 154
agcauagcaa guuaaaauaa ggcuaguccg uuaucaacuu gaaaaagugg caccgagucg      60
gugcuuu                                                                67

<210> SEQ ID NO 155
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (24)..(24)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 155
agcauagcaa guuaaaauaa ggcuaguccg uuaucaacuu gaaaaagugg caccgagucg      60
gugcuuu                                                                67

<210> SEQ ID NO 156
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
```

<223> OTHER INFORMATION: 2'-O-methyl nucleotide
<220> FEATURE:
<221> NAME/KEY: modified_base
<222> LOCATION: (25)..(25)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 156
agcauagcaa guuaaaauaa ggcuaguccg uuaucaacuu gaaaaagugg caccgagucg    60
gugcuuu                                                              67

<210> SEQ ID NO 157
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (26)..(26)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 157
agcauagcaa guuaaaauaa ggcuaguccg uuaucaacuu gaaaaagugg caccgagucg    60
gugcuuu                                                              67

<210> SEQ ID NO 158
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (27)..(27)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide

```
<220> FEATURE:
<221> NAME/KEY: misc_feature
<222> LOCATION: (65)..(67)
<223> OTHER INFORMATION: Phosphorothioate linkage

<400> SEQUENCE: 158
agcauagcaa guuaaaauaa ggcuaguccg uuaucaacuu gaaaaagugg caccgagucg    60
gugcuuu                                                              67

<210> SEQ ID NO 159
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (28)..(28)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 159
agcauagcaa guuaaaauaa ggcuaguccg uuaucaacuu gaaaaagugg caccgagucg    60
gugcuuu                                                              67

<210> SEQ ID NO 160
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (29)..(29)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 160
agcauagcaa guuaaaauaa ggcuaguccg uuaucaacuu gaaaaagugg caccgagucg    60
``` gugcuuu                                                                67

<210> SEQ ID NO 161
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (30)..(30)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 161
agcauagcaa guuaaaauaa ggcuaguccg uuaucaacuu gaaaaagugg caccgagucg      60
gugcuuu                                                                67

<210> SEQ ID NO 162
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (31)..(31)
<223> OTHER INFORMATION: 2'-O-methyl nucleotide
<220> FEATURE:
<221> NAME/KEY: modified_base
<222> LOCATION: (33)..(67)
<223> OTHER INFORMATION: 2'-O-methyl nucleotide
<220> FEATURE:
<221> NAME/KEY: misc_feature
<222> LOCATION: (65)..(67)
<223> OTHER INFORMATION: Phosphorothioate linkage

<400> SEQUENCE: 162
agcauagcaa guuaaaauaa ggcuaguccg uuaucaacuu gaaaaagugg caccgagucg      60
gugcuuu                                                                67

<210> SEQ ID NO 163
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: 5' C3 spacer
<220> FEATURE:
<223> OTHER INFORMATION: 3' C3 spacer

<400> SEQUENCE: 163
uuauauccaa cacuucgugg uuuuagagcu augcu                              35

<210> SEQ ID NO 164
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: misc_feature
<222> LOCATION: (32)..(35)
<223> OTHER INFORMATION: Phosphorothioate linkage

<400> SEQUENCE: 164
uuauauccaa cacuucgugg uuuuagagcu augcu                              35

<210> SEQ ID NO 165
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(24)
<223> OTHER INFORMATION: 2'-O-methyl nucleotide

<400> SEQUENCE: 165
uuauauccaa cacuucgugg uuuuagagcu augcu                              35

<210> SEQ ID NO 166
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(6)
<223> OTHER INFORMATION: 2'-O-methyl nucleotide

<400> SEQUENCE: 166
uuauauccaa cacuucgugg uuuuagagcu augcu                              35

<210> SEQ ID NO 167
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(34)
<223> OTHER INFORMATION: 2'-O-methyl nucleotide

<400> SEQUENCE: 167
uuauauccaa cacuucgugg uuuuagagcu augcu                                      35

<210> SEQ ID NO 168
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(28)
<223> OTHER INFORMATION: 2'-O-methyl nucleotide
<220> FEATURE:
<221> NAME/KEY: modified_base
<222> LOCATION: (30)..(30)
<223> OTHER INFORMATION: 2'-O-methyl nucleotide
<220> FEATURE:
<221> NAME/KEY: modified_base
<222> LOCATION: (32)..(32)
<223> OTHER INFORMATION: 2'-O-methyl nucleotide
<220> FEATURE:
<221> NAME/KEY: modified_base
<222> LOCATION: (34)..(34)
<223> OTHER INFORMATION: 2'-O-methyl nucleotide

<400> SEQUENCE: 168
uuauauccaa cacuucgugg uuuuagagcu augcu                                      35

<210> SEQ ID NO 169
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(27)
<223> OTHER INFORMATION: 2'-O-methyl nucleotide
<220> FEATURE:
<221> NAME/KEY: modified_base
<222> LOCATION: (29)..(29)
<223> OTHER INFORMATION: 2'-O-methyl nucleotide
<220> FEATURE:
<221> NAME/KEY: modified_base
<222> LOCATION: (31)..(31)
<223> OTHER INFORMATION: 2'-O-methyl nucleotide
<220> FEATURE:
<221> NAME/KEY: modified_base
<222> LOCATION: (33)..(33)
<223> OTHER INFORMATION: 2'-O-methyl nucleotide
<220> FEATURE:
<221> NAME/KEY: modified_base
<222> LOCATION: (35)..(35)
<223> OTHER INFORMATION: 2'-O-methyl nucleotide

<400> SEQUENCE: 169
uuauauccaa cacuucgugg uuuuagagcu augcu                                      35

<210> SEQ ID NO 170
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(17)
<223> OTHER INFORMATION: 2'-O-methyl nucleotide

<400> SEQUENCE: 170
uuauauccaa cacuucgugg uuuuagagcu augcu                                      35

<210> SEQ ID NO 171
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(8)
<223> OTHER INFORMATION: 2'-O-methyl nucleotide

<400> SEQUENCE: 171
uuauauccaa cacuucgugg uuuuagagcu augcu                                      35

<210> SEQ ID NO 172
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl nucleotide
<220> FEATURE:
<221> NAME/KEY: modified_base
<222> LOCATION: (4)..(4)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (10)..(10)
<223> OTHER INFORMATION: 2'-O-methyl nucleotide
<220> FEATURE:
<221> NAME/KEY: modified_base
<222> LOCATION: (12)..(12)
<223> OTHER INFORMATION: 2'-O-methyl nucleotide

<400> SEQUENCE: 172
uuauauccaa cacuucgugg uuuuagagcu augcu                                      35

<210> SEQ ID NO 173
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(27)
<223> OTHER INFORMATION: 2'-O-methyl nucleotide

<400> SEQUENCE: 173
uuauauccaa cacuucgugg uuuuagagcu augcu                                      35

<210> SEQ ID NO 174
<211> LENGTH: 36
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-O-methyl nucleotide

<400> SEQUENCE: 174
cuuauaucca acacuucgug guuuuagagc uaugcu                                    36

<210> SEQ ID NO 175
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(36)
<223> OTHER INFORMATION: 2'-O-methyl nucleotide

<400> SEQUENCE: 175
cuuauaucca acacuucgug guuuuagagc uaugcu                                    36

<210> SEQ ID NO 176
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (34)..(36)
<223> OTHER INFORMATION: 2'-O-methyl nucleotide

<400> SEQUENCE: 176
cuuauaucca acacuucgug guuuuagagc uaugcu                                    36

<210> SEQ ID NO 177
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: misc_feature
<222> LOCATION: (33)..(36)
<223> OTHER INFORMATION: Phosphorothioate linkage

<400> SEQUENCE: 177
cuuauaucca acacuucgug guuuuagagc uaugcu                                    36

<210> SEQ ID NO 178
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: misc_feature
<222> LOCATION: (33)..(36)
<223> OTHER INFORMATION: Phosphorothioate linkage

<400> SEQUENCE: 178
cuuauaucca acacuucgug guuuuagagc uaugcu                                36

<210> SEQ ID NO 179
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer

<400> SEQUENCE: 179
cuuauaucca acacuucgug guuuuagagc uaugcu                                36

<210> SEQ ID NO 180
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' C3 spacer

<400> SEQUENCE: 180
cuuauaucca acacuucgug guuuuagagc uaugcu                                36

<210> SEQ ID NO 181
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<223> OTHER INFORMATION: 3' C3 spacer

<400> SEQUENCE: 181
cuuauaucca acacuucgug guuuuagagc uaugcu                                36

<210> SEQ ID NO 182
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier

<400> SEQUENCE: 182
cuuauaucca acacuucgug guuuuagagc uaugcu                                36

<210> SEQ ID NO 183
<211> LENGTH: 36
<212> TYPE: RNA
```

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 3' ZEN modifier

<400> SEQUENCE: 183
cuuauaucca acacuucgug guuuuagagc uaugcu                          36

<210> SEQ ID NO 184
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 184
cuuauaucca acacuucgug guuuuagagc uaugcu                          36

<210> SEQ ID NO 185
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 5' ZEN modifier
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (34)..(36)
<223> OTHER INFORMATION: 2'-O-methyl nucleotide
<220> FEATURE:
<223> OTHER INFORMATION: 3' ZEN modifier

<400> SEQUENCE: 185
cuuauaucca acacuucgug guuuuagagc uaugcu                          36

<210> SEQ ID NO 186
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 186
uuauauccaa cacuucgugg uuuuagagcu augcu                                35

<210> SEQ ID NO 187
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (13)..(14)
<223> OTHER INFORMATION: 2'-O-methyl nucleotide
<220> FEATURE:
<221> NAME/KEY: modified_base
<222> LOCATION: (17)..(18)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 187
cuuauauuca acacuucgug guuuuagagc uaugcu                               36

<210> SEQ ID NO 188
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (22)..(25)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 188
cuuauauuca acacuucgug guuuuagagc uaugcu                               36

<210> SEQ ID NO 189

```
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (33)..(36)
<223> OTHER INFORMATION: 2'-O-methyl nucleotide

<400> SEQUENCE: 189
cuuauaucca acacuucgug guuuuagagc uaugcu                                 36

<210> SEQ ID NO 190
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (32)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 190
cuuauaucca acacuucgug guuuuagagc uaugcu                                 36

<210> SEQ ID NO 191
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (31)..(36)
<223> OTHER INFORMATION: 2'-O-methyl nucleotide
<220> FEATURE:
<221> NAME/KEY: misc_feature
<222> LOCATION: (33)..(36)
```

<223> OTHER INFORMATION: Phosphorothioate linkage

<400> SEQUENCE: 191
cuuauaucca acacuucgug guuuuagagc uaugcu                                36

<210> SEQ ID NO 192
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (30)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 192
cuuauaucca acacuucgug guuuuagagc uaugcu                                36

<210> SEQ ID NO 193
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (29)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 193
cuuauaucca acacuucgug guuuuagagc uaugcu                                36

<210> SEQ ID NO 194
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)

<223> OTHER INFORMATION: 2'-O-methyl nucleotide
<220> FEATURE:
<221> NAME/KEY: modified_base
<222> LOCATION: (28)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 194
cuuauaucca acacuucgug guuuuagagc uaugcu                                    36

<210> SEQ ID NO 195
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (27)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 195
cuuauaucca acacuucgug guuuuagagc uaugcu                                    36

<210> SEQ ID NO 196
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 196
cuuauaucca acacuucgug guuuuagagc uaugcu                                    36

<210> SEQ ID NO 197
<211> LENGTH: 36
<212> TYPE: RNA
<213> ORGANISM: Artificial Sequence
<220> FEATURE:
<223> OTHER INFORMATION: Description of Artificial Sequence: Synthetic

```
              oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(5)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 197
cuuauaucca acacuucgug guuuuagagc uaugcu                                    36

<210> SEQ ID NO 198
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 198
cuuauaucca acacuucgug guuuuagagc uaugcu                                    36

<210> SEQ ID NO 199
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(7)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 199
cuuauaucca acacuucgug guuuuagagc uaugcu                                    36
```

```
<210> SEQ ID NO 200
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 200
cuuauaucca acacuucgug guuuuagagc uaugcu                                  36

<210> SEQ ID NO 201
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(9)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 201
cuuauaucca acacuucgug guuuuagagc uaugcu                                  36

<210> SEQ ID NO 202
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
```

<220> FEATURE:
<221> NAME/KEY: modified_base
<222> LOCATION: (34)..(36)
<223> OTHER INFORMATION: 2'-O-methyl nucleotide

<400> SEQUENCE: 202
cuuauaucca acacuucgug guuuuagagc uaugcu    36

<210> SEQ ID NO 203
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 203
cuuauaucca acacuucgug guuuuagagc uaugcu    36

<210> SEQ ID NO 204
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (27)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 204
cuuauaucca acacuucgug guuuuagagc uaugcu    36

<210> SEQ ID NO 205
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage

```
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (17)..(18)
<223> OTHER INFORMATION: 2'-O-methyl nucleotide
<220> FEATURE:
<221> NAME/KEY: modified_base
<222> LOCATION: (27)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 205
cuuauaucca acacuucgug guuuuagagc uaugcu                                36

<210> SEQ ID NO 206
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (26)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 206
cuuauaucca acacuucgug guuuuagagc uaugcu                                36

<210> SEQ ID NO 207
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 207
cuuauaucca acacuucgug guuuuagagc uaugcu                                36
```

```
<210> SEQ ID NO 208
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (24)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 208
cuuauaucca acacuucgug guuuuagagc uaugcu                               36

<210> SEQ ID NO 209
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (23)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 209
cuuauaucca acacuucgug guuuuagagc uaugcu                               36

<210> SEQ ID NO 210
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (22)..(36)
<223> OTHER INFORMATION: 2'-O-methyl nucleotide
<220> FEATURE:
```

<221> NAME/KEY: misc_feature
<222> LOCATION: (33)..(36)
<223> OTHER INFORMATION: Phosphorothioate linkage

<400> SEQUENCE: 210
cuuauaucca acacuucgug guuuuagagc uaugcu                                    36

<210> SEQ ID NO 211
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (21)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 211
cuuauaucca acacuucgug guuuuagagc uaugcu                                    36

<210> SEQ ID NO 212
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 212
cuuauaucca acacuucgug guuuuagagc uaugcu                                    36

<210> SEQ ID NO 213
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:

```
<221> NAME/KEY: modified_base
<222> LOCATION: (1)..(13)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 213
cuuauaucca acacuucgug guuuuagagc uaugcu                               36

<210> SEQ ID NO 214
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 214
cuuauaucca acacuucgug guuuuagagc uaugcu                               36

<210> SEQ ID NO 215
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(15)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 215
cuuauaucca acacuucgug guuuuagagc uaugcu                               36

<210> SEQ ID NO 216
<211> LENGTH: 36
<212> TYPE: RNA
<213> ORGANISM: Artificial Sequence
```

<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(16)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 216
cuuauaucca acacuucgug guuuuagagc uaugcu                                    36

<210> SEQ ID NO 217
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(17)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 217
cuuauaucca acacuucgug guuuuagagc uaugcu                                    36

<210> SEQ ID NO 218
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(18)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 218 cuuauauucca acacuucgug guuuuagagc uaugcu                             36

<210> SEQ ID NO 219
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(19)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 219 cuuauauucca acacuucgug guuuuagagc uaugcu                             36

<210> SEQ ID NO 220
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(20)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 220 cuuauauucca acacuucgug guuuuagagc uaugcu                             36

<210> SEQ ID NO 221
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: LNA nucleotide
<220> FEATURE:
<221> NAME/KEY: misc_feature
<222> LOCATION: (1)..(3)

```
<223> OTHER INFORMATION: Phosphorothioate linkage
<220> FEATURE:
<221> NAME/KEY: misc_feature
<222> LOCATION: (34)..(36)
<223> OTHER INFORMATION: Phosphorothioate linkage
<220> FEATURE:
<221> NAME/KEY: modified_base
<222> LOCATION: (35)..(36)
<223> OTHER INFORMATION: LNA nucleotide

<400> SEQUENCE: 221
ctuauaucca acacuucgug guuuuagagc uaugct                         36

<210> SEQ ID NO 222
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 222
cuuauaucca acacuucgug guuuuagagc uaugcu                         36

<210> SEQ ID NO 223
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (26)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 223
cuuauaucca acacuucgug guuuuagagc uaugcu                         36

<210> SEQ ID NO 224
<211> LENGTH: 36
<212> TYPE: RNA
<213> ORGANISM: Artificial Sequence
<220> FEATURE:
<223> OTHER INFORMATION: Description of Artificial Sequence: Synthetic
```

```
            oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (17)..(18)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 224
cuuauaucca acacuucgug guuuuagagc uaugcu                              36

<210> SEQ ID NO 225
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (16)..(18)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 225
cuuauaucca acacuucgug guuuuagagc uaugcu                              36

<210> SEQ ID NO 226
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (17)..(19)
<223> OTHER INFORMATION: 2'-O-methyl nucleotide
```

```
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 226
cuuauaucca acacuucgug guuuuagagc uaugcu                              36

<210> SEQ ID NO 227
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (17)..(20)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 227
cuuauaucca acacuucgug guuuuagagc uaugcu                              36

<210> SEQ ID NO 228
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (17)..(21)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 228
cuuauaucca acacuucgug guuuuagagc uaugcu                              36
```

```
<210> SEQ ID NO 229
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (17)..(22)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 229
cuuauaucca acacuucgug guuuuagagc uaugcu                                 36

<210> SEQ ID NO 230
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (17)..(23)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 230
cuuauaucca acacuucgug guuuuagagc uaugcu                                 36

<210> SEQ ID NO 231
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
```

```
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (23)..(23)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 231
cuuauaucca acacuucgug guuuuagagc uaugcu                              36

<210> SEQ ID NO 232
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (22)..(22)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 232
cuuauaucca acacuucgug guuuuagagc uaugcu                              36

<210> SEQ ID NO 233
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (21)..(21)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
```

```
<222> LOCATION: (33)..(36)
<223> OTHER INFORMATION: Phosphorothioate linkage

<400> SEQUENCE: 233
cuuauaucca acacuucgug guuuuagagc uaugcu                                    36

<210> SEQ ID NO 234
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 234
cuuauaucca acacuucgug guuuuagagc uaugcu                                    36

<210> SEQ ID NO 235
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2'-O-methyl nucleotide
<220> FEATURE:
<221> NAME/KEY: modified_base
<222> LOCATION: (34)..(36)
<223> OTHER INFORMATION: 2'-O-methyl nucleotide
<220> FEATURE:
<223> OTHER INFORMATION: 3' C3 spacer

<400> SEQUENCE: 235
cuuauaucca acacuucgug guuuuagagc uaugcu                                    36

<210> SEQ ID NO 236
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
```

-continued

```
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (26)..(36)
<223> OTHER INFORMATION: 2'-O-methyl nucleotide
<220> FEATURE:
<223> OTHER INFORMATION: 3' C3 spacer

<400> SEQUENCE: 236
cuuauaucca acacuucgug guuuuagagc uaugcu                              36

<210> SEQ ID NO 237
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' C3 spacer
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2'-O-methyl nucleotide
<220> FEATURE:
<221> NAME/KEY: modified_base
<222> LOCATION: (34)..(36)
<223> OTHER INFORMATION: 2'-O-methyl nucleotide
<220> FEATURE:
<221> NAME/KEY: modified_base
<222> LOCATION: (37)..(37)
<223> OTHER INFORMATION: Inverted-dT
<220> FEATURE:
<223> OTHER INFORMATION: 3' C3 spacer

<400> SEQUENCE: 237
cuuauaucca acacuucgug guuuuagagc uaugcut                             37

<210> SEQ ID NO 238
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (20)..(21)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
```

-continued

```
<400> SEQUENCE: 238
cuuauaucca acacuucgug guuuuagagc uaugcu                                 36

<210> SEQ ID NO 239
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (17)..(18)
<223> OTHER INFORMATION: 2'-O-methyl nucleotide
<220> FEATURE:
<221> NAME/KEY: modified_base
<222> LOCATION: (20)..(21)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 239
cuuauaucca acacuucgug guuuuagagc uaugcu                                 36

<210> SEQ ID NO 240
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (20)..(21)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<223> OTHER INFORMATION: 3' C3 spacer

<400> SEQUENCE: 240
cuuauaucca acacuucgug guuuuagagc uaugcu                                 36

<210> SEQ ID NO 241
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: 5' C3 spacer
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (17)..(18)
<223> OTHER INFORMATION: 2'-O-methyl nucleotide
<220> FEATURE:
<221> NAME/KEY: modified_base
<222> LOCATION: (20)..(21)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<223> OTHER INFORMATION: 3' C3 spacer

<400> SEQUENCE: 241
cuuauaucca acacuucgug guuuuagagc uaugcu                                    36

<210> SEQ ID NO 242
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (20)..(21)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<223> OTHER INFORMATION: 3' ZEN modifier

<400> SEQUENCE: 242
cuuauaucca acacuucgug guuuuagagc uaugcu                                    36

<210> SEQ ID NO 243
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (17)..(18)
<223> OTHER INFORMATION: 2'-O-methyl nucleotide
<220> FEATURE:
<221> NAME/KEY: modified_base
<222> LOCATION: (20)..(21)
<223> OTHER INFORMATION: 2'-O-methyl nucleotide
<220> FEATURE:
<221> NAME/KEY: modified_base
<222> LOCATION: (25)..(36)
```

```
<223> OTHER INFORMATION: 2'-O-methyl nucleotide
<220> FEATURE:
<223> OTHER INFORMATION: 3' ZEN modifier

<400> SEQUENCE: 243
cuuauaucca acacuucgug guuuuagagc uaugcu                                  36

<210> SEQ ID NO 244
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 244
cuuauaucca acacuucgug guuuuagagc uaugcu                                  36

<210> SEQ ID NO 245
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 245
cuuauaucca acacuucgug guuuuagagc uaugcu                                  36

<210> SEQ ID NO 246
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
```

```
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 246
cuuauaucca acacuucgug guuuuagagc uaugcu                              36

<210> SEQ ID NO 247
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 247
cuuauaucca acacuucgug guuuuagagc uaugcu                              36

<210> SEQ ID NO 248
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 248
cuuauaucca acacuucgug guuuuagagc uaugcu                              36

<210> SEQ ID NO 249
<211> LENGTH: 36
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 249
cuuauaucca acacuucgug guuuuagagc uaugcu                                36

<210> SEQ ID NO 250
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 250
cuuauaucca acacuucgug guuuuagagc uaugcu                                36

<210> SEQ ID NO 251
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 251
```

-continued cuuauauccaacacuucguguguuuagagcuaugcu        36

<210> SEQ ID NO 252
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 252
cuuauaucca acacuucgug guuuuagagc uaugcu        36

<210> SEQ ID NO 253
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (15)..(24)
<223> OTHER INFORMATION: 2'-fluoro nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 253
cuuauaucca acacuucgug guuuuagagc uaugcu        36

<210> SEQ ID NO 254
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base -continued

```
<222> LOCATION: (1)..(14)
<223> OTHER INFORMATION: 2'-O-methyl nucleotide
<220> FEATURE:
<221> NAME/KEY: modified_base
<222> LOCATION: (15)..(20)
<223> OTHER INFORMATION: 2'-fluoro nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 254
cuuauaucca acacuucgug guuuuagagc uaugcu                         36

<210> SEQ ID NO 255
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(14)
<223> OTHER INFORMATION: 2'-O-methyl nucleotide
<220> FEATURE:
<221> NAME/KEY: modified_base
<222> LOCATION: (21)..(24)
<223> OTHER INFORMATION: 2'-fluoro nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 255
cuuauaucca acacuucgug guuuuagagc uaugcu                         36

<210> SEQ ID NO 256
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<223> OTHER INFORMATION: 3' C3 spacer

<400> SEQUENCE: 256
cuuauaucca acacuucgug guuuuagagc uaugcu                         36

<210> SEQ ID NO 257
```

```
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<223> OTHER INFORMATION: 3' C3 spacer

<400> SEQUENCE: 257
cuuauaucca acacuucgug guuuuagagc uaugcu                                    36

<210> SEQ ID NO 258
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 258
cuuauaucca acacuucgug guuuuagagc uaugcu                                    36

<210> SEQ ID NO 259
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(35)
<223> OTHER INFORMATION: 2'-O-methyl nucleotide
<220> FEATURE:
<221> NAME/KEY: misc_feature
<222> LOCATION: (32)..(35)
<223> OTHER INFORMATION: Phosphorothioate linkage

<400> SEQUENCE: 259
``` cuuauauucca acacuucgug guuuuagagc uaugc                                35

<210> SEQ ID NO 260
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(34)
<223> OTHER INFORMATION: 2'-O-methyl nucleotide
<220> FEATURE:
<221> NAME/KEY: misc_feature
<222> LOCATION: (31)..(34)
<223> OTHER INFORMATION: Phosphorothioate linkage

<400> SEQUENCE: 260 cuuauauucca acacuucgug guuuuagagc uaug                                 34

<210> SEQ ID NO 261
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(33)
<223> OTHER INFORMATION: 2'-O-methyl nucleotide
<220> FEATURE:
<221> NAME/KEY: misc_feature
<222> LOCATION: (30)..(33)
<223> OTHER INFORMATION: Phosphorothioate linkage

<400> SEQUENCE: 261 cuuauauucca acacuucgug guuuuagagc uau                                  33

<210> SEQ ID NO 262
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(32)

```
<223> OTHER INFORMATION: 2'-O-methyl nucleotide
<220> FEATURE:
<221> NAME/KEY: misc_feature
<222> LOCATION: (29)..(32)
<223> OTHER INFORMATION: Phosphorothioate linkage

<400> SEQUENCE: 262
cuuauaucca acacuucgug guuuuagagc ua                                     32

<210> SEQ ID NO 263
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(31)
<223> OTHER INFORMATION: 2'-O-methyl nucleotide
<220> FEATURE:
<221> NAME/KEY: misc_feature
<222> LOCATION: (28)..(31)
<223> OTHER INFORMATION: Phosphorothioate linkage

<400> SEQUENCE: 263
cuuauaucca acacuucgug guuuuagagc u                                      31

<210> SEQ ID NO 264
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (21)..(21)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 264
cuuauaucca acacuucgug guuuuagagc uaugcu                                 36

<210> SEQ ID NO 265
<211> LENGTH: 36
<212> TYPE: RNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: misc_feature
<222> LOCATION: (21)..(25)
<223> OTHER INFORMATION: Phosphorothioate linkage
<220> FEATURE:
<221> NAME/KEY: modified_base
<222> LOCATION: (21)..(21)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 265
cuuauaucca acacuucgug guuuuagagc uaugcu                                 36

<210> SEQ ID NO 266
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: misc_feature
<222> LOCATION: (10)..(21)
<223> OTHER INFORMATION: Phosphorothioate linkage
<220> FEATURE:
<221> NAME/KEY: modified_base
<222> LOCATION: (21)..(21)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 266
cuuauaucca acacuucgug guuuuagagc uaugcu                                 36

<210> SEQ ID NO 267
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
```

```
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: misc_feature
<222> LOCATION: (10)..(21)
<223> OTHER INFORMATION: Phosphorothioate linkage
<220> FEATURE:
<221> NAME/KEY: modified_base
<222> LOCATION: (21)..(21)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 267
cuuauaucca acacuucgug guuuuagagc uaugcu                              36

<210> SEQ ID NO 268
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (21)..(21)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<223> OTHER INFORMATION: 3' C3 spacer

<400> SEQUENCE: 268
cuuauaucca acacuucgug guuuuagagc uaugcu                              36

<210> SEQ ID NO 269
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: misc_feature
<222> LOCATION: (21)..(25)
<223> OTHER INFORMATION: Phosphorothioate linkage
<220> FEATURE:
<221> NAME/KEY: modified_base
<222> LOCATION: (21)..(21)
<223> OTHER INFORMATION: 2'-O-methyl nucleotide
<220> FEATURE:
<221> NAME/KEY: modified_base
<222> LOCATION: (25)..(36)
```

```
<223> OTHER INFORMATION: 2'-O-methyl nucleotide
<220> FEATURE:
<223> OTHER INFORMATION: 3' C3 spacer

<400> SEQUENCE: 269
cuuauaucca acacuucgug guuuuagagc uaugcu                                36

<210> SEQ ID NO 270
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: misc_feature
<222> LOCATION: (10)..(21)
<223> OTHER INFORMATION: Phosphorothioate linkage
<220> FEATURE:
<221> NAME/KEY: modified_base
<222> LOCATION: (21)..(21)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<223> OTHER INFORMATION: 3' C3 spacer

<400> SEQUENCE: 270
cuuauaucca acacuucgug guuuuagagc uaugcu                                36

<210> SEQ ID NO 271
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: misc_feature
<222> LOCATION: (10)..(25)
<223> OTHER INFORMATION: Phosphorothioate linkage
<220> FEATURE:
<221> NAME/KEY: modified_base
<222> LOCATION: (21)..(21)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<223> OTHER INFORMATION: 3' C3 spacer

<400> SEQUENCE: 271
cuuauaucca acacuucgug guuuuagagc uaugcu                                36

<210> SEQ ID NO 272
<211> LENGTH: 36
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 2'-O-methyl nucleotide

<400> SEQUENCE: 272
cuuauaucca acacuucgug guuuuagagc uaugcu                                    36

<210> SEQ ID NO 273
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: 2'-O-methyl nucleotide

<400> SEQUENCE: 273
cuuauaucca acacuucgug guuuuagagc uaugcu                                    36

<210> SEQ ID NO 274
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 2'-O-methyl nucleotide

<400> SEQUENCE: 274
cuuauaucca acacuucgug guuuuagagc uaugcu                                    36

<210> SEQ ID NO 275
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 2'-O-methyl nucleotide

<400> SEQUENCE: 275
cuuauaucca acacuucgug guuuuagagc uaugcu                                    36

<210> SEQ ID NO 276
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: 2'-O-methyl nucleotide

<400> SEQUENCE: 276
cuuauaucca acacuucgug guuuuagagc uaugcu                                    36
```

<210> SEQ ID NO 277
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: 2'-O-methyl nucleotide

<400> SEQUENCE: 277
cuuauaucca acacuucgug guuuuagagc uaugcu        36

<210> SEQ ID NO 278
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: 2'-O-methyl nucleotide

<400> SEQUENCE: 278
cuuauaucca acacuucgug guuuuagagc uaugcu        36

<210> SEQ ID NO 279
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: 2'-O-methyl nucleotide

<400> SEQUENCE: 279
cuuauaucca acacuucgug guuuuagagc uaugcu        36

<210> SEQ ID NO 280
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: 2'-O-methyl nucleotide

<400> SEQUENCE: 280
cuuauaucca acacuucgug guuuuagagc uaugcu        36

<210> SEQ ID NO 281
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (20)..(20)
<223> OTHER INFORMATION: 2'-O-methyl nucleotide

<400> SEQUENCE: 281
cuuauaucca acacuucgug guuuuagagc uaugcu                                   36

<210> SEQ ID NO 282
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: 2'-O-methyl nucleotide

<400> SEQUENCE: 282
cuuauaucca acacuucgug guuuuagagc uaugcu                                   36

<210> SEQ ID NO 283
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: 2'-O-methyl nucleotide

<400> SEQUENCE: 283
cuuauaucca acacuucgug guuuuagagc uaugcu                                   36

<210> SEQ ID NO 284
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: 2'-O-methyl nucleotide

<400> SEQUENCE: 284
cuuauaucca acacuucgug guuuuagagc uaugcu                                   36

<210> SEQ ID NO 285
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(24)
<223> OTHER INFORMATION: 2'-O-methyl nucleotide

<400> SEQUENCE: 285
cuuauaucca acacuucgug guuuuagagc uaugcu                                   36

<210> SEQ ID NO 286
<211> LENGTH: 36
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(25)
<223> OTHER INFORMATION: 2'-O-methyl nucleotide

<400> SEQUENCE: 286
cuuauaucca acacuucgug guuuuagagc uaugcu                                  36

<210> SEQ ID NO 287
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(7)
<223> OTHER INFORMATION: 2'-O-methyl nucleotide
<220> FEATURE:
<221> NAME/KEY: modified_base
<222> LOCATION: (22)..(33)
<223> OTHER INFORMATION: 2'-O-methyl nucleotide
<220> FEATURE:
<221> NAME/KEY: misc_feature
<222> LOCATION: (30)..(33)
<223> OTHER INFORMATION: Phosphorothioate linkage

<400> SEQUENCE: 287
auauccaaca cuucgugguu uuagagcuau gcu                                     33

<210> SEQ ID NO 288
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (21)..(33)
<223> OTHER INFORMATION: 2'-O-methyl nucleotide
<220> FEATURE:
<221> NAME/KEY: misc_feature
<222> LOCATION: (30)..(33)
<223> OTHER INFORMATION: Phosphorothioate linkage

<400> SEQUENCE: 288
uauccaacac uucgugguuu uagagcuaug cu                                      32

<210> SEQ ID NO 289
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(2)
<223> OTHER INFORMATION: LNA nucleotide
<220> FEATURE:
<221> NAME/KEY: modified_base
<222> LOCATION: (3)..(7)
<223> OTHER INFORMATION: 2'-O-methyl nucleotide
<220> FEATURE:
<221> NAME/KEY: modified_base
<222> LOCATION: (22)..(33)
<223> OTHER INFORMATION: 2'-O-methyl nucleotide
<220> FEATURE:
<221> NAME/KEY: misc_feature
<222> LOCATION: (30)..(33)
<223> OTHER INFORMATION: Phosphorothioate linkage

<400> SEQUENCE: 289
atauccaaca cuucgugguu uuagagcuau gcu                                   33

<210> SEQ ID NO 290
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(2)
<223> OTHER INFORMATION: LNA nucleotide
<220> FEATURE:
<221> NAME/KEY: modified_base
<222> LOCATION: (3)..(6)
<223> OTHER INFORMATION: 2'-O-methyl nucleotide
<220> FEATURE:
<221> NAME/KEY: modified_base
<222> LOCATION: (21)..(32)
<223> OTHER INFORMATION: 2'-O-methyl nucleotide
<220> FEATURE:
<221> NAME/KEY: misc_feature
<222> LOCATION: (29)..(32)
<223> OTHER INFORMATION: Phosphorothioate linkage

<400> SEQUENCE: 290
tauccaacac uucgugguuu uagagcuaug cu                                    32

<210> SEQ ID NO 291
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
```

```
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 291
uccauuucau agucuuuccu guuuuagagc uaugcu                            36

<210> SEQ ID NO 292
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 292
uuuuguaauu aacagcuugc guuuuagagc uaugcu                            36

<210> SEQ ID NO 293
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 293
cuuagagaau auuuguagag guuuuagagc uaugcu                            36

<210> SEQ ID NO 294
<211> LENGTH: 36
<212> TYPE: RNA
<213> ORGANISM: Artificial Sequence
<220> FEATURE:
<223> OTHER INFORMATION: Description of Artificial Sequence: Synthetic
```

```
        oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 294
uugacuauaa ugaauacuuc guuuuagagc uaugcu                                    36

<210> SEQ ID NO 295
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 295
caaaacacgc auaaaaauuu guuuuagagc uaugcu                                    36

<210> SEQ ID NO 296
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 296
aauuaugggg auuacuagga guuuuagagc uaugcu                                    36
```

<210> SEQ ID NO 297
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 297
ggucacuuuu aacacaccca guuuuagagc uaugcu                                 36

<210> SEQ ID NO 298
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 298
ggcuuauauc caacacuucg guuuuagagc uaugcu                                 36

<210> SEQ ID NO 299
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

```
<220> FEATURE:
<221> NAME/KEY: modified_base
<222> LOCATION: (34)..(36)
<223> OTHER INFORMATION: 2'-O-methyl nucleotide

<400> SEQUENCE: 299
auuucacaua aaacucuuuu guuuuagagc uaugcu                               36

<210> SEQ ID NO 300
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 300
ucaaauuaug aggugcugga guuuuagagc uaugcu                               36

<210> SEQ ID NO 301
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 301
uacagcuuua ugugacuaau guuuuagagc uaugcu                               36

<210> SEQ ID NO 302
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
```

```
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 302
uccauuucau agucuuuccu guuuuagagc uaugcu                                   36

<210> SEQ ID NO 303
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 303
uuuuguaauu aacagcuugc guuuuagagc uaugcu                                   36

<210> SEQ ID NO 304
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 304
cuuagagaau auuuguagag guuuuagagc uaugcu                                   36

<210> SEQ ID NO 305
<211> LENGTH: 36
<212> TYPE: RNA
```

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 305
uugacuauaa ugaauacuuc guuuuagagc uaugcu                                  36

<210> SEQ ID NO 306
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 306
caaaacacgc auaaaaauuu guuuuagagc uaugcu                                  36

<210> SEQ ID NO 307
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 307
aauuaugggg auuacuagga guuuuagagc uaugcu                                    36

<210> SEQ ID NO 308
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 308
ggucacuuuu aacacaccca guuuuagagc uaugcu                                    36

<210> SEQ ID NO 309
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 309
cuuauaucca acacuucgug guuuuagagc uaugcu                                    36

<210> SEQ ID NO 310
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(4)
<223> OTHER INFORMATION: 2'-O-methyl nucleotide
<220> FEATURE:

```
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 310
ggcuuauauc caacacuucg guuuuagagc uaugcu                                  36

<210> SEQ ID NO 311
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 311
auuucacaua aaacucuuuu guuuuagagc uaugcu                                  36

<210> SEQ ID NO 312
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 312
ucaaauuaug aggugcugga guuuuagagc uaugcu                                  36

<210> SEQ ID NO 313
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 313
uacagcuuua ugugacuaau guuuuagagc uaugcu                           36

<210> SEQ ID NO 314
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 314
uccauuucau agucuuuccu guuuuagagc uaugcu                           36

<210> SEQ ID NO 315
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 315
uuuuguaauu aacagcuugc guuuuagagc uaugcu                           36
```

```
<210> SEQ ID NO 316
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 316
cuuagagaau auuguagag guuuuagagc uaugcu                         36

<210> SEQ ID NO 317
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 317
uugacuauaa ugaauacuuc guuuuagagc uaugcu                        36

<210> SEQ ID NO 318
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
```

```
<222> LOCATION: (33)..(36)
<223> OTHER INFORMATION: Phosphorothioate linkage

<400> SEQUENCE: 318
caaaacacgc auaaaaauuu guuuuagagc uaugcu                                36

<210> SEQ ID NO 319
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 319
aauuaugggg auuacuagga guuuuagagc uaugcu                                36

<210> SEQ ID NO 320
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 320
ggucacuuuu aacacaccca guuuuagagc uaugcu                                36

<210> SEQ ID NO 321
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
```

```
<222> LOCATION: (1)..(6)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 321
cuuauaucca acacuucgug guuuuagagc uaugcu                          36

<210> SEQ ID NO 322
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 322
ggcuuauauc caacacuucg guuuuagagc uaugcu                          36

<210> SEQ ID NO 323
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 323
auuucacaua aaacucuuuu guuuuagagc uaugcu                          36

<210> SEQ ID NO 324
<211> LENGTH: 36
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 324
ucaaauuaug aggugcugga guuuuagagc uaugcu                               36

<210> SEQ ID NO 325
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 325
uacagcuuua ugugacuaau guuuuagagc uaugcu                               36

<210> SEQ ID NO 326
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 326
```
uccauuucau agucuuuccu guuuuagagc uaugcu                36

<210> SEQ ID NO 327
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 327
uuuuguaauu aacagcuugc guuuuagagc uaugcu                36

<210> SEQ ID NO 328
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 328
cuuagagaau auuuguagag guuuuagagc uaugcu                36

<210> SEQ ID NO 329
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (25)..(36)

<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 329
uugacuauaa ugaauacuuc guuuuagagc uaugcu                                   36

<210> SEQ ID NO 330
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 330
caaaacacgc auaaaaauuu guuuuagagc uaugcu                                   36

<210> SEQ ID NO 331
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 331
aauuaugggg auuacuagga guuuuagagc uaugcu                                   36

<210> SEQ ID NO 332
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)

```
<223> OTHER INFORMATION: Phosphorothioate linkage
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 332
ggucacuuuu aacacaccca guuuuagagc uaugcu                               36

<210> SEQ ID NO 333
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 333
cuuauaucca acacuucgug guuuuagagc uaugcu                               36

<210> SEQ ID NO 334
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 334
ggcuuauauc caacacuucg guuuuagagc uaugcu                               36

<210> SEQ ID NO 335
<211> LENGTH: 36
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 335
auuucacaua aaacucuuuu guuuuagagc uaugcu                              36

<210> SEQ ID NO 336
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 336
ucaaauuaug aggugcugga guuuuagagc uaugcu                              36

<210> SEQ ID NO 337
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
```

<400> SEQUENCE: 337
uacagcuuua ugugacuaau guuuuagagc uaugcu        36

<210> SEQ ID NO 338
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 338
uccauuucau agucuuuccu guuuuagagc uaugcu        36

<210> SEQ ID NO 339
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 339
uuuuguaauu aacagcuugc guuuuagagc uaugcu        36

<210> SEQ ID NO 340
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 340
cuuagagaau auuuguagag guuuuagagc uaugcu                              36

<210> SEQ ID NO 341
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 341
uugacuauaa ugaauacuuc guuuuagagc uaugcu                              36

<210> SEQ ID NO 342
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 342
caaaacacgc auaaaaauuu guuuuagagc uaugcu                              36

<210> SEQ ID NO 343
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 343
aauuaugggg auuacuagga guuuuagagc uaugcu                              36

<210> SEQ ID NO 344
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 344
ggucacuuuu aacacaccca guuuuagagc uaugcu                              36

<210> SEQ ID NO 345
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 345
cuuauaucca acacuucgug guuuuagagc uaugcu                              36
```

```
<210> SEQ ID NO 346
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 346
ggcuuauauc caacacuucg guuuuagagc uaugcu                              36

<210> SEQ ID NO 347
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 347
auuucacaua aaacucuuuu guuuuagagc uaugcu                              36

<210> SEQ ID NO 348
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
```

-continued

```
<221> NAME/KEY: misc_feature
<222> LOCATION: (33)..(36)
<223> OTHER INFORMATION: Phosphorothioate linkage

<400> SEQUENCE: 348
ucaaauuaug aggugcugga guuuuagagc uaugcu                              36

<210> SEQ ID NO 349
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 349
uacagcuuua ugugacuaau guuuuagagc uaugcu                              36

<210> SEQ ID NO 350
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 350
uccauuucau agucuuuccu guuuuagagc uaugcu                              36

<210> SEQ ID NO 351
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
```

```
<221> NAME/KEY: modified_base
<222> LOCATION: (1)..(12)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 351
uuuuguaauu aacagcuugc guuuuagagc uaugcu                                    36

<210> SEQ ID NO 352
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 352
cuuagagaau auuuguagag guuuuagagc uaugcu                                    36

<210> SEQ ID NO 353
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 353
uugacuauaa ugaauacuuc guuuuagagc uaugcu                                    36

<210> SEQ ID NO 354
<211> LENGTH: 36
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 354
caaaacacgc auaaaaauuu guuuuagagc uaugcu                              36

<210> SEQ ID NO 355
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 355
aauuaugggg auuacuagga guuuuagagc uaugcu                              36

<210> SEQ ID NO 356
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 356
```

-continued ggucacuuuu aacacaccca guuuuagagc uaugcu                36

<210> SEQ ID NO 357
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 357
cuuauaucca acacuucgug guuuuagagc uaugcu                36

<210> SEQ ID NO 358
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 358
ggcuuauauc caacacuucg guuuuagagc uaugcu                36

<210> SEQ ID NO 359
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: modified_base

```
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 359
auuucacaua aaacucuuuu guuuuagagc uaugcu                              36

<210> SEQ ID NO 360
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 360
ucaaauuaug aggugcugga guuuuagagc uaugcu                              36

<210> SEQ ID NO 361
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 361
uacagcuuua ugugacuaau guuuuagagc uaugcu                              36

<210> SEQ ID NO 362
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
```

```
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 362
uccauuucau agucuuuccu guuuuagagc uaugcu                           36

<210> SEQ ID NO 363
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 363
uuuuguaauu aacagcuugc guuuuagagc uaugcu                           36

<210> SEQ ID NO 364
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 364
cuuagagaau auuuguagag guuuuagagc uaugcu                           36

<210> SEQ ID NO 365
```

```
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 365
uugacuauaa ugaauacuuc guuuuagagc uaugcu                            36

<210> SEQ ID NO 366
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 366
caaaacacgc auaaaaauuu guuuuagagc uaugcu                            36

<210> SEQ ID NO 367
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
```

<223> OTHER INFORMATION: Phosphorothioate linkage

<400> SEQUENCE: 367
aauuaugggg auuacuagga guuuuagagc uaugcu                                    36

<210> SEQ ID NO 368
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 368
ggucacuuuu aacacaccca guuuuagagc uaugcu                                    36

<210> SEQ ID NO 369
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 369
cuuauaucca acacuucgug guuuuagagc uaugcu                                    36

<210> SEQ ID NO 370
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)

```
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 370
ggcuuauauc caacacuucg guuuuagagc uaugcu                                36

<210> SEQ ID NO 371
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 371
auuucacaua aaacucuuuu guuuuagagc uaugcu                                36

<210> SEQ ID NO 372
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 372
ucaaauuaug aggugcugga guuuuagagc uaugcu                                36

<210> SEQ ID NO 373
<211> LENGTH: 36
<212> TYPE: RNA
<213> ORGANISM: Artificial Sequence
<220> FEATURE:
<223> OTHER INFORMATION: Description of Artificial Sequence: Synthetic
```

```
    oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 373
uacagcuuua ugugacuaau guuuuagagc uaugcu                                 36

<210> SEQ ID NO 374
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 374
uccauuucau agucuuuccu guuuuagagc uaugcu                                 36

<210> SEQ ID NO 375
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 375
uuuuguaauu aacagcuugc guuuuagagc uaugcu                                 36
```

<210> SEQ ID NO 376
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 376
cuuagagaau auuguagag guuuuagagc uaugcu                                      36

<210> SEQ ID NO 377
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 377
uugacuauaa ugaauacuuc guuuuagagc uaugcu                                     36

<210> SEQ ID NO 378
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide

```
<220> FEATURE:
<221> NAME/KEY: misc_feature
<222> LOCATION: (33)..(36)
<223> OTHER INFORMATION: Phosphorothioate linkage

<400> SEQUENCE: 378
caaaacacgc auaaaaauuu guuuuagagc uaugcu                              36

<210> SEQ ID NO 379
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 379
aauuaugggg auuacuagga guuuuagagc uaugcu                              36

<210> SEQ ID NO 380
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 380
ggucacuuuu aacacaccca guuuuagagc uaugcu                              36

<210> SEQ ID NO 381
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
```

-continued

```
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 381
ggcuuauauc caacacuucg guuuuagagc uaugcu                             36

<210> SEQ ID NO 382
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 382
auuucacaua aaacucuuuu guuuuagagc uaugcu                             36

<210> SEQ ID NO 383
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 383
ucaaauuaug aggugcugga guuuuagagc uaugcu                             36

<210> SEQ ID NO 384
<211> LENGTH: 36
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 384
uacagcuuua ugugacuaau guuuuagagc uaugcu                                 36

<210> SEQ ID NO 385
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<223> OTHER INFORMATION: 3' C3 spacer

<400> SEQUENCE: 385
uccauuucau agucuuuccu guuuuagagc uaugcu                                 36

<210> SEQ ID NO 386
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<223> OTHER INFORMATION: 3' C3 spacer

<400> SEQUENCE: 386
uuuuguaauu aacagcuugc guuuuagagc uaugcu                                 36

<210> SEQ ID NO 387
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<223> OTHER INFORMATION: 3' C3 spacer

<400> SEQUENCE: 387
cuuagagaau auuuguagag guuuuagagc uaugcu                                 36

<210> SEQ ID NO 388
<211> LENGTH: 36
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<223> OTHER INFORMATION: 3' C3 spacer

<400> SEQUENCE: 388
uugacuauaa ugaauacuuc guuuuagagc uaugcu                              36

<210> SEQ ID NO 389
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<223> OTHER INFORMATION: 3' C3 spacer

<400> SEQUENCE: 389
caaaacacgc auaaaaauuu guuuuagagc uaugcu                              36

<210> SEQ ID NO 390
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<223> OTHER INFORMATION: 3' C3 spacer

<400> SEQUENCE: 390
aauuaugggg auuacuagga guuuuagagc uaugcu                              36

<210> SEQ ID NO 391
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<223> OTHER INFORMATION: 3' C3 spacer

<400> SEQUENCE: 391
ggucacuuuu aacacaccca guuuuagagc uaugcu                              36

<210> SEQ ID NO 392
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<223> OTHER INFORMATION: 3' C3 spacer

<400> SEQUENCE: 392
```
ggcuuauauc caacacuucg guuuuagagc uaugcu                  36

<210> SEQ ID NO 393
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<223> OTHER INFORMATION: 3' C3 spacer

<400> SEQUENCE: 393
auuucacaua aaacucuuuu guuuuagagc uaugcu                  36

<210> SEQ ID NO 394
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<223> OTHER INFORMATION: 3' C3 spacer

<400> SEQUENCE: 394
ucaaauuaug aggugcugga guuuuagagc uaugcu                  36

<210> SEQ ID NO 395
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<223> OTHER INFORMATION: 3' C3 spacer

<400> SEQUENCE: 395
uacagcuuua ugugacuaau guuuuagagc uaugcu                  36

<210> SEQ ID NO 396
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 396
uccauuucau agucuuuccu guuuuagagc uaugcu                  36

<210> SEQ ID NO 397
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: 5' ZEN modifier
<220> FEATURE:
<223> OTHER INFORMATION: 3' ZEN modifier

<400> SEQUENCE: 397
uuuuguaauu aacagcuugc guuuuagagc uaugcu                            36

<210> SEQ ID NO 398
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 398
cuuagagaau auuuguagag guuuuagagc uaugcu                            36

<210> SEQ ID NO 399
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 399
uugacuauaa ugaauacuuc guuuuagagc uaugcu                            36

<210> SEQ ID NO 400
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 400
caaaacacgc auaaaaauuu guuuuagagc uaugcu                            36

<210> SEQ ID NO 401
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 401
aauuaugggg auuacuagga guuuuagagc uaugcu                            36

<210> SEQ ID NO 402
```

```
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 402
ggucacuuuu aacacaccca guuuuagagc uaugcu                        36

<210> SEQ ID NO 403
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 403
ggcuuauauc caacacuucg guuuuagagc uaugcu                        36

<210> SEQ ID NO 404
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 404
auuucacaua aaacucuuuu guuuuagagc uaugcu                        36

<210> SEQ ID NO 405
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 405
ucaaauuaug aggugcugga guuuuagagc uaugcu                        36

<210> SEQ ID NO 406
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier
```

-continued

```
<400> SEQUENCE: 406
uacagcuuua ugugacuaau guuuuagagc uaugcu                                    36

<210> SEQ ID NO 407
<211> LENGTH: 1367
<212> TYPE: PRT
<213> ORGANISM: Streptococcus pyogenes

<400> SEQUENCE: 407
```

| | | | | | | | | | | | | | | |
|---|---|---|---|---|---|---|---|---|---|---|---|---|---|---|
|Met|Asp|Lys|Lys|Tyr|Ser|Ile|Gly|Leu|Asp|Ile|Gly|Thr|Asn|Ser|Val
|1| | | |5| | | | |10| | | | |15| |
|Gly|Trp|Ala|Val|Ile|Thr|Asp|Glu|Tyr|Lys|Val|Pro|Ser|Lys|Lys|Phe
| | | |20| | | | |25| | | | |30| | |
|Lys|Val|Leu|Gly|Asn|Thr|Asp|Arg|His|Ser|Ile|Lys|Lys|Asn|Leu|Ile
| | |35| | | | |40| | | | |45| | | |
|Gly|Ala|Leu|Leu|Phe|Asp|Ser|Gly|Glu|Thr|Ala|Glu|Ala|Thr|Arg|Leu
| |50| | | | |55| | | | |60| | | | |
|Lys|Arg|Thr|Ala|Arg|Arg|Arg|Tyr|Thr|Arg|Arg|Lys|Asn|Arg|Ile|Cys
|65| | | | |70| | | | |75| | | | |80|
|Tyr|Leu|Gln|Glu|Ile|Phe|Ser|Asn|Glu|Met|Ala|Lys|Val|Asp|Asp|Ser
| | | | |85| | | | |90| | | | |95| | |
|Phe|Phe|His|Arg|Leu|Glu|Glu|Ser|Phe|Leu|Val|Glu|Glu|Asp|Lys|Lys
| | | |100| | | | |105| | | | |110| | |
|His|Glu|Arg|His|Pro|Ile|Phe|Gly|Asn|Ile|Val|Asp|Glu|Val|Ala|Tyr
| | |115| | | | |120| | | | |125| | | |
|His|Glu|Lys|Tyr|Pro|Thr|Ile|Tyr|His|Leu|Arg|Lys|Lys|Leu|Val|Asp
| |130| | | | |135| | | | |140| | | | |
|Ser|Thr|Asp|Lys|Ala|Asp|Leu|Arg|Leu|Ile|Tyr|Leu|Ala|Leu|Ala|His
|145| | | | |150| | | | |155| | | | |160|
|Met|Ile|Lys|Phe|Arg|Gly|His|Phe|Leu|Ile|Glu|Gly|Asp|Leu|Asn|Pro
| | | | |165| | | | |170| | | | |175| | |
|Asp|Asn|Ser|Asp|Val|Asp|Lys|Leu|Phe|Ile|Gln|Leu|Val|Gln|Thr|Tyr
| | | |180| | | | |185| | | | |190| | | |
|Asn|Gln|Leu|Phe|Glu|Glu|Asn|Pro|Ile|Asn|Ala|Ser|Gly|Val|Asp|Ala
| | |195| | | | |200| | | | |205| | | |
|Lys|Ala|Ile|Leu|Ser|Ala|Arg|Leu|Ser|Lys|Ser|Arg|Arg|Leu|Glu|Asn
| |210| | | | |215| | | | |220| | | | |
|Leu|Ile|Ala|Gln|Leu|Pro|Gly|Glu|Lys|Lys|Asn|Gly|Leu|Phe|Gly|Asn
|225| | | | |230| | | | |235| | | | |240|
|Leu|Ile|Ala|Leu|Ser|Leu|Gly|Leu|Thr|Pro|Asn|Phe|Lys|Ser|Asn|Phe
| | | | |245| | | | |250| | | | |255| | |
|Asp|Leu|Ala|Glu|Asp|Ala|Lys|Leu|Gln|Leu|Ser|Lys|Asp|Thr|Tyr|Asp
| | | |260| | | | |265| | | | |270| | | |
|Asp|Asp|Leu|Asp|Asn|Leu|Leu|Ala|Gln|Ile|Gly|Asp|Gln|Tyr|Ala|Asp
| | |275| | | | |280| | | | |285| | | |
|Leu|Phe|Leu|Ala|Ala|Lys|Asn|Leu|Ser|Asp|Ala|Ile|Leu|Leu|Ser|Asp
| |290| | | | |295| | | | |300| | | | |
|Ile|Leu|Arg|Val|Asn|Thr|Glu|Ile|Thr|Lys|Ala|Pro|Leu|Ser|Ala|Ser
|305| | | | |310| | | | |315| | | | |320|
|Met|Ile|Lys|Arg|Tyr|Asp|Glu|His|His|Gln|Asp|Leu|Thr|Leu|Leu|Lys
| | | | |325| | | | |330| | | | |335| | |
|Ala|Leu|Val|Arg|Gln|Gln|Leu|Pro|Glu|Lys|Tyr|Lys|Glu|Ile|Phe|Phe
| | | |340| | | | |345| | | | |350| | | |
|Asp|Gln|Ser|Lys|Asn|Gly|Tyr|Ala|Gly|Tyr|Ile|Asp|Gly|Gly|Ala|Ser

-continued

```
                355                 360                 365
Gln Glu Glu Phe Tyr Lys Phe Ile Lys Pro Ile Leu Glu Lys Met Asp
370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ile Leu Arg Arg Gln Glu Asp Phe Tyr Pro Phe Leu
                420                 425                 430
Lys Asp Asn Arg Glu Lys Ile Glu Lys Ile Leu Thr Phe Arg Ile Pro
                435                 440                 445
Tyr Tyr Val Gly Pro Leu Ala Arg Gly Asn Ser Arg Phe Ala Trp Met
                450                 455                 460
Thr Arg Lys Ser Glu Glu Thr Ile Thr Pro Trp Asn Phe Glu Glu Val
465                 470                 475                 480
Val Asp Lys Gly Ala Ser Ala Gln Ser Phe Ile Glu Arg Met Thr Asn
                485                 490                 495
Phe Asp Lys Asn Leu Pro Asn Glu Lys Val Leu Pro Lys His Ser Leu
                500                 505                 510
Leu Tyr Glu Tyr Phe Thr Val Tyr Asn Glu Leu Thr Lys Val Lys Tyr
                515                 520                 525
Val Thr Glu Gly Met Arg Lys Pro Ala Phe Leu Ser Gly Glu Gln Lys
                530                 535                 540
Lys Ala Ile Val Asp Leu Leu Phe Lys Thr Asn Arg Lys Val Thr Val
545                 550                 555                 560
Lys Gln Leu Lys Glu Asp Tyr Phe Lys Lys Ile Glu Cys Phe Asp Ser
                565                 570                 575
Val Glu Ile Ser Gly Val Glu Asp Arg Phe Asn Ala Ser Leu Gly Thr
                580                 585                 590
Tyr His Asp Leu Leu Lys Ile Ile Lys Asp Lys Asp Phe Leu Asp Asn
                595                 600                 605
Glu Glu Asn Glu Asp Ile Leu Glu Asp Ile Val Leu Thr Leu Thr Leu
                610                 615                 620
Phe Glu Asp Arg Glu Met Ile Glu Glu Arg Leu Lys Thr Tyr Ala His
625                 630                 635                 640
Leu Phe Asp Asp Lys Val Met Lys Gln Leu Lys Arg Arg Arg Tyr Thr
                645                 650                 655
Gly Trp Gly Arg Leu Ser Arg Lys Leu Ile Asn Gly Ile Arg Asp Lys
                660                 665                 670
Gln Ser Gly Lys Thr Ile Leu Asp Phe Leu Lys Ser Asp Gly Phe Ala
                675                 680                 685
Asn Arg Asn Phe Met Gln Leu Ile His Asp Asp Ser Leu Thr Phe Lys
                690                 695                 700
Glu Asp Ile Gln Lys Ala Gln Val Ser Gly Gln Gly Asp Ser Leu His
705                 710                 715                 720
Glu His Ile Ala Asn Leu Ala Gly Ser Pro Ala Ile Lys Lys Gly Ile
                725                 730                 735
Leu Gln Thr Val Lys Val Val Asp Glu Leu Val Lys Val Met Gly Arg
                740                 745                 750
His Lys Pro Glu Asn Ile Val Ile Glu Met Ala Arg Glu Asn Gln Thr
                755                 760                 765
Thr Gln Lys Gly Gln Lys Asn Ser Arg Glu Arg Met Lys Arg Ile Glu
                770                 775                 780
```

-continued

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
        805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
850                 855                 860

Lys Ser Asp Asn Val Pro Ser Glu Glu Val Val Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

```
Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 408
<211> LENGTH: 1416
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Met Gly Ser Ser Ala Pro Lys Lys Lys Arg Lys Val Gly Ile His Gly
1               5                   10                  15

Val Pro Ala Ala Met Asp Lys Lys Tyr Ser Ile Gly Leu Asp Ile Gly
                20                  25                  30

Thr Asn Ser Val Gly Trp Ala Val Ile Thr Asp Glu Tyr Lys Val Pro
            35                  40                  45

Ser Lys Lys Phe Lys Val Leu Gly Asn Thr Asp Arg His Ser Ile Lys
        50                  55                  60

Lys Asn Leu Ile Gly Ala Leu Leu Phe Asp Ser Gly Glu Thr Ala Glu
65                  70                  75                  80

Ala Thr Arg Leu Lys Arg Thr Ala Arg Arg Arg Tyr Thr Arg Arg Lys
                85                  90                  95

Asn Arg Ile Cys Tyr Leu Gln Glu Ile Phe Ser Asn Glu Met Ala Lys
            100                 105                 110

Val Asp Asp Ser Phe Phe His Arg Leu Glu Glu Ser Phe Leu Val Glu
        115                 120                 125

Glu Asp Lys Lys His Glu Arg His Pro Ile Phe Gly Asn Ile Val Asp
    130                 135                 140

Glu Val Ala Tyr His Glu Lys Tyr Pro Thr Ile Tyr His Leu Arg Lys
145                 150                 155                 160

Lys Leu Val Asp Ser Thr Asp Lys Ala Asp Leu Arg Leu Ile Tyr Leu
                165                 170                 175
```

```
Ala Leu Ala His Met Ile Lys Phe Arg Gly His Phe Leu Ile Glu Gly
            180                 185                 190

Asp Leu Asn Pro Asp Asn Ser Asp Val Asp Lys Leu Phe Ile Gln Leu
            195                 200                 205

Val Gln Thr Tyr Asn Gln Leu Phe Glu Glu Asn Pro Ile Asn Ala Ser
210                 215                 220

Gly Val Asp Ala Lys Ala Ile Leu Ser Ala Arg Leu Ser Lys Ser Arg
225                 230                 235                 240

Arg Leu Glu Asn Leu Ile Ala Gln Leu Pro Gly Glu Lys Lys Asn Gly
            245                 250                 255

Leu Phe Gly Asn Leu Ile Ala Leu Ser Leu Gly Leu Thr Pro Asn Phe
            260                 265                 270

Lys Ser Asn Phe Asp Leu Ala Glu Asp Ala Lys Leu Gln Leu Ser Lys
            275                 280                 285

Asp Thr Tyr Asp Asp Asp Leu Asp Asn Leu Leu Ala Gln Ile Gly Asp
            290                 295                 300

Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
                325                 330                 335

Leu Ser Ala Ser Met Ile Lys Arg Tyr Asp Glu His His Gln Asp Leu
                340                 345                 350

Thr Leu Leu Lys Ala Leu Val Arg Gln Gln Leu Pro Glu Lys Tyr Lys
            355                 360                 365

Glu Ile Phe Phe Asp Gln Ser Lys Asn Gly Tyr Ala Gly Tyr Ile Asp
            370                 375                 380

Gly Gly Ala Ser Gln Glu Glu Phe Tyr Lys Phe Ile Lys Pro Ile Leu
385                 390                 395                 400

Glu Lys Met Asp Gly Thr Glu Glu Leu Leu Val Lys Leu Asn Arg Glu
                405                 410                 415

Asp Leu Leu Arg Lys Gln Arg Thr Phe Asp Asn Gly Ser Ile Pro His
            420                 425                 430

Gln Ile His Leu Gly Glu Leu His Ala Ile Leu Arg Arg Gln Glu Asp
            435                 440                 445

Phe Tyr Pro Phe Leu Lys Asp Asn Arg Glu Lys Ile Glu Lys Ile Leu
            450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
                485                 490                 495

Asn Phe Glu Glu Val Val Asp Lys Gly Ala Ser Ala Gln Ser Phe Ile
            500                 505                 510

Glu Arg Met Thr Asn Phe Asp Lys Asn Leu Pro Asn Glu Lys Val Leu
            515                 520                 525

Pro Lys His Ser Leu Leu Tyr Glu Tyr Phe Thr Val Tyr Asn Glu Leu
            530                 535                 540

Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
                565                 570                 575

Arg Lys Val Thr Val Lys Gln Leu Lys Glu Asp Tyr Phe Lys Lys Ile
            580                 585                 590
```

```
Glu Cys Phe Asp Ser Val Glu Ile Ser Gly Val Glu Asp Arg Phe Asn
            595                 600                 605

Ala Ser Leu Gly Thr Tyr His Asp Leu Leu Lys Ile Ile Lys Asp Lys
610                 615                 620

Asp Phe Leu Asp Asn Glu Glu Asn Glu Asp Ile Leu Glu Asp Ile Val
625                 630                 635                 640

Leu Thr Leu Thr Leu Phe Glu Asp Arg Glu Met Ile Glu Glu Arg Leu
            645                 650                 655

Lys Thr Tyr Ala His Leu Phe Asp Asp Lys Val Met Lys Gln Leu Lys
            660                 665                 670

Arg Arg Arg Tyr Thr Gly Trp Gly Arg Leu Ser Arg Lys Leu Ile Asn
            675                 680                 685

Gly Ile Arg Asp Lys Gln Ser Gly Lys Thr Ile Leu Asp Phe Leu Lys
            690                 695                 700

Ser Asp Gly Phe Ala Asn Arg Asn Phe Met Gln Leu Ile His Asp Asp
705                 710                 715                 720

Ser Leu Thr Phe Lys Glu Asp Ile Gln Lys Ala Gln Val Ser Gly Gln
            725                 730                 735

Gly Asp Ser Leu His Glu His Ile Ala Asn Leu Ala Gly Ser Pro Ala
            740                 745                 750

Ile Lys Lys Gly Ile Leu Gln Thr Val Lys Val Val Asp Glu Leu Val
            755                 760                 765

Lys Val Met Gly Arg His Lys Pro Glu Asn Ile Val Ile Glu Met Ala
            770                 775                 780

Arg Glu Asn Gln Thr Thr Gln Lys Gly Gln Lys Asn Ser Arg Glu Arg
785                 790                 795                 800

Met Lys Arg Ile Glu Glu Gly Ile Lys Glu Leu Gly Ser Gln Ile Leu
            805                 810                 815

Lys Glu His Pro Val Glu Asn Thr Gln Leu Gln Asn Glu Lys Leu Tyr
            820                 825                 830

Leu Tyr Tyr Leu Gln Asn Gly Arg Asp Met Tyr Val Asp Gln Glu Leu
            835                 840                 845

Asp Ile Asn Arg Leu Ser Asp Tyr Asp Val Asp His Ile Val Pro Gln
850                 855                 860

Ser Phe Leu Lys Asp Asp Ser Ile Asp Asn Lys Val Leu Thr Arg Ser
865                 870                 875                 880

Asp Lys Asn Arg Gly Lys Ser Asp Asn Val Pro Ser Glu Glu Val Val
            885                 890                 895

Lys Lys Met Lys Asn Tyr Trp Arg Gln Leu Leu Asn Ala Lys Leu Ile
            900                 905                 910

Thr Gln Arg Lys Phe Asp Asn Leu Thr Lys Ala Glu Arg Gly Gly Leu
            915                 920                 925

Ser Glu Leu Asp Lys Ala Gly Phe Ile Lys Arg Gln Leu Val Glu Thr
            930                 935                 940

Arg Gln Ile Thr Lys His Val Ala Gln Ile Leu Asp Ser Arg Met Asn
945                 950                 955                 960

Thr Lys Tyr Asp Glu Asn Asp Lys Leu Ile Arg Glu Val Lys Val Ile
            965                 970                 975

Thr Leu Lys Ser Lys Leu Val Ser Asp Phe Arg Lys Asp Phe Gln Phe
            980                 985                 990

Tyr Lys Val Arg Glu Ile Asn Asn Tyr His His Ala His Asp Ala Tyr
            995                 1000                1005

Leu Asn Ala Val Val Gly Thr Ala Leu Ile Lys Lys Tyr Pro Lys
```

-continued

```
                    1010                1015                1020
Leu Glu Ser Glu Phe Val Tyr Gly Asp Tyr Lys Val Tyr Asp Val
            1025                1030                1035
Arg Lys Met Ile Ala Lys Ser Glu Gln Glu Ile Gly Lys Ala Thr
            1040                1045                1050
Ala Lys Tyr Phe Phe Tyr Ser Asn Ile Met Asn Phe Phe Lys Thr
            1055                1060                1065
Glu Ile Thr Leu Ala Asn Gly Glu Ile Arg Lys Arg Pro Leu Ile
            1070                1075                1080
Glu Thr Asn Gly Glu Thr Gly Glu Ile Val Trp Asp Lys Gly Arg
            1085                1090                1095
Asp Phe Ala Thr Val Arg Lys Val Leu Ser Met Pro Gln Val Asn
            1100                1105                1110
Ile Val Lys Lys Thr Glu Val Gln Thr Gly Gly Phe Ser Lys Glu
            1115                1120                1125
Ser Ile Leu Pro Lys Arg Asn Ser Asp Lys Leu Ile Ala Arg Lys
            1130                1135                1140
Lys Asp Trp Asp Pro Lys Lys Tyr Gly Gly Phe Asp Ser Pro Thr
            1145                1150                1155
Val Ala Tyr Ser Val Leu Val Val Ala Lys Val Glu Lys Gly Lys
            1160                1165                1170
Ser Lys Lys Leu Lys Ser Val Lys Glu Leu Leu Gly Ile Thr Ile
            1175                1180                1185
Met Glu Arg Ser Ser Phe Glu Lys Asn Pro Ile Asp Phe Leu Glu
            1190                1195                1200
Ala Lys Gly Tyr Lys Glu Val Lys Lys Asp Leu Ile Ile Lys Leu
            1205                1210                1215
Pro Lys Tyr Ser Leu Phe Glu Leu Glu Asn Gly Arg Lys Arg Met
            1220                1225                1230
Leu Ala Ser Ala Gly Glu Leu Gln Lys Gly Asn Glu Leu Ala Leu
            1235                1240                1245
Pro Ser Lys Tyr Val Asn Phe Leu Tyr Leu Ala Ser His Tyr Glu
            1250                1255                1260
Lys Leu Lys Gly Ser Pro Glu Asp Asn Glu Gln Lys Gln Leu Phe
            1265                1270                1275
Val Glu Gln His Lys His Tyr Leu Asp Glu Ile Ile Glu Gln Ile
            1280                1285                1290
Ser Glu Phe Ser Lys Arg Val Ile Leu Ala Asp Ala Asn Leu Asp
            1295                1300                1305
Lys Val Leu Ser Ala Tyr Asn Lys His Arg Asp Lys Pro Ile Arg
            1310                1315                1320
Glu Gln Ala Glu Asn Ile Ile His Leu Phe Thr Leu Thr Asn Leu
            1325                1330                1335
Gly Ala Pro Ala Ala Phe Lys Tyr Phe Asp Thr Thr Ile Asp Arg
            1340                1345                1350
Lys Arg Tyr Thr Ser Thr Lys Glu Val Leu Asp Ala Thr Leu Ile
            1355                1360                1365
His Gln Ser Ile Thr Gly Leu Tyr Glu Thr Arg Ile Asp Leu Ser
            1370                1375                1380
Gln Leu Gly Gly Asp Ala Ala Pro Lys Lys Lys Arg Lys Val Asp
            1385                1390                1395
Pro Lys Lys Lys Arg Lys Val Ala Ala Ala Leu Glu His His His
            1400                1405                1410
```

His His His
   1415

<210> SEQ ID NO 409
<211> LENGTH: 4251
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 409

| | | | | | |
|---|---|---|---|---|---|
| atgggcagca | gcgccccaaa | gaagaagcgg | aaggtcggta | tccacggagt | cccagcagcc | 60 |
| atggacaaaa | agtactctat | tggcctggat | atcgggacca | acagcgtcgg | gtgggctgtt | 120 |
| atcaccgacg | agtataaagt | accttcgaaa | aagttcaaag | tgctgggcaa | caccgatcgc | 180 |
| cattcaatca | aaagaacttt | gattggtgcg | ctgttgtttg | actccgggga | aaccgccgag | 240 |
| gcgactcgcc | ttaaacgtac | agcacgtcgc | cggtacactc | ggcgtaagaa | tcgcatttgc | 300 |
| tatttgcagg | aaatctttag | caacgagatg | gcaaagtcg | atgactcgtt | tttccaccgc | 360 |
| ctcgaggaaa | gctttctggt | ggaggaagac | aaaaagcatg | agcgtcaccc | gatcttcggc | 420 |
| aacattgtcg | atgaagtagc | gtatcatgaa | aaatacccaa | ccatttacca | cttacgcaaa | 480 |
| aagctggtgg | acagcactga | caaagctgat | ttgcgcctta | tctatttagc | cctggcacat | 540 |
| atgattaagt | ttcgtggtca | cttcctgatc | gaaggagact | aaatcccga | caacagtgat | 600 |
| gttgataaat | tgtttattca | gcttgtccaa | acttacaatc | aactgttcga | ggaaaacccg | 660 |
| atcaatgcct | ccggtgtgga | tgcaaaagcc | attttaagtg | cacgccttag | caagtcccgt | 720 |
| cgcttagaaa | accttatcgc | gcagctgccc | ggcgagaaaa | agaatggttt | gtttgggaac | 780 |
| cttattgcct | tgagcttagg | cctcaccccg | aatttcaaaa | gtaatttcga | tcttgcagaa | 840 |
| gacgccaaat | tacaactgtc | gaaggatact | tatgatgacg | atctcgataa | tctgttagcg | 900 |
| cagattggtg | accaatacgc | cgatctttt | ctggcggcta | aaaatctgag | cgacgccatc | 960 |
| ttgctttcgg | atattctccg | cgttaacacc | gaaatcacga | aagcgcctct | tagtgccagc | 1020 |
| atgattaaac | gttatgatga | acaccaccag | gacctgacct | tactcaaagc | gttggttcgc | 1080 |
| cagcaactgc | cagagaagta | caaagaaatc | ttctttgatc | agtcaaagaa | tggttatgcc | 1140 |
| ggctatattg | acggggggtgc | aagccaagag | gaattctaca | aatttatcaa | gcctattctg | 1200 |
| gagaaaatgg | atggcaccga | agagttattg | gtgaagctta | accgtgaaga | cctcctgcgg | 1260 |
| aaacagcgca | cattcgataa | tggttcgatc | ccacaccaaa | tccatttggg | ggagttacac | 1320 |
| gctattttgc | gtcgccagga | agactttac | ccttttcctga | aggataaccg | ggagaaaatt | 1380 |
| gagaagatcc | ttaccttcg | tattccgtat | tacgtaggcc | ccttagcacg | gggtaatagc | 1440 |
| cgtttcgcgt | ggatgacacg | gaagtcggaa | gagacgatca | ccccgtggaa | cttcgaagag | 1500 |
| gtagtcgaca | agggcgcatc | agcgcagtct | tttattgaac | gtatgacgaa | tttcgataaa | 1560 |
| aacttgccca | atgagaaggt | gcttccgaaa | cattccttgt | tatatgaata | ttttacagtt | 1620 |
| tacaacgagc | tgaccaaggt | taaatacgtg | acggaaggaa | tgcgcaagcc | cgcttttctt | 1680 |
| agcggtgagc | aaaaaaaggc | gatcgtcgac | ctgttattca | aaacgaatcg | taaggtgact | 1740 |
| gtaaagcaac | tcaaagaaga | ttacttcaaa | aagattgagt | gcttcgacag | cgtcgaaatc | 1800 |
| tctggggtag | aggatcggtt | taacgcaagt | ttaggtacct | accatgacct | gcttaaaatc | 1860 |
| attaaggata | aagacttctt | agataatgaa | gagaacgaag | atattctcga | ggacatcgtc | 1920 |

```
ttgacgttaa ccttatttga ggatcgtgaa atgattgagg aacgcctcaa aacttatgcc    1980
cacctgttcg acgataaggt gatgaagcag ctgaaacgtc ggcgctacac aggatggggc    2040
cgcttgagtc gcaaacttat taacggaatc cgtgacaagc aatccggcaa aacgattctg    2100
gatttcttga agtcggacgg atttgctaat cgcaacttca tgcagttgat ccatgatgac    2160
tccctgactt ttaaagagga tattcaaaag gcgcaggtta gtggtcaagg cgacagctta    2220
cacgaacaca tcgcaaattt ggctggttcg ccggccatta aaaaggggat cctccagacc    2280
gtgaaagttg tagatgagct tgttaaggtc atgggtcgtc ataagcccga aacatcgtg    2340
attgaaatgg cgcgggagaa tcaaacgacc cagaaaggac aaaagaatag ccgtgaacgg    2400
atgaagcgga tcgaggaagg cattaaagag ctggggtctc aaatcttgaa ggaacaccct    2460
gtggagaaca ctcagctcca aaatgaaaaa ctttacctgt actatttgca gaacggacgc    2520
gatatgtacg tggaccaaga gttggatatt aatcggctga gtgactacga cgttgatcat    2580
atcgtcccgc agagcttcct caaagacgat tctattgaca ataaggtact gacgcgctct    2640
gataaaaacc gtggtaagtc ggacaacgtg ccctccgaag aggttgtgaa aaagatgaaa    2700
aattattggc gccagctttt aaacgcgaag ctgatcacac aacgtaaatt cgataatttg    2760
accaaggctg aacggggtgg cctgagcgag ttagataagg caggatttat taaacgccag    2820
ttagtggaga ctcgtcaaat caccaaacat gtcgcgcaga ttttggacag ccggatgaac    2880
accaagtacg atgaaaatga caaactgatc cgtgaggtga agtcattac tctgaagtcc    2940
aaattagtta gtgatttccg gaaggacttt caattctaca agtccgtgaa attaataac    3000
tatcatcacg cacatgacgc gtacctgaat gcagtggttg ggaccgccct tatcaagaaa    3060
tatcctaagc tggagtcgga gtttgtctat ggcgactata aggtatacga tgttcgcaaa    3120
atgattgcga aatctgagca ggagatcggt aaggcaaccg caaatatttt cttttactca    3180
aacattatga atttctttaa gacagaaatc actctggcca acggggagat tcgcaaacgt    3240
ccgttgatcg aaacaaacgg cgagactggc gaaattgttt gggacaaagg gcgtgatttc    3300
gcgacggtgc gcaaggtact gagcatgcct caagtcaata ttgttaagaa aaccgaagtg    3360
cagacgggcg ggttttccaa ggaaagcatc ttacccaaac gtaattcaga taaacttatt    3420
gcacgcaaaa aggactggga tccgaaaaag tatggaggct tcgacagtcc aaccgtagcc    3480
tactctgttc tcgttgtagc gaaagtagaa aagggtaaat ccaagaaact gaaatctgtc    3540
aaggagttgc ttggaatcac cattatggag cgtagctcct tcgagaagaa cccgattgac    3600
tttctggaag ccaaaggata taagaggtc aagaaagatc ttatcattaa gctgcctaag    3660
tattcactct tcgagctgga aaatggtcgt aaacgcatgc tcgcttctgc cggcgagttg    3720
cagaagggca atgaattagc acttccatca aagtacgtta acttcctgta tttggccagc    3780
cattacgaga aactgaaggg gtctccagag gacaacgaac agaaacaatt atttgtagag    3840
cagcacaagc attatcttga tgaaatcatt gagcaaattt ccgaattcag taaacgcgta    3900
atcctggccg atgcaaacct cgacaaggtg ctgagcgctt acaataagca tcgcgacaaa    3960
cctatccgtg agcaggctga aaatatcatt caccgttca cattaacgaa cctgggcgct    4020
ccggccgctt ttaaatattt cgacacgaca atcgaccgta agcgctatac cagtacgaaa    4080
gaagtgttgg atgcgaccct tattcaccag tcaattacag gattatatga gacccgtatc    4140
gaccttagcc aattaggtgg ggatgcggcc ccgaagaaaa aacgcaaagt ggatccgaag    4200
aaaaaacgca aagtggcggc cgcactcgag caccaccacc accaccactg a              4251
```

```
<210> SEQ ID NO 410
<211> LENGTH: 1429
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410

Met Gly Lys Pro Ile Pro Asn Pro Leu Leu Gly Leu Asp Ser Thr Ala
1               5                   10                  15

Pro Lys Lys Lys Arg Lys Val Gly Ile His Gly Val Pro Ala Ala Asp
                20                  25                  30

Lys Lys Tyr Ser Ile Gly Leu Asp Ile Gly Thr Asn Ser Val Gly Trp
            35                  40                  45

Ala Val Ile Thr Asp Glu Tyr Lys Val Pro Ser Lys Lys Phe Lys Val
50                  55                  60

Leu Gly Asn Thr Asp Arg His Ser Ile Lys Lys Asn Leu Ile Gly Ala
65                  70                  75                  80

Leu Leu Phe Asp Ser Gly Glu Thr Ala Glu Ala Thr Arg Leu Lys Arg
                85                  90                  95

Thr Ala Arg Arg Arg Tyr Thr Arg Arg Lys Asn Arg Ile Cys Tyr Leu
            100                 105                 110

Gln Glu Ile Phe Ser Asn Glu Met Ala Lys Val Asp Asp Ser Phe Phe
        115                 120                 125

His Arg Leu Glu Glu Ser Phe Leu Val Glu Glu Asp Lys Lys His Glu
    130                 135                 140

Arg His Pro Ile Phe Gly Asn Ile Val Asp Glu Val Ala Tyr His Glu
145                 150                 155                 160

Lys Tyr Pro Thr Ile Tyr His Leu Arg Lys Lys Leu Val Asp Ser Thr
                165                 170                 175

Asp Lys Ala Asp Leu Arg Leu Ile Tyr Leu Ala Leu Ala His Met Ile
            180                 185                 190

Lys Phe Arg Gly His Phe Leu Ile Glu Gly Asp Leu Asn Pro Asp Asn
        195                 200                 205

Ser Asp Val Asp Lys Leu Phe Ile Gln Leu Val Gln Thr Tyr Asn Gln
    210                 215                 220

Leu Phe Glu Glu Asn Pro Ile Asn Ala Ser Gly Val Asp Ala Lys Ala
225                 230                 235                 240

Ile Leu Ser Ala Arg Leu Ser Lys Ser Arg Arg Leu Glu Asn Leu Ile
                245                 250                 255

Ala Gln Leu Pro Gly Glu Lys Lys Asn Gly Leu Phe Gly Asn Leu Ile
            260                 265                 270

Ala Leu Ser Leu Gly Leu Thr Pro Asn Phe Lys Ser Asn Phe Asp Leu
        275                 280                 285

Ala Glu Asp Ala Lys Leu Gln Leu Ser Lys Asp Thr Tyr Asp Asp Asp
    290                 295                 300

Leu Asp Asn Leu Leu Ala Gln Ile Gly Asp Gln Tyr Ala Asp Leu Phe
305                 310                 315                 320

Leu Ala Ala Lys Asn Leu Ser Asp Ala Ile Leu Leu Ser Asp Ile Leu
                325                 330                 335

Arg Val Asn Thr Glu Ile Thr Lys Ala Pro Leu Ser Ala Ser Met Ile
            340                 345                 350

Lys Arg Tyr Asp Glu His His Gln Asp Leu Thr Leu Leu Lys Ala Leu
        355                 360                 365
```

```
Val Arg Gln Gln Leu Pro Glu Lys Tyr Lys Glu Ile Phe Phe Asp Gln
            370                 375                 380

Ser Lys Asn Gly Tyr Ala Gly Tyr Ile Asp Gly Gly Ala Ser Gln Glu
385                 390                 395                 400

Glu Phe Tyr Lys Phe Ile Lys Pro Ile Leu Glu Lys Met Asp Gly Thr
                    405                 410                 415

Glu Glu Leu Leu Val Lys Leu Asn Arg Glu Asp Leu Leu Arg Lys Gln
                420                 425                 430

Arg Thr Phe Asp Asn Gly Ser Ile Pro His Gln Ile His Leu Gly Glu
            435                 440                 445

Leu His Ala Ile Leu Arg Arg Gln Glu Asp Phe Tyr Pro Phe Leu Lys
450                 455                 460

Asp Asn Arg Glu Lys Ile Glu Lys Ile Leu Thr Phe Arg Ile Pro Tyr
465                 470                 475                 480

Tyr Val Gly Pro Leu Ala Arg Gly Asn Ser Arg Phe Ala Trp Met Thr
                485                 490                 495

Arg Lys Ser Glu Glu Thr Ile Thr Pro Trp Asn Phe Glu Glu Val Val
                500                 505                 510

Asp Lys Gly Ala Ser Ala Gln Ser Phe Ile Glu Arg Met Thr Asn Phe
            515                 520                 525

Asp Lys Asn Leu Pro Asn Glu Lys Val Leu Pro Lys His Ser Leu Leu
530                 535                 540

Tyr Glu Tyr Phe Thr Val Tyr Asn Glu Leu Thr Lys Val Lys Tyr Val
545                 550                 555                 560

Thr Glu Gly Met Arg Lys Pro Ala Phe Leu Ser Gly Glu Gln Lys Lys
                565                 570                 575

Ala Ile Val Asp Leu Leu Phe Lys Thr Asn Arg Lys Val Thr Val Lys
            580                 585                 590

Gln Leu Lys Glu Asp Tyr Phe Lys Lys Ile Glu Cys Phe Asp Ser Val
            595                 600                 605

Glu Ile Ser Gly Val Glu Asp Arg Phe Asn Ala Ser Leu Gly Thr Tyr
610                 615                 620

His Asp Leu Leu Lys Ile Ile Lys Asp Lys Asp Phe Leu Asp Asn Glu
625                 630                 635                 640

Glu Asn Glu Asp Ile Leu Glu Asp Ile Val Leu Thr Leu Thr Leu Phe
                645                 650                 655

Glu Asp Arg Glu Met Ile Glu Glu Arg Leu Lys Thr Tyr Ala His Leu
            660                 665                 670

Phe Asp Asp Lys Val Met Lys Gln Leu Lys Arg Arg Arg Tyr Thr Gly
            675                 680                 685

Trp Gly Arg Leu Ser Arg Lys Leu Ile Asn Gly Ile Arg Asp Lys Gln
690                 695                 700

Ser Gly Lys Thr Ile Leu Asp Phe Leu Lys Ser Asp Gly Phe Ala Asn
705                 710                 715                 720

Arg Asn Phe Met Gln Leu Ile His Asp Asp Ser Leu Thr Phe Lys Glu
                725                 730                 735

Asp Ile Gln Lys Ala Gln Val Ser Gly Gln Gly Asp Ser Leu His Glu
            740                 745                 750

His Ile Ala Asn Leu Ala Gly Ser Pro Ala Ile Lys Lys Gly Ile Leu
            755                 760                 765

Gln Thr Val Lys Val Val Asp Glu Leu Val Lys Val Met Gly Arg His
770                 775                 780

Lys Pro Glu Asn Ile Val Ile Glu Met Ala Arg Glu Asn Gln Thr Thr
```

```
              785                 790                 795                 800
        Gln Lys Gly Gln Lys Asn Ser Arg Glu Arg Met Lys Arg Ile Glu Glu
                        805                 810                 815
        Gly Ile Lys Glu Leu Gly Ser Gln Ile Leu Lys Glu His Pro Val Glu
                        820                 825                 830
        Asn Thr Gln Leu Gln Asn Glu Lys Leu Tyr Leu Tyr Tyr Leu Gln Asn
                        835                 840                 845
        Gly Arg Asp Met Tyr Val Asp Gln Glu Leu Asp Ile Asn Arg Leu Ser
                850                 855                 860
        Asp Tyr Asp Val Asp His Ile Val Pro Gln Ser Phe Leu Lys Asp Asp
        865                 870                 875                 880
        Ser Ile Asp Asn Lys Val Leu Thr Arg Ser Asp Lys Asn Arg Gly Lys
                        885                 890                 895
        Ser Asp Asn Val Pro Ser Glu Glu Val Val Lys Lys Met Lys Asn Tyr
                900                 905                 910
        Trp Arg Gln Leu Leu Asn Ala Lys Leu Ile Thr Gln Arg Lys Phe Asp
                        915                 920                 925
        Asn Leu Thr Lys Ala Glu Arg Gly Gly Leu Ser Glu Leu Asp Lys Ala
                930                 935                 940
        Gly Phe Ile Lys Arg Gln Leu Val Glu Thr Arg Gln Ile Thr Lys His
        945                 950                 955                 960
        Val Ala Gln Ile Leu Asp Ser Arg Met Asn Thr Lys Tyr Asp Glu Asn
                        965                 970                 975
        Asp Lys Leu Ile Arg Glu Val Lys Val Ile Thr Leu Lys Ser Lys Leu
                        980                 985                 990
        Val Ser Asp Phe Arg Lys Asp Phe Gln Phe Tyr Lys Val Arg Glu Ile
                        995                 1000                1005
        Asn Asn Tyr His His Ala His Asp Ala Tyr Leu Asn Ala Val Val
                        1010                1015                1020
        Gly Thr Ala Leu Ile Lys Lys Tyr Pro Lys Leu Glu Ser Glu Phe
                        1025                1030                1035
        Val Tyr Gly Asp Tyr Lys Val Tyr Asp Val Arg Lys Met Ile Ala
                        1040                1045                1050
        Lys Ser Glu Gln Glu Ile Gly Lys Ala Thr Ala Lys Tyr Phe Phe
                        1055                1060                1065
        Tyr Ser Asn Ile Met Asn Phe Phe Lys Thr Glu Ile Thr Leu Ala
                        1070                1075                1080
        Asn Gly Glu Ile Arg Lys Arg Pro Leu Ile Glu Thr Asn Gly Glu
                        1085                1090                1095
        Thr Gly Glu Ile Val Trp Asp Lys Gly Arg Asp Phe Ala Thr Val
                        1100                1105                1110
        Arg Lys Val Leu Ser Met Pro Gln Val Asn Ile Val Lys Lys Thr
                        1115                1120                1125
        Glu Val Gln Thr Gly Gly Phe Ser Lys Glu Ser Ile Leu Pro Lys
                        1130                1135                1140
        Arg Asn Ser Asp Lys Leu Ile Ala Arg Lys Lys Asp Trp Asp Pro
                        1145                1150                1155
        Lys Lys Tyr Gly Gly Phe Asp Ser Pro Thr Val Ala Tyr Ser Val
                        1160                1165                1170
        Leu Val Val Ala Lys Val Glu Lys Gly Lys Ser Lys Lys Leu Lys
                        1175                1180                1185
        Ser Val Lys Glu Leu Leu Gly Ile Thr Ile Met Glu Arg Ser Ser
                        1190                1195                1200
```

```
Phe Glu Lys Asn Pro Ile Asp Phe Leu Glu Ala Lys Gly Tyr Lys
    1205                1210                1215

Glu Val Lys Lys Asp Leu Ile Ile Lys Leu Pro Lys Tyr Ser Leu
    1220                1225                1230

Phe Glu Leu Glu Asn Gly Arg Lys Arg Met Leu Ala Ser Ala Gly
    1235                1240                1245

Glu Leu Gln Lys Gly Asn Glu Leu Ala Leu Pro Ser Lys Tyr Val
    1250                1255                1260

Asn Phe Leu Tyr Leu Ala Ser His Tyr Glu Lys Leu Lys Gly Ser
    1265                1270                1275

Pro Glu Asp Asn Glu Gln Lys Gln Leu Phe Val Glu Gln His Lys
    1280                1285                1290

His Tyr Leu Asp Glu Ile Ile Glu Gln Ile Ser Glu Phe Ser Lys
    1295                1300                1305

Arg Val Ile Leu Ala Asp Ala Asn Leu Asp Lys Val Leu Ser Ala
    1310                1315                1320

Tyr Asn Lys His Arg Asp Lys Pro Ile Arg Glu Gln Ala Glu Asn
    1325                1330                1335

Ile Ile His Leu Phe Thr Leu Thr Asn Leu Gly Ala Pro Ala Ala
    1340                1345                1350

Phe Lys Tyr Phe Asp Thr Thr Ile Asp Arg Lys Arg Tyr Thr Ser
    1355                1360                1365

Thr Lys Glu Val Leu Asp Ala Thr Leu Ile His Gln Ser Ile Thr
    1370                1375                1380

Gly Leu Tyr Glu Thr Arg Ile Asp Leu Ser Gln Leu Gly Gly Asp
    1385                1390                1395

Ser Arg Ala Asp Pro Lys Lys Lys Arg Lys Val Glu Phe His His
    1400                1405                1410

Thr Gly Leu Val Asp Pro Ser Ser Val Pro Ser Leu Ser Leu Asn
    1415                1420                1425

Arg

<210> SEQ ID NO 411
<211> LENGTH: 4290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 411
atgggcaagc ccatccctaa ccccctgttg gggctggaca gcaccgctcc caaaaagaaa      60
aggaaggtgg gcattcacgg cgtgcctgcg gccgacaaaa agtacagcat cggccttgat     120
atcggcacca atagcgtggg ctgggccgtt atcacagacg aatacaaggt acccagcaag     180
aagttcaagg tgctggggaa tacagacagg cactctatca agaaaaacct tatcggggct     240
ctgctgtttg actcaggcga gaccgccgag gccaccaggt tgaagaggac cgcaaggcga     300
aggtacaccc ggaggaagaa caggatctgc tatctgcagg agatcttcag caacgagatg     360
gccaaggtgg acgacagctt cttccacagg ctggaggaga gcttccttgt cgaggaggat     420
aagaagcacg aacgacaccc catcttcggc aacatagtcg acgaggtcgc ttatcacgag     480
aagtacccca ccatctacca cctgcgaaag aaattggtgg atagcaccga taaagccgac     540
ttgcgactta tctacttggc tctggcgcac atgattaagt tcaggggcca cttcctgatc     600
```

```
gagggcgacc ttaaccccga caacagtgac gtagacaaat tgttcatcca gcttgtacag    660
acctataacc agctgttcga ggaaaaccct attaacgcca gcggggtgga tgcgaaggcc    720
atacttagcg ccaggctgag caaaagcagg cgcttggaga acctgatagc ccagctgccc    780
ggtgaaaaga agaacggcct cttcggtaat ctgattgccc tgagcctggg cctgaccccc    840
aacttcaaga gcaacttcga cctggcagaa gatgccaagc tgcagttgag taaggacacc    900
tatgacgacg acttggacaa tctgctcgcc caaatcggcg accagtacgc tgacctgttc    960
ctcgccgcca agaacctttc tgacgcaatc ctgcttagcg atatccttag ggtgaacaca   1020
gagatcacca aggcccccct gagcgccagc atgatcaaga ggtacgacga gcaccatcag   1080
gacctgaccc ttctgaaggc cctggtgagg cagcaactgc ccgagaagta caaggagatc   1140
tttttcgacc agagcaagaa cggctacgcc ggctacatcg acggcggagc cagccaagag   1200
gagttctaca agttcatcaa gcccatcctg agaagatgga tggcaccga ggagctgctg    1260 gtgaagctga acaggaaga tttgctccgg aagcagagga cctttgacaa cggtagcatc   1320
ccccaccaga tccacctggg cgagctgcac gcaatactga ggcgacagga ggatttctac   1380
cccttcctca aggacaatag ggagaaaatc gaaaagattc tgaccttcag gatcccctac   1440
tacgtgggcc ctcttgccag gggcaacagc cgattcgctt ggatgacaag aaagagcgag   1500
gagaccatca ccccctggaa cttcgaggaa gtggtggaca aggagcaag cgcgcagtct    1560 ttcatcgaac ggatgaccaa tttcgacaaa aacctgccta cgagaaggt gctgcccaag    1620 cacagcctgc tttacgagta cttcaccgtg tacaacgagc tcaccaaggt gaaatatgtg   1680
accgagggca tgcgaaaacc cgcttttcctg agcggcgagc agaagaaggc catcgtggac   1740
ctgctgttca agaccaacag gaaggtgacc gtgaagcagc tgaaggagga ctacttcaag   1800
aagatcgagt gctttgatag cgtggaaata gcggcgtgg aggacaggtt caacgccagc    1860
ctgggcacct accacgactt gttgaagata atcaaagaca aggatttcct ggataatgag   1920
gagaacgagg atatactcga ggacatcgtg ctgactttga ccctgtttga ggaccgagag   1980
atgattgaag aaaggctcaa aacctacgcc cacctgttcg acgacaaagt gatgaaacaa   2040
ctgaagagac gaagatacac cggctgggc agactgtcca ggaagctcat caacggcatt    2100
agggacaagc agagcggcaa gaccatcctg gatttcctga agtccgacgg cttcgccaac   2160
cgaaacttca tgcagctgat tcacgatgac agcttgacct tcaaggagga catccagaag   2220
gcccaggtta gcggccaggg cgactccctg cacgaacata ttgcaaacct ggcaggctcc   2280
cctgcgatca gaagggcat actgcagacc gttaaggttg tggacgaatt ggtcaaggtc    2340
atgggcaggc acaagcccga aaacatagtt atagagatgg ccagagagaa ccagaccacc   2400
caaaagggcc agaagaacag ccgggagcgc atgaaaagga tcgaggaggg tatcaaggaa   2460
ctcggaagcc agatcctcaa agagcacccc gtggagaata cccagctcca gaacgagaag   2520
ctgtacctgt actacctgca gaacggcagg gacatgtacg ttgaccagga gttgacatc    2580 aacaggcttt cagactatga cgtggatcac atagtgcccc agagctttct taaagacgat   2640
agcatcgaca caaggtcct gacccgctcc gacaaaaaca ggggcaaaag cgacaacgtg   2700
ccaagcgaag aggtggttaa aaagatgaag aactactgga ggcaactgct caacgcgaaa   2760
ttgatcaccc agagaaagtt cgataacctg accaaggccg agaggggcgg actctccgaa   2820
cttgacaaag cgggcttcat aaagaggcag ctggtcgaga cccgacagat cacgaagcac   2880
gtggcccaaa tcctcgacag cagaatgaat accaagtacg atgagaatga caaactcatc   2940
agggaagtga aagtgattac cctgaagagc aagttggtgt ccgactttcg caaagatttc   3000
```

| | |
|---|---|
| cagttctaca aggtgaggga gatcaacaac taccaccatg cccacgacgc atacctgaac | 3060 |
| gccgtggtcg gcaccgccct gattaagaag tatccaaagc tggagtccga atttgtctac | 3120 |
| ggcgactaca aagtttacga tgtgaggaag atgatcgcta agagcgaaca ggagatcggc | 3180 |
| aaggccaccg ctaagtattt cttctacagc aacatcatga cttttttcaa gaccgagatc | 3240 |
| acacttgcca acggcgaaat caggaagagg ccgcttatcg agaccaacgg tgagaccggc | 3300 |
| gagatcgtgt gggacaaggg cagggacttc gccaccgtga ggaaagtcct gagcatgccc | 3360 |
| caggtgaata ttgtgaaaaa aactgaggtg cagacaggcg gctttagcaa ggaatccatc | 3420 |
| ctgcccaaga ggaacagcga caagctgatc gcccggaaga aggactggga ccctaagaag | 3480 |
| tatggaggct cgacagccc accgtagcc tacagcgtgc tggtggtcgc gaaggtagag | 3540 |
| aaggggaaga gcaagaaact gaagagcgtg aaggagctgc tcggcataac catcatggag | 3600 |
| aggtccagct ttgagaagaa ccccattgac ttttttggaag ccaagggcta caaagaggtc | 3660 |
| aaaaaggacc tgatcatcaa actccccaag tactccctgt ttgaattgga gaacggcaga | 3720 |
| aagaggatgc tggcgagcgc tggggaactg caaaagggca cgaactggc gctgcccagc | 3780 |
| aagtacgtga attttctgta cctggcgtcc cactacgaaa agctgaaagg cagccccgag | 3840 |
| gacaacgagc agaagcagct gttcgtggag cagcacaagc attacctgga cgagataatc | 3900 |
| gagcaaatca gcgagttcag caagagggtg attctggccg acgcgaacct ggataaggtc | 3960 |
| ctcagcgcct acaacaagca ccgagacaaa cccatcaggg agcaggccga aatatcata | 4020 |
| cacctgttca ccctgacaaa tctgggcgca cctgcggcat tcaaatactt cgataccacc | 4080 |
| atcgacagga aaggtacac tagcactaag gaggtgctgg atgccaccttt gatccaccag | 4140 |
| tccattaccg gcctgtatga gaccaggatc gacctgagcc agcttggagg cgactctagg | 4200 |
| gcggacccaa aaagaaaag gaaggtggaa ttccaccaca ctggactagt ggatccgagc | 4260 |
| tcggtaccaa gcttaagttt aaaccgctga | 4290 |

<210> SEQ ID NO 412
<211> LENGTH: 4601
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 412

| | |
|---|---|
| taatacgact cactataggg agacccaagc tggctagcgt ttaaacgggc cctctagact | 60 |
| cgagcggccg ccaccatggg caagcccatc cctaacccccc tgttggggct ggacagcacc | 120 |
| gctcccaaaa agaaaaggaa ggtgggcatt cacggcgtgc ctgcggccga caaaaagtac | 180 |
| agcatcggcc ttgatatcgg caccaatagc gtgggctggg ccgttatcac agacgaatac | 240 |
| aaggtacccca gcaagaagtt caaggtgctg gggaatacag acaggcactc tatcaagaaa | 300 |
| aaccttatcg gggctctgct gtttgactca ggcgagaccg ccgaggccac caggttgaag | 360 |
| aggaccgcaa ggcgaaggta cacccggagg aagaacagga tctgctatct gcaggagatc | 420 |
| ttcagcaacg agatggccaa ggtggacgac agcttcttcc acaggctgga ggagagcttc | 480 |
| cttgtcgagg aggataagaa gcacgaacga caccccatct tcggcaacat agtcgacgag | 540 |
| gtcgcttatc acgagaagta ccccaccatc taccacctgc gaaagaaatt ggtggatagc | 600 |
| accgataaag ccgacttgcg acttatctac ttggctctgg cgcacatgat taagttcagg | 660 |
| ggccacttcc tgatcgaggg cgaccttaac cccgacaaca gtgacgtaga caaattgttc | 720 |

```
atccagcttg tacagaccta taaccagctg ttcgaggaaa accctattaa cgccagcggg      780
gtggatgcga aggccatact tagcgccagg ctgagcaaaa gcaggcgctt ggagaacctg      840
atagcccagc tgcccggtga aaagaagaac ggcctcttcg gtaatctgat tgccctgagc      900
ctgggcctga cccccaactt caagagcaac ttcgacctgg cagaagatgc caagctgcag      960
ttgagtaagg acacctatga cgacgacttg acaatctgc tcgcccaaat cggcgaccag     1020
tacgctgacc tgttcctcgc cgccaagaac ctttctgacg caatcctgct tagcgatatc     1080
cttagggtga acacagagat caccaaggcc cccctgagcg ccagcatgat caagaggtac     1140
gacgagcacc atcaggacct gacccttctg aaggccctgg tgaggcagca actgcccgag     1200
aagtacaagg agatcttttt cgaccagagc aagaacggct acgccggcta catcgacggc     1260
ggagccagcc aagaggagtt ctacaagttc atcaagccca tcctggagaa gatggatggc     1320
accgaggagc tgctggtgaa gctgaacagg gaagatttgc tccggaagca gaggaccttt     1380
gacaacggta gcatccccca ccagatccac ctgggcgagc tgcacgcaat actgaggcga     1440
caggaggatt tctacccctt cctcaaggac aatagggaga aaatcgaaaa gattctgacc     1500
ttcaggatcc cctactacgt gggccctctt gccaggggca cagccgatt cgcttggatg     1560 acaagaaaga gcgaggagac catcaccccc tggaacttcg aggaagtggt ggacaaagga     1620
gcaagcgcgc agtctttcat cgaacggatg accaatttcg acaaaaacct gcctaacgag     1680
aaggtgctgc ccaagcacag cctgctttac gagtacttca ccgtgtacaa cgagctcacc     1740
aaggtgaaat atgtgaccga gggcatgcga aaacccgctt tcctgagcgg cgagcagaag     1800
aaggccatcg tggacctgct gttcaagacc aacaggaagg tgaccgtgaa gcagctgaag     1860
gaggactact tcaagaagat cgagtgcttt gatagcgtgg aaataagcgg cgtggaggac     1920
aggttcaacg ccagcctggg cacctaccac gacttgttga agataatcaa agacaaggat     1980
ttcctggata tgaggagaa cgaggatata ctcgaggaca tcgtgctgac tttgaccctg     2040
tttgaggacc gagagatgat tgaagaaagg ctcaaaacct acgcccacct gttcgacgac     2100
aaagtgatga acaactgaa gagacgaaga taccccggct ggggcagact gtccaggaag     2160
ctcatcaacg gcattaggga caagcagagc ggcaagacca tcctggatt cctgaagtcc     2220 gacggcttcg ccaaccgaaa cttcatgcag ctgattcacg atgacagctt gaccttcaag     2280
gaggacatcc agaaggccca ggttagcggc cagggcgact ccctgcacga acatattgca     2340
aacctggcag gctcccctgc gatcaagaag ggcatactgc agaccgttaa ggttgtggac     2400
gaattggtca aggtcatggg caggcacaag cccgaaaaca tagttataga gatggccaga     2460
gagaaccaga ccacccaaaa gggccagaag aacagccggg agcgcatgaa aaggatcgag     2520
gagggtatca aggaactcgg aagccagatc ctcaaagagc accccgtgga aataccccag     2580
ctccagaacg agaagctgta cctgtactac ctgcagaacg caggacat gtacgttgac     2640 caggagttgg acatcaacag gctttcagac tatgacgtgg atcacatagt gccccagagc     2700
tttcttaaag acgatagcat cgacaacaag gtcctgaccc gctccgacaa aaacagggc     2760 aaaagcgaca acgtgccaag cgaagaggtg gttaaaaaga tgaagaacta ctggaggcaa     2820
ctgctcaacg cgaaattgat cacccagaga aagttcgata acctgaccaa ggccgagagg     2880
ggcggactct ccgaacttga caaagcgggc ttcataaaga gcagctggt cgagacccga     2940 cagatcacga agcacgtggc ccaaatcctc gacagcagaa tgaataccaa gtacgatgag     3000
aatgacaaac tcatcaggga agtgaaagtg attaccctga gagcaagtt ggtgtccgac     3060
```

```
tttcgcaaag atttccagtt ctacaaggtg agggagatca acaactacca ccatgcccac    3120
gacgcatacc tgaacgccgt ggtcggcacc gccctgatta agaagtatcc aaagctggag    3180
tccgaatttg tctacggcga ctacaaagtt tacgatgtga ggaagatgat cgctaagagc    3240
gaacaggaga tcggcaaggc caccgctaag tatttcttct acagcaacat catgaacttt    3300
ttcaagaccg agatcacact tgccaacggc gaaatcagga gaggccgct tatcgagacc    3360 aacggtgaga ccggcgagat cgtgtgggac aagggcaggg acttcgccac cgtgaggaaa    3420
gtcctgagca tgccccaggt gaatattgtg aaaaaaactg aggtgcagac aggcggcttt    3480
agcaaggaat ccatcctgcc caagaggaac agcgacaagc tgatcgcccg gaagaaggac    3540
tgggacccta gaagtatgg aggcttcgac agccccaccg tagcctacag cgtgctggtg    3600
gtcgcgaagg tagagaaggg gaagagcaag aaactgaaga gcgtgaagga gctgctcggc    3660
ataaccatca tggagaggtc cagctttgag aagaaccccca ttgacttttt ggaagccaag    3720
ggctacaaag aggtcaaaaa ggacctgatc atcaaactcc ccaagtactc cctgtttgaa    3780
ttggagaacg gcagaaagag gatgctggcg agcgctgggg aactgcaaaa gggcaacgaa    3840
ctggcgctgc ccagcaagta cgtgaatttt ctgtacctgg cgtcccacta cgaaaagctg    3900
aaaggcagcc ccgaggacaa cgagcagaag cagctgttcg tggagcagca caagcattac    3960
ctggacgaga taatcgagca aatcagcgag ttcagcaaga gggtgattct ggccgacgcg    4020
aacctggata aggtcctcag cgcctacaac aagcaccgag acaaacccat cagggagcag    4080
gccgagaata tcatacacct gttcacccctg acaaatctgg gcgcacctgc ggcattcaaa    4140
tacttcgata ccaccatcga caggaaaaagg tacactagca ctaaggaggt gctggatgcc    4200
accttgatcc accagtccat taccggcctg tatgagacca ggatcgacct gagccagctt    4260
ggaggcgact ctagggcgga cccaaaaaag aaaaggaagg tggaattcca ccacactgga    4320
ctagtggatc cgagctcggt accaagctta agtttaaacc gctgatcagc ctcgactgtg    4380
ccttctagtt gccagccatc tgttgtttgc ccctcccccg tgccttcctt gaccctggaa    4440
ggtgccactc ccactgtcct ttcctaataa aatgaggaaa ttgcatcgca ttgtctgagt    4500
aggtgtcatt ctattctggg gggtggggtg ggcaggaca gcaaggggga ggattgggaa    4560
gacaatagca ggcatgctgg ggatgcggtg ggctctatgg c                       4601

<210> SEQ ID NO 413
<211> LENGTH: 4584
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 413
gggagaccca agcuggcuag cguuuaaacg ggcccucuag acucgagcgg ccgccaccau      60
gggcaagccc aucccuaacc cccuguuggg gcugacagc accgcuccca aaagaaaag     120 gaaggugggc auucacggcg ugccugcggc cgacaaaaag uacagcaucg gccuugauau     180
cggcaccaau agcguggggcu gggccguuau cacagacgaa uacaagguac ccagcaagaa     240
guucaaggug cuggggaaua cagacaggca cucuaucaag aaaaaccuua ucggggcucu     300
gcuguuugac ucaggcgaga ccgccgaggc caccagguug aagaggaccg caaggcgaag     360
guacacccgg aggaagaaca ggaucugcua ucucgcaggag aucuucagca acgagauggc     420 caaggugggac gacagcuucu uccacaggcu ggaggagagc uuccuugucg aggaggauaa     480
```

```
gaagcacgaa cgacacccca ucuucggcaa cauagucgac gaggucgcuu aucacgagaa      540
guaccccacc aucuaccacc ugcgaaagaa auuggugqau agcaccgaua aagccgacuu      600
gcgacuuauc uacuuggcuc uggcgcacau gauuaaguuc aggggccacu uccugaucga      660
gggcgacauu aacccccgaca acagugacgu agacaaauug uucauccagc uguacagac      720 cuauaaccag cuguucgagg aaaacccuau uaacgccagc ggggyggaug cgaaggccau      780
acuuagcgcc aggcugagca aaagcaggcg cuuggagaac cugauagccc agcugccggg      840
ugaaaagaag aacggccucu ucgguaaucu gauugcccug agccugggcc ugaccccaa       900 cuucaagagc aacuucgacc uggcagaaga ugccaagcug caguugagua aggacaccua      960
ugacgacgac uuggacaauc ugcucgccca aaucggcgac caguacgcug accguuccu     1020 cgccgccaag aaccuuucug acgcaauccu gcuuagcgau auccuuaggg ugaacacaga     1080
gaucaccaag gccccccuga cgccagcau gaucaagagg uacgacgagc accaucagga     1140
ccugacccuu cugaaggccc uggugaggca gcaacugccc gagaaguaca aggagaucuu     1200
uuucgaccag agcaagaacg gcuacgccgg cuacaucgac ggcggagcca gccaagagga     1260
guucuacaag uucaucaagc ccauccugga aagauggau ggcaccgagg agcugcuggu     1320
gaagcugaac agggaagauu ugcuccgaa gcagaggacc uuugacaacg guagcauccc     1380
ccaccagauc caccugggcg agcugcacgc aauacugagg cgacaggagg auuucuaccc     1440
cuuccucaag gacaauaggg agaaaaucga aagauucug accuucagga ucccuacua     1500 cguggggcccu cuugccaggg gcaacagccg auucgcuugg augacaagaa agagcgagga     1560
gaccaucacc cccuggaacu ucgaggaagu gguggacaaa ggagcaagcg cgcagcucuu     1620
caucgaacgg augaccaauu ucgacaaaaa ccugccuaac gagaagguge ugcccaagca     1680 cagccugcuu uacagauacu ucaccgugua caacgagccuc accaaggua aauaugugac     1740 cgagggcaug cgaaaacccg cuuuccugag cggcgagcag aagaaggcca ucguggaccu     1800
gcuguucaag accaacagga aggugaccgu gaagcagcug aaggaggacu acuucaagaa     1860
gaucgagugc uuugauagcg uggaaauaag cggcguggag acaggyuca acgccagccu     1920 gggcaccuac cacgacuugu ugaagauaau caaagacaag gauuuccugg auaaugagga     1980
gaacgaggau auacucgagg acaucgugcu gacuuugacc cuguuugagg accgagagau     2040
gauugaagaa aggcucaaaa ccuacgccca ccuguucgac gacaaaguga ugaacaacu     2100 gaagagacga agauacaccg gcuggggcag acuguccagg aagcucauca acggcauuag     2160
ggacaagcag agcggcaaga ccauccugga uuuccgaag uccgacggcu cgccaaccg     2220 aaacuucaug cagcugauuc acgaugacag cuugaccuuc aaggaggaca uccagaaggc     2280
ccagguuagc ggccagggcg acuccccgca cgaacauauu gcaaaccugg caggcucccc     2340
ugcgaucaag aagggcauac ugcagaccgu uaagguugug gacgaauugg ucaaggucau     2400
gggcaggcac aagcccgaaa acauaguuau agagauggcc agagagaacc agaccacca      2460 aaagggcca agaacagcc gggagcgcau gaaaaggauc gaggagggua ucaaggaacu     2520
cggaagccag auccucaaag agcaccccgu ggagaauacc cagcuccaga acgagaagcu      2580
guaccuguac uaccgcagca acggcaggga caugacguu gaccaggagu uggacaucaa     2640
caggcuuuca gacuaugacg uggaucacau agugcccag agcuuucua aagacgauag     2700 caucgacaac aagguccuga cccgcucccga caaaacagg ggcaaaagcg acaacgugcc     2760
aagcgaagag guggyuaaaa agaugaagaa cuacuggagg caacugcuca acgcgaaauu     2820
gaucacccag agaaaguucg auaaccugac caaggccgag aggggcggac ucuccgaacu     2880
```

```
ugacaaagcg ggcuucauaa agaggcagcu ggucgagacc cgacagauca cgaagcacgu    2940
ggcccaaauc cucgacagca gaaugaauac caaguacgau gagaaugaca aacucaucag    3000
ggaagugaaa gugauuaccc ugaagagcaa guugguqucc gacuuucgca aagauuucca    3060
guucuacaag gugagggaga ucaacaacua ccaccaugcc cacgacgcau accugaacgc    3120
cguggucggc accgcccuga uuaagaagua uccaaagcug gaguccgaau uugcuacgg     3180 cgacuacaaa guuacgaug ugaggaagau gaucgcuaag agcgaacagg agaucggcaa     3240
ggccaccgcu aaguauuucu cuacagcaa caucaugaac uuuuucaaga ccgagaucac    3300
acuugccaac ggcgaaauca ggaagaggcc gcuuaucgag accaacggug agaccggcga    3360
gaucgugugg acaagggca gggacuucgc caccgugagg aaaguccuga gcaugcccca    3420
ggugaauauu gugaaaaaaa cugaggugca gacaggcggc uuuagcaagg aauccauccu    3480
gcccaagagg aacagcgaca agcugaucgc ccggaagaag gacugggacc cuaagaagua    3540
uggaggcuuc gacagcccca ccguagccua cagcgugcug guggucgcga agguagagaa    3600
ggggaagagc aagaaacuga gagcgugaa ggagcugcuc ggcauaacca ucauggagag     3660
guccagcuuu gagaagaacc ccauugacuu uuuggaagcc aagggcuaca agaggucaa     3720 aaaggaccug aucaucaaac uccccaagua ucccuguuu gaauuggaga acggcagaaa     3780
gaggaugcug gcgagcgcug gggaacugca aaagggcaac gaacuggcgc ugcccagcaa    3840
guacgugaau uuucuguacc uggcgucca cuacgaaaag cugaaaggca gccccgagga    3900
caacgagcag aagcagcugu ucguggagca gcacaagcau uaccuggacg agauaaucga    3960
gcaaaucagc gaguucagca agagggugau ucuggccgac gcgaaccugg auaagguccu    4020
cagcgccuac aacaagcacc gagacaaacc caucagggag caggccgaga auaucauaca    4080
ccuguucacc cugacaaauc ugggcgcacc ugcggcauuc aaauacuucg auaccaccau    4140
cgacaggaaa agguacacua gcacuaagga ggugcuggau gccaccuuga uccaccaguc    4200
cauuaccggc cuguaugaga ccaggaucga ccugagccag cuggaggcg acucuagggc    4260 ggacccaaaa aagaaaagga agguggaauu ccaccacacu ggacuagugg auccgagcuc    4320
gguaccaagc uuaaguuuaa accgcugauc agccucgacu gugccuucua guugccagcc    4380
aucuguuguu ugcccuccc ccgugccuuc cuugacccug gaaggugcca cucccacugu    4440
ccuuuccuaa uaaaaugagg aaauugcauc gcauugucug aguaggugu auucuauucu    4500 gggggugggg gugggcagg acagcaaggg ggaggauugg gaagacaaua gcaggcaugc    4560
uggggaugcg gugggcucua uggc                                          4584
```

<210> SEQ ID NO 414
<211> LENGTH: 104
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5' Triphosphate

<400> SEQUENCE: 414

```
gcuuauaucc aacacuucgu gguuuuagag cuagaaauag caaguaaaa uaaggcuagu    60 ccguuaucaa cuugaaaaag uggcaccgag ucggugcuuu uuuu                   104
```

<210> SEQ ID NO 415
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
gactttgctt tccttggtca g                                              21

<210> SEQ ID NO 416
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
ggcttatatc caacacttcg tggg                                           24

<210> SEQ ID NO 417
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' FAM
<220> FEATURE:
<223> OTHER INFORMATION: 3' ZEN modifier

<400> SEQUENCE: 417 atggtcaag                                                             9

<210> SEQ ID NO 418
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
tgtgcagaag gatggagt                                                  18

<210> SEQ ID NO 419
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
ctggtgcttc tctcaggata                                                20

<210> SEQ ID NO 420
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' HEX
<220> FEATURE:
<223> OTHER INFORMATION: 3' ZEN modifier
```

<400> SEQUENCE: 420 tggaatatg                                                              9

<210> SEQ ID NO 421
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
ctcttcttga actggtgctg tctg                                            24

<210> SEQ ID NO 422
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422
caggatgaat ccaatggtca tgagg                                           25

<210> SEQ ID NO 423
<211> LENGTH: 9
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' ZEN modifier

<400> SEQUENCE: 423 aagtgcctg                                                              9

<210> SEQ ID NO 424
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
ccattgtctg gatttaagcg g                                               21

<210> SEQ ID NO 425
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 425
gccacaaaaa atcacaagcc a                                               21

<210> SEQ ID NO 426
<211> LENGTH: 9
<212> TYPE: DNA
<213> ORGANISM: Artificial Sequence
<220> FEATURE:

```
<223> OTHER INFORMATION: Description of Artificial Sequence: Synthetic
      probe
<220> FEATURE:
<223> OTHER INFORMATION: 5' HEX modifier
<220> FEATURE:
<223> OTHER INFORMATION: 3' ZEN modifier

<400> SEQUENCE: 426 tttctttgc                                                                  9

<210> SEQ ID NO 427
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
agcauagcaa guuaaaauaa ggcuaguccg ucaacuugaa aaaguggcac cgagucggug          60
cuuu                                                                      64

<210> SEQ ID NO 428
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
cuuauaucca acacuucgug guuuuagagc uagaaauagc aaguuaaaau aaggcuaguc          60
cguuaucaac uugaaaaagu ggcaccgagu cggugcuuu                                 99

<210> SEQ ID NO 429
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 429
nnnnnnnnnn nnnnnnnnnn guuuuagagc uaugcu                                   36

<210> SEQ ID NO 430
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (1)..(20)
<223> OTHER INFORMATION: a, c, u, g, unknown or other
<220> FEATURE:
```

```
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 430
nnnnnnnnnn nnnnnnnnnn guuuuagagc uaugcu                                  36

<210> SEQ ID NO 431
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 431
nnnnnnnnnn nnnnnnnnnn guuuuagagc uaugcu                                  36

<210> SEQ ID NO 432
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 432
nnnnnnnnnn nnnnnnnnnn guuuuagagc uaugcu                                  36
```

-continued

```
<210> SEQ ID NO 433
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(8)
<223> OTHER INFORMATION: 2'-O-methyl nucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 433
nnnnnnnnnn nnnnnnnnnn guuuuagagc uaugcu                              36

<210> SEQ ID NO 434
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (1)..(10)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 434
nnnnnnnnnn nnnnnnnnnn guuuuagagc uaugcu                              36

<210> SEQ ID NO 435
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
```

```
<222> LOCATION: (1)..(20)
<223> OTHER INFORMATION: a, c, u, g, unknown or other
<220> FEATURE:
<221> NAME/KEY: modified_base
<222> LOCATION: (1)..(12)
<223> OTHER INFORMATION: 2'-O-methyl nucleotide
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 435
nnnnnnnnnn nnnnnnnnnn guuuuagagc uaugcu                              36

<210> SEQ ID NO 436
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(13)
<223> OTHER INFORMATION: 2'-O-methyl nucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 436
nnnnnnnnnn nnnnnnnnnn guuuuagagc uaugcu                              36

<210> SEQ ID NO 437
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(15)
<223> OTHER INFORMATION: 2'-O-methyl nucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (25)..(36)
<223> OTHER INFORMATION: 2'-O-methyl nucleotide
<220> FEATURE:
<221> NAME/KEY: misc_feature
<222> LOCATION: (33)..(36)
```

<223> OTHER INFORMATION: Phosphorothioate linkage

<400> SEQUENCE: 437
nnnnnnnnnn nnnnnnnnnn guuuuagagc uaugcu                            36

<210> SEQ ID NO 438
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' C3 spacer
<220> FEATURE:
<221> NAME/KEY: modified_base
<222> LOCATION: (1)..(20)
<223> OTHER INFORMATION: a, c, u, g, unknown or other
<220> FEATURE:
<223> OTHER INFORMATION: 3' C3 spacer

<400> SEQUENCE: 438
nnnnnnnnnn nnnnnnnnnn guuuuagagc uaugcu                            36

<210> SEQ ID NO 439
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<221> NAME/KEY: modified_base
<222> LOCATION: (1)..(20)
<223> OTHER INFORMATION: a, c, u, g, unknown or other
<220> FEATURE:
<223> OTHER INFORMATION: 5' ZEN modifier

<400> SEQUENCE: 439
nnnnnnnnnn nnnnnnnnnn guuuuagagc uaugcu                            36

<210> SEQ ID NO 440
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (1)..(21)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage

<400> SEQUENCE: 440
nnnnnnnnnn nnnnnnnnnn guuuuagagc uaugcu                            36

<210> SEQ ID NO 441

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 441
gtcgcaagct tgctggt                                                   17

<210> SEQ ID NO 442
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 442
ccctgcgtaa actgga                                                    16

<210> SEQ ID NO 443
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 443
aacatctggg ccctgatt                                                  18

<210> SEQ ID NO 444
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ZEN modifier
<220> FEATURE:
<223> OTHER INFORMATION: 3' ZEN modifier

<400> SEQUENCE: 444
ttcccctaag gcaggctg                                                  18

<210> SEQ ID NO 445
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
```

<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 445
aauuaugggg auuacuagga guuuuagagc uaugcu        36

<210> SEQ ID NO 446
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 446
uuuuguaauu aacagcuugc guuuuagagc uaugcu        36

<210> SEQ ID NO 447
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: misc_feature
<222> LOCATION: (33)..(36)
<223> OTHER INFORMATION: Phosphorothioate linkage
<220> FEATURE:
<221> NAME/KEY: modified_base
<222> LOCATION: (34)..(36)
<223> OTHER INFORMATION: 2'-O-methyl nucleotide

<400> SEQUENCE: 447
ggucacuuuu aacacaccca guuuuagagc uaugcu        36

<210> SEQ ID NO 448
<211> LENGTH: 36
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(10)
<223> OTHER INFORMATION: 2'-fluoro nucleotide
<220> FEATURE:
<221> NAME/KEY: modified_base
<222> LOCATION: (25)..(36)
<223> OTHER INFORMATION: 2'-fluoro nucleotide
<220> FEATURE:
<221> NAME/KEY: misc_feature
<222> LOCATION: (33)..(36)
<223> OTHER INFORMATION: Phosphorothioate linkage

<400> SEQUENCE: 448
cuuauaucca acacuucgug guuuuagagc uaugcu                                 36

<210> SEQ ID NO 449
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-fluoro nucleotide
<220> FEATURE:
<221> NAME/KEY: modified_base
<222> LOCATION: (33)..(67)
<223> OTHER INFORMATION: 2'-fluoro nucleotide
<220> FEATURE:
<221> NAME/KEY: misc_feature
<222> LOCATION: (65)..(67)
<223> OTHER INFORMATION: Phosphorothioate linkage

<400> SEQUENCE: 449
agcauagcaa guuaaaauaa ggcuaguccg uuaucaacuu gaaaaagugg caccgagucg       60
gugcuuu                                                                 67

<210> SEQ ID NO 450
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(9)
<223> OTHER INFORMATION: 2'-fluoro nucleotide
<220> FEATURE:
<221> NAME/KEY: modified_base
<222> LOCATION: (58)..(67)
<223> OTHER INFORMATION: 2'-fluoro nucleotide
<220> FEATURE:
<221> NAME/KEY: misc_feature
<222> LOCATION: (65)..(67)
<223> OTHER INFORMATION: Phosphorothioate linkage
```

<400> SEQUENCE: 450
agcauagcaa guuaaaauaa ggcuaguccg uuaucaacuu gaaaaagugg caccgagucg    60
gugcuuu    67

<210> SEQ ID NO 451
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (1)..(11)
<223> OTHER INFORMATION: 2'-O-methyl nucleotide
<220> FEATURE:
<221> NAME/KEY: modified_base
<222> LOCATION: (14)..(14)
<223> OTHER INFORMATION: 2'-O-methyl nucleotide
<220> FEATURE:
<221> NAME/KEY: modified_base
<222> LOCATION: (16)..(17)
<223> OTHER INFORMATION: 2'-O-methyl nucleotide
<220> FEATURE:
<221> NAME/KEY: modified_base
<222> LOCATION: (18)..(22)
<223> OTHER INFORMATION: 2'-O-methyl nucleotide
<220> FEATURE:
<221> NAME/KEY: modified_base
<222> LOCATION: (25)..(25)
<223> OTHER INFORMATION: 2'-O-methyl nucleotide
<220> FEATURE:
<221> NAME/KEY: modified_base
<222> LOCATION: (29)..(29)
<223> OTHER INFORMATION: 2'-O-methyl nucleotide
<220> FEATURE:
<221> NAME/KEY: modified_base
<222> LOCATION: (33)..(62)
<223> OTHER INFORMATION: 2'-fluoro nucleotide
<220> FEATURE:
<221> NAME/KEY: misc_feature
<222> LOCATION: (60)..(62)
<223> OTHER INFORMATION: Phosphorothioate linkage

<400> SEQUENCE: 451
agcauagcaa guuaaaauaa ggcuaguccg uuaucaacuu gaaaaagugg caccgagucg    60
gu    62

CRISPR-BASED COMPOSITIONS AND METHODS OF USE

CROSS-REFERENCE TO RELATED APPLICATIONS

This application claims benefit of priority under 35 U.S.C. 119 to U.S. provisional patent applications bearing Ser. Nos. 62/093,588 and 62/239,546, filed Dec. 18, 2014 and Oct. 9, 2015, and entitled "CRISPR-BASED COMPOSITIONS AND METHODS OF USE," the contents of which are herein incorporated by reference in its entirety.

SEQUENCE LISTING

The instant application contains a Sequence Listing that has been submitted in ASCII format via EFS-Web and is hereby incorporated by reference in its entirety. The ASCII copy, created on Jun. 16, 2017, is named IDT01-008-US_ST25.txt, and is 280,061 bytes in size.

FIELD OF THE INVENTION

This invention pertains to modified compositions for use in CRISPR systems, and their methods of use.

BACKGROUND OF THE INVENTION

The use of clustered regularly interspaced short palindromic repeats (CRISPR) and associated Cas proteins (CRISPR-Cas system) for site-specific DNA cleavage has shown great potential for a number of biological applications. CRISPR is used for genome editing; the genome-scale-specific targeting of transcriptional repressors (CRISPRi) and activators (CRISPRa) to endogenous genes; and other applications of RNA-directed DNA targeting with Cas enzymes.

CRISPR-Cas systems are native to bacteria and *Archaea* to provide adaptive immunity against viruses and plasmids. There are three classes of CRISPR-Cas systems that could potentially be adapted for research and therapeutic reagents, but Type-II CRISPR systems have a desirable characteristic in utilizing a single CRISPR associated (Cas) nuclease (specifically Cas9) in a complex with the appropriate guide RNAs—either a 2-part RNA system similar to the natural complex in bacteria comprising a CRISPR-activating RNA: trans-activating crRNA (crRNA:tracrRNA) pair or an artificial chimeric single-guide-RNA (sgRNA)—to mediate double-stranded cleavage of target DNA. In mammalian systems, these RNAs have been introduced by transfection of DNA cassettes containing RNA Pol III promoters (such as U6 or H1) driving RNA transcription, viral vectors, and single-stranded RNA following in vitro transcription (see Xu, T., et al., Appl Environ Microbiol, 2014. 80(5): p. 1544-52).

In the CRISPR-Cas9 system, using, for example, the system present in *Streptococcus pyogenes* as an example (S. py. or Spy), native crRNAs are about 42 bp long, containing a 5'-region of about 20 bases complementary to a target sequence (also referred to as a protospacer sequence) and a 3' region typically about 22 bases long that corresponds to a complementary region of the tracrRNA sequence. The native tracrRNAs are about 85-90 bases long, having a 5'-region containing the region complementary to the crRNA as well as about a 10-base region 5'-upstream. The remaining 3' region of the tracrRNA includes secondary structures (herein referred to as the "tracrRNA 3'-tail").

Jinek et al. extensively investigated the portions of the crRNA and tracrRNA that are required for proper functioning of the CRISPR-Cas9 system (Science, 2012. 337(6096): p. 816-21). They devised a truncated crRNA:tracrRNA fragment that could still function in CRISPR-Cas9 wherein the crRNA was the wild type 42 nucleotides and the tracrRNA was truncated to 75 nucleotides. They also developed an embodiment wherein the crRNA and tracrRNA are attached with a linker loop, forming a single guide RNA (sgRNA), which varies between 99-123 nucleotides in different embodiments. The configuration of the native 2-part crRNA:tracrRNA complex is shown in FIG. 1 and the 99 nucleotide embodiment of the artificial sgRNA single guide is shown in FIG. 2.

At least two groups have elucidated the crystal structure of *Streptococcus pyogenes* Cas9 (SpyCas9). In Jinek, M., et al., the structure did not show the nuclease in complex with either a guide RNA or target DNA. They carried out molecular modeling experiments to reveal predictive interactions between the protein in complex with RNA and DNA (Science, 2014. 343, p. 1215, DOI: 10.1126/science/1247997).

In Nishimasu, H., et al., the crystal structure of SpyCas9 is shown in complex with sgRNA and its target DNA at 2.5 angstrom resolution (Cell, 2014. 156(5): p. 935-49, incorporated herein in its entirety). The crystal structure identified two lobes to the Cas9 enzyme: a recognition lobe (REC) and a nuclease lobe (NUC). The sgRNA:target DNA heteroduplex (negatively charged) sits in the positively charged groove between the two lobes. The REC lobe, which shows no structural similarity with known proteins and therefore likely a Cas9-specific functional domain, interacts with the portions of the crRNA and tracrRNA that are complementary to each other.

Another group, Briner et al. (Mol Cell, 2014. 56(2): p. 333-9, incorporated herein in its entirety), identified and characterized the six conserved modules within native crRNA:tracrRNA duplexes and sgRNA.

The CRISPR-Cas9 system is utilized in genomic engineering as follows: a portion of the crRNA hybridizes to a target sequence, a portion of the tracrRNA hybridizes to a portion of the crRNA, and the Cas9 nuclease binds to the entire construct and directs cleavage. The Cas9 contains two domains homologous to endonucleases HNH and RuvC, wherein the HNH domain cleaves the DNA strand complementary to the crRNA and the RuvC-like domain cleaves the noncomplementary strand. This results in a double-stranded break in the genomic DNA. When repaired by non-homologous end joining (NHEJ) the break is typically shifted by 1 or more bases, leading to disruption of the natural DNA sequence and in many cases leading to a frameshift mutation if the event occurs in the coding exon of a protein-encoding gene. The break by also be repaired by homology dependent recombination (HDR), which permits insertion of new genetic material via experimental manipulation into the cut site created by Cas9 cleavage.

Some of the current methods for guide RNA delivery into mammalian cells include transfection of double-stranded DNA (dsDNA) containing RNA Pol III promoters for endogenous transcription, viral delivery, transfection of RNAs as in vitro transcription (IVT) products, or microinjection of IVT products. There are disadvantages to each of these methods. Unmodified exogenous RNA introduced into mammalian cells is known to initiate the innate immune response via recognition by Toll-like Receptors (TLRs), RIG-I, OASI and others receptors that recognize pathogen-associated molecular patterns (PAMPs). However, in most published studies, RNA which has been in vitro transcribed (IVT) by a T7 RNA polymerase is delivered to the cells. This type of RNA payload has been shown to be a trigger for the innate immune response. The alternative delivery methods described above each have their own disadvantages as well. For example, dsDNA cassettes can lead to integration, guide RNA transcription driven endogenously by a RNA Pol II promoter can persist constitutively, and the amount of RNA transcribed is uncontrollable.

RNA is quickly degraded by nucleases present in serum and in cells. Unmodified CRISPR RNA triggers (crRNAs, tracrRNAs, and sgRNAs) made by IVT methods or chemical synthesis are quickly degraded during delivery or after delivery to mammalian cells. Greater activity would be realized if the RNA was chemically modified to gain nuclease resistance. The most potent degradative activity present in serum and in cells is a 3'-exonuclease (Eder et al., Antisense Research and Development 1:141-151, 1991). Thus "end blocking" a synthetic oligonucleotide often improves nuclease stability. Chemical modification of single-stranded antisense oligonucleotides (ASOs) and double-stranded small interfering RNAs (siRNAs) has been well studied and successful approaches are in practice today (for reviews, see: Kurreck, Eur. J. Biochem., 270:1628-1644, 2003; Behlke, Oligonucleotides, 18:305-320, 2008; Lennox et al., Gene Therapy, 18:1111-1120, 2011). It is therefore desirable to devise chemical modification strategies for use with the RNA components of CRISPR/Cas. While the basic toolbox of chemical modifications available is well known to those with skill in the art, the effects that site-specific modification have on the interaction of a RNA species and an effector protein are not easily predicted and effective modification patterns usually must be empirically determined. In some cases, sequence of the RNA may influence the effectiveness of a modification pattern, requiring adjustment of the modification pattern employed for different sequence contexts, making practical application of such methods more challenging.

There is therefore a need to modify the guide RNA to reduce its toxicity to cells and to extend lifespan and functionality in mammalian cells while still performing their intended purpose in the CRISPR-Cas system. The methods and compositions of the invention described herein provide RNA and modified RNA oligonucleotides for use in a CRISPR-Cas system. These and other advantages of the invention, as well as additional inventive features, will be apparent from the description of the invention provided herein.

BRIEF SUMMARY OF THE INVENTION

This invention pertains to modified compositions for use in CRISPR systems, and their methods of use. The compositions include modified internucleotide linkages and 2'-O-alkyl and 2'-O-fluoro modified RNA oligonucleotides to serve as the guides strands (crRNA:tracrRNA or sgRNA) for the CRISPR-Cas system. Compositions also include end-modifications such as an inverted-dT base or other non-nucleotide modifiers that impeded exonuclease attack (such as the propanediol group (C3 spacer), napthyl-azo modifier, or others as are well known in the art).

In a first aspect, isolated tracrRNA including a length-modified form of SEQ ID NO.: 18 is provided. The isolated tracrRNA displays activity in a Clustered Regularly Interspaced Short Palindromic Repeats (CRISPR)-CRISPR associated (Cas) (CRISPR-Cas) endonuclease system.

In a second aspect, an isolated crRNA including a length-modified form of formula (I) is provided:

5'-X—Z-3'     (I), wherein X represents sequences comprising a target-specific protospacer domain comprising about 20 target-specific nucleotides, and Z represents sequences comprising a universal tracrRNA-binding domain comprising about 20 nucleotides. The isolated crRNA displays activity in a Clustered Regularly Interspaced Short Palindromic Repeats (CRISPR)-CRISPR associated (Cas) (CRISPR-Cas) endonuclease system.

In a third aspect, an isolated tracrRNA including a chemically-modified form of one of SEQ ID NOs.: 2, 18, 30-33 and 36-39 is provided. The isolated tracrRNA displays activity in a Clustered Regularly Interspaced Short Palindromic Repeats (CRISPR)-CRISPR associated (Cas) (CRISPR-Cas) endonuclease system.

In a fourth aspect, isolated crRNA including a chemically-modified form of formula (I) is provided:

5'-X—Z-3'     (I), wherein X represents sequences comprising a target-specific protospacer domain comprising from about 17 nucleotides to about 20 nucleotides, and Z represents sequences comprising a universal tracrRNA-binding domain comprising about 12 nucleotides to about 19 nucleotides. The isolated crRNA displays activity in a Clustered Regularly Interspaced Short Palindromic Repeats (CRISPR)-CRISPR associated (Cas) (CRISPR-Cas) endonuclease system.

BRIEF DESCRIPTION OF THE DRAWINGS

FIG. 1 is an illustration of a wild-type (WT) natural 2-part crRNA:tracrRNA complex with a 42 base unmodified crRNA (SEQ ID No. 46) and an 89 base unmodified tracrRNA (SEQ ID No. 18). Lowercase letters represent RNA.

FIG. 2 is an illustration of a 99 base artificial single-guide RNA (SEQ ID NO: 428) (sgRNA) that fuses the crRNA and tracrRNA elements into a single sequence through the addition of a new hairpin loop. Lowercase letters represent RNA.

FIG. 3 shows an alignment of the full-length and truncated tracrRNA species studied in Example 2. Sequences are RNA and are shown 5'-3'. Alignment is based upon the 89 base WT tracrRNA sequence at the top (SEQ ID No. 18). Internal gaps represent sites of internal truncation/deletion. Uppercase letters represent RNA.

FIG. 4 shows an alignment of the full-length and truncated crRNA and tracrRNA species studied in Example 3. Alignment is based upon the 42 base WT crRNA (SEQ ID No. 46) and 89 base WT tracrRNA (SEQ ID No. 18) sequences at the top of their respective groupings. The 20 base 5'-domain in the crRNAs is sequence-specific and targets human HPRT1. The 3'-domain in underlined and binds to a region towards the 5'-end of the tracrRNA. The 5'-domain in the tracrRNA is underlined that binds the 3'-end of the crRNA. Uppercase letters represent RNA.

FIG. 5 is an illustration of a truncated 2-part crRNA:tracrRNA complex with a 36 base crRNA (SEQ ID No. 48) and a 67 base tracrRNA (SEQ ID No. 2). Lowercase letters represent RNA.

FIG. 8 is a schematic showing structure of one embodiment of the optimized truncated/modified crRNA:tracrRNA complex as employed in Example 8. The crRNA is positioned at the top with the 5'-protospacer domain 20 base underlined, which in this case is specific for target human HPRT1 site 38285; the 3'-end is the 16 base tracrRNA binding domain. The tracrRNA is aligned below. RNA is lower case, 2'OMe RNA is uppercase, and "*" indicates a phosphorothioate internucleotide linkage modification. This figure shows the complex formed by crRNA SEQ ID No. 178 and tracrRNA SEQ ID No. 100.

FIG. 9 is a schematic showing structure of one embodiment of the optimized truncated/modified crRNA:tracrRNA complex that is highly modified. The crRNA is positioned at the top with the 5'-protospacer domain 20 base underlined, which in this case is specific for target human HPRT1 site 38285; the 3'-end is the 16 base tracrRNA binding domain. The tracrRNA is aligned below. RNA is lower case, 2'OMe RNA is uppercase, and "*" indicates a phosphorothioate internucleotide linkage modification. This figure shows the complex formed by crRNA SEQ ID No. 446 and tracrRNA SEQ ID No. 134.

FIG. 10 is a schematic showing the crRNA modification patterns employed in Example 10. Oligonucleotide sequences (SEQ ID NOS 429-439, respectively, in order of appearance) are shown 5'-3'. Lowercase=RNA; Underlined=2'-O-methyl RNA; C3=C3 spacer (propanediol modifier); *=phosphorothioate internucleotide linkage; ZEN=napthyl-azo modifier. The 5'-target specific protospacer domain is indicated. Bases are indicated by "N" in this domain as sequence is different for each target site, although the modification pattern employed remains constant. The 3'-universal tracrRNA binding domain is indicated. Modification patterns are numbered for reference between Table 10 and FIG. 10.

FIG. 12 is a schematic showing structure of one embodiment of the optimized truncated/modified crRNA:tracrRNA complex that is highly modified using crRNA Mod Pattern 6 that is universal and can be applied in any sequence context. The crRNA (SEQ ID NO: 440) is positioned at the top with the 5'-protospacer domain 20 base underlined (N-bases); the 3'-end is the 16 base tracrRNA binding domain. The tracrRNA is aligned below (SEQ ID No. 134). RNA is lower case, 2'OMe RNA is uppercase, and "*" indicates a phosphorothioate internucleotide linkage modification.

DETAILED DESCRIPTION OF THE INVENTION

Figure 6:
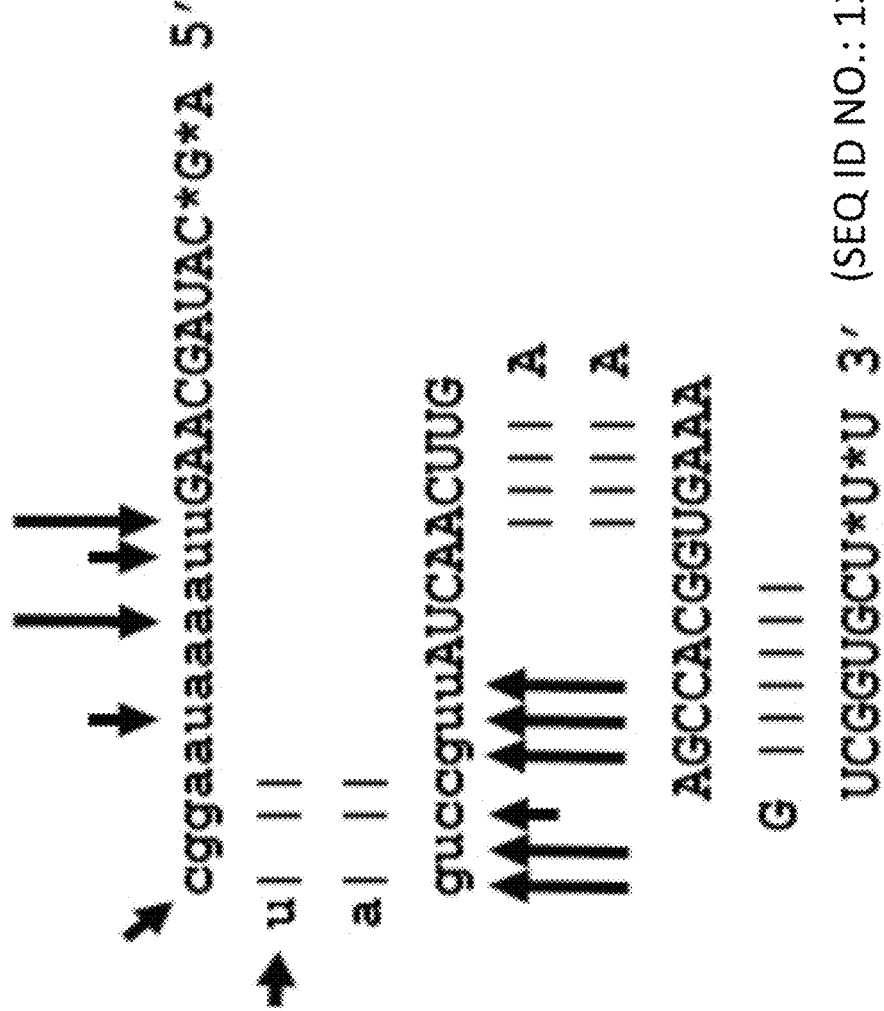
FIG. 6 is a schematic showing structure of one embodiment of an optimized truncated and chemically-modified tracrRNA (SEQ ID No. 134). Length is 67 bases. RNA is lower case and 2'OMe RNA is uppercase. Phosphorothioate (PS) internucleotide linkages are indicated by "*". Residues which lead to substantial loss of function when converted from RNA to 2'OMe RNA are identified by large arrows and residues which lead to a moderate loss of function when converted from RNA to 2'OMe RNA are identified by small arrows.

Aspects of this invention relate to modified compositions for use in CRISPR systems, and their methods of use.

The term "oligonucleotide," as used herein, refer to polydeoxyribonucleotides (containing 2-deoxy-D-ribose), polyribonucleotides (containing D-ribose), and to any other type of polynucleotide which is an N glycoside of a purine or pyrimidine base (a single nucleotide is also referred to as a "base" or "residue"). There is no intended distinction in length between the terms "nucleic acid", "oligonucleotide" and "polynucleotide", and these terms can be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs. An oligonucleotide may comprise ribonucleotides, deoxyribonucleotides, modified nucleotides (e.g., nucleotides with 2' modifications, synthetic base analogs, etc.) or combinations thereof.

Compositions of the present invention include any modification that potentially reduces activation of the innate immune system. Modifications can be placed or substituted at a conventional phosphodiester linkage, at the ribose sugar, or at the nucleobase of RNA. Such compositions could include, for example, a modified nucleotide such as 2'-O-methyl-modified RNAs.

More broadly, the term "modified nucleotide" refers to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications include those naturally occurring that result from modification by enzymes that modify nucleotides, such as methyltransferases. Modified nucleotides also include synthetic or non-naturally occurring nucleotides. Modifications also include base analogs and universal bases. Synthetic or non-naturally occurring modifications in nucleotides include those with 2' modifications, e.g., 2'-O-alkyl (including 2'-O-methyl), 2'-fluoro, 2'-methoxyethoxy, 2'-allyl, 2'-O-[2-(methylamino)-2-oxoethyl], 4'-thio, bicyclic nucleic acids, 4'-CH2-O-2'-bridge, 4'-(CH2)2-O-2'-bridge, 2'-LNA, and 2'-O—(N-methylcarbamate) or those comprising base analogs. Such modified groups are described, e.g., in Eckstein et al., U.S. Pat. No. 5,672,695 and Matulic-Adamic et al., U.S. Pat. No. 6,248,878.

The use of 2'-O-methyl has been documented in siRNA literature (See Behlke, M. A., Oligonucleotides, 2008. 18(4): p. 305-19) as well as in mRNA delivery (see Sahin, U. et al., Nat Rev Drug Discov, 2014. 13(10): p. 759-80). Sahin et al., describes modifications of mRNA therapeutics that extend beyond 2'-OMe modification and "non-immunogenic" mRNA.

The term "ribonucleotide" encompasses natural and synthetic, unmodified and modified ribonucleotides. Modifications include changes to the sugar moiety, to the base moiety and/or to the linkages between ribonucleotides in the oligonucleotide.

The term "Cas9 protein" encompasses wild-type and mutant forms of Cas9 having biochemical and biological activity when combined with a suitable guide RNA (for example sgRNA or dual crRNA:tracrRNA compositions) to form an active CRISPR-Cas endonuclease system. This includes orthologs and Cas9 variants having different amino acid sequences from the *Streptococcus pyogenese* Cas9 employed as example in the present invention.

The term "length-modified," as that term modifies RNA, refers to a shortened or truncated form of a reference RNA lacking nucleotide sequences or an elongated form of a reference RNA including additional nucleotide sequences.

The term "chemically-modified," as that term modifies RNA, refers to a form of a reference RNA containing a chemically-modified nucleotide or a non-nucleotide chemical group covalently linked to the RNA. Chemically-modified RNA, as described herein, generally refers to synthetic RNA prepared using oligonucleotide synthesis procedures wherein modified nucleotides are incorporated during synthesis of an RNA oligonucleotide. However, chemically-modified RNA also includes synthetic RNA oligonucleotides modified with suitable modifying agents post-synthesis.

Applicants have discovered novel crRNA and tracrRNA oligonucleotide compositions that display robust activity in the Clustered Regularly Interspaced Short Palindromic Repeats (CRISPR)-CRISPR associated (Cas) (CRISPR-Cas) endonuclease system. The oligonucleotide compositions include length-modified forms of crRNA and tracrRNA, as well as chemically-modified forms of crRNA and tracrRNA. The length-modified forms of crRNA and tracrRNA enable one to prepare active forms of these RNAs with cost-effective and efficient oligonucleotide synthesis protocols routinely available. The chemically-modified forms of crRNA and tracrRNA provide one with active agents tunable with certain specific properties, such as improved stability in cellular and in vivo contexts. The length-modified forms of crRNA and tracrRNA can also include modifications, thereby enabling access to a broad range of compositions having activity in CRISPR-Cas endonuclease system contexts. These oligonucleotide compositions and their properties in the CRISPR-Cas endonuclease system are described below.

Length-Modified Forms of crRNA and tracrRNA

FIG. 1 depicts a representation of the wild-type *S. pyogenes* crRNA:tracrRNA complex, wherein an exemplary isolated crRNA (SEQ ID No. 46) is paired with an isolated tracrRNA (SEQ ID No. 18). In a first aspect, an isolated tracrRNA including a length-modified form of SEQ ID NO.: 18 is provided. The isolated tracrRNA displays activity in the CRISPR-Cas endonuclease system. In one respect, the isolated tracrRNA includes a length-modified form of SEQ ID NO.: 18 nucleotide having deleted sequence information. In some embodiments, the length-modified form of SEQ ID NO.: 18 includes shortened or truncated forms of SEQ ID NO.: 18, wherein SEQ ID NO.: 18 can be shortened by 1 to 20 nucleotides at the 5'-end and by 1-10 nucleotides at the 3'-end. Such shortened or truncated forms of SEQ ID NO.: 18 retain activity when paired with a functionally competent crRNA in the CRISPR-Cas endonuclease system. Where shortening of the 5'-end of the tracrRNA is performed and extends into sequence that pairs with the 3'-end of the crRNA, improved activity may be obtained using chemical modification that enhance binding affinity in these domains. Where shortening of the 3'-end of the crRNA is performed and extends into sequence that pairs with the 5'-end of the tracrRNA, improved activity may be obtained using chemical modification that enhance binding affinity in these domains. Preferred examples of a length-modified form of SEQ ID NO.: 18 having a shortened or truncated form include SEQ ID NOs: 2, 30-33 and 36-39. A highly preferred example of a length-modified form of SEQ ID NO.: 18 having a shortened or truncated form includes SEQ ID NO:2. For each of the foregoing exemplary length-modified forms of SEQ ID NO.: 18 having a shortened or truncated form, SEQ ID NOs.: 2, 30-33 and 36-69 can consist of chemically non-modified nucleotides.

In a second aspect, an isolated crRNA comprising a length-modified form of formula (I) is provided:

$$5'\text{-X}—\text{Z-}3' \qquad (I),$$

wherein X represents sequences including a target-specific protospacer domain, and Z represents sequences including a tracrRNA-binding domain.

The target-specific protospacer domain (X domain of formula (I)) typically includes about twenty nucleotides having complementarity to a region of DNA targeted by the CRISPR-Cas endonuclease system. The tracrRNA-binding domain (the Z domain of formula (I)) typically includes about 20 nucleotides in most CRISPR endonuclease systems (in the native S. py. version, this domain is 22 nucleotides). The isolated crRNA displays activity in the CRISPR-Cas endonuclease system.

In one respect, the isolated crRNA includes a length-modified form of formula (I) having deleted sequence information. In some embodiments, the length-modified form of formula (I) includes shortened or truncated forms of formula (I), wherein formula (I) can be shortened by 1-8 nucleotides at the 3'-end of the Z domain. The length-modified form of formula (I) can be shortened at the 5-end of the X-domain to accommodate a target-specific protospacer domain having 17, 18, 19 or 20 nucleotides. Highly preferred examples of such length-modified form of formula (I) include target-specific protospacer domain having 19 or 20 nucleotides. The exemplary length-modified forms of formula (I) having a shortened or truncated form with a target-specific protospacer (X-domain) of 17-20 nucleotides in length and/or lacking 1-8 nucleotides at the 3'-end of the Z-domain can consist of chemically non-modified nucleotides.

Such shortened or truncated forms of formula (I) retain activity when paired with a competent tracrRNA in the CRISPR-Cas endonuclease system. Preferred embodiments of isolated crRNA of formula (I) having a length-modified form of formula (I) can include chemically non-modified nucleotides and chemically modified nucleotides.

Chemically-Modified Forms of crRNA and tracrRNA

In a third aspect, an isolated tracrRNA including a chemically-modified nucleotide or a non-nucleotide chemical modifier is provided. The isolated tracrRNA displays activity in the CRISPR-Cas endonuclease system. In one respect, the isolated tracrRNA includes a chemically-modified nucleotide having a modification selected from a group consisting of a ribose modification, an end-modifying group, and internucleotide modifying linkages. Exemplary ribose modifications include 2'O-alkyl (e.g., 2'OMe), 2'F, bicyclic nucleic acid, and locked nucleic acid (LNA). Exemplary end-modifying groups include a propanediol (C3) spacer and napthyl-azo modifier (N,N-diethyl-4-(4-nitronaphthalen-1-ylazo)-phenylamine, or "ZEN"), and an inverted-dT residue. Exemplary internucleotide modifying linkages include phosphorothioate modification. In one respect, the isolated tracrRNA having a chemically-modified form include SEQ ID NO.: 46 and length-modified forms thereof, such as shortened or truncated forms of SEQ ID NO.: 46. Preferred shortened or truncated forms of SEQ ID NO.: 46 having a chemically-modified nucleotide include SEQ ID NOs: 2, 30-33 and 36-39 having a chemically-modified nucleotide. Yet other examples of isolated tracrRNA having a chemically-modified nucleotide with robust activity in the CRISPR-Cas endonuclease system are presented in the Examples.

In a fourth aspect, an isolated crRNA including a chemically-modified nucleotide is provided. The isolated crRNA displays activity in the CRISPR-Cas endonuclease system. In one respect, the isolated crRNA includes a chemically-modified nucleotide having a modification selected from a group consisting of a ribose modification, an end-modifying group, and internucleotide modifying linkage. Exemplary ribose modifications include 2'O-alkyl (e.g., 2'OMe), 2'F, bicyclic nucleic acid, and locked nucleic acid (LNA). Exemplary end-modifying groups include a propanediol (C3) spacer and napthyl-azo modifier (N,N-diethyl-4-(4-nitronaphthalen-1-ylazo)-phenylamine, or "ZEN"), and an inverted-dT residue. Exemplary internucleotide modifying linkages include phosphorothioate modification. In one respect, the isolated crRNA having a chemically-modified form include crRNA of formula (I) and length-modified forms thereof. Preferred shortened or truncated forms of crRNA of formula (I) having a chemically-modified nucleotide include SEQ ID NOs.: 429-439. Highly preferred examples of an isolated crRNA having a chemically-modified nucleotide include SEQ ID NOs.: 434 and 435. These particular isolated crRNA species represent "universal" crRNAs having a chemically-modified nucleotide showing high activity when combined with a competent tracrRNA in the CRISPR-Cas endonuclease system. Yet other examples of isolated crRNA having a chemically-modified nucleotide with robust activity in the CRISPR-Cas endonuclease system are presented in the Examples.

The foregoing isolated, length-modified and chemically-modified of crRNA and tracrRNA preferably include chemical modifications at the 2'-OH groups (for example, 2'OMe, 2'F, bicyclic nucleic acid, locked nucleic acid, among others) and end-blocking modifications (for example, ZEN, C3 spacer, inverted-dT). Use of both types of general modifications provides isolated, length-modified and chemically-modified of crRNA and tracrRNA with biochemical stability and immunologic tolerance for isolated, length-modified and chemically-modified of crRNA and tracrRNA in biological contexts.

The foregoing isolated, length-modified and chemically-modified of crRNA and tracrRNA can be mixed in different combinations to form active crRNA:tracrRNA as the guide RNA for Cas9. For example, an isolated, length-modified tracrRNA can be combined with an isolated chemically-modified crRNA to form an active crRNA:tracrRNA as the guide RNA for Cas9. The Examples provide illustrations of different combinations of isolated, length-modified and chemically-modified of crRNA and tracrRNA resulting in active crRNA:tracrRNA as the guide RNA for Cas9.

The extent to which one needs particular chemically-modified nucleotides included in one (or both) of the isolated, length-modified and chemically-modified crRNA and tracrRNA depends upon the application for which the resultant active crRNA:tracrRNA serves as the guide RNA for Cas9. In certain biochemical assays of the CRISPR-Cas endonuclease system, particularly where nucleases can be minimized or absent, one may not need extensively chemically-modified crRNA and tracrRNA to effect robust activity of the resultant guide RNA for Cas9 of the CRISPR-Cas endonuclease system. This is attributed to the fact that chemically-modified nucleotides that confer resistance to nucleases are not necessary when nucleases are minimal or absent. In certain biological (in vivo) contexts, wherein a mixture including crRNA and tracrRNA is delivered to cells inside carrier vehicles, such as liposome nanoparticles, the isolated length-modified and chemically-modified crRNA and tracrRNA may require less extensive chemically-modified nucleotides than mixtures of crRNA and tracrRNA delivered directly into the blood stream or injected into organ systems as isolated, "naked," RNA mixtures. The extent of chemical modification present in chemically-modified crRNA and tracrRNA can dictate the half-life of the relevant RNA molecules in vivo (that is, in the relevant biological context, such as, for example, in the blood stream or inside cells). Accordingly, the modification profile of chemically-modified crRNA and tracrRNA can be used to fine tune the biochemical and biological activity of the resultant crRNA:tracrRNA duplexes as a guide RNA for Cas9 in the CRISPR-Cas endonuclease system.

Although the prior art focuses on the structure of Cas9 as it interacts with a sgRNA, the disclosed design patterns described herein contemplate the aforementioned crRNA:tracrRNA dual RNA systems. A single strand guide RNA offers several benefits, such as simplicity of a therapeutic design. However, standard solid phase phosphoramidite RNA synthesis shows diminishing yields for oligonucleotides as length increases and this problem becomes more apparent as length exceeds 60-70 bases. This precludes robust, cost-effective synthesis of some tracrRNAs as well as the chimeric sgRNA, especially at larger scales needed for some commercial or therapeutic applications. For this reason, the invention contemplates embodiments of not only sgRNA, but also alternate dual crRNA:tracrRNA as the guide RNA for Cas9. However, an isolated guide RNA having robust activity when combined with Cas9 in the CRISPR-Cas endonuclease system can be engineered by linkage or synthesis of appropriate crRNA and tracrRNA as an artificial, unimolecular sgRNA based upon the isolated, length-modified and chemically-modified forms of crRNA and tracrRNA provided herein. Long single guides of this type may be obtained by direct synthesis or by post-synthetic chemical conjugation of shorter strands.

The design of length-modified and chemically-modified tracrRNA compositions addresses the potential synthetic issues associated with tracrRNA oligonucleotides that are >80 nucleotides in length. The coupling efficiency of 2'-OMe-modified RNA monomers (effectively containing a protecting group on the 2'-OH) is greater than RNA monomer coupling. Incorporating 2'-OMe modified RNAs provides some advantages. First, it allows for longer oligonucleotides to be synthesized as either full 2'-OMe or RNA/2'-OMe mixed oligonucleotides. Secondly, the methods and compositions of the invention lead to synthesis and transfection of crRNA:tracrRNA that can evade detection by the immune system. It is well known that exogenous, unmodified RNAs trigger an innate immune response in mammalian cells as well as whole animals. Using 2'OMe-modified oligonucleotides can confer RNA stability to nucleases (a third advantage) as well as reduce cell death and toxicity associated with immunogenic triggers. These advantages are not unique to 2'-OMe modification, per se, as the other disclosed modified nucleotides having different chemical moieties (for example, 2'F, other 2'O-alkyls, LNA, and other bicyclic nucleotides) can offer similar benefits and advantages in terms of conferring resistance to nucleases.

In another embodiment, the tracrRNA portion complementary to the crRNA contains at least one modified nucleotide, and in a further embodiment the tracrRNA portion complementary to the crRNA is comprised of more than 10% modified residues, and in a further embodiment the tracrRNA portion not complementary to the crRNA is comprised of more than 50% modified residues, and a further embodiment the tracrRNA portion not complementary to the crRNA is comprised of more than 90% modified residues.

In another embodiment, the crRNA portion is unmodified and the tracrRNA portion is comprised of at least one modified nucleotide. In a further embodiment the crRNA portion is unmodified and the tracrRNA portion is comprised of more than 10% modified bases.

Figure 7:
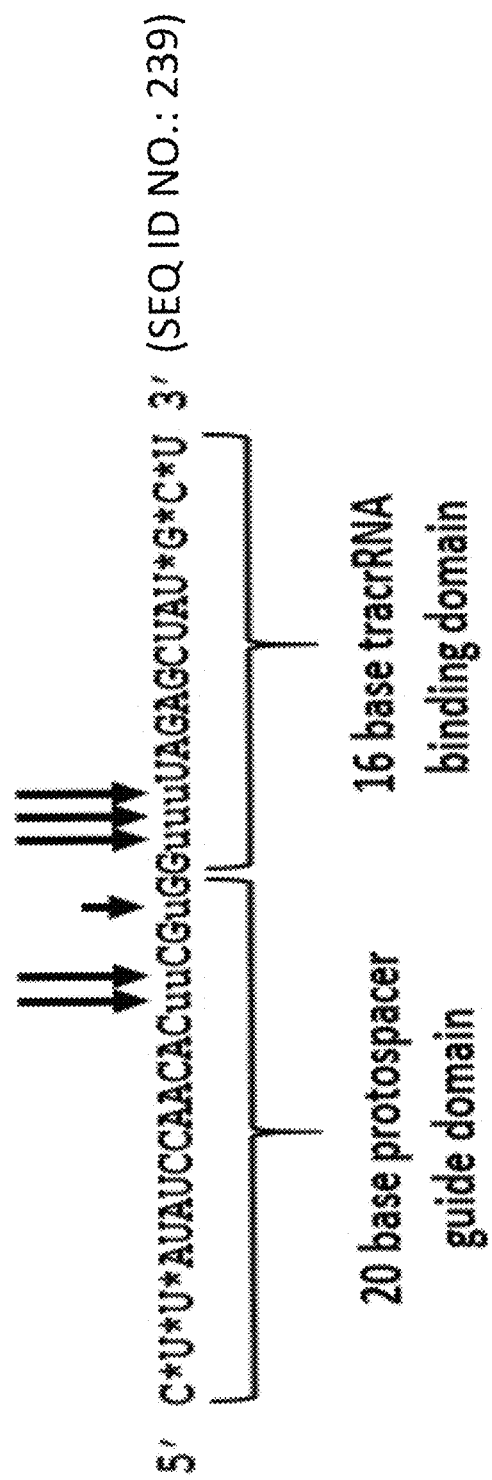
FIG. 7 is a schematic showing structure of one embodiment of an optimized truncated and chemically-modified crRNA (SEQ ID No. 239). Length is 36 bases. RNA is lower case and 2'OMe RNA is uppercase. Phosphorothioate (PS) internucleotide linkages are indicated by "*". Residues which lead to substantial loss of function when converted from RNA to 2'OMe RNA are identified by large arrows and residues which lead to a moderate loss of function when converted from RNA to 2'OMe RNA are identified by small arrows. The 5'-end 20 base protospacer target-specific guide domain is indicated, which in this case is sequence specific to the human HPRT1 gene. The 3'-end 16 base tracrRNA binding domain is indicated.

In another embodiment, an isolated crRNA of formula (I) is designed with modifications that are empirically determined. As depicted in FIGS. 7 and 10, the 12 nucleotides at the 3'-end of the Z domain (the tracrRNA-binding domain) and the 10-12 nucleotides at the 5'-end of the X domain (within the protospacer domain) represent universal nucleotides amenable to substitution with chemically-modified nucleotides, wherein the resultant RNAs retain robust activity in the CRISPR-Cas endonuclease system. Yet other nucleotides within the 5'-end of the Z domain (the tracrRNA-binding domain) are intolerant to substitution with chemically-modified nucleotides (FIG. 7). Yet the ability of other sites within an isolated crRNA of formula (I) to accept chemically-modified nucleotides and retain activity in the CRISPR-Cas endonuclease system is largely determined empirically. The tracrRNA binding domain (Z domain) of the crRNA is constant (i.e., sequence does not change as target site varies), so the modifications patterns described herein are universal to all crRNAs regardless of target site and can be broadly applied. The protospacer (X domain) of the crRNA varies with target, and the tolerance of some of the base positions within this domain to chemical modification vary with sequence context and, if maximal chemical modification of a site is desired, may benefit from empiric optimization. However, some of the residues within the target-specific protospacer (X) domain can be modified without consideration to sequence context. The 10-12 residues at the 5'-end of this domain can be substituted with 2'-modified residues with the expectation that full activity of the modified crRNA will be maintained. The remaining 8-10 bases towards the 3'-end of the protospacer (X) domain may tolerate modification or may not, depending on sequence context. One sequence context where 17 out of the 20 bases of the protospacer (X) domain can be modified while maintaining full activity are shown in FIG. 7. Sites were modification compromised activity are indicated.

The applications of Cas9-based tools are many and varied. They include, but are not limited to: plant gene editing, yeast gene editing, rapid generation of knockout/knockin animal lines, generating an animal model of disease state, correcting a disease state, inserting a reporter gene, and whole genome functional screening.

The utility of the present invention is further expanded by including mutant versions of Cas enzymes, such as a D10A and H840a double mutant of Cas9 as a fusion protein with transcriptional activators (CRISPRa) and repressors (CRISPRi) (see Xu, T., et al., Appl Environ Microbiol, 2014. 80(5): p. 1544-52). The Cas9-sgRNA complex also can be used to target single-stranded mRNA as well (see O'Connell, M. R., et al., Nature, 516:263, 2014). In the same way as targeting dsDNA, crRNA:tracrRNA can be used with a PAMmer DNA oligonucleotide to direct Cas9 cleavage to the target mRNA or use it in the mRNA capture assay described by O'Connell.

By utilizing an approach to deliver synthetic RNA oligonucleotides for CRISPR/Cas9 applications, it is possible to 1) use mass spectroscopy to confirm discrete RNA sequences, 2) selectively insert 2'-OMe modified RNAs in well-tolerated locations to confer stability and avoid immunogenicity yet retain functional efficacy, 3) specifically control the amount of RNA that is introduced into cells for a controlled transient effect, and 4) eliminate concern over introducing dsDNA that would be endogenously transcribed to RNA but could also become substrate in either homology-directed repair pathway or in non-homologous end joining resulting in an integration event. These integration events can lead to long term undesired expression of crRNA or tracrRNA elements. Further, integration can disrupt other genes in a random and unpredictable fashion, changing the genetic material of the cell in undesired and potentially deleterious ways. The present invention is therefore desirable as a means to introduce transient expression of elements of the CRISPR pathway in cells in a way which is transient and leaves no lasting evidence or change in the genome outside of whatever alteration is intended as directed by the crRNA guide.

CRISPR-Cas Endonuclease Systems

A competent CRISPR-Cas endonuclease system includes a ribonucleoprotein (RNP) complex formed with isolated Cas9 protein and isolated guide RNA selected from one of a dual crRNA:tracrRNA combination and a chimeric sgRNA. In some embodiments, isolated length-modified and/or chemically-modified forms of crRNA and tracrRNA are combined with purified Cas9 protein (for example, SEQ ID NOs.: 407-410), an isolated mRNA encoding Cas9 protein (for example, SEQ ID NO.: 413), or a gene encoding Cas9 protein (for example, SEQ ID NOs.: 411 and 412) in an expression vector. In certain assays, isolated length-modified and/or chemically-modified forms of crRNA and tracrRNA can be introduced into cell lines that stably express Cas9 protein from an endogenous expression cassette encoding the Cas9 gene. In other assays, a mixture of length-modified and/or chemically-modified forms of crRNA and tracrRNA in combination with either Cas9 mRNA or Cas9 protein can be introduced into cells.

EXAMLE 1

This example illustrates functioning of chemically modified and truncated guide RNAs in an in vitro Cas9 DNA cleavage assay.

CrRNA and tracrRNA oligonucleotides were synthesized having various chemical modifications and truncations relative to the WT sequences as indicated (Table 1).

TABLE 1

In vitro biochemical studies of cleavage of HPRT1 target DNA by Cas9 endonuclease with various crRNA and tracrRNA pairs.

| cr/tracr RNA pair | SEQ ID No. | crRNA Sequence tracrRNA Sequence | Length | Cleavage |
|---|---|---|---|---|
| 1A | 1 | uuauauccaacacuucgugguuuuagagcuaugcu | 35 | +++ |
|  | 2 | agcauagcaaguuaaaauaaggcuaguccguuaucaacuug aaaaaguggcaccgagucggugcuuu | 67 |  |
| 1B | 1 | uuauauccaacacuucgugguuuuagagcuaugcu | 35 | − |
|  | 3 | guuggaaccauucaaaacagcauagcaaguuaaaauaaggc uaguccguuaucaacuugaaaaaguggcaccgagucggugc uuuuuuu | 89 |  |
| 1C | 1 | uuauauccaacacuucgugguuuuagagcuaugcu | 35 | − |
|  | 4 | agcauagcaaguuaaaauaaggcuaguccguuaucaacuug aaaaagugqcaccgagucggugcuuu | 67 |  |
| 2A | 5 | uuauauccaacacuucgugguuuuagagcuaugcuguuuug | 41 | +++ |
|  | 2 | agcauagcaaguuaaaauaaggcuaguccguuaucaacuug aaaaaguggcaccgagucggugcuuu | 67 |  |
| 2B | 5 | uuauauccaacacuucgugguuuuagagcuaugcuguuuug | 41 | − |
|  | 6 | guuggaaccauucaaaacagcauagcaaguuaaaauaaggc uaguccguuaucaacuugaaaaaguggcaccgagucggugc uuuuuuu | 89 |  |
| 2C | 5 | uuauauccaacacuucgugguuuuagagcuaugcuguuuug | 41 | − |
|  | 4 | agcauagcaaguuaaaauaaggcuaguccguuaucaacuug aaaaagugqcaccgagucggugcuuu | 67 |  |
| 3A | 7 | uuauauccaacacuucgugguuuuagagcuaugcuguuuug | 41 | − |
|  | 2 | agcauagcaaguuaaaauaaggcuaguccguuaucaacuug aaaaaguggcaccgagucggugcuuu | 67 |  |
| 3B | 7 | uuauauccaacacuucgugguuuuagagcuaugcuguuuug | 41 | − |
|  | 6 | guuggaaccauucaaaacagcauagcaaguuaaaauaaggc uaguccguuaucaacuugaaaaaguggcaccgagucggugc uuuuuuu | 89 |  |
| 3C | 7 | uuauauccaacacuucgugguuuuagagcuaugcuguuuug | 41 | − |
|  | 4 | agcauagcaaguuaaaauaaggcuaguccguuaucaacuug aaaaagugqcaccgagucggugcuuu | 67 |  |
| 4A | 8 | uuauauccaacacuucgugguuuuagagcuaugcuguuuug | 41 | − |
|  | 2 | agcauagcaaguuaaaauaaggcuaguccguuaucaacuug aaaaaguggcaccgagucggugcuuu | 67 |  |
| 4B | 8 | uuauauccaacacuucgugguuuuagagcuaugcuguuuug | 41 | − |
|  | 6 | guuggaaccauucaaaacagcauagcaaguuaaaauaaggc uaguccguuaucaacuugaaaaaguggcaccgagucggugc uuuuuuu | 89 |  |
| 4C | 8 | uuauauccaacacuucgugguuuuagagcuaugcuguuuug | 41 | − |
|  | 4 | agcauagcaaguuaaaauaaggcuaguccguuaucaacuug aaaaagugqcaccgagucggugcuuu | 67 |  |
| 5A | 9 | uuauauccaacacuucgugguuuuagagcuaugcu | 35 | − |
|  | 2 | agcauagcaaguuaaaauaaggcuaguccguuaucaacuug aaaaaguggcaccgagucggugcuuu | 67 |  |
| 5B | 9 | uuauauccaacacuucgugguuuuagagcuaugcu | 35 | − |
|  | 6 | guuggaaccauucaaaacagcauagcaaguuaaaauaaggc uaguccguuaucaacuugaaaaaguggcaccgagucggugc uuuuuuu | 89 |  |
| 5C | 9 | uuauauccaacacuucgugguuuuagagcuaugcu | 35 | − |
|  | 4 | agcauagcaaguuaaaauaaggcuaguccguuaucaacuug aaaaagugqcaccgagucggugcuuu | 67 |  |
| 6A | 10 | uuauauccaacacuucgugguuuuagagcuaugcu | 35 | − |
|  | 2 | agcauagcaaguuaaaauaaggcuaguccguuaucaacuug aaaaaguggcaccgagucggugcuuu | 67 |  |
| 6B | 10 | uuauauccaacacuucgugguuuuagagcuaugcu | 35 | − |
|  | 6 | guuggaaccauucaaaacagcauagcaaguuaaaauaaggc uaguccguuaucaacuugaaaaaguggcaccgagucggugc uuuuuuu | 89 |  |

TABLE 1-continued

In vitro biochemical studies of cleavage of HPRT1 target DNA by Cas9 endonuclease with various crRNA and tracrRNA pairs.

| cr/tracr RNA pair | SEQ ID No. | crRNA Sequence tracrRNA Sequence | Length | Cleavage |
|---|---|---|---|---|
| 6C | 10 | uuauauccaacacuucgugguuuuagagcuaugcu | 35 | − |
|  | 4 | agcauagcaaguuaaaauaaggcuaguccguuaucaacuug aaaaaguggcaccgagucggugcuuu | 67 |  |
| 1G | 1 | uuauauccaacacuucgugguuuuagagcuaugcu | 35 | +++ |
|  | 11 | agcauagcaaguuaaaauaaggcuaguccguuaucaacuug aaaaaguggcaccgagucggugcuuu | 67 |  |
| 1K | 1 | uuauauccaacacuucgugguuuuagagcuaugcu | 35 | ++ |
|  | 12 | agcauagcaaguuaaaauaaggcuaguccguuaucaacuug aaaaaguggcaccgagucggugcuuu | 67 |  |
| 1L | 1 | uuauauccaacacuucgugguuuuagagcuaugcu | 35 | +++ |
|  | 13 | agcauagcaaguuaaaauaaggcuaguccguuaucaacuug aaaaaguggcaccgagucggugcuuu | 67 |  |
| 14A | 14 | uuauauccaacacuucgugguuuuagagcuaugcu | 35 | +++ |
|  | 2 | agcauagcaaguuaaaauaaggcuaguccguuaucaacuug aaaaaguggcaccgagucggugcuuu | 67 |  |
| 14G | 14 | uuauauccaacacuucgugguuuuagagcuaugcu | 35 | +++ |
|  | 11 | agcauagcaaguuaaaauaaggcuaguccguuaucaacuug aaaaaguggcaccgagucggugcuuu | 67 |  |
| 14K | 14 | uuauauccaacacuucgugguuuuagagcuaugcu | 35 | +++ |
|  | 12 | agcauagcaaguuaaaauaaggcuaguccguuaucaacuug aaaaaguggcaccgagucggugcuuu | 67 |  |
| 14L | 14 | uuauauccaacacuucgugguuuuagagcuaugcu | 35 | +++ |
|  | 13 | agcauagcaaguuaaaauaaggcuaguccguuaucaacuug aaaaaguggcaccgagucggugcuuu | 67 |  |
| 15A | 15 | uuauauccaacacuucgugguuuuagagcuaugcu | 35 | +++ |
|  | 2 | agcauagcaaguuaaaauaaggcuaguccguuaucaacuug aaaaaguggcaccgagucggugcuuu | 67 |  |
| 15G | 15 | uuauauccaacacuucgugguuuuagagcuaugcu | 35 | +++ |
|  | 11 | agcauagcaaguuaaaauaaggcuaguccguuaucaacuug aaaaaguggcaccgagucggugcuuu | 67 |  |
| 15K | 15 | uuauauccaacacuucgugguuuuagagcuaugcu | 35 | +++ |
|  | 12 | agcauagcaaguuaaaauaaggcuaguccguuaucaacuug aaaaaguggcaccgagucggugcuuu | 67 |  |
| 15L | 15 | uuauauccaacacuucgugguuuuagagcuaugcu | 35 | +++ |
|  | 13 | agcauagcaaguuaaaauaaggcuaguccguuaucaacuug aaaaaguggcaccgagucggugcuuu | 67 |  |
| 16A | 16 | uuauauccaacacuucgugguuuuagagcuaugcu | 35 | +++ |
|  | 2 | agcauagcaaguuaaaauaaggcuaguccguuaucaacuug aaaaaguggcaccgagucggugcuuu | 67 |  |
| 16G | 16 | uuauauccaacacuucgugguuuuagagcuaugcu | 35 | +++ |
|  | 11 | agcauagcaaguuaaaauaaggcuaguccguuaucaacuug aaaaaguggcaccgagucggugcuuu | 67 |  |
| 16K | 16 | uuauauccaacacuucgugguuuuagagcuaugcu | 35 | +++ |
|  | 12 | agcauagcaaguuaaaauaaggcuaguccguuaucaacuug aaaaaguggcaccgagucggugcuuu | 67 |  |
| 16L | 16 | uuauauccaacacuucgugguuuuagagcuaugcu | 35 | +++ |
|  | 13 | agcauagcaaguuaaaauaaggcuaguccguuaucaacuug aaaaaguggcaccgagucggugcuuu | 67 |  |
| 1H | 1 | uuauauccaacacuucgugguuuuagagcuaugcu | 35 | +++ |
|  | 17 | agcauagcaaguuaaaauaaggcuaguccguuaucaacuug aaaaaguggcaccgagucggugcuuu | 67 |  |
| 2D | 5 | uuauauccaacacuucgugguuuuagagcuaugcuguuuug | 41 | +++ |
|  | 18 | guuggaaccauucaaaacagcauagcaaguuaaaauaaggc uaguccguuaucaacuugaaaaaguggcaccgagucggugc uuuuuuu | 89 |  |

TABLE 1-continued

In vitro biochemical studies of cleavage of HPRT1 target DNA by Cas9 endonuclease with various crRNA and tracrRNA pairs.

| cr/tracr RNA pair | SEQ ID No. | crRNA Sequence tracrRNA Sequence | Length | Cleavage |
|---|---|---|---|---|
| 2E | 5<br>19 | uuauauccaacacuucgugguuuuagagcuaugcuguuug<br>guuggaaccauucaaaacagcauagcaaguuaaaauaaggc<br>uaguccguuaucaacuugaaaaaguggcaccgagucggugc<br>uuuuuuu | 41<br>89 | +++ |
| 2F | 5<br>20 | uuauauccaacacuucgugguuuuagagcuaugcuguuug<br>guuggaaccauucaaaacagcauagcaaguuaaaauaaggc<br>uaguccguuaucaacuugaaaaaguggcaccgagucggugc<br>uuuuuuu | 41<br>89 | +++ |
| 2I | 5<br>21 | uuauauccaacacuucgugguuuuagagcuaugcuguuug<br>guuggaaccauucaaaacagcauagcaaguuaaaauaaggc<br>uaguccguuaucaacuugaaaaaguggcaccgagucggugc<br>uuuuuuu | 41<br>89 | +++ |
| 7A | 22<br>2 | uuauauccaacacuucgugguuuuagagcuaugcu<br>agcauagcaaguuaaaauaaggcuaguccguuaucaacuug<br>aaaaaguggcaccgagucggugcuuu | 35<br>67 | – |
| 9A | 23<br>2 | uuauauccaacacuucgugguuuuagagcuaugcu<br>agcauagcaaguuaaaauaaggcuaguccguuaucaacuug<br>aaaaaguggcaccgagucggugcuuu | 35<br>67 | +++ |
| 10A | 24<br>2 | uuauauccaacacuucgugguuuuagagcuaugcu<br>agcauagcaaguuaaaauaaggcuaguccguuaucaacuug<br>aaaaaguggcaccgagucggugcuuu | 35<br>67 | +++ |
| 3D | 7<br>18 | uuauauccaacacuucgugguuuuagagcuaugcuguuug<br>guuggaaccauucaaaacagcauagcaaguuaaaauaaggc<br>uaguccguuaucaacuugaaaaaguggcaccgagucggugc<br>uuuuuuu | 41<br>89 | – |
| 4D | 8<br>18 | uuauauccaacacuucgugguuuuagagcuaugcuguuug<br>guuggaaccauucaaaacagcauagcaaguuaaaauaaggc<br>uaguccguuaucaacuugaaaaaguggcaccgagucggugc<br>uuuuuuu | 41<br>89 | – |
| 8D | 25<br>18 | uuauauccaacacuucgugguuuuagagcuaugcuguuug<br>guuggaaccauucaaaacagcauagcaaguuaaaauaaggc<br>uaguccguuaucaacuugaaaaaguggcaccgagucggugc<br>uuuuuuu | 41<br>89 | – |
| 13D | 26<br>18 | uuauauccaacacuucgugguuuuagagcuaugcuguuug<br>guuggaaccauucaaaacagcauagcaaguuaaaauaaggc<br>uaguccguuaucaacuugaaaaaguggcaccgagucggugc<br>uuuuuuu | 41<br>89 | +++ |
| 13I | 26<br>21 | uuauauccaacacuucgugguuuuagagcuaugcuguuug<br>guuggaaccauucaaaacagcauagcaaguuaaaauaaggc<br>uaguccguuaucaacuugaaaaaguggcaccgagucggugc<br>uuuuuuu | 41<br>89 | +++ |

Oligonucleotide sequences are shown 5'-3'.
Lowercase = RNA,
Underlined = 2'-O-methyl RNA,
Italics = 2'-fluoro RNA.
Lengths of the RNA oligonucleotides are indicated (bases). The relative efficiency of cleavage of the DNA target by recombinant Cas9 with each of the crRNA: tracrRNA pairs as visualized by agarose gel electrophoresis is indicated with "+++" indicating complete cleavage, "++" and "+" indicating intermediate levels of cleavage, and "–" indicating no cleavage.

The crRNAs contained a 19 base protospacer guide sequence matching a site in the human HPRT1 gene adjacent to a suitable 'NGG" PAM site. A 938 base pair region from the human HPRT1 gene was cloned into the pCR-Blunt vector (Life Technologies). The plasmid was linearized by digestion with the restriction endonuclease XmaI (New England BioLabs) prior to use in the Cas9 cleavage assay. Sequence of the HPRT1 target fragment is shown below. The target PAM site is indicated in bold font and the protospacer guide sequence binding site is underlined.

HPRT1 Target Sequence. SEQ ID No. 27.

GAATGTTGTGATAAAAGGTGATGCTCACCTCTCCCACACCCTTTTATAG
TTTAGGGATTGTATTTCCAAGGTTTCTAGACTGAGAGCCCTTTTCATCT

-continued
TTGCTCATTGACACTCTGTACCCATTAATCCTCCTTATTAGCTCCCCTT

CAATGGACACATGGGTAGTCAGGGTGCAGGTCTCAGAACTGTCCTTCAG

GTTCCAGGTGATCAACCAAGTGCCTTGTCTGTAGTGTCAACTCATTGCT

GCCCCTTCCTAGTAATCCCCATAATTTAGCTCTCCATTTCATAGTCTTT

CCTTGGGTGTGTTAAAAGTGACCATGGTACACTCAGCACGGATGAAATG

AAACAGTGTTTAGAAACGTCAGTCTTCTCTTTTGTAATGCCCTGTAGTC

TCTCTGTATGTTATATGTCACATTTTGTAATTAACAGCTTGCTGGTGAA

AAGGACCCCACGAAGTGTTGGATATAAGCCAGACTGTAAGTGAATTACT

TTTTTTGTCAATCATTTAACCATCTTTAACCTAAAAGAGTTTTATGTGA

AATGGCTTATAATTGCTTAGAGAATATTTGTAGAGAGGCACATTTGCCA

GTATTAGATTTAAAAGTGATGTTTTCTTTATCTAAATGATGAATTATGA

TTCTTTTTAGTTGTTGGATTTGAAATTCCAGACAAGTTTGTTGTAGGAT

ATGCCCTTGACTATAATGAATACTTCAGGGATTTGAATGTAAGTAATTG

CTTCTTTTTCTCACTCATTTTTCAAAACACGCATAAAAATTTAGGAAAG

AGAATTGTTTTCTCCTTCCAGCACCTCATAATTTGAACAGACTGATGGT

TCCCATTAGTCACATAAAGCTGTAGTCTAGTACAGACGTCCTTAGAACT

GGAACCTGGCCAGGCTAGGGTGACACTTCTTGTTGGCTGAAATAGTTGA

ACAGCTT

The crRNA and tracrRNA pairs were tested for the ability to direct degradation of a linearized plasmid DNA containing a cloned fragment of the human HPRT1 gene by recombinant Spy Cas9 (New England BioLabs). The crRNA:tracrRNA were annealed in Duplex Buffer (30 mM HEPES pH 7.5, 100 mM potassium acetate) at 150 nM concentration. Spy Cas9 (15 nM) was preincubated with the crRNA:tracrRNA for 10 min at 37° C. at a 1:1 molar ratio. Subsequently, 3 nM of the linearized target plasmid was added and incubated at 37° C. for 1 hour. The reaction products were separated on a 1% agarose gel at 125 V for 1 hour. Bands were visualized by GelRed (Biotium) post-staining according to the manufacturer's protocol. The gel was imaged on a UV-transilluminator and results are summarized in Table 1 above.

Native wild-type (WT) CRISPR RNAs have a 19-20 base protospacer domain (guide, which binds to a target nucleic acid) at the 5'-end and a 22 base domain at the 3'-end that binds to the tracrRNA. Thus WT crRNAs are 41-42 bases long. The WT tracrRNA is 89 bases long. We observed that a WT type crRNA:tracrRNA pair supported full cleavage of the target DNA (cr/tracrRNA pair 2D). We additionally observed that a truncated version of the reagents with a 35 base crRNA (19 base protospacer and 16 base tracrRNA binding domain) paired with a 67 base tracrRNA supported full cleavage of the target RNA (cr/tracrRNA pair 1A). The crRNA tracrRNA binding region was truncated 6 bases at the 3'-end (SEQ ID No. 1). The tracrRNA was truncated at both ends (SEQ ID No. 2). Pairwise combinations of the short crRNA with the long tracrRNA showed cleavage as well as the long crRNA with the short tracrRNA (pair 2A). These findings are significant as it permits use of shorter RNA components to direct Cas9 target recognition and cleavage. Shorter RNA oligonucleotides are less expensive and less difficult for chemical synthesis, requiring less purification and giving higher yields than longer RNA oligonucleotides.

Some elements of the native crRNA and tracrRNA (FIG. 1) were deleted to make a functional sgRNA (FIG. 2). However, the amount of duplex nucleic acid binding the crRNA to the tracrRNA in the sgRNA is limited to 11 base pairs, which is typically too short for duplex formation in biological salt conditions. The complex is stable in sgRNA format due to the unimolecular hairpin structure, however the same sequences split into 2 RNAs would be unstable. It was therefore unclear what length of duplex domain was needed to make a minimal yet functional 2-molecule (2-part) CRISPR complex, or if this complex would function to direct target cleavage by Cas9. The present example demonstrates that having as little of 15 bases base paired permits a function 2-part crRNA:tracrRNA complex that is competent to direct Cas9 nuclease activity against a target complementary to the crRNA protospacer domain (SEQ ID Nos. 1 and 2).

Complete chemical modification of the crRNA with 2'OMe RNA was not tolerated (pair 3A and pair 5A). Further, complete 2'OMe modification of the 22 base tracrRNA binding domain of the crRNA did not support target cleavage (pair 4A, pair 6A) and complete 2'OMe modification of the protospacer guide domain did not support cleavage (pair 7A). Complete chemical modification of the tracrRNA with 2'OMe RNA was also not tolerated (pair 1B, 1C and pair 2B, 2C).

Importantly, some highly 2'OMe-modified versions of both CRISPR RNA species did support cleavage. Pair 1K shows high cleavage activity with a tracrRNA having 29 2'OMe residues at the 3'-end (SEQ ID No. 11). Pair 1 L shows high cleavage activity with 9 2'OMe residues at the 5'-end and 29 2'OMe residues at the 3'-end (SEQ ID No. 13). Thus 38 out of 67 RNA residues in the short version of the tracrRNA can be converted to 2'OMe RNA (57%) with no loss of activity in an in vitro cleavage assay.

Pair 14A demonstrates that 11 bases at the 3'-end of the crRNA (50% of the 22 base tracrRNA binding domain) can be modified with 2'OMe RNA and support target cleavage (SEQ ID No. 14). The modified crRNA retains full activity when paired with the modified tracrRNA (pair 14L, Seq ID Nos. 13 and 14). Modification of 11 bases towards the 5'-end of the crRNA (in the guide, protospacer domain, bases 2-12) supports target cleavage (pair 15A) and this modification is also functional when paired with the modified tracrRNA (pair 15L, SEQ ID Nos. 13 and 15). The 2'OMe modifications towards the 5'-end and 3'-end of the crRNA can be combined (SEQ ID No. 16) such that 22 out of 35 residues are modified (63%) and still support cleavage (pair 16A), even when paired with the modified tracrRNA (pair 16L, SEQ ID Nos. 13 and 16).

The crRNA:tracrRNA pairs mentioned above all employed 2'OMe RNA as the modifier. Additional studies showed that 2'F modification was also tolerated by Cas9 and enabled cleavage of a target DNA. Pair 9A employs a crRNA with 2'F modification at all pyrimidine bases (SEQ ID No. 23) and this design supported complete target cleavage. Likewise complete 2'F modification of the crRNA supported complete target cleavage (pair 10A, SEQ ID No. 24). Combined use of 2'OMe and 2'F modifications may permit complete modification of both the crRNA and tracrRNA. The studies in the present example utilized in vitro biochemical analyses. Performance may vary in the context of mammalian gene editing where the sequences have to function in the milieu of a cell nucleus.

EXAMPLE 2

This example demonstrates functioning of truncated tracrRNAs to direct genome editing by the Spy Cas9 nuclease in mammalian cells.

Both functional Cas9 nuclease and the RNA triggers (a single sgRNA or dual crRNA:tracrRNA pair) must be present in the nucleus of mammalian cells for CRISPR genome editing to take place. Transfection of large plasmid vectors expressing Cas9 is inefficient and adds variability to experimental results. In order to accurately assess the impact that changes in length and chemical composition of the crRNA and tracrRNA have in mammalian cells in the absence of other variables, a cell line that stably expresses Spy Cas9 was constructed.

A HEK293 cell line having constitutive expression of SpyCas9 (human codon-optimized) with stable vector integration and selection under G418 was developed as described below. Human optimized Spy Cas9 was ligated into a pcDNA3.1 expression vector (Life Technologies) and transfected into HEK293 cells using Lipofectamine2000 (Life Technologies). The transfected cells were allowed to grow for 2 days before being placed under selective pressure using Neomycin. After 7 days, cells were plated to single colonies using limiting dilution techniques. Monoclonal colonies were screened for Cas9 activity and the clone having highest level of expression was used for future studies. A single copy integration event for Cas9 was determined using droplet digital PCR (ddPCR). Western blot using an anti-Cas9 antibody showed low but constant expression of Cas9 protein. This cell line is henceforth referred to as "HEK-Cas9".

The HEK-Cas9 cell line was employed in subsequent studies. In a reverse transfection format, anti-HPRT1 crRNA:tracrRNA complexes were mixed with Lipofectamine RNAiMAX (Life Technologies) and transfected into the HEK-Cas9 cells. Transfections were done with 40,000 cells per well in 96 well plate format. RNAs were introduced at a final concentration of 30 nM in 0.75 µl of the lipid reagent. Cells were incubated at 37° C. for 48 hours. Genomic DNA was isolated using QuickExtract solution (Epicentre). Genomic DNA was amplified with KAPA HiFi DNA Polymerase (Roche) and primers targeting the HPRT region of interest (HPRT forward primer:

(SEQ ID No. 28)
AAGAATGTTGTGATAAAAGGTGATGCT;

HPRT reverse primer:

(SEQ ID No. 29))
ACACATCCATGGGACTTCTGCCTC.

PCR products were melted and re-annealed in NEB buffer 2 (New England BioLabs) to allow for heteroduplex formation followed by digestion with 2 units of T7 endonuclease 1 (T7EI; New England BioLabs) for 1 hour at 37° C. The digested products were visualized on a Fragment Analyzer (Advanced Analytics). Percent cleavage of targeted DNA was calculated as the average molar concentration of the cut products/(average molar concentration of the cut products+ molar concentration of the uncut band)×100.

TracrRNAs (Table 2) were synthesized having deletions at the 5'-end, 3'-end, internal or combinations thereof. The tracrRNAs were complexed with unmodified truncated anti-HPRT1 crRNA SEQ ID No. 1 (Table 1) which has a 19 base protospacer domain targeting HPRT1 at the 5'-end and a 16 base tracrRNA binding domain at the 3'-end. The paired crRNA:tracrRNA RNA oligonucleotides were transfected into the HEK-Cas9 cells and processed as described above. Relative gene editing activities were assessed by comparing cleavage rates in the HPRT1 gene using the T7EI mismatch endonuclease cleavage assay with quantitative measurement of products done using the Fragment Analyzer. A representation of the wild-type *S. pyogenes* crRNA:tracrRNA complex is shown in FIG. 1 (which pairs crRNA SEQ ID No. 46 with tracrRNA SEQ ID No. 18). The relative location of deletions in the tracrRNA tested in this example are shown in sequence alignment format in FIG. 3.

TABLE 2

Effect of length truncations in the tracrRNA on efficiency of gene editing in mammalian cells by Cas9 endonuclease.

| SEQ ID No. | tracrRNA Sequence 5'-3' | Cleavage (%) | Length | Truncation positions |
| --- | --- | --- | --- | --- |
| 18 | guuggaaccauucaaaacagcauagcaaguuaaaauaaggcuaguccguuaucaacuugaaaaaguggcaccgagucggugcuuuuuuu | 38 | 89 | — |
| 30 | caaaacagcauagcaaguuaaaauaaggcuaguccguuaucaacuugaaaaaguggcaccgagucggugcuuuu | 26 | 74 | 5'-12 bases<br>3'-3 bases |
| 31 | aacagcauagcaaguuaaaauaaggcuaguccguuaucaacuugaaaaaguggcaccgagucggugcuuu | 32 | 70 | 5'-15 bases<br>3'-4 bases |
| 2 | agcauagcaaguuaaaauaaggcuaguccguuaucaacuugaaaaaguggcaccgagucggugcuuu | 57 | 67 | 5'-18 bases<br>3'-4 bases |
| 32 | agcauagcaaguuaaaauaaggcuaguccguuaucaacuugaaaaaguggcaccgagucggugcu | 47 | 65 | 5'-18 bases<br>3'-6 bases |
| 33 | cauagcaaguuaaaauaaggcuaguccguuaucaacuugaaaaaguggcaccgagucggugcu | 27 | 63 | 5'-20 bases<br>3'-6 bases |
| 34 | agcauagcaaguuaaaauaguuaucaacuugaaaaaguggcaccgagucggugcu | 0 | 55 | 5'-18 bases<br>Int-10 bases<br>3'-6 bases |
| 35 | agcauagcaaguuaaaauaaacuugaaaaaguggcaccgagucggugcu | 0 | 49 | 5'-18 bases<br>Int-16 bases<br>3'-6 bases |

TABLE 2-continued

Effect of length truncations in the tracrRNA on efficiency
of gene editing in mammalian cells by Cas9 endonuclease.

| SEQ ID No. | tracrRNA Sequence 5'-3' | Cleavage (%) | Length | Truncation positions |
|---|---|---|---|---|
| 36 | agcauagcaaguuaaaauaaggcuaguccguuaucaacuuga aaaaguggcaccgagucggugc | 53 | 64 | 5'-18 bases<br>3'-7 bases |
| 37 | agcauagcaaguuaaaauaaggcuaguccguuaucaacuuga aaaaguggcaccgagucggug | 56 | 63 | 5'-18 bases<br>3'-8 bases |
| 38 | agcauagcaaguuaaaauaaggcuaguccguuaucaacuuga aaaaguggcaccgagucggu | 56 | 62 | 5'-18 bases<br>3'-9 bases |
| 39 | agcauagcaaguuaaaauaaggcuaguccguuaucaacuuga aaaaguggcaccgagucgg | 53 | 61 | 5'-18 bases<br>3'-10 bases |
| 40 | agcauagcaaguuaaaauaaggcuaguccguuaucaacuuga aaaagugccgagucgg | 5 | 58 | 5'-18 bases<br>Int-3 bases<br>3'-10 bases |
| 41 | agcauagcaaguuaaaauaaggcuaguccaacuugaaaaagu ggcaccgagucggugcu | 0 | 59 | 5'-18 bases<br>Int-6 bases<br>3'-6 bases |
| 42 | agcauagcaaguuaaaauaaggcuaguccaacuugaaaaagu ggcaccgagucgg | 0 | 55 | 5'-18 bases<br>Int-6 bases<br>3'-10 bases |
| 43 | agcauagcaaguuaaaauaaggcuaguccaacuugaaaaagu gccgagucgg | 0 | 52 | 5'-18 bases<br>Int-9 bases<br>3'-10 bases |
| 44 | agcauagcaaguuaaaauaaggcuaguccguuaucaacuuga aaaagug | 0 | 49 | 5'-18 bases<br>3'-22 bases |
| 45 | agcauagcaaguuaaaauaaggcuaguccguuaucagcaccg agucggugcu | 0 | 52 | 5'-18 bases<br>Int-13 bases<br>3'-6 bases |
| 427 | agcauagcaaguuaaaauaaggcuaguccgucaacuugaaaa aguggcaccgagucggugcuuu | 4 | 64 | 5'-18 bases<br>Int-3 bases<br>3'-4 bases |

Oligonucleotide sequences are shown 5'-3'.
Lowercase = RNA.
Lengths of the RNA oligonucleotides are indicated (bases). The number of RNA residues removed in truncation studies at the 5'-end, 3'-end, and internal (int) are indicated. The relative functional activity of each species is indicated by the % cleavage in a T7EI heteroduplex assay.

This example demonstrates that for purposes of gene editing in mammalian cells that the tracrRNA can tolerate significant deletions from both the 5'-end and 3'-end and retain full functionality. Deletion of 18 bases from the 5'-end was well tolerated. Deletion of 20 bases from the 5'-end led to reduced activity, possibly due to lower affinity of binding of the crRNA. It is possible that this reduced length or even shorter might be functional if Tm-enhancing modifications were employed to stabilize the short duplex forming region. Deletion of up to 10 bases from the 3'-end was well tolerated. Additional deletions resulted in loss of activity. Internal deletions that disrupted hairpin elements or spacing between hairpin elements were not functional.

In summary, this example demonstrates that truncation of the tracrRNA from the 89 base length of the wild-type (WT, SEQ ID No. 18) to a 67 base length (SEQ ID No. 2) or to a 62 base length (SEQ ID No. 38), or to a 61 base length (SEQ ID No. 39) retained high functional activity. Use of shortened tracrRNAs of this kind will be less costly and easier to manufacture by chemical methods than the WT 89 base RNA. Some of the truncated species (SEQ ID No. 2, SEQ ID No. 38, and SEQ ID No. 39) showed increased functional activity over the 89 base WT tracrRNA. Therefore in addition to being less costly and easier to manufacture by chemical methods, the shortened tracrRNAs of the present invention showed improved activity.

EXAMPLE 3

Examples 1 and 2 demonstrated that crRNA:tracrRNA complexes shorter than the WT lengths of 42 and 89 bases, respectively, can show higher functional activity in mammalian gene editing. The present example shows further optimization of the lengths of these RNA species.

A series of crRNAs and tracrRNAs (Table 3) were synthesized having different lengths as indicated. Truncations were made at the 3'-end of the crRNA, the 5'-end of the tracrRNA, and/or the 3'-end of the tracrRNA. The crRNAs and tracrRNA were paired as indicated in Table 3. The crRNAs all employed a 20 base protospacer domain targeting HPRT1 at the 5'-end and variable length 3'-ends (tracrRNA binding domains). An alignment of the crRNA and tracrRNA sequences studied in this example is shown in FIG. 4 to make clear the positions of truncations relative to each functional domain.

The paired crRNA:tracrRNA RNA oligonucleotides were transfected into the HEK-Cas9 cells and processed as described in Example 2. Relative gene editing activities were assessed by comparing cleavage rates in the HPRT1 gene using the T7EI mismatch endonuclease cleavage assay with quantitative measurement of products done using the Fragment Analyzer. Results are shown in Table 3. The relative location of deletions are shown in sequence alignment format in FIG. 4.

TABLE 3

Effect of length truncations in both the crRNA and tracrRNA on efficiency of gene editing in mammalian cells by Cas9 endonuclease.

| cr/tracr RNA pair | SEQ ID No. | crRNA Sequence tracrRNA Sequence | Length | Cleavage % |
|---|---|---|---|---|
| 42/89 | 46 | cuuauauccaacacuucgugguuuuagagcuaugcuguuug | 42 | 25 |
|  | 18 | guuggaaccauucaaaacagcauagcaaguuaaaauaaggcuaguccguuaucaacuugaaaaaguggcaccgagucggugcuuuuuuu | 89 |  |
| 39/89 | 47 | cuuauauccaacacuucgugguuuuagagcuaugcuguu | 39 | 31 |
|  | 18 | guuggaaccauucaaaacagcauagcaaguuaaaauaaggcuaguccguuaucaacuugaaaaaguggcaccgagucggugcuuuuuuu | 89 |  |
| 36/89 | 48 | cuuauauccaacacuucgugguuuuagagcuaugcu | 36 | 38 |
|  | 18 | guuggaaccauucaaaacagcauagcaaguuaaaauaaggcuaguccguuaucaacuugaaaaaguggcaccgagucggugcuuuuuuu | 89 |  |
| 34/89 | 49 | cuuauauccaacacuucgugguuuuagagcuaug | 34 | 21 |
|  | 18 | guuggaaccauucaaaacagcauagcaaguuaaaauaaggcuaguccguuaucaacuugaaaaaguggcaccgagucggugcuuuuuuu | 89 |  |
| 42/74 | 46 | cuuauauccaacacuucgugguuuuagagcuaugcuguuug | 42 | 35 |
|  | 50 | caaaacagcauagcaaguuaaaauaaggcuaguccguuaucaacuugaaaaaguggcaccgagucggugcuuuuu | 74 |  |
| 39/74 | 47 | cuuauauccaacacuucgugguuuuagagcuaugcuguu | 39 | 34 |
|  | 50 | caaaacagcauagcaaguuaaaauaaggcuaguccguuaucaacuugaaaaaguggcaccgagucggugcuuuuu | 74 |  |
| 36/74 | 48 | cuuauauccaacacuucgugguuuuagagcuaugcu | 36 | 26 |
|  | 50 | caaaacagcauagcaaguuaaaauaaggcuaguccguuaucaacuugaaaaaguggcaccgagucggugcuuuuu | 74 |  |
| 34/74 | 49 | cuuauauccaacacuucgugguuuuagagcuaug | 34 | 20 |
|  | 50 | caaaacagcauagcaaguuaaaauaaggcuaguccguuaucaacuugaaaaaguggcaccgagucggugcuuuuu | 74 |  |
| 42/70 | 46 | cuuauauccaacacuucgugguuuuagagcuaugcuguuug | 42 | 55 |
|  | 51 | aacagcauagcaaguuaaaauaaggcuaguccguuaucaacuugaaaaaguggcaccgagucggugcuuu | 70 |  |
| 39/70 | 47 | cuuauauccaacacuucgugguuuuagagcuaugcuguu | 39 | 48 |
|  | 51 | aacagcauagcaaguuaaaauaaggcuaguccguuaucaacuugaaaaaguggcaccgagucggugcuuu | 70 |  |
| 36/70 | 48 | cuuauauccaacacuucgugguuuuagagcuaugcu | 36 | 32 |
|  | 51 | aacagcauagcaaguuaaaauaaggcuaguccguuaucaacuugaaaaaguggcaccgagucggugcuuu | 70 |  |
| 34/70 | 49 | cuuauauccaacacuucgugguuuuagagcuaug | 34 | 9 |
|  | 51 | aacagcauagcaaguuaaaauaaggcuaguccguuaucaacuugaaaaaguggcaccgagucggugcuuu | 70 |  |
| 42/67 | 46 | cuuauauccaacacuucgugguuuuagagcuaugcuguuug | 42 | 36 |
|  | 2 | agcauagcaaguuaaaauaaggcuaguccguuaucaacuugaaaaguggcaccgagucggugcuuu | 67 |  |
| 39/67 | 47 | cuuauauccaacacuucgugguuuuagagcuaugcuguu | 39 | 41 |
|  | 2 | agcauagcaaguuaaaauaaggcuaguccguuaucaacuugaaaaguggcaccgagucggugcuuu | 67 |  |
| 36/67 | 48 | cuuauauccaacacuucgugguuuuagagcuaugcu | 36 | 57 |
|  | 2 | agcauagcaaguuaaaauaaggcuaguccguuaucaacuugaaaaguggcaccgagucggugcuuu | 67 |  |
| 34/67 | 49 | cuuauauccaacacuucgugguuuuagagcuaug | 34 | 44 |
|  | 2 | agcauagcaaguuaaaauaaggcuaguccguuaucaacuugaaaaguggcaccgagucggugcuuu | 67 |  |

TABLE 3-continued

Effect of length truncations in both the crRNA and tracrRNA on efficiency of gene editing in mammalian cells by Cas9 endonuclease.

| cr/tracr RNA pair | SEQ ID No. | crRNA Sequence tracrRNA Sequence | Length | Cleavage % |
|---|---|---|---|---|
| 42/65 | 46 | cuuauauccaacacuucgugguuuuagagcuaugcuguuuug | 42 | 50 |
| | 52 | agcauagcaaguuaaaauaaggcuaguccguuaucaacuuga aaaaguggcaccgagucggugcu | 65 | |
| 39/65 | 47 | cuuauauccaacacuucgugguuuuagagcuaugcuguu | 39 | 46 |
| | 52 | agcauagcaaguuaaaauaaggcuaguccguuaucaacuuga aaaaguggcaccgagucggugcu | 65 | |
| 36/65 | 48 | cuuauauccaacacuucgugguuuuagagcuaugcu | 36 | 47 |
| | 52 | agcauagcaaguuaaaauaaggcuaguccguuaucaacuuga aaaaguggcaccgagucggugcu | 65 | |
| 34/65 | 49 | cuuauauccaacacuucgugguuuuagagcuaug | 34 | 16 |
| | 52 | agcauagcaaguuaaaauaaggcuaguccguuaucaacuuga aaaaguggcaccgagucggugcu | 65 | |
| 42/63 | 46 | cuuauauccaacacuucgugguuuuagagcuaugcuguuuug | 42 | 6 |
| | 53 | cauagcaaguuaaaauaaggcuaguccguuaucaacuugaaa aaguggcaccgagucggugcu | 63 | |
| 39/63 | 47 | cuuauauccaacacuucgugguuuuagagcuaugcuguu | 39 | 13 |
| | 53 | cauagcaaguuaaaauaaggcuaguccguuaucaacuugaaa aaguggcaccgagucggugcu | 63 | |
| 36/63 | 48 | cuuauauccaacacuucgugguuuuagagcuaugcu | 36 | 28 |
| | 53 | cauagcaaguuaaaauaaggcuaguccguuaucaacuugaaa aaguggcaccgagucggugcu | 63 | |
| 34/63 | 49 | cuuauauccaacacuucgugguuuuagagcuaug | 34 | 33 |
| | 53 | cauagcaaguuaaaauaaggcuaguccguuaucaacuugaaa aaguggcaccgagucggugcu | 63 | |

Oligonucleotide sequences are shown 5'-3'.
Lowercase = RNA.
Lengths of the RNA oligonucleotides are indicated (bases). The relative functional activity of each crRNA: tracrRNA pair is indicated by the % cleavge in a T7EI heteroduplex assay.

All of the compounds studied directed CRISPR/Cas editing at the HPRT1 locus in HEK-Cas9 cells. Efficiency varied widely from 6% to 57%. The most effective crRNA+tracrRNA combination was the 36 base crRNA (SEQ ID No. 48) with the 67mer tracrRNA (SEQ ID No. 2). A schematic representation of the truncated, optimized crRNA:tracrRNA complex is shown in FIG. 5. In this case the tracrRNA binding domain of the crRNA was truncated to 16 bases from the WT 22 base sequence (3'-end). This hybridizes to the crRNA binding domain at the 5'-end of the tracrRNA. The tracrRNA was truncated 18 bases at the 5'-end and 4 bases at the 3'-end to product the active 67 base product. For this pair, a blunt end is formed upon hybridization of the 3'-end of the crRNA with the 5'-end of the tracrRNA. Other versions also showed high activity, including the 42 base (WT) crRNA (SEQ ID No. 46) paired with the 70 base tracrRNA (SEQ ID No. 51).

The shortest crRNA tested was 34 bases in length (SEQ ID No. 49) and, in general, showed lower activity than the longer variants. The shorter duplex domain formed between this variant and the tracrRNA has reduced binding affinity (Tm) compared to the 36 base crRNA variant and that 34 base complex was less stable at 37° C. Use of chemical modification that increase binding affinity (Tm), such as 2'OMe RNA, 2'F RNA, or LNA residues, will increase stability of this short duplex domain and will lead to improved activity, permitting use of very short crRNAs of this design. Extensive use of Tm-enhancing modifications will permit use of even shorter tracrRNA binding domains in the crRNA, such as 13 base, or 12 base, or 11 base, or 10 base, or 9 base, or 8 base or shorter, depending on the kind and number of modified residues employed.

EXAMPLE 4

Examples 1, 2, and 3 demonstrated that crRNA:tracrRNA complexes shorter than the WT lengths of 42 and 89 bases, respectively, can show higher functional activity in mammalian gene editing. In those examples, all truncations were made in the universal domains of the RNAs. The present example tests the effects that truncations have on the target-specific protospacer domain of the guide crRNA.

A series of crRNAs (Table 4) were synthesized having protospacer domain lengths of 20, 19, 18, or 17 bases as indicated. Truncations were made at the 5'-end of the crRNA, using a 16mer universal tracrRNA binding sequence at the 3'-end. The crRNAs were paired with an unmodified 67mer tracrRNA (SEQ ID No. 2). The crRNAs targeted 4 different sites in the same exon of the human HPRT1 gene.

The paired crRNA:tracrRNA RNA oligonucleotides were transfected into the HEK-Cas9 cells and processed as described in Example 2. Relative gene editing activities were assessed by comparing cleavage rates in the HPRT1 gene using the T7EI mismatch endonuclease cleavage assay with quantitative measurement of products done using the Fragment Analyzer. Results are shown in Table 4.

TABLE 4

Effect of length truncations in the 5'-protospacer domain of the crRNA on efficiency of gene editing in mammalian cells by Cas9 endonuclease.

| SEQ ID No. | crRNA Sequence 5'-3' | Length Protospacer domain | Cleavage (%) | HPRT1 site |
|---|---|---|---|---|
| 48 | cuuauauccaacacuucgugguuuuagagcuaugcu | 20 | 64 | 38285 |
| 1 | uuauauccaacacuucgugguuuuagagcuaugcu | 19 | 62 | |
| 54 | uauauccaacacuucgugguuuuagagcuaugcu | 18 | 57 | |
| 55 | auauccaacacuucgugguuuuagagcuaugcu | 17 | 42 | |
| 56 | aauuauggggauuacuaggaguuuuagagcuaugcu | 20 | 78 | 38087 |
| 57 | auuauggggauuacuaggaguuuuagagcuaugcu | 19 | 81 | |
| 58 | uuauggggauuacuaggaguuuuagagcuaugcu | 18 | 82 | |
| 59 | uauggggauuacuaggaguuuuagagcuaugcu | 17 | 82 | |
| 60 | auuucauaaaacucuuuuguuuuagagcuaugcu | 20 | 52 | 38358 |
| 61 | uuucacauaaaacucuuuuguuuuagagcuaugcu | 19 | 30 | |
| 62 | uucacauaaaacucuuuuguuuuagagcuaugcu | 18 | 12 | |
| 63 | ucacauaaaacucuuuuguuuuagagcuaugcu | 17 | 0 | |
| 64 | uccauuucauagucuuuccuguuuuagagcuaugcu | 20 | 70 | 38094 |
| 65 | ccauuucauagucuuuccuguuuuagagcuaugcu | 19 | 71 | |
| 66 | cauuucauagucuuuccuguuuuagagcuaugcu | 18 | 52 | |
| 67 | auuucauagucuuuccuguuuuagagcuaugcu | 17 | 0 | |

Oligonucleotide sequences are shown 5'-3'.
Lowercase = RNA.
The target-specific protospacer domain is underlined and length is indicated (bases).
The relative functional activity of each species is indicated by the % cleavage in a T7EI heteroduplex assay.

Of the 4 sites studied, one (site 38087) showed high activity for all 4 crRNAs with no changes seen as the protospacer domain was shortened. Site 38285 similar efficacy for the 20 and 19 base protospacer crRNAs (SEQ ID Nos. 48 and 1), a slight decrease for the 18 base version (SEQ ID No. 54), and a large decrease for the 17 base version (SEQ ID No. 55). Site 38094 showed similar efficacy for the 20 and 19 base protospacer crRNAs (SEQ ID Nos. 64 and 65), a moderate decrease for the 18 base version (SEQ ID No. 66), and no activity for the 17 base version (SEQ ID No. 67). Site 38358 showed good activity for the 20 base version (SEQ ID No. 60), lower activity for the 19 base version (SEQ ID No. 61), even lower activity for the 18 base version (SEQ ID No. 62) and no activity for the 17 base version (SEQ ID No. 63).

The use of shortened 17 base protospacer guide domains can lower the occurrence of undesired off-target events compared to the wild-type 20 base domain (Fu et al., Nature Biotechnol., 32:279, 2014). We observe that on-target efficacy varies in a sequence-context specific fashion and that 20 base and 19 base protospacer guide domains are generally effective but that activity begins to decrease when 18 base protospacer domains are used and activity significantly decreases when 17 base protospacer domains are used. Therefore, to maintain desired on-target efficiency, use of 20 and 19 base target-specific protospacer guide domains are employed herein. Significant truncation of the protospacer guide domain in many cases lowers on-target cleavage of a DNA target by the Cas9 endonuclease. Use of chemical modifications that enhance Tm (increase binding affinity of the protospacer target-specific domain of the crRNA to the target DNA sequence) may permit use of shorter sequences such that a 17 base protospacer guide may show similar on-target efficacy as an unmodified 20 base protospacer guide domain.

EXAMPLE 5

This example demonstrates that truncated crRNA:tracrRNA complex show improved gene editing activity at multiple sites. The prior examples studied efficacy of the truncated RNAs as triggers of CRISPR gene editing in mammalian cells at a single site in the human HRPT1 gene. Site/sequence specific effects may exist. The present example demonstrates improved performance of the truncated species of the present invention at 12 sites in an exon of the human HPRT1 gene.

A series of crRNAs (Table 5) were synthesized having a protospacer domain lengths of 20 bases specific to 12 sites in the human HPRT1 gene with a 16mer universal tracrRNA binding sequence at the 3'-end. The crRNAs were paired with an unmodified 67mer tracrRNA (SEQ ID No. 2). The same 12 sites were studied using WT length crRNA:tracrRNA complexes wherein the crRNA comprised a 20 base protospacer guide paired with a 22mer universal tracrRNA binding sequence at the 3'-end complexed with the WT 89mer tracrRNA (SEQ ID No. 18).

The paired crRNA:tracrRNA RNA oligonucleotides were transfected into the HEK-Cas9 cells and processed as described in Example 2. Relative gene editing activities were assessed by comparing cleavage rates in the HPRT1 gene using the T7EI mismatch endonuclease cleavage assay with quantitative measurement of products done using the Fragment Analyzer. Results are shown in Table 5.

TABLE 5

Effect of length truncations in both the crRNA and tracrRNA on efficiency of gene editing in mammalian cells by Cas9 endonuclease.

| cr/tracr RNA pair | SEQ ID No. | crRNA Sequence tracrRNA Sequence | Length | Cleavage % |
|---|---|---|---|---|
| 38094 short | 64 2 | uccauuucauagucuuuccuguuuuagagcuaugcu<br>agcauagcaaguuaaaauaaggcuaguccguuaucaacuuga<br>aaaaguggcaccgagucggugcuuu | 36<br>67 | 55 |
| 38094 long | 68 18 | uccauuucauagucuuuccuguuuuagagcuaugcuguuuug<br>guuggaaccauucaaaacagcauagcaaguuaaaauaaggcu<br>aguccguuaucaacuugaaaaaguggcaccgagucggugcuu<br>uuuuu | 42<br>89 | 31 |
| 38231 short | 69 2 | uuuuguaauuaacagcuugcguuuuagagcuaugcu<br>agcauagcaaguuaaaauaaggcuaguccguuaucaacuuga<br>aaaaguggcaccgagucggugcuuu | 36<br>67 | 7 |
| 38231 long | 70 18 | uuuuguaauuaacagcuugcguuuuagagcuaugcuguuuug<br>guuggaaccauucaaaacagcauagcaaguuaaaauaaggcu<br>aguccguuaucaacuugaaaaaguggcaccgagucggugcuu<br>uuuuu | 42<br>89 | 0 |
| 38371 short | 71 2 | cuuagagaauauuuguagagguuuuagagcuaugcu<br>agcauagcaaguuaaaauaaggcuaguccguuaucaacuuga<br>aaaaguggcaccgagucggugcuuu | 36<br>67 | 57 |
| 37371 long | 72 18 | cuuagagaauauuuguagagguuuuagagcuaugcuguuuug<br>guuggaaccauucaaaacagcauagcaaguuaaaauaaggcu<br>aguccguuaucaacuugaaaaaguggcaccgagucggugcuu<br>uuuuu | 42<br>89 | 27 |
| 38509 short | 73 2 | uugacuauaaugaauacuucguuuuagagcuaugcu<br>agcauagcaaguuaaaauaaggcuaguccguuaucaacuuga<br>aaaaguggcaccgagucggugcuuu | 36<br>67 | 56 |
| 38509 long | 74 18 | uugacuauaaugaauacuucguuuuagagcuaugcuguuuug<br>guuggaaccauucaaaacagcauagcaaguuaaaauaaggcu<br>aguccguuaucaacuugaaaaaguggcaccgagucggugcuu<br>uuuuu | 42<br>89 | 7 |
| 38574 short | 75 2 | caaaacacgcauaaaaauuuguuuuagagcuaugcu<br>agcauagcaaguuaaaauaaggcuaguccguuaucaacuuga<br>aaaaguggcaccgagucggugcuuu | 36<br>67 | 58 |
| 38574 long | 76 18 | caaaacacgcauaaaaauuuguuuuagagcuaugcuguuuug<br>guuggaaccauucaaaacagcauagcaaguuaaaauaaggcu<br>aguccguuaucaacuugaaaaaguggcaccgagucggugcuu<br>uuuuu | 42<br>89 | 22 |
| 38087 short | 56 2 | aauuauggggauuacuaggaguuuuagagcuaugcu<br>agcauagcaaguuaaaauaaggcuaguccguuaucaacuuga<br>aaaaguggcaccgagucggugcuuu | 36<br>67 | 60 |
| 38087 long | 77 18 | aauuauggggauuacuaggaguuuuagagcuaugcuguuuug<br>guuggaaccauucaaaacagcauagcaaguuaaaauaaggcu<br>aguccguuaucaacuugaaaaaguggcaccgagucggugcuu<br>uuuuu | 42<br>89 | 53 |
| 38133 short | 78 2 | ggucacuuuuaacacacccaguuuuagagcuaugcu<br>agcauagcaaguuaaaauaaggcuaguccguuaucaacuuga<br>aaaaguggcaccgagucggugcuuu | 36<br>67 | 53 |
| 38133 long | 79 18 | ggucacuuuuaacacacccaguuuuagagcuaugcuguuuug<br>guuggaaccauucaaaacagcauagcaaguuaaaauaaggcu<br>aguccguuaucaacuugaaaaaguggcaccgagucggugcuu<br>uuuuu | 42<br>89 | 37 |
| 38285 short | 48 2 | cuuauauccaacacuucgugguuuuagagcuaugcu<br>agcauagcaaguuaaaauaaggcuaguccguuaucaacuuga<br>aaaaguggcaccgagucggugcuuu | 36<br>67 | 38 |
| 38285 long | 46 18 | cuuauauccaacacuucgugguuuuagagcuaugcuguuuug<br>guuggaaccauucaaaacagcauagcaaguuaaaauaaggcu<br>aguccguuaucaacuugaaaaaguggcaccgagucggugcuu<br>uuuuu | 42<br>89 | 8 |

TABLE 5-continued

Effect of length truncations in both the crRNA and tracrRNA on efficiency of gene editing in mammalian cells by Cas9 endonuclease.

| cr/tracr RNA pair | SEQ ID No. | crRNA Sequence tracrRNA Sequence | Length | Cleavage % |
|---|---|---|---|---|
| 38287 short | 80 2 | ggcuuauauccaacacuucgguuuuagagcuaugcu agcauagcaaguuaaaauaaggcuaguccguuaucaacuuga aaaaguggcaccgagucggugcuuu | 36 67 | 48 |
| 38287 long | 81 18 | ggcuuauauccaacacuucgguuuuagagcuaugcuguuug guuggaaccauucaaaacagcauagcaaguuaaaauaaggcu aguccguuaucaacuugaaaaaguggcaccgagucggugcuu uuuuu | 42 89 | 6 |
| 38358 short | 60 2 | auuucacauaaaacucuuuugeuuuuagagcuaugcu agcauagcaaguuaaaauaaggcuaguccguuaucaacuuga aaaaguggcaccgagucggugcuuu | 36 67 | 42 |
| 38358 long | 82 18 | auuucacauaaaacucuuuugeuuuuagagcuaugcuguuug guuggaaccauucaaaacagcauagcaaguuaaaauaaggcu aguccguuaucaacuugaaaaaguggcaccgagucggugcuu uuuuu | 42 89 | 8 |
| 38636 short | 83 2 | ucaaauuaugaggugcuggaguuuuagagcuaugcu agcauagcaaguuaaaauaaggcuaguccguuaucaacuuga aaaaguggcaccgagucggugcuuu | 36 67 | 26 |
| 38636 long | 84 18 | ucaaauuaugaggugcuggaguuuuagagcuaugcuguuug guuggaaccauucaaaacagcauagcaaguuaaaauaaggcu aguccguuaucaacuugaaaaaguggcaccgagucggugcuu uuuuu | 42 89 | 16 |
| 38673 short | 85 2 | uacagcuuuaugugacuaauguuuuagagcuaugcu agcauagcaaguuaaaauaaggcuaguccguuaucaacuuga aaaaguggcaccgagucggugcuuu | 36 67 | 45 |
| 38673 long | 86 18 | uacagcuuuaugugacuaauguuuuagagcuaugcuguuug guuggaaccauucaaaacagcauagcaaguuaaaauaaggcu aguccguuaucaacuugaaaaaguggcaccgagucggugcuu uuuuu | 42 89 | 32 |

Oligonucleotide sequences are shown 5'-3'.
Lowercase = RNA.
Lengths of the RNA oligonucleotides are indicated (bases). The relative functional activity of each crRNA: tracrRNA pair is indicated by the % cleavage in a T7EI heteroduplex assay.

The relative efficiency of CRISPR mediated gene editing in the HEK-Cas9 cells varied with sequence context. However, in all cases the shorter optimized RNA guides (36mer crRNA and 67mer tracrRNA) showed higher efficiency than the WT RNAs (42mer crRNA and 89mer tracrRNA). Use of the shortened, optimized guide RNAs of the present invention improve Cas9 cleavage of targeted DNAs relative to the WT RNAs, improving the gene editing rates.

EXAMPLE 6

Example 1 described chemical modification patterns that functioned with Cas9 in an in vitro biochemical target DNA cleavage assay. This example demonstrates functioning of chemically modified tracrRNAs to direct genome editing by the Spy Cas9 nuclease in mammalian cells. Optimal modification patterns differ between in vitro and in vivo use.

A series of tracrRNAs (Table 6) were synthesized having a variety of chemical modifications, including: the ribose modifications 2'OMe RNA and LNA; the end-modifying groups propanediol spacer and napthyl-azo modifier (N,N-diethyl-4-(4-nitronaphthalen-1-ylazo)-phenylamine, or "ZEN"); and select internucleotide linkages with phosphorothioate modifications. See: Lennox et al., Molecular Therapy Nucleic Acids 2:e117 2013 for structure of the napthyl-azo modified and use of the napthyl-azo modifier and propanediol modifier for use as end-groups to block exonuclease attack. The tracrRNAs listed in Table 6 were complexed with unmodified truncated anti-HPRT1 crRNA SEQ ID No. 1 (Table 1) which has a 19 base protospacer domain targeting HPRT1 at the 5'-end and a 16 base tracrRNA binding domain at the 3'-end. The paired crRNA: tracrRNA RNA oligonucleotides were transfected into the HEK-Cas9 cells and processed as described above. Relative gene editing activities were assessed by comparing cleavage rates in the HPRT1 gene using the T7EI mismatch endonuclease cleavage assay with quantitative measurement of products done using the Fragment Analyzer.

TABLE 6

Optimization of tracrRNA oligonucleotide modification patterns in mammalian cells.

| SEQ ID No. | tracrRNA Sequence (5'-3') | Cleavage (%) |
|---|---|---|
| 2 | agcauagcaaguuaaaauaaggcuaguccguuaucaacuugaaaaaguggcaccgagucggugcuuu | 65 |
| 4 | <u>agcauagcaaguuaaaauaaggcuaguccguuaucaacuugaaaaagugqcaccgagucggugcuuu</u> | 0 |
| 11 | agcauagcaaguuaaaauaaggcuaguccguuaucaac<u>uugaaaaagugqcaccgagucggugcuuu</u> | 56 |
| 17 | agcauagcaaguuaaaauaaggcuaguccguuaucaac<u>uu</u>ga<u>aaa</u>g<u>ugqc</u>a<u>cc</u>gagu<u>cggugcuuu</u> | 12 |
| 12 | <u>agcauagca</u>aguuaaa<u>a</u>uaa<u>ggcu</u>agu<u>cc</u>guuaucaa<u>cuugaaaaagugqcaccgagucggugcuuu</u> | 20 |
| 13 | <u>agcauagca</u>aguuaaaauaaggcuaguccguuaucaa<u>cuugaaaaagugqcaccgagucggugcuuu</u> | 64 |
| 87 | <u>agcau</u>agcaaguuaaaauaaggcuaguccguuaucaacuugaaaaaguggcaccgagucggugcuuu | 61 |
| 88 | agcauagcaaguuaaaauaaggcuaguccguuaucaacuugaaaaaguggcaccgagucggugc<u>uuu</u> | 60 |
| 89 | <u>agcau</u>agcaaguuaaaauaaggcuaguccguuaucaacuugaaaaaguggcaccgagucggugc<u>uuu</u> | 64 |
| 90 | <u>agcauag</u>caaguuaaaauaaggcuaguccguuaucaacuugaaaaaguggcaccgagucggugcu | 60 |
| 91 | agcauagcaaguuaaaauaaggcuaguccguuaucaacuugaaaaaguggcaccgagucggugcu | 61 |
| 92 | agcauagcaaguuaaaauaaggcuaguccguuaucaacuugaaa<u>aagugqcaccg</u>agucggugcu | 59 |
| 93 | agcauagcaaguuaaaauaaggcuaguccguuaucaa<u>cuugaaaaagugqcaccg</u>agucggugcu | 57 |
| 94 | agcauagcaaguuaaaauaaggcuaguccguuaucaa<u>cuugaaaaagugqcaccg</u>agucggugcu | 57 |
| 95 | <u>agcauagc</u>aaguuaaaauaaggcuaguccguuaucaa<u>cuugaaaaagugqcaccg</u>agu<u>cggugcu</u> | 62 |
| 96 | agcauagcaaguuaaaauaaggcuaguccguuaucaacuu<u>gaaa</u>aaguggcaccg<u>agu</u> cggugcu | 62 |
| 97 | C3-agcauagcaaguuaaaauaaggcuaguccguuaucaacuugaaaaaguggcaccgagucggugcuuu-C3 | 53 |
| 98 | a*g*cauagcaaguuaaaauaaggcuaguccguuaucaacuugaaaaaguggcaccgagucggugcu*u*u | 58 |
| 99 | C3-<u>agcauagc</u>aaguuaaaauaaggcuaguccguuaucaa<u>cuugaaaaagugqcaccg</u>agucggugcuuu-C3 | 20 |
| 100 | <u>a*g</u>*cauagcaaguuaaaauaaggcuaguccguuaucaa<u>cuugaaaaagugqcaccga</u> <u>gucggugcu</u>*u*u | 63 |
| 101 | a*g*c*auagcaaguuaaaauaaggcuaguccguuaucaacuugaaaaaguggcaccgagucggugc*u*u*u | 55 |
| 102 | <u>agc</u>auagcaaguuaaaauaaggcuaguccguuaucaacuugaaaaaguggcaccgagucggugc<u>uuu</u> | 39 |
| 103 | <u>a*g*c</u>*auagcaaguuaaaauaaggcuaguccguuaucaacuugaaaaaguggcaccgagucggugc*<u>u</u>*<u>u</u>*<u>u</u> | 54 |
| 104 | agcauagcaaguuaaaauaaggcuaguccguuaucaacuugaaaaaguggcaccgagucggugcuuu-ZEN | 55 |
| 105 | ZEN-agcauagcaaguuaaaauaaggcuaguccguuaucaacuugaaaaaguggcaccgagucggugcuuu-ZEN | 23 |

TABLE 6-continued

Optimization of tracrRNA oligonucleotide modification patterns in mammalian cells.

| SEQ ID No. | tracrRNA Sequence (5'-3') | Cleavage (%) |
|---|---|---|
| 106 | <u>a</u>*<u>g</u>*<u>cauagcaa</u>aguuaaaauaaggcuaguccguuaucaa<u>cuug</u>aaaaa<u>guggcaccga gucg</u>*<u>g</u>*<u>u</u> | 58 |
| 107 | <u>a</u>*<u>g</u>*<u>cauagcaa</u>guuaaaauaaggcuaguccg<u>uu</u>aucaa<u>cuug</u>aaaaa<u>guggcaccga gucggugcu</u>*<u>u</u>*<u>u</u> | 8 |
| 108 | <u>a</u>*<u>g</u>*<u>cauagcaa</u>guuaaaauaaggcuaguccguuaucaa<u>cuug</u>aaaaa<u>guggcaccga gucggugcu</u>*<u>u</u>*<u>u</u> | 0 |
| 109 | <u>a</u>*<u>g</u>*<u>cauagcaa</u>guua<u>aaau</u>aaggcuaguccguuaucaa<u>cuug</u>aaaaa<u>guggcaccga gucggugcu</u>*<u>u</u>*<u>u</u> | 11 |
| 110 | <u>a</u>*<u>g</u>*<u>cauagcaa</u>guuaaaauaaggcuaguccguuauca<u>acuug</u>aaaaa<u>guggcaccga gucggugcu</u>*<u>u</u>*<u>u</u> | 61 |
| 111 | <u>a</u>*<u>g</u>*<u>cauagcaa</u>guuaaaauaaggcuaguccguuauc<u>aacuug</u>aaaaa<u>guggcaccga gucggugcu</u>*<u>u</u>*<u>u</u> | 61 |
| 112 | <u>a</u>*<u>g</u>*<u>cauagcaa</u>guuaaaauaaggcuaguccguuau<u>caacuug</u>aaaaa<u>guggcaccga gucggugcu</u>*<u>u</u>*<u>u</u> | 62 |
| 113 | <u>a</u>*<u>g</u>*<u>cauagcaa</u>guuaaaauaaggcuaguccgu<u>uaacuug</u>aaaaa<u>guggcaccga gucggugcu</u>*<u>u</u>*<u>u</u> | 62 |
| 114 | <u>a</u>*<u>g</u>*<u>cauagcaa</u>guuaaaauaaggcuaguccgu<u>uaucaacuug</u>aaaaa<u>guggcaccga gucggugcu</u>*<u>u</u>*<u>u</u> | 61 |
| 115 | <u>a</u>*<u>g</u>*<u>cauagcaa</u>guuaaaauaaggcuaguccgu<u>uaucaacuug</u>aaaaa<u>guggcaccga gucggugcu</u>*<u>u</u>*<u>u</u> | 14 |
| 116 | <u>a</u>*<u>g</u>*<u>cauagcaa</u>guuaaaauaaggcuaguccguuauca<u>acuug</u>aaaaa<u>guggcaccga gucggugcu</u>*<u>u</u>*<u>u</u> | 60 |
| 117 | <u>a</u>*<u>g</u>*<u>cauagcaa</u>guuaaaauaaggcuaguccguuauca<u>acuug</u>aaaaa<u>guggcaccga gucggugcu</u>*<u>u</u>*<u>u</u> | 60 |
| 118 | <u>a</u>*<u>g</u>*<u>cauagcaa</u>g<u>uu</u>aaaauaaggcuaguccguuaucaa<u>cuug</u>aaaaa<u>guggcaccga gucggugcu</u>*<u>u</u>*<u>u</u> | 15 |
| 119 | <u>a</u>*<u>g</u>*<u>cauagcaag</u>uuaaaauaaggcuaguccguuaucaa<u>cuug</u>aaaaa<u>guggcaccga gucggugcu</u>*<u>u</u>*<u>u</u> | 0 |
| 120 | a*g*cauagcaaguuaaaauaaggcuaguccguuaucaacuugaaaaaguggcaccga <u>gucggugcu</u>*<u>u</u>*<u>u</u> | 7 |
| 121 | <u>a</u>*<u>g</u>*<u>cauagcaa</u>guu<u>aaaau</u>aaggcuaguccguuaucaa<u>cuug</u>aaaaa<u>guggcaccga gucggugcu</u>*<u>u</u>*<u>u</u> | 14 |
| 122 | <u>a</u>*<u>g</u>*<u>cauagcaa</u>gu<u>uaaaauaa</u>ggcuaguccguuaucaa<u>cuug</u>aaaaa<u>guggcaccga gucggugcu</u>*<u>u</u>*<u>u</u> | 11 |
| 123 | <u>a</u>*<u>g</u>*<u>cauagcaa</u>g<u>uuaaaauaa</u>ggcuaguccguuaucaa<u>cuug</u>aaaaa<u>guggcaccga gucggugcu</u>*<u>u</u>*<u>u</u> | 0 |
| 124 | <u>a</u>*<u>g</u>*<u>cauagcaag</u>uuaaaauaaggcuaguccguuaucaa<u>cuug</u>aaaaa<u>guggcaccga gucggugcu</u>*<u>u</u>*<u>u</u> | 0 |
| 125 | <u>a</u>*<u>g</u>*<u>cauagcaagu</u>uaaaauaaggcuaguccguuaucaa<u>cuug</u>aaaaa<u>guggcaccga gucggugcu</u>*<u>u</u>*<u>u</u> | 0 |
| 126 | <u>a</u>*<u>g</u>*<u>cauagcaa</u>guuaaaauaag<u>gc</u>uaguccguuaucaa<u>cuug</u>aaaaa<u>guggcaccga gucggugcu</u>*<u>u</u>*<u>u</u> | 64 |
| 127 | <u>a</u>*<u>g</u>*<u>cauagcaa</u>guuaaaauaagg<u>cuaguccg</u>uuaucaa<u>cuug</u>aaaaa<u>guggcaccga gucggugcu</u>*<u>u</u>*<u>u</u> | 0 |
| 128 | <u>a</u>*<u>g</u>*<u>cauagcaa</u>guuaaaauaagg<u>c</u>uaguccguuaucaa<u>cuug</u>aaaaa<u>guggcaccga gucggugcu</u>*<u>u</u>*<u>u</u> | 0 |
| 129 | +a*+g*cauagcaaguuaaaauaaggcuaguccguuaucaacuugaaaaaguggcacc gagucggugcu*+t*+t | 57 |

TABLE 6-continued

Optimization of tracrRNA oligonucleotide modification patterns in mammalian cells.

| SEQ ID No. | tracrRNA Sequence (5'-3') | Cleavage (%) |
|---|---|---|
| 130 | C3-<u>agcauagca</u>aguuaaaauaaggcuaguccguuaucaa<u>cuugaaaaaguggcaccg agucgguqcuuu</u>-InvT | |
| 131 | C3-<u>agcauagca</u>aguuaaaauaaggcuaguccguuaucaa<u>cuugaaaaaguggcaccg agucggu</u>-C3 | 58 |
| 132 | C3-<u>agcauagca</u>aguuaaaauaaggcuaguccguuaucaa<u>cuugaaaaaguggcaccg agucggu</u>-InvT | 59 |
| 133 | agcauagca*a*g*u*u*a*a*a*a*u*a*a*g*g*c*u*a*g*u*c*c*g*u*u*a* u*c*a*a*<u>cuugaaaaaguggcaccgagucggugcuuu</u> | 0 |
| 134 | <u>a</u>*<u>g</u>*<u>cauagcaa</u>guuaaaauaaggcuaguccguu<u>aucaacuugaaaaaguggcaccga gucggugcu</u>*<u>u</u>*<u>u</u> | 58 |
| 135 | <u>a</u>*<u>g</u>*<u>cauagcaa</u>guuaaaauaaggcuaguccguu<u>aucaacuugaaaaaguggcaccga gucggugcu</u>*<u>u</u>*<u>u</u> | 19 |
| 136 | <u>a</u>*<u>g</u>*<u>cauagcaa</u>guuaaaauaaggcuaguccguu<u>aucaacuugaaaaaguggcaccga gucg</u>*<u>g</u>*<u>u</u> | 54 |
| 137 | <u>a</u>*<u>g</u>*<u>cauagcaa</u>guuaaaauaaggcuaguccguu<u>aucaacuugaaaaaguggcaccga gucg</u>*<u>g</u>*<u>u</u> | 13 |
| 138 | <u>a</u>*<u>g</u>*<u>cauagcaag</u>TTAAAATAAGGCTAGTCCGTT<u>aucaacuugaaaaaguggcaccga gucggugcu</u>*<u>u</u>*<u>u</u> | 0 |
| 139 | <u>a</u>*<u>g</u>*<u>cauagcaag</u>TTAAAATAAGgcuaguccguu<u>aucaacuugaaaaaguggcaccga gucggugcu</u>*<u>u</u>*<u>u</u> | 0 |
| 140 | a*g*cauagcaaguuaaaauaagGCTAGTCCGTT<u>aucaacuugaaaaaguggcaccga gucggugcu</u>*<u>u</u>*<u>u</u> | 0 |
| 141 | <u>a</u>*<u>g</u>*<u>cauagcaag</u>uu<u>aaaauaagg</u>cuaguccguu<u>aucaacuugaaaaaguggcaccga gucggugcu</u>*<u>u</u>*<u>u</u> | 0 |
| 142 | <u>a</u>*<u>g</u>*<u>cauagcaag</u>uuaaaauaaggcuaguccguu<u>aucaacuugaaaaaguggcaccga gucggugcu</u>*<u>u</u>*<u>u</u> | 4 |
| 143 | <u>a</u>*<u>g</u>*<u>cauagcaag</u>uuaaaauaagg<i>cuaguccguu</i><u>aucaacuugaaaaaguggcaccga gucggugcu</u>*<u>u</u>*<u>u</u> | 0 |
| 144 | <u>a</u>*<u>g</u>*<u>cauagcaagu</u>u<u>aaaauaagg</u>cuaguccguu<u>aucaacuugaaaaaguggcaccga gucggugcu</u>*<u>u</u>*<u>u</u> | 52 |
| 145 | <u>a</u>*<u>g</u>*<u>cauagcaagu</u>u<u>a</u>aaauaaggcuaguccguu<u>aucaacuugaaaaaguggcaccga gucggugcu</u>*<u>u</u>*<u>u</u> | 63 |
| 146 | <u>a</u>*<u>g</u>*<u>cauagcaag</u>uu<u>a</u>aaauaaggcuaguccguu<u>aucaacuugaaaaaguggcaccga gucggugcu</u>*<u>u</u>*<u>u</u> | 0 |
| 147 | <u>a</u>*<u>g</u>*<u>cauagcaag</u>uuaa<u>a</u>auaaggcuaguccguu<u>aucaacuugaaaaaguggcaccga gucggugcu</u>*<u>u</u>*<u>u</u> | 62 |
| 148 | <u>a</u>*<u>g</u>*<u>cauagcaag</u>uuaa<u>a</u>auaaggcuaguccguu<u>aucaacuugaaaaaguggcaccga gucggugcu</u>*<u>u</u>*<u>u</u> | 57 |
| 149 | <u>a</u>*<u>g</u>*<u>cauagcaag</u>uuaaaa<u>u</u>aaggcuaguccguu<u>aucaacuugaaaaaguggcaccga gucggugcu</u>*<u>u</u>*<u>u</u> | 47 |
| 150 | <u>a</u>*<u>g</u>*<u>cauagcaag</u>uuaaaau<u>a</u>aggcuaguccguu<u>aucaacuugaaaaaguggcaccga gucggugcu</u>*<u>u</u>*<u>u</u> | 61 |
| 151 | <u>a</u>*<u>g</u>*<u>cauagcaag</u>uuaaaa<u>a</u>aggcuaguccguu<u>aucaacuugaaaaaguggcaccga gucggugcu</u>*<u>u</u>*<u>u</u> | 61 |
| 152 | <u>a</u>*<u>g</u>*<u>cauagcaag</u>uuaaaauaaggcuaguccguu<u>aucaacuugaaaaaguggcaccga gucggugcu</u>*<u>u</u>*<u>u</u> | 61 |
| 153 | <u>a</u>*<u>g</u>*<u>cauagcaag</u>uuaaaauaaggcuaguccguu<u>aucaacuugaaaaaguggcaccga gucggugcu</u>*<u>u</u>*<u>u</u> | 61 |

TABLE 6-continued

Optimization of tracrRNA oligonucleotide modification patterns in mammalian cells.

| SEQ ID No. | tracrRNA Sequence (5'-3') | Cleavage (%) |
|---|---|---|
| 154 | a*g*cauagcaaguuaaaauaaggcuaguccguuaucaacuugaaaaagu ggcaccgagucggugcu*u*u | 50 |
| 155 | a*g*cauagcaaguuaaaauaaggcuaguccguuaucaacuugaaaaagu ggcaccgagucggugcu*u*u | 46 |
| 156 | a*g*cauagcaaguuaaaauaaggcuaguccguuaucaacuugaaaaagu ggcaccgagucggugcu*u*u | 59 |
| 157 | a*g*cauagcaaguuaaaauaaggcuaguccguuaucaacuugaaaaagu ggcaccgagucggugcu*u*u | 2 |
| 158 | a*g*cauagcaaguuaaaauaaggcuagu ccguuaucaacuugaaaaaguggcaccgagucggugcu*u*u | 18 |
| 159 | a*g*cauagcaaguuaaaauaaggcuaguccguuaucaacuugaaaaagu ggcaccgagucggugcu*u*u | 50 |
| 160 | a*g*cauagcaaguuaaaauaaggcuaguccguuaucaacuugaaaaaguggcaccgagucggugcu*u*u | 58 |
| 161 | a*g*cauagcaaguuaaaauaaggcuaguccguuaucaacuugaaaaagu ggcaccgagucggugcu*u*u | 14 |
| 162 | a*g*cauagcaaguuaaaauaaggcuaguccguuaucaacuugaaaaagu ggcaccgagucggugcu*u*u | 8 |

Oligonucleotide sequences are shown 5'-3'.
Uppercase = DNA;
Lowercase = RNA;
Underlined = 2'-O-methyl RNA;
Italics = 2'-fluoro RNA;
+a, +c, +g = LNA; C3 = C3 spacer (propanediol modifier);
* = phosphorothioate internucleotide linkage;
ZEN-napthyl-azo modifier;
Inv-dT = inverted-dT.
The relative functional activity of each species is indicated by the % cleavage in a T7EI heteroduplex assay.

Modification is usually necessary for synthetic nucleic acids to function well in an intracellular environment due to the presence of exonucleases and endonucleases that degrade unmodified oligonucleotides. A wide range of modifications have been described that confer nuclease resistance to oligonucleotides. The precise combination and order of modifications employed that works well for a given application can vary with sequence context and the nature of the protein interactions required for biological function. Extensive prior work has been done relating to chemical modification of antisense oligonucleotides (which interact with RNase H1) and siRNAs (which interact with DICER, AGO2, and other proteins). It is expected that chemical modification will improve function of the CRISPR crRNA: tracrRNA complex. However, it is not possible to predict what modifications and/or pattern of modifications will be compatible with functional complexation of the synthetic RNAs with Cas9. The present invention defines minimal, moderate, and extensive chemical modification patterns for the tracrRNA that retain high levels of function to direct Cas9 mediated gene editing in mammalian cells.

The results in Table 6 demonstrate that extensive modification is tolerated throughout the 5' and 3' end domains of the tracrRNA. Modification of the internal domains of the tracrRNA showed reduced activity, likely due to altered structure of the folded RNA and/or blocking of protein contact points with the 2'-OH of key RNA residues by the 2'OMe modification. For example, compound SEQ ID No. 100 has 39/67 residues modified with 2'OMe RNA (58%) and retains full activity compared with the unmodified sequence. SEQ ID No. 134 has 46/67 residues modified with 2'OMe RNA (69%) and retains near full activity compared with the unmodified sequence (FIG. 6). SEQ ID No. 134 is a truncated 67mer variant of the tracrRNA. Using SEQ ID No. 134 as a model, modification of 11 sequential residues in the 5'-domain with 2'OMe RNA was tolerated with no loss of activity. Modification of 35 sequential residues in the 3'-domain with 2'OMe RNA was tolerated with not loss of activity. Of note, the two hairpin structures present in the 3'-domain are necessary for function as deletion of either of these features results in loss of activity (Example 2, FIG. 3), yet both of these domains can be completely modified with 2'OMe RNA without compromising function. Note that both SEQ ID Nos. 134 and 100 also have phosphorothioate (PS) modified internucleotide linkages at the 5'- and 3'-ends, which provides additional protection against exonuclease attack.

Specific residues were identified that led to large reductions or complete loss of activity when modified. Using the 67 base tracrRNA (for example, SEQ ID No. 134) as reference, starting from the 5'-end of the sequence substitution of 2'OMe RNA for the natural RNA at residues U12, A15, G26, U27, G30, U31, and U32 led to substantial loss of activity (FIG. 6). Specific residues were also identified that led to smaller yet significant reductions in activity when modified. Using the 67 base tracrRNA (for example, SEQ ID No. 134) as reference, starting from the 5'-end of the sequence substitution of 2'OMe RNA for the natural RNA at residues U13, U18, C23, U24, and C28 led to reduced activity (FIG. 6). This study was performed using 2'OMe RNA. Use of other modifications, such as 2'F, LNA, DNA, etc. at these positions may be better tolerated. The central 21 residue domain of unmodified RNA in SEQ ID No. 134 was modified with 2'-F RNA either completely (SEQ ID No. 141) or partially (SEQ ID Nos. 142 and 143). These variants were not functional. The central 21 residue domain of unmodified RNA in SEQ ID No. 134 was modified with DNA either completely (SEQ ID No. 138) or partially (SEQ ID Nos. 139 and 140). These variants were not functional. Modification of isolated residues in this domain may work, however large continuous blocks of modification in this domain reduce activity of the tracrRNA.

To further investigate which individual residues can be modified using 2'OMe RNA within the central domain of the tracrRNA, a single base modification 2'OMe RNA 'walk' was done (SEQ ID Nos. 144-162). Within this series, modification as residues A14, A19, A20, G21, G22, A25, and C29 showed no loss of activity and are candidates for modification.

Antisense oligonucleotides are often made using complete PS modification, where every internucleotide linkage is phosphorothioate modified. This extensive level of modification is possible because the protein effector molecule RNase H1 (which mediates ASO-directed mRNA degradation) tolerates the PS modification in the ASO when forming a functional substrate/enzyme complex. On the other hand, siRNAs do not tolerate full PS modification; extensive PS modification disrupts productive interaction with the effector protein AGO2 (which mediates siRNA-directed mRNA degradation). Extensive PS modification of the tracrRNA in the internal RNA loops disrupts functional interaction with Cas9 (Seq ID No. 133; 29 PS modifications). Limited PS end-modification can be done with no loss of activity (SEQ ID Nos. 98 and 101; 2-3 PP linkages on each end). Less extensive PS modification may be tolerated in the central domain. In particular, RNase cleavage mapping (where incubation of the tracrRNA in a series of serum or cell extract dilutions are used to find the sites that are most sensitive to RNase attack) may be used to identify critical sites where PS modification of only one or a few linkages may stabilize the RNA without disrupting function.

There are applications where the PS modification contributes to chemical toxicity. In this case use of other methods to block exonuclease attack are desirable. Options include end-modifiers such as inverted-dT or abasic groups such as dSpacer, C3 spacer (propanediol), ZEN (napthyl-azo modifier), and others. Placement of such end-modifying groups can eliminate the need for terminal PS internucleotide linkages.

EXAMPLE 7

Example 1 described chemical modification patterns that functioned with Cas9 in an in vitro biochemical target DNA cleavage assay. This example demonstrates functioning of chemically modified crRNAs to direct genome editing by the Spy Cas9 nuclease in mammalian cells. Optimal modification patterns differ between in vitro and in vivo use.

A series of crRNAs (Table 7) were synthesized having a variety of chemical modifications, including: the ribose modifications 2'OMe RNA, 2'F, and LNA; the end-modifying groups propanediol spacer and napthyl-azo modifier (N,N-diethyl-4-(4-nitronaphthalen-1-ylazo)-phenylamine, or "ZEN"), and an inverted-dT residue; and select internucleotide linkages with phosphorothioate modifications. See: Lennox et al., Molecular Therapy Nucleic Acids 2:e117 2013 for structure of the napthyl-azo modified and use of the napthyl-azo modifier and propanediol modifier for use as end-groups to block exonuclease attack. The crRNAs had either a 19 base protospacer domain targeting HPRT1 at the 5'-end (SEQ ID Nos. 1, 9 10, 14-16, 22-24, 163-173) or a 20 base protospacer domain targeting the same site (SEQ ID Nos. 48, 174-237) with a 16 base tracrRNA binding domain at the 3'-end. The crRNAs listed in Table 7 were complexed with unmodified truncated (67 base) tracrRNA SEQ ID No. 2 (Table 1) or chemically-modified truncated (67 base) tracrRNA SEQ ID No. 100 (Table 6). The use of two tracrRNAs enables determination if function of chemical modified crRNAs varies if paired with a modified tracrRNA. The paired crRNA:tracrRNA RNA oligonucleotides were transfected into the HEK-Cas9 cells and processed as described previously. Relative gene editing activities were assessed by comparing cleavage rates in the HPRT1 gene using the T7EI mismatch endonuclease cleavage assay, with quantitative measurement of products done using the Fragment Analyzer.

TABLE 7

Optimization of crRNA oligonucleotide modification patterns in mammalian cells.

| SEQ ID No. | crRNA Sequence (5'-3') | Cleavage % tracrRNA SEQ ID No 2 | Cleavage % tracrRNA SEQ ID No. 100 |
|---|---|---|---|
| 1 | uuauauccaacacuucgugguuuuagagcuaugcu | 63 | 61 |
| 9 | uuauauccaacacuucgugguuuuagagcuaugcu | 1 | 0 |
| 10 | uuauauccaacacuucgugguuuuagagcuaugcu | 0 | 1 |
| 22 | uuauauccaacacuucgugguuuuagagcuaugcu | 1 | 1 |
| 23 | uuauauccaacacuucgugguuuuagagcuaugcu | 5 | ND |
| 24 | uuauauccaacacuucgugguuuuagagcuaugcu | 3 | 5 |
| 14 | uuauauccaacacuucgugguuuuagagcuaugcu | 63 | 26 |
| 15 | uuauauccaacacuucgugguuuuagagcuaugcu | 5 | 3 |
| 16 | uuauauccaacacuucgugguuuuagagcuaugcu | 5 | 5 |

TABLE 7-continued

Optimization of crRNA oligonucleotide modification patterns in mammalian cells.

| SEQ ID No. | crRNA Sequence (5'-3') | Cleavage % tracrRNA SEQ ID No 2 | Cleavage % tracrRNA SEQ ID No. 100 |
|---|---|---|---|
| 163 | C3-uuauauccaacacuucgugguuuuagagcuaugcu-C3 | 65 | 49 |
| 164 | u*u*a*uauccaacacuucgugguuuuagagcuau*g*c*u | 65 | 65 |
| 165 | uuauauccaacacuucgugguuuuagagcuaugcu | 0 | 3 |
| 166 | uuauauccaacacuucgugguuuuagagcuaugcu | 54 | 42 |
| 167 | uuauauccaacacuucgugguuuuagagcuaugcu | 49 | 58 |
| 168 | uuauauccaacacuucgugguuuuagagcuaugcu | 64 | 60 |
| 169 | uuauauccaacacuucgugguuuuagagcuaugcu | 16 | 16 |
| 170 | uuauauccaacacuucgugguuuuagagcuaugcu | 3 | 3 |
| 171 | uuauauccaacacuucgugguuuuagagcuaugcu | 42 | 62 |
| 172 | uuauauccaacacuucgugguuuuagagcuaugcu | 4 | 13 |
| 173 | uuauauccaacacuucgugguuuuagagcuaugcu | 1 | 1 |
| 48 | cuuauauccaacacuucgugguuuuagagcuaugcu | 61 | 60 |
| 174 | cuuauauccaacacuucgugguuuuagagcuaugcu | 60 | 59 |
| 175 | cuuauauccaacacuucgugguuuuagagcuaugcu | 62 | 60 |
| 176 | cuuauauccaacacuucgugguuuuagagcuaugcu | 61 | 59 |
| 177 | c*u*u*auauccaacacuucgugguuuuagagcuau*g*c*u | 60 | 59 |
| 178 | c*u*u*auauccaacacuucgugguuuuagagcuau*g*c*u | 61 | 59 |
| 179 | C3-cuuauauccaacacuucgugguuuuagagcuaugcu | 61 | 58 |
| 180 | cuuauauccaacacuucgugguuuuagagcuaugcu-C3 | 57 | 59 |
| 181 | C3-cuuauauccaacacuucgugguuuuagagcuaugcu-C3 | 62 | 59 |
| 182 | ZEN-cuuauauccaacacuucgugguuuuagagcuaugcu | 64 | 62 |
| 183 | cuuauauccaacacuucgugguuuuagagcuaugcu-ZEN | 62 | 60 |
| 184 | ZEN-cuuauauccaacacuucgugguuuuagagcuaugcu-ZEN | 64 | 64 |
| 185 | ZEN-cuuauauccaacacuucgugguuuuagagcuaugcu-ZEN | 60 | 63 |
| 186 | u*u*a*uauccaacacuucgugguuuuagagcuau*g*c*u | 64 | 62 |
| 187 | c*u*u*auauccaacacuucgugguuuuagagcuau*g*c*u | 65 | 65 |
| 188 | c*u*u*auauccaacacuucgugguuuuagagcuau*g*c*u | 0 | 0 |
| 189 | c*u*u*auauccaacacuucgugguuuuagagcuau*g*c*u | 63 | 64 |
| 190 | c*u*u*auauccaacacuucgugguuuuagagcuau*g*c*u | 64 | 62 |
| 191 | c*u*u*auauccaacacuucgugguuuuagagcuau*g*c*u | 64 | 63 |
| 192 | c*u*u*auauccaacacuucgugguuuuagagcuau*g*c*u | 64 | 64 |
| 193 | c*u*u*auauccaacacuucgugguuuuagagcuau*g*c*u | 64 | 65 |
| 194 | c*u*u*auauccaacacuucgugguuuuagagcuau*g*c*u | 60 | 63 |
| 195 | c*u*u*auauccaacacuucgugguuuuagagcuau*g*c*u | 63 | 62 |
| 196 | c*u*u*auauccaacacuucgugguuuuagagcuau*g*c*u | 62 | 63 |
| 197 | c*u*u*auauccaacacuucgugguuuuagagcuau*g*c*u | 61 | 64 |
| 198 | c*u*u*auauccaacacuucgugguuuuagagcuau*g*c*u | 61 | 64 |

TABLE 7-continued

Optimization of crRNA oligonucleotide modification patterns in mammalian cells.

| SEQ ID No. | crRNA Sequence (5'-3') | Cleavage % tracrRNA SEQ ID No 2 | Cleavage % tracrRNA SEQ ID No. 100 |
|---|---|---|---|
| 199 | c*u*u*auauccaacacuucgugguuuuagagcuau*g*c*u | 63 | 68 |
| 200 | c*u*u*auauccaacacuucgugguuuuagagcuau*g*c*u | 59 | 67 |
| 201 | c*u*u*auauccaacacuucgugguuuuagagcuau*g*c*u | 63 | 67 |
| 202 | c*u*u*auauccaacacuucgugguuuuagagcuau*g*c*u | 60 | 69 |
| 203 | c*u*u*auauccaacacuucgugguuuuagagcuau*g*c*u | 53 | 67 |
| 204 | c*u*u*auauccaacacuucgugguuuuagagcuau*g*c*u | 54 | 67 |
| 205 | c*u*u*auauccaacacuucgugguuuuagagcuau*g*c*u | 59 | 62 |
| 206 | c*u*u*auauccaacacuucgugguuuuagagcuau*g*c*u | 58 | 61 |
| 207 | c*u*u*auauccaacacuucgugguuuuagagcuau*g*c*u | 50 | 60 |
| 208 | c*u*u*auauccaacacuucgugguuuuagagcuau*g*c*u | 0 | 7 |
| 209 | c*u*u*auauccaacacuucgugguuuuagagcuau*g*c*u | 0 | 0 |
| 210 | c*u*u*auauccaacacuucgugguuuuagagcuau*g*c*u | 0 | 0 |
| 211 | c*u*u*auauccaacacuucgugguuuuagagcuau*g*c*u | 0 | 0 |
| 212 | c*u*u*auauccaacacuucgugguuuuagagcuau*g*c*u | 56 | 68 |
| 213 | c*u*u*auauccaacacuucgugguuuuagagcuau*g*c*u | 41 | 64 |
| 214 | c*u*u*auauccaacacuucgugguuuuagagcuau*g*c*u | 53 | 67 |
| 215 | c*u*u*auauccaacacuucgugguuuuagagcuau*g*c*u | 0 | 2 |
| 216 | c*u*u*auauccaacacuucgugguuuuagagcuau*g*c*u | 0 | 0 |
| 217 | c*u*u*auauccaacacuucgugguuuuagagcuau*g*c*u | 0 | 0 |
| 218 | c*u*u*auauccaacacuucgugguuuuagagcuau*g*c*u | 0 | 0 |
| 219 | c*u*u*auauccaacacuucgugguuuuagagcuau*g*c*u | 0 | 0 |
| 220 | c*u*u*auauccaacacuucgugguuuuagagcuau*g*c*u | 0 | 0 |
| 221 | +c*+t*uauauccaacacuucgugguuuuagagcuaug*+c*+t | 58 | 61 |
| 222 | c*u*u*auauccaacacuucgugguuuuagagcuau*g*c*u | 31 | 54 |
| 223 | c*u*u*auauccaacacuucgugguuuuagagcuau*g*c*u | 6 | 60 |
| 224 | c*u*u*auauccaacacuucgugguuuuagagcuau*g*c*u | 27 | 57 |
| 225 | c*u*u*auauccaacacuucgugguuuuagagcuau*g*c*u | 0 | 2 |
| 226 | c*u*u*auauccaacacuucgugguuuuagagcuau*g*c*u | 2 | 25 |
| 227 | c*u*u*auauccaacacuucgugguuuuagagcuau*g*c*u | 3 | 31 |
| 228 | c*u*u*auauccaacacuucgugguuuuagagcuau*g*c*u | 4 | 35 |
| 229 | c*u*u*auauccaacacuucgugguuuuagagcuau*g*c*u | 0 | 0 |
| 230 | c*u*u*auauccaacacuucgugguuuuagagcuau*g*c*u | 0 | 0 |
| 231 | c*u*u*auauccaacacuucgugguuuuagagcuau*g*c*u | 0 | 1 |
| 232 | c*u*u*auauccaacacuucgugguuuuagagcuau*g*c*u | 0 | 0 |
| 233 | c*u*u*auauccaacacuucgugguuuuagagcuau*g*c*u | 33 | 67 |
| 234 | c*u*u*auauccaacacuucgugguuuuagagcuau*g*c*u | 24 | 66 |
| 235 | C3-cuuauauccaacacuucgugguuuuagagcuaugcu-C3 | 56 | 65 |

TABLE 7-continued

Optimization of crRNA oligonucleotide modification patterns in mammalian cells.

| SEQ ID No. | crRNA Sequence (5'-3') | Cleavage % tracrRNA SEQ ID No 2 | Cleavage % tracrRNA SEQ ID No. 100 |
|---|---|---|---|
| 236 | C3-cuuauauccaacacuucgugguuuuagagcuaugcu-C3 | 11 | 55 |
| 237 | C3-cuuauauccaacacuucgugguuuuagagcuaugcu-InvT | 62 | 65 |
| 238 | c*u*u*auauccaacacuucgugguuuuagagcuau*g*c*u | 17 | 67 |
| 239 | c*u*u*auauccaacacuucgugguuuuagagcuau*g*c*u | 39 | 66 |
| 240 | C3-cuuauauccaacacuucgugguuuuagagcuaugcu-C3 | 27 | 63 |
| 241 | C3-cuuauauccaacacuucgugguuuuagagcuaugcu-C3 | 14 | 46 |
| 242 | ZEN-cuuauauccaacacuucgugguuuuagagcuaugcu-ZEN | 41 | 67 |
| 243 | ZEN-cuuauauccaacacuucgugguuuuagagcuaugcu-ZEN | 23 | 24 |
| 244 | c*u*u*auauccaacacuucgugguuuuagagcuau*g*c*u | ND | 60 |
| 245 | c*u*u*auauccaacacuucgugguuuuagagcuau*g*c*u | ND | 65 |
| 246 | c*u*u*auauccaacacuucgugguuuuagagcuau*g*c*u | ND | 64 |
| 247 | c*u*u*auauccaacacuucgugguuuuagagcuau*g*c*u | ND | 64 |
| 248 | c*u*u*auauccaacacuucgugguuuuagagcuau*g*c*u | ND | 63 |
| 249 | c*u*u*auauccaacacuucgugguuuuagagcuau*g*c*u | ND | 53 |
| 250 | c*u*u*auauccaacacUUCGUGGUUUuagagcuau*g*c*u | 0 | 2 |
| 251 | c*u*u*auauccaacacUUCGUGguuuuagagcuau*g*c*u | 0 | 0 |
| 252 | c*u*u*auauccaacacuucgugGUUUuagagcuau*g*c*u | 0 | 18 |
| 253 | c*u*u*auauccaacacuucgugguuuuagagcuau*g*c*u | 0 | 3 |
| 254 | c*u*u*auauccaacacuucgugguuuuagagcuau*g*c*u | 5 | 0 |
| 255 | c*u*u*auauccaacacuucgugguuuuagagcuau*g*c*u | 0 | 0 |
| 256 | C3-cuuauauccaacacuucgugguuuuagagcuaugcu-C3 | 27 | 53 |
| 257 | C3-cuuauauccaacacuucgugguuuuagagcuaugcu-C3 | 10 | 50 |
| 258 | c*u*u*auauccaacacuucgugguuuuagagcuau*g*c*u | 29 | 47 |
| 259 | c*u*u*auauccaacacuucgugguuuuagagcua*u*g*c | 7 | 45 |
| 260 | c*u*u*auauccaacacuucgugguuuuagagcu*a*u*g | 0 | 4 |
| 261 | c*u*u*auauccaacacuucgugguuuuagagc*u*a*u | 0 | 0 |
| 262 | c*u*u*auauccaacacuucgugguuuuag*c*u*a | 0 | 0 |
| 263 | c*u*u*auauccaacacuucgugguuuuaga*g*c*u | 0 | 0 |
| 264 | c*u*u*auauccaacacuucgugguuuuagagcuau*g*c*u | 50 | 62 |
| 265 | c*u*u*auauccaacacuucgugg*u*u*u*uagagcuau*g*c*u | 45 | 59 |
| 266 | c*u*u*auaucca*a*c*a*c*u*u*c*g*u*g*guuuuagagcuau*g*c*u | 26 | 36 |
| 267 | c*u*u*auaucca*a*c*a*c*u*u*c*g*u*g*g*u*u*u*uagagcuau*g*c*u | 20 | 34 |
| 268 | C3-cuuauauccaacacuucgugguuuuagagcuaugcu-C3 | 27 | 59 |
| 269 | C3-cuuauauccaacacuucgugg*u*u*u*uagagcuaugcu-C3 | 45 | 60 |
| 270 | C3-cuuauaucca*a*c*a*c*u*u*c*g*u*g*guuuuagagcuaugcu-C3 | 16 | 43 |
| 271 | C3-cuuauaucca*a*c*a*c*u*u*c*g*u*g*g*u*u*u*uagagcuaugcu-C3 | 22 | 45 |
| 272 | cuuauauccaacacuucgugguuuuagagcuaugcu | 63 | 57 |

TABLE 7-continued

Optimization of crRNA oligonucleotide modification patterns in mammalian cells.

| SEQ ID No. | crRNA Sequence (5'-3') | Cleavage % tracrRNA SEQ ID No 2 | Cleavage % tracrRNA SEQ ID No. 100 |
|---|---|---|---|
| 273 | cuuauauccaa<u>c</u>acuucgugguuuuagagcuaugcu | 59 | 60 |
| 274 | cuuauauccaac<u>a</u>cuucgugguuuuagagcuaugcu | 63 | 63 |
| 275 | cuuauauccaaca<u>c</u>uucgugguuuuagagcuaugcu | 64 | 62 |
| 276 | cuuauauccaacac<u>u</u>ucgugguuuuagagcuaugcu | 0 | 1 |
| 277 | cuuauauccaacacu<u>u</u>cgugguuuuagagcuaugcu | 5 | 16 |
| 278 | cuuauauccaacacuu<u>c</u>gugguuuuagagcuaugcu | 64 | 61 |
| 279 | cuuauauccaacacuuc<u>g</u>ugguuuuagagcuaugcu | 64 | 63 |
| 280 | cuuauauccaacacuucg<u>u</u>gguuuuagagcuaugcu | 30 | 49 |
| 281 | cuuauauccaacacuucgu<u>g</u>guuuuagagcuaugcu | 56 | 60 |
| 282 | cuuauauccaacacuucgug<u>g</u>uuuuagagcuaugcu | 53 | 61 |
| 283 | cuuauauccaacacuucgugg<u>u</u>uuuagagcuaugcu | 0 | 3 |
| 284 | cuuauauccaacacuucguggu<u>u</u>uuagagcuaugcu | 0 | 2 |
| 285 | cuuauauccaacacuucgugguu<u>u</u>uagagcuaugcu | 2 | 8 |
| 286 | cuuauauccaacacuucgugguuu<u>u</u>agagcuaugcu | 48 | 61 |
| 287 | <u>a</u>*<u>u</u>*<u>a</u>*<u>u</u>*<u>cc</u>aacacuucgugguuu<u>uagagcuau</u>*<u>g</u>*<u>c</u>*<u>u</u> | 0 | 0 |
| 288 | <u>u</u>*<u>a</u>*<u>u</u>*<u>cc</u>aacacuucgugguuu<u>uagagcuau</u>*<u>g</u>*<u>c</u>*<u>u</u> | 0 | 0 |
| 289 | +A*+T*<u>a</u>*<u>ucc</u>aacacuucgugguuu<u>uagagcuau</u>*<u>g</u>*<u>c</u>*<u>u</u> | 2 | 14 |
| 290 | +T*+A*<u>u</u>*<u>cc</u>aacacuucgugguuu<u>uagagcuau</u>*<u>g</u>*<u>c</u>*<u>u</u> | 0 | 0 |

Oligonucleotide sequences are shown 5'-3'.
Uppercase = DNA;
Lowercase = RNA;
Underlined = 2'-O-methyl RNA;
Italics = 2'-fluoro RNA;
+a, +c, +g = LNA;
C3 = C3 spacer (propanediol modifier);
* = phosphorothioate internucleotide linkage;
ZEN = napthyl-azo modifier;
InvT = inverted-dT.
The relative functional activity of each species is indicated by the % cleavage in a T7EI heteroduplex assay when the indicated crRNA is paired with the indicated tracrRNA.
ND = not determined.

Some kind of chemical modification is usually necessary for synthetic nucleic acids to function well in an intracellular environment due to the presence of exonucleases and endonucleases that degrade unmodified oligonucleotides. A wide range of modifications have been described that confer nuclease resistance to oligonucleotides. The precise combination and order of modifications employed that works well for a given application can vary with sequence context and the nature of the protein interactions required for biological function. Extensive prior work has been done relating to chemical modification of antisense oligonucleotides (which interact with RNase H1) and siRNAs (which interact with DICER, AGO2, and other proteins). It is expected that chemical modification will improve function of the CRISPR crRNA:tracrRNA complex. However, it is not possible to predict what modifications and/or pattern of modifications will be compatible with association of the RNAs with Cas9 in a functional way. The present invention defines minimal, moderate, and extensive chemical modification patterns for the crRNA that retain high levels of function to direct Cas9 mediated gene editing in mammalian cells. The survey in Example 7 was performed targeting a single site in the human HPRT1 gene. Note that modification patterns of the 20 base 5'-end protospacer guide domain of the crRNA that perform well may vary with sequence context. However, it is likely that modification patterns of the 3'-end tracrRNA binding domain that perform well as defined herein will be affected when the sequence of the adjacent protospacer domain changes when different sites are targeted, so the 3'-domain modification patterns shown here will be "universal".

The results in Table 7 demonstrate that extensive modification is tolerated throughout the 5' and 3' ends of the crRNA. Modification of certain select positions within internal domains of the crRNA lead to reduced activity or totally blocks activity, likely due to altered structure of the folded RNA and/or blocking of protein contact points with the 2'-OH of key RNA residues by the 2'OMe modification. For example, compound SEQ ID No. 204 has 21/36 residues modified with 2'OMe RNA (58%) and retains full activity compared with the unmodified sequence. Compound SEQ ID No. 239 has 30/36 residues modified with 2'OMe RNA (83%) and retains full activity compared with the unmodified sequence. Both of these compounds also have 3 phosphorothioate (PS) modified internucleotide linkages at the 5'- and 3'-ends, which provides additional protection against exonuclease attack. In contrast, SEQ ID No. 165 has only 4/36 residues modified with 2'OMe RNA (11%) yet has totally lost activity.

Large blocks of sequence were tolerant to 2'OMe modification at the 5'-end and 3'-end of the crRNA, however modification of certain residues in the central portion of the molecule led to inactivation. To further investigate which individual residues can be modified using 2'OMe RNA within the central domain of the crRNA, a single base modification 2'OMe RNA 'walk' was done (SEQ ID Nos. 272-286). Specific residues (positions within the crRNA) were identified that led to large reductions or complete loss of activity. Using the 36 base crRNA SEQ ID No. 239 as model and numbering from the 5'-end of the sequence, substitution of 2'OMe RNA for the natural RNA of residues U15 and U16 lead to substantial loss of activity and residue U19 led to a moderate loss of activity (FIG. 7). These 3 sites lie within the target-specific protospacer guide domain, so sequence varies with target (residues 15, 16, and 19, FIG. 7). It is possible that in certain sequence contexts that these sites will be tolerant to modification. Within the universal tracrRNA-binding domain (residues 21-36), substitution of 2'OMe RNA for the natural RNA of residues U22, U23, and U24 led to substantial loss of activity. Given that this domain does not change with sequence context, it is likely that these sites will not vary in modification tolerance as target sequence changes. Sequence-specific effects of modification in the 20-base target-specific protospacer guide domain are studies in greater detail in Example 10.

Antisense oligonucleotide are often made with complete PS modification, where every internucleotide linkage is phosphorothioate modified. This extensive level of modification is possible because the protein effector molecule RNase H1 tolerates the PS modification in the ASO when forming a functional substrate/enzyme complex. On the other hand, siRNAs do not tolerate full PS modification; extensive PS modification disrupts productive interaction with the effector protein AGO2. Limited PS end modification of the crRNA can be done with no loss of activity (SEQ ID Nos. 177, 178, 239, etc., have 3 PS linkages on each end). End-modification is desirable as this adds additional protection from exonuclease attack. PS modification of select internal sites may also be tolerated and may provide additional protection from endonuclease attack. Using SEQ ID No. 264 as a base modification pattern, internal linkages were PS modified in the tracrRNA-binding domain (SEQ ID No. 265), in the 3'-end of the protospacer guide domain (seed region) (SEQ ID No. 266), or both regions (SEQ ID No. 267). Increasing level of PS modification led to reduced functional activity, with SEQ ID No. 267 having ~50% the activity of the less modified SEQ ID No. 264 variant. SEQ ID No 267 has 21 out of 35 internucleotide linkages modified and will be stable to nuclease exposure. In cases where exposure to a high nuclease environment is needed (such as direct IV administration for research or therapeutic indications), this highly modified variant may actually show higher activity than the less modified variants, which will be degraded more quickly.

There are experimental settings where the PS modification contributes to chemical toxicity. In this case use of other methods to block exonuclease attack are desirable. The crRNA can have a C3 spacer (propanediol modifier) or a ZEN (napthyl-azo modifier) placed on either or both the 5'-end and 3'-end to block exonuclease attack, obviating the need the PS modification. This strategy can be employed to eliminate the PS-end block modification (See SEQ ID Nos. 179-186). This strategy can be used to reduce PS content of more highly modified crRNA variants. SEQ ID No. 271 has the internal protospacer domain and tracrRNA binding domain PS-modified in the same pattern as SEQ ID No. 267, yet employs only 15 PS internucleotide linkages (instead of 21) and shows improved activity. Therefore combination of non-base end-blocks with internal PS modification may be used to increase nuclease stability while maintaining high activity.

EXAMPLE 8

The following example demonstrates improved potency of the modified CRISPR crRNAs and tracrRNAs of the present invention. Examples 2-7 employed transfection of crRNA:tracrRNA complexes into human HEK-Cas9 cells at 30 nM concentration. Experimental testing had previously shown that this dose represented the upper shoulder of the dose response curve such that using higher doses of RNA did not improve gene editing efficiency but use of lower doses resulted lower gene editing efficiency. Those measurements were done using unmodified RNAs. The present example re-examines the dose response of new optimized chemically modified RNAs of the present invention compared with unmodified RNAs and demonstrates that chemical modification (i.e., nuclease stabilization) results in more potent compounds which can be used at lower dose.

Example 5 demonstrated that the truncated guide RNAs of the present invention performed superior to WT RNAs at 12 sites in the human HPRT1 gene. Four of these sites (38087, 38231, 38133, and 38285) were chosen for comparison of unmodified vs. modified RNA in the present example. Unmodified crRNAs were paired with the unmodified tracrRNA (SEQ ID No. 2) at a 1:1 molar ratio. Unmodified crRNAs were paired with the modified tracrRNA (SEQ ID No. 100) at a 1:1 molar ratio. Modified crRNAs were paired with the modified tracrRNA (SEQ ID No. 100) at a 1:1 molar ratio. Sequences are shown in Table 8. RNAs were transfected into HEK-Cas9 cells as described previously at 30 nM, 10 nM, and 3 nM concentrations. Cells were incubated for 48 hours at 37° C., then were processed for DNA and studied for evidence of gene editing activity comparing cleavage rates at the HPRT1 locus in the T7EI mismatch endonuclease assay, with quantitative measurement of products done using the Fragment Analyzer as previously described. Results are shown in Table 8.

TABLE 8

Increased potency of modified vs. unmodified crRNA: tracrRNA complexes to direct Cas9-mediated gene editing in mammalian cells.

| cr/tracr RNA pair | SEQ ID No. | crRNA Sequence tracrRNA Sequence | 30 nM Cleavage % | 10 nM Cleavage % | 3 nM Cleavage % |
|---|---|---|---|---|---|
| 38087 Un-cr Un-tr | 56 2 | aauuauggggauuacuaggaguuuuagagcuaugcu agcauagcaaguuaaaauaaggcuaguccguuaucaacuuga aaaaguggcaccgagucggugcuuu | 80 | 76 | 35 |
| 38087 Un-cr Mod-tr | 56 100 | aauuauggggauuacuaggaguuuuagagcuaugcu a*g*cauagcaaguuaaaauaaggcuaguccguuaucaacuu gaaaaaguggcaccgagucggugcu*u*u | 83 | 76 | 50 |
| 38087 Mod-cr Mod-tr | 445 100 | a*a*u*uauggggauuacuaggaguuuuagagcuau*g*c*u a*g*cauagcaaguuaaaauaaggcuaguccguuaucaacuu gaaaaaguggcaccgagucggugcu*u*u | 77 | 77 | 54 |
| 38231 Un-cr Un-tr | 69 2 | uuuuguaauuaacagcuugcguuuuagagcuaugcu agcauagcaaguuaaaauaaggcuaguccguuaucaacuuga aaaaguggcaccgagucggugcuuu | 41 | 4 | 0 |
| 38231 Un-cr Mod-tr | 69 100 | uuuuguaauuaacagcuugcguuuuagagcuaugcu a*g*cauagcaaguuaaaauaaggcuaguccguuaucaacuu gaaaaaguggcaccgagucggugcu*u*u | 45 | 14 | 1 |
| 38231 Mod-cr Mod-tr | 446 100 | u*u*u*uguaauuaacagcuugcguuuuagagcuau*g*c*u a*g*cauagcaaguuaaaauaaggcuaguccguuaucaacuu gaaaaaguggcaccgagucggugcu*u*u | 48 | 25 | 4 |
| 38133 Un-cr Un-tr | 78 2 | ggucacuuuuaacacacccaguuuuagagcuaugcu agcauagcaaguuaaaauaaggcuaguccguuaucaacuuga aaaaguggcaccgagucggugcuuu | 73 | 61 | 27 |
| 38133 Un-cr Mod-tr | 78 100 | ggucacuuuuaacacacccaguuuuagagcuaugcu a*g*cauagcaaguuaaaauaaggcuaguccguuaucaacuu gaaaaaguggcaccgagucggugcu*u*u | 74 | 61 | 37 |
| 38133 Mod-cr Mod-tr | 447 100 | g*g*u*cacuuuuaacacacccaguuuuagagcuau*g*c*u a*g*cauagcaaguuaaaauaaggcuaguccguuaucaacuu gaaaaaguggcaccgagucggugcu*u*u | 75 | 66 | 55 |
| 38285 Un-cr Un-tr | 48 2 | cuuauauccaacacuucgugguuuuagagcuaugcu agcauagcaaguuaaaauaaggcuaguccguuaucaacuuga aaaaguggcaccgagucggugcuuu | 66 | 16 | 2 |
| 38285 Un-cr Mod-tr | 48 100 | cuuauauccaacacuucgugguuuuagagcuaugcu a*g*cauagcaaguuaaaauaaggcuaguccguuaucaacuu gaaaaaguggcaccgagucggugcu*u*u | 67 | 16 | 5 |
| 38285 Mod-cr Mod-tr | 178 100 | c*u*u*auauccaacacuucgugguuuuagagcuau*g*c*u a*g*cauagcaaguuaaaauaaggcuaguccguuaucaacuu gaaaaaguggcaccgagucggugcu*u*u | 62 | 80 | 26 |

Oligonucleotide sequences are shown 5'-3'.
Lowercase = RNA;
Underlined = 2'-O-methyl RNA;
* = phosphorothioate internucleotide linkage.
Unmodified crRNA = Un-cr.
Unmodified tracrRNA = Un-tr.
Modified crRNA = Mod-cr. Modified tracrRNA = Mod-tr.
The relative functional activity of each species is indicated by the % cleavage in a T7EI heteroduplex assay for each dose studied.

In general, modification of the crRNA and tracrRNA had a small impact on gene editing efficiency when the RNAs were transfected at high dose where the RNAs are present in excess. At lower doses, the modified reagents showed improved potency and, in some cases, markedly improved potency. The degree of improvement varied with site. The very potent site 38087 showed highly efficiency gene editing at the 30 nM and 10 nM doses with all crRNA/tracrRNA variants tested, but at the 3 nM use of the modified tracrRNA (with either of the crRNAs) showed improved activity. A low potency site, such as 38231, showed improved gene editing efficiency even at the highest dose tested (30 nM) using the modified RNAs. Modification of the tracrRNA alone showed benefit, but the greatest benefit was realized when both the crRNA and tracrRNA were modified. FIG. 8 shows a schematic of one effective modified crRNA (SEQ ID No. 178) paired with modified tracrRNA (SEQ ID No. 100), specific for HPRT1 site 38285. FIG. 9 shows a schematic of a more highly modified pair that is also highly functional, crRNA (SEQ ID No. 239) paired with modified tracrRNA (SEQ ID No. 134), also specific for HPRT1 site 38285.

The present example employed transfection of the crRNA:tracrRNA complex into HEK-Cas9 cells, where Cas9 protein is constitutively expressed. Therefore transfected RNAs can bind Cas9 protein immediately, minimizing risk of degradation in the cytoplasm by nucleases. It is anticipated that the benefit of chemical modification of the crRNA and/or tracrRNA will be greater in cases where the transfected RNAs must survive exposure to cellular nucleases while Cas9 protein is being made, as occurs when using protocols where Cas9 mRNA or a Cas9 expression vector is co-transfected with the targeting RNAs, such that Cas9 is not already expressed in the cells. The benefits of using highly modified RNAs will be greatest for in vivo applications (such as medical therapeutics) where the RNAs may be exposed to both nucleases present in serum (following IV administration) and cellular cytoplasmic nucleases.

HPRT1 locus in the T7EI mismatch endonuclease assay, with quantitative measurement of products done using the Fragment Analyzer as previously described. Results are shown in Table 9.

TABLE 9

Increased potency of modified vs. unmodified crRNA: tracrRNA complexes to direct Cas9-mediated gene editing in mammalian cells.

| cr/tracr RNA pair | SEQ ID No. | crRNA Sequence tracrRNA Sequence | 10 nM Cleavage % |
|---|---|---|---|
| 38285 Un-cr Un-tr | 48 2 | cuuauauccaacacuucgugguuuuagagcuaugcu agcauagcaaguuaaaauaaggcuaguccguuaucaacuugaa aaaguggcaccgagucggugcuuu | 42 |
| 38285 Un-cr Mod-tr | 48 100 | cuuauauccaacacuucgugguuuuagagcuaugcu a*g*cauagcaaguuaaaauaaggcuaguccguuaucaacuug aaaaaguggcaccgagucggugcu*u*u | 41 |
| 38285 Mod-cr Mod-tr | 178 100 | c*u*u*auauccaacacuucgugguuuuagagcuau*g*c*u a*g*cauagcaaguuaaaauaaggcuaguccguuaucaacuug aaaaaguggcaccgagucggugcu*u*u | 54 |

Oligonucleotide sequences are shown 5'-3'.
Lowercase = RNA;
Underlined = 2'-O-methyl RNA;
* = phosphorothioate internucleotide linkage.
Unmodified crRNA = Un-cr.
Unmodified tracrRNA = Un-tr.
Modified crRNA = Mod-cr.
Modified tracrRNA = Mod-tr.
The relative functional activity of each complex is indicated by the % cleavage in a T7EI heteroduplex assay for each dose studied.

EXAMPLE 9

Examples 2-8 demonstrate activity of truncated and/or chemically-modified CRISPR crRNAs and/or tracrRNAs to trigger Cas9-mediated genome editing in mammalian cells that constitutively express Cas9. The present example demonstrates that the truncated, modified RNA compositions of the present invention can bind Cas9 protein and this complex can be transfected into human cells and further that transfection of the ribonuclear protein (RNP) complex is sufficient to trigger highly efficient genome editing.

Reagents specific for human HPRT1 site 38285 were employed in the present example. Unmodified crRNA was paired with unmodified tracrRNA at a 1:1 molar ratio. Unmodified crRNA was paired with modified tracrRNA at a 1:1 molar ratio. Modified crRNA was paired with modified tracrRNA at a 1:1 molar ratio. Sequences are shown in Table 9. RNAs were transfected into unmodified HEK293 cells as described above except that a 1:1 complex of Cas9 protein (Caribou Biosciences) with crRNA:tracrRNA were employed at 10 nM concentration using increased amounts of RNAiMAX lipid transfection reagent (1.2 μL, increased over the 0.75 μL amount used per 100 μL transfection in 96 well format for the 30 nM RNA-alone transfections in HEK-Cas9 cells). Cells were incubated for 48 hours at 37° C., then were processed for DNA and studied for evidence of gene editing activity comparing cleavage rates at the All 3 CRISPR RNA complexes performed well in the RNP-transfection protocol for mammalian genome editing. The unmodified crRNA+unmodified tracrRNA pair (SEQ ID Nos. 48 and 2) and the unmodified crRNA+modified tracrRNA pair (SEQ ID Nos. 48 and 100) performed 2.5× better at 10 nM dose in the RNP protocol than in the HEK-Cas9 protocol, consistent with the less modified RNAs suffering degradation between transfection and eventual complexation with Cas9 protein in the cytoplasm or nucleus. Thus higher doses are needed for unmodified RNAs and in some settings it is likely that unmodified RNAs will fail to direct any genome editing activity. The modified crRNA+ modified tracrRNA (SEQ ID NOs. 178 and 100), on the other hand, worked with high efficiency in both protocols.

The modified, truncated CRISPR RNAs of the present invention work well with direct Cas9 RNP transfection methods.

EXAMPLE 10

The chemical modification optimization studies performed in Examples 6 and 7 studied the activity of crRNAs having various modification patterns paired with a tracrRNA having various modification patterns. The tracrRNA is universal and the same sequence is employed at all target sites. It is expected that the performance of various modification patterns for the tracrRNA will be similar between different target sites. The crRNA, however, varies sequence between different target sites. In the optimized version tested in Examples 7 and 8, the 5'-20 bases of the crRNA are target-specific (i.e., the "protospacer domain") and the 3'-16 bases are universal (i.e., "the tracrRNA binding domain"). Like the tracrRNA, it is expected that the performance of various modification patterns in the universal 16 base 3'-domain of the crRNA will be similar at all target sites.

However, it is possible that performance of different modification patterns may be influenced by the sequence context present in the 5'-20 base target-specific domain.

It is well established that effective modification patterns for small interfering RNAs (siRNAs) are affected by sequence context (Behlke, Oligonucleotides 18:305-320, 2008). For siRNAs, certain "limited modification" patterns can be applied to all sites, whereas for "heavy modification" it is not possible to predict which patterns will be functional for a given sequence and empiric testing is necessary. The present example studies the effect that sequence context has on the crRNA, testing different modification patterns within the 5'-20 base target-specific domain at different sites.

The modification studies in Examples 6 and 7 employed a single crRNA PAM site in the human HPRT1 gene. The present study examines 12 sites in the human HPRT1 gene, including the site previously examined, comparing functional performance of different modification patterns and establishes a single modification pattern that can be employed with good results at all sites. See Example 5 for other studies relating to these 12 sites.

A series of crRNAs (Table 10) were synthesized having a protospacer domain lengths of 20 bases specific to 12 sites in the human HPRT1 gene with a 16mer universal tracrRNA binding sequence at the 3'-end. The crRNAs were made using a variety of chemical modifications, including: the ribose modifications 2'OMe RNA, the end-modifying groups propanediol spacer and napthyl-azo modifier (N,N-diethyl-4-(4-nitronaphthalen-1-ylazo)-phenylamine, or "ZEN"), an inverted-dT residue; and select internucleotide linkages with phosphorothioate modifications. A schematic representation of the different modification patterns employed is shown in FIG. 10.

Figure 11:
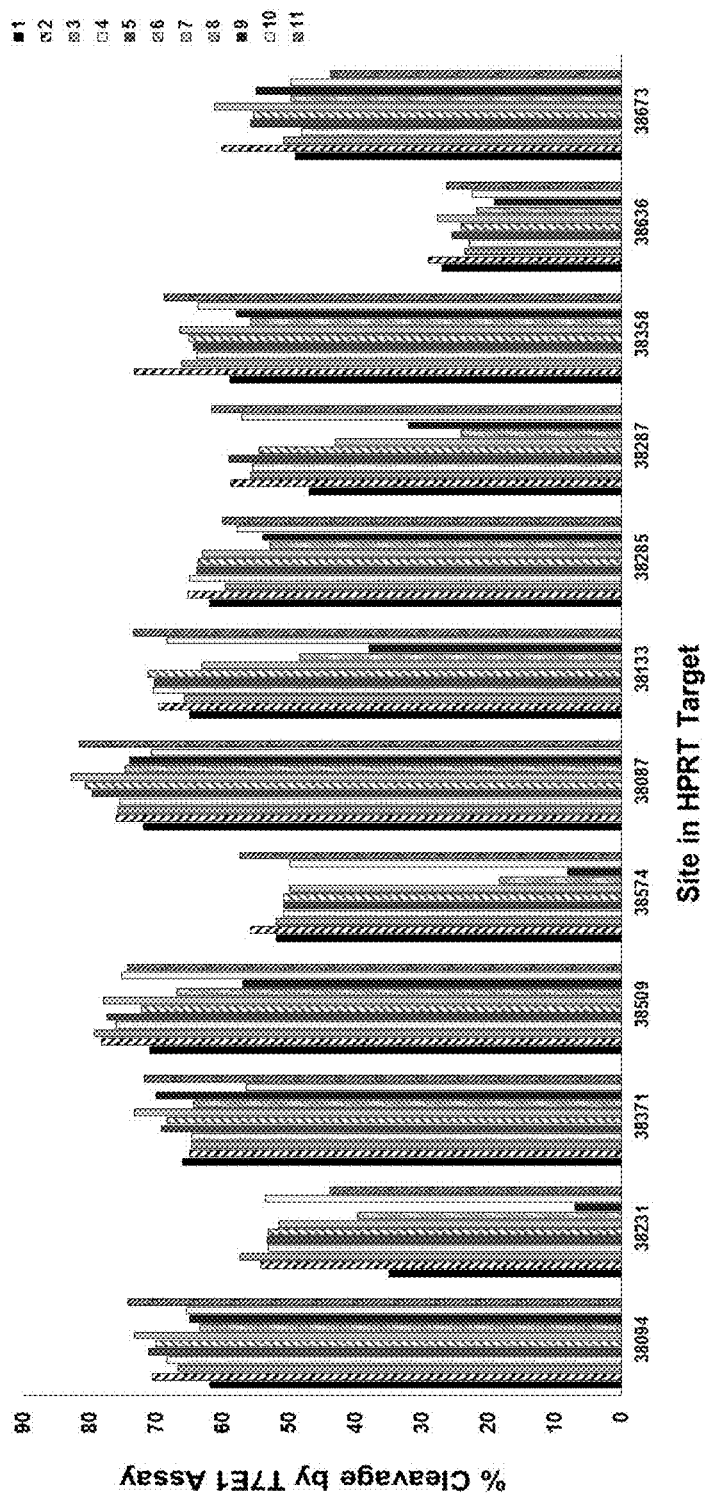
FIG. 11 is a plot of the data in Table 10 showing the functional gene editing observed using the T7E1 assay in mammalian cells using crRNAs made with 11 different modification patterns tested at 12 different sites in the human HPRT1 gene. All crRNA variants were paired with an optimized, modified tracrRNA (SEQ ID No. 100).

The crRNAs were paired with a highly modified 67mer tracrRNA (SEQ ID No. 100). The paired crRNA:tracrRNA RNA oligonucleotides were transfected into the HEK-Cas9 cells and processed as described in Example 2. Relative gene editing activities were assessed by comparing cleavage rates in the HPRT1 gene using the T7EI mismatch endonuclease cleavage assay with quantitative measurement of products done using the Fragment Analyzer. Results are shown in Table 10 and in FIG. 11.

TABLE 10

Optimization of crRNA oligonucleotide modification patterns in mammalian cells across 12 target sites.

| HPRT1 Target site | SEQ ID No. | Mod Pattern | crRNA Sequence (5'-3') | Cleavage % tracrRNA SEQ ID No. 100 |
|---|---|---|---|---|
| 38094 | 64 | 1 | uccauuucauagucuuuccuguuuuagagcuaugcu | 62 |
| 38231 | 69 | 1 | uuuuguaauuaacagcuugcguuuuagagcuaugcu | 35 |
| 38371 | 71 | 1 | cuuagagaauauuuguagagguuuuagagcuaugcu | 66 |
| 38509 | 73 | 1 | uugacuauaaugaauacuucguuuuagagcuaugcu | 71 |
| 38574 | 75 | 1 | caaaacacgcauaaaaauuuguuuuagagcuaugcu | 52 |
| 38087 | 56 | 1 | aauuauggggauuacuaggaguuuuagagcuaugcu | 72 |
| 38133 | 78 | 1 | ggucacuuuuaacacacccaguuuuagagcuaugcu | 65 |
| 38285 | 48 | 1 | cuuauauccaacacuucguggguuuuagagcuaugcu | 62 |
| 38287 | 80 | 1 | ggcuuauauccaacacuucgguuuuagagcuaugcu | 47 |
| 38358 | 60 | 1 | auuucacauaaaacucuuuuguuuuagagcuaugcu | 59 |
| 38636 | 83 | 1 | ucaaauuaugaggugcuggaguuuuagagcuaugcu | 27 |
| 38673 | 85 | 1 | uacagcuuuaugugacuaauguuuuagagcuaugcu | 49 |
| 38094 | 291 | 2 | u*c*c*auuucauagucuuuccuguuuuagagcuau*g*c*u | 71 |
| 38231 | 292 | 2 | u*u*u*uguaauuaacagcuugcguuuuagagcuau*g*c*u | 54 |
| 38371 | 293 | 2 | c*u*u*agagaauauuuguagagguuuuagagcuau*g*c*u | 65 |
| 38509 | 294 | 2 | u*u*g*acuauaaugaauacuucguuuuagagcuau*g*c*u | 78 |
| 38574 | 295 | 2 | c*a*a*aacacgcauaaaaauuuguuuuagagcuau*g*c*u | 56 |
| 38087 | 296 | 2 | a*a*u*uauggggauuacuaggaguuuuagagcuau*g*c*u | 76 |
| 38133 | 297 | 2 | g*g*u*cacuuuuaacacacccaguuuuagagcuau*g*c*u | 70 |
| 38285 | 178 | 2 | c*u*u*auauccaacacuucguggguuuuagagcuau*g*c*u | 65 |
| 38287 | 298 | 2 | g*g*c*uuauauccaacacuucgguuuuagagcuau*g*c*u | 59 |
| 38358 | 299 | 2 | a*u*u*ucacauaaaacucuuuuguuuuagagcuau*g*c*u | 73 |
| 38636 | 300 | 2 | u*c*a*aauuaugaggugcuggaguuuuagagcuau*g*c*u | 29 |

TABLE 10-continued

Optimization of crRNA oligonucleotide modification patterns in mammalian cells across 12 target sites.

| HPRT1 Target site | SEQ ID No. | Mod Pattern | crRNA Sequence (5'-3') | Cleavage % tracrRNA SEQ ID No. 100 |
|---|---|---|---|---|
| 38673 | 301 | 2 | u*a*c*agcuuuaugugacuaauguuuuagagcuau*g*c*u | 60 |
| 38094 | 302 | 3 | u*c*c*auuucauagucuuuccuguuuuagagcuau*g*c*u | 67 |
| 38231 | 303 | 3 | u*u*u*uguaauuaacagcuugcguuuuagagcuau*g*c*u | 57 |
| 38371 | 304 | 3 | c*u*u*agagaauauuuguagagguuuuagagcuau*g*c*u | 65 |
| 38509 | 305 | 3 | u*u*g*acuauaaugaauacuucguuuuagagcuau*g*c*u | 79 |
| 38574 | 306 | 3 | c*a*a*aacacgcauaaaaauuuguuuuagagcuau*g*c*u | 52 |
| 38087 | 307 | 3 | a*a*u*uaugggauuacuaggaguuuuagagcuau*g*c*u | 76 |
| 38133 | 308 | 3 | g*g*u*cacuuuuaacacacccaguuuuagagcuau*g*c*u | 66 |
| 38285 | 309 | 3 | c*u*u*auauccaacacuucgugguuuuagagcuau*g*c*u | 60 |
| 38287 | 310 | 3 | g*g*c*uuauauccaacacuucgguuuuagagcuau*g*c*u | 56 |
| 38358 | 311 | 3 | a*u*u*ucacauaaaacucuuuuguuuuagagcuau*g*c*u | 66 |
| 38636 | 312 | 3 | u*c*a*aauuaugaggugcuggaguuuuagagcuau*g*c*u | 24 |
| 38673 | 313 | 3 | u*a*c*agcuuuaugugacuaauguuuuagagcuau*g*c*u | 51 |
| 38094 | 314 | 4 | u*c*c*auuucauagucuuuccuguuuuagagcuau*g*c*u | 68 |
| 38231 | 315 | 4 | u*u*u*uguaauuaacagcuugcguuuuagagcuau*g*c*u | 53 |
| 38371 | 316 | 4 | c*u*u*agagaauauuuguagagguuuuagagcuau*g*c*u | 65 |
| 38509 | 317 | 4 | u*u*g*acuauaaugaauacuucguuuuagagcuau*g*c*u | 76 |
| 38574 | 318 | 4 | c*a*a*aacacgcauaaaaauuuguuuuagagcuau*g*c*u | 51 |
| 38087 | 319 | 4 | a*a*u*uaugggauuacuaggaguuuuagagcuau*g*c*u | 76 |
| 38133 | 320 | 4 | g*g*u*cacuuuuaacacacccaguuuuagagcuau*g*c*u | 70 |
| 38285 | 321 | 4 | c*u*u*auauccaacacuucgugguuuuagagcuau*g*c*u | 65 |
| 38287 | 322 | 4 | g*g*c*uuauauccaacacuucgguuuuagagcuau*g*c*u | 56 |
| 38358 | 323 | 4 | a*u*u*ucacauaaaacucuuuuguuuuagagcuau*g*c*u | 64 |
| 38636 | 324 | 4 | u*c*a*aauuaugaggugcuggaguuuuagagcuau*g*c*u | 23 |
| 38673 | 325 | 4 | u*a*c*agcuuuaugugacuaauguuuuagagcuau*g*c*u | 48 |
| 38094 | 326 | 5 | u*c*c*auuucauagucuuuccuguuuuagagcuau*g*c*u | 71 |
| 38231 | 327 | 5 | u*u*u*uguaauuaacagcuugcguuuuagagcuau*g*c*u | 53 |
| 38371 | 328 | 5 | c*u*u*agagaauauuuguagagguuuuagagcuau*g*c*u | 69 |
| 38509 | 329 | 5 | u*u*g*acuauaaugaauacuucguuuuagagcuau*g*c*u | 77 |
| 38574 | 330 | 5 | c*a*a*aacacgcauaaaaauuuguuuuagagcuau*g*c*u | 51 |
| 38087 | 331 | 5 | a*a*u*uaugggauuacuaggaguuuuagagcuau*g*c*u | 80 |
| 38133 | 332 | 5 | g*g*u*cacuuuuaacacacccaguuuuagagcuau*g*c*u | 70 |
| 38285 | 333 | 5 | c*u*u*auauccaacacuucgugguuuuagagcuau*g*c*u | 64 |
| 38287 | 334 | 5 | g*g*c*uuauauccaacacuucgguuuuagagcuau*g*c*u | 59 |
| 38358 | 335 | 5 | a*u*u*ucacauaaaacucuuuuguuuuagagcuau*g*c*u | 64 |
| 38636 | 336 | 5 | u*c*a*aauuaugaggugcuggaguuuuagagcuau*g*c*u | 25 |
| 38673 | 337 | 5 | u*a*c*agcuuuaugugacuaauguuuuagagcuau*g*c*u | 56 |

TABLE 10-continued

Optimization of crRNA oligonucleotide modification patterns in mammalian cells across 12 target sites.

| HPRT1 Target site | SEQ ID No. | Mod Pattern | crRNA Sequence (5'-3') | Cleavage % tracrRNA SEQ ID No. 100 |
|---|---|---|---|---|
| 38094 | 338 | 6 | u*c*c*auuucauagucuuuccuguuuuagagcuau*g*c*u | 70 |
| 38231 | 339 | 6 | u*u*u*uguaauuaacagcuugcguuuuagagcuau*g*c*u | 53 |
| 38371 | 340 | 6 | c*u*u*agagaauauuuguagagguuuuagagcuau*g*c*u | 68 |
| 38509 | 341 | 6 | u*u*g*acuauaaugaauacuucguuuuagagcuau*g*c*u | 72 |
| 38574 | 342 | 6 | c*a*a*aacacgcauaaaaauuuguuuuagagcuau*g*c*u | 51 |
| 38087 | 343 | 6 | a*a*u*uaugggauuacuaggaguuuuagagcuau*g*c*u | 81 |
| 38133 | 344 | 6 | g*g*u*cacuuuuaacacacccaguuuuagagcuau*g*c*u | 71 |
| 38285 | 345 | 6 | c*u*u*auauccaacacuucgugguuuuagagcuau*g*c*u | 64 |
| 38287 | 346 | 6 | g*g*c*uuauauccaacacuucgguuuuagagcuau*g*c*u | 55 |
| 38358 | 347 | 6 | a*u*u*ucacauaaaacucuuuuguuuuagagcuau*g*c*u | 65 |
| 38636 | 348 | 6 | u*c*a*aauuaugaggugcuggaguuuuagagcuau*g*c*u | 24 |
| 38673 | 349 | 6 | u*a*c*agcuuuaugugacuaauguuuuagagcuau*g*c*u | 55 |
| 38094 | 350 | 7 | u*c*c*auuucauagucuuuccuguuuuagagcuau*g*c*u | 73 |
| 38231 | 351 | 7 | u*u*u*uguaauuaacagcuugcguuuuagagcuau*g*c*u | 51 |
| 38371 | 352 | 7 | c*u*u*agagaauauuuguagagguuuuagagcuau*g*c*u | 73 |
| 38509 | 353 | 7 | u*u*g*acuauaaugaauacuucguuuuagagcuau*g*c*u | 78 |
| 38574 | 354 | 7 | c*a*a*aacacgcauaaaaauuuguuuuagagcuau*g*c*u | 50 |
| 38087 | 355 | 7 | a*a*u*uaugggauuacuaggaguuuuagagcuau*g*c*u | 83 |
| 38133 | 356 | 7 | g*g*u*cacuuuuaacacacccaguuuuagagcuau*g*c*u | 63 |
| 38285 | 357 | 7 | c*u*u*auauccaacacuucgugguuuuagagcuau*g*c*u | 63 |
| 38287 | 358 | 7 | g*g*c*uuauauccaacacuucgguuuuagagcuau*g*c*u | 43 |
| 38358 | 359 | 7 | a*u*u*ucacauaaaacucuuuuguuuuagagcuau*g*c*u | 66 |
| 38636 | 360 | 7 | u*c*a*aauuaugaggugcuggaguuuuagagcuau*g*c*u | 28 |
| 38673 | 361 | 7 | u*a*c*agcuuuaugugacuaauguuuuagagcuau*g*c*u | 61 |
| 38094 | 362 | 8 | u*c*c*auuucauagucuuuccuguuuuagagcuau*g*c*u | 63 |
| 38231 | 363 | 8 | u*u*u*uguaauuaacagcuugcguuuuagagcuau*g*c*u | 40 |
| 38371 | 364 | 8 | c*u*u*agagaauauuuguagagguuuuagagcuau*g*c*u | 64 |
| 38509 | 365 | 8 | u*u*g*acuauaaugaauacuucguuuuagagcuau*g*c*u | 67 |
| 38574 | 366 | 8 | c*a*a*aacacgcauaaaaauuuguuuuagagcuau*g*c*u | 18 |
| 38087 | 367 | 8 | a*a*u*uaugggauuacuaggaguuuuagagcuau*g*c*u | 75 |
| 38133 | 368 | 8 | g*g*u*cacuuuuaacacacccaguuuuagagcuau*g*c*u | 48 |
| 38285 | 369 | 8 | c*u*u*auauccaacacuucgugguuuuagagcuau*g*c*u | 53 |
| 38287 | 370 | 8 | g*g*c*uuauauccaacacuucgguuuuagagcuau*g*c*u | 24 |
| 38358 | 371 | 8 | a*u*u*ucacauaaaacucuuuuguuuuagagcuau*g*c*u | 56 |
| 38636 | 372 | 8 | u*c*a*aauuaugaggugcuggaguuuuagagcuau*g*c*u | 22 |
| 38673 | 373 | 8 | u*a*c*agcuuuaugugacuaauguuuuagagcuau*g*c*u | 50 |

TABLE 10-continued

Optimization of crRNA oligonucleotide modification patterns in mammalian cells across 12 target sites.

| HPRT1 Target site | SEQ ID No. | Mod Pattern | crRNA Sequence (5'-3') | Cleavage % tracrRNA SEQ ID No. 100 |
|---|---|---|---|---|
| 38094 | 374 | 9 | u*c*c*auuucauagucuuuccuguuu<u>uagagcuau</u>*g*c*u | 65 |
| 38231 | 375 | 9 | u*u*u*uguaauuaacagcuugcguuu<u>uagagcuau</u>*g*c*u | 7 |
| 38371 | 376 | 9 | c*u*u*agagaauauuuguagagguuu<u>uagagcuau</u>*g*c*u | 70 |
| 38509 | 377 | 9 | u*u*g*acuauaaugaauacuucguuu<u>uagagcuau</u>*g*c*u | 57 |
| 38574 | 378 | 9 | c*a*a*aacacgcauaaaaauuuguuu<u>uagagcuau</u>*g*c*u | 8 |
| 38087 | 379 | 9 | a*a*u*uaugggggauuacuaggaguuu<u>uagagcuau</u>*g*c*u | 74 |
| 38133 | 380 | 9 | g*g*u*cacuuuaacacacccaguuu<u>uagagcuau</u>*g*c*u | 38 |
| 38285 | 222 | 9 | c*u*u*auauccaacacuucguggguuu<u>uagagcuau</u>*g*c*u | 54 |
| 38287 | 381 | 9 | g*g*c*uuauauccaacacuucgguuu<u>uagagcuau</u>*g*c*u | 32 |
| 38358 | 382 | 9 | a*u*u*ucacauaaaacucuuuuguuu<u>uagagcuau</u>*g*c*u | 58 |
| 38636 | 383 | 9 | u*c*a*aauuaugaggugcuggaguuu<u>uagagcuau</u>*g*c*u | 19 |
| 38673 | 384 | 9 | u*a*c*agcuuuaugugacuaauguuu<u>uagagcuau</u>*g*c*u | 55 |
| 38094 | 385 | 10 | C3-uccauuucauagucuuuccuguuuuagagcuaugcu-C3 | 66 |
| 38231 | 386 | 10 | C3-uuuuguaauuaacagcuugcguuuuagagcuaugcu-C3 | 54 |
| 38371 | 387 | 10 | C3-cuuagagaauauuuguagagguuuuagagcuaugcu-C3 | 57 |
| 38509 | 388 | 10 | C3-uugacuauaaugaauacuucguuuuagagcuaugcu-C3 | 75 |
| 38574 | 389 | 10 | C3-caaaacacgcauaaaaauuuguuuuagagcuaugcu-C3 | 50 |
| 38087 | 390 | 10 | C3-aauuaugggggauuacuaggaguuuuagagcuaugcu-C3 | 71 |
| 38133 | 391 | 10 | C3-ggucacuuuaacacacccaguuuuagagcuaugcu-C3 | 68 |
| 38285 | 181 | 10 | C3-cuuauauccaacacuucguggguuuuagagcuaugcu-C3 | 58 |
| 38287 | 392 | 10 | C3-ggcuuauauccaacacuucgguuuuagagcuaugcu-C3 | 57 |
| 38358 | 393 | 10 | C3-auuucacauaaaacucuuuuguuuuagagcuaugcu-C3 | 64 |
| 38636 | 394 | 10 | C3-ucaaauuaugaggugcuggaguuuuagagcuaugcu-C3 | 22 |
| 38673 | 395 | 10 | C3-uacagcuuuaugugacuaauguuuuagagcuaugcu-C3 | 50 |
| 38094 | 396 | 11 | ZEN-uccauuucauagucuuuccuguuuuagagcuaugcu-ZEN | 74 |
| 38231 | 397 | 11 | ZEN-uuuuguaauuaacagcuugcguuuuagagcuaugcu-ZEN | 44 |
| 38371 | 398 | 11 | ZEN-cuuagagaauauuuguagagguuuuagagcuaugcu-ZEN | 72 |
| 38509 | 399 | 11 | ZEN-uugacuauaaugaauacuucguuuuagagcuaugcu-ZEN | 74 |
| 38574 | 400 | 11 | ZEN-caaaacacgcauaaaaauuuguuuuagagcuaugcu-ZEN | 57 |
| 38087 | 401 | 11 | ZEN-aauuaugggggauuacuaggaguuuuagagcuaugcu-ZEN | 82 |
| 38133 | 402 | 11 | ZEN-ggucacuuuaacacacccaguuuuagagcuaugcu-ZEN | 73 |
| 38285 | 184 | 11 | ZEN-cuuauauccaacacuucguggguuuuagagcuaugcu-ZEN | 60 |
| 38287 | 403 | 11 | ZEN-ggcuuauauccaacacuucgguuuuagagcuaugcu-ZEN | 62 |
| 38358 | 404 | 11 | ZEN-auuucacauaaaacucuuuuguuuuagagcuaugcu-ZEN | 69 |

TABLE 10-continued

Optimization of crRNA oligonucleotide modification
patterns in mammalian cells across 12 target sites.

| HPRT1 Target site | SEQ ID No. | Mod Pattern | crRNA Sequence (5'-3') | Cleavage % tracrRNA SEQ ID No. 100 |
|---|---|---|---|---|
| 38636 | 405 | 11 | ZEN-ucaaauuaugaggugcuggaguuuuagagcuaugcu-ZEN | 26 |
| 38673 | 406 | 11 | ZEN-uacagcuuuaugugacuaauguuuuagagcuaugcu-ZEN | 44 |

Oligonucleotide sequences are shown 5'-3'.
Lowercase = RNA;
Underlined = 2'-O-methyl RNA;
C3 = C3 spacer (propanediol modifier);
* = phosphorothioate internucleotide linkage;
ZEN = napthyl-azo modifier.
The relative functional activity of each species is indicated by the % cleavage in a T7EI heteroduplex assay when the indicated crRNA is paired with the indicated tracrRNA at each of 12 sites in human HRPT1.

The modified crRNAs employed a fixed modification pattern in the 16-base 3'-end domain which is universal and binds the tracrRNA. Different modification pattern were tested/compared in the 5'-end domain that is target specific (i.e., sequence varies with target site). The test set comprised variants having 0, 3, 4, 6, 8, 10, 12, 13, or 14 contiguous 2'OMe RNA residues starting at the 5'-end and walking towards the 3'-end. The modification patterns avoided positions previously demonstrated to reduce functional performance of the crRNA (Example 7). Use of only non-base modifier end groups (C3 spacer or ZEN) were also tested (without additional modification). When functional activity is compared across all 12 sites in the survey, all sites tested showed full activity when 0-10 RNA residues at the 5'-end were replaced with 2'OMe RNA residues. Only 1/12 sites showed a slight reduction in activity with 12 residues modified, however 3/12 sites showed a reduction in activity when 13 residues were modified and 4/12 sites showed a reduction in activity when 14 residues were modified. The end-modifiers (C3, ZEN) showed full activity at all sites.

The highest level of crRNA modification that showed full activity at all sites tested included Mod Patterns 6 and 7 (FIG. 10). This represents 61% and 67% of the bases in the crRNA modified with 2'OMe RNA, respectively.

Mod Pattern 6
(SEQ ID NO.: 434)
n*n*n*nnnnnnnnnnnnnnnnnguuuuagagcuau*g*c*u

Mod Pattern 7
(SEQ ID NO.: 435)
n*n*n*nnnnnnnnnnnnnnnnnguuuuagagcuau*g*c*u

The data in the present example also demonstrates that individual sites can be modified at higher levels and retain potency. For example, 8 of the 12 sites studied showed full activity using Mod Pattern 8, which has 72% of the residues modified. Further, example 7 demonstrates that the crRNA targeting site 38285 in HPRT1 (SEQ ID No. 239) has full activity and has 30/36 residues modified (83%, with only 6 unmodified RNA residues remaining). A base modification pattern such as Mod Pattern 6 or Mod Pattern 7 can be used as a starting point for studies to empirically ascertain the extent that a particular sequence can be modified before activity is lost. FIG. 12 shows a schematic where a Mod Pattern 6 crRNA is paired with a highly modified tracrRNA, SEQ ID No. 134.

EXAMPLE 11

The Examples herein employ the Cas9 endonuclease from *Streptococcus pyogenes*. The native amino acid sequence of S. py. Cas9 (SpyCas9) is shown below (SEQ ID No. 407).

The native Cas9 DNA sequence was codon optimized for expression in *E. coli* bacteria and had elements added for mammalian nuclear localization (nuclease localization signals) and aid protein purification (His-tag). The final amino-acid sequence of the recombinant protein is shown (SEQ ID No 408). The DNA sequence employed to express the recombinant protein in *E. coli* is shown (SEQ ID No. 409).

The native Cas9 DNA sequence was codon optimized for expression in human cells and had elements added for antibody recognition (V5 epitope) and mammalian nuclear localization (nuclease localization signals, NLS) added. The final amino-acid sequence is shown (SEQ ID No. 410) and DNA sequence follows (SEQ ID No 411).

The native S. py Cas9 DNA sequence codon was optimized for expression in human cells and assembled as a T7 RNA polymerase expression cassette (SEQ ID No. 412). The sequence contains a T7 RNA polymerase promoter, a V5 epitope tag, a nuclear localization signal, the codon optimized Cas9 sequence, a second nuclear localization signal, and the BGH (bovine growth hormone) gene 3'-UTR element with a polyadenylation signal. Sequence of mRNA made from this expression cassette is shown (SEQ ID No. 413).

S. py. Cas9 Amino Acid Sequence (SEQ ID No. 407).

MDKKYSIGLDIGINSVGWAVITDEYKVPSKKEKVLGNTDRHSIKKNLIG

ALLFDSGETAEATRLKRTARRRYTRRKNRICYLQEIFSNEMAKVDDSFF

HRLEESFLVEEDKKHERHPIFGNIVDEVAYHEKYPTIYHLRKKLVDSTD

KADLRLIYLALAHMIKFRGHFLIEGDLNPDNSDVDKLFIQLVQTYNQLF

EENPINASGVDAKAILSARLSKSRRLENLIAQLPGEKKNGLEGNLIALS

LGLIPNEKSNEDLAEDAKLQLSKDTYDDDLDNLLAQIGDQYADLFLAAK

NLSDAILLSDILRVNTEITKAPLSASMIKRYDEHHQDLTLLKALVRQQL

PEKYKEIFFDQSKNGYAGYIDGGASQEEFYKFIKPILEKMDGTEELLVK

LNREDLLRKQRTFDNGSIPHQIHLGELHILRRQEDFYPFLKDNREKIEK

ILTFRIPYYVGPLARGNSRFAWMTRKSEETITPWNFEEVVDKGASAQSF

-continued

IERMTNEDKNLPNEKVLPKHSLLYEYFTVYNELTKVKYVTEGMRKPAFL

SGEQKKAIVDLLFKINRKVIVKQLKEDYFKKIECFDSVEISGVEDRFNA

SLGTYHDLLKIIKDKDFLDNEENEDILEDIVLTLTLFEDREMIEERLKT

YAHLFDDKVMKQLKRRRYTGWGRLSRKLINGIRDKQSGKTILDFLKSDG

FANRNFMQLIHDDSLTFKEDIQKAQVSGQGDSLHEHIANLAGSPAIKKG

ILQTVKVVDELVKVMGRHKPENIVIEMARENQTTQKGQKNSRERMKRIE

EGIKELGSQILKEHPVENTQLQNEKLYLYYLQNGRDMYVDQELDINRLS

DYDVDHIVPQSFLKDDSIDNKVLTRSDKNRGKSDNVPSEEVVKKMKNYW

RQLLNAKLITQRKEDNLIKAERGGLSELDKAGFIKRQLVETRQITKHVA

QILDSRMNTKYDENDKLIREVKVITLKSKLVSDERKDFQFYKVREINNY

HHAHDAYLNAVVGTALIKKYPKLESEFVYGDYKVYDVRKMIAKSEQEIG

KATAKYFFYSNIMNFFKTEITLANGEIRKRPLIETNGETGEIVWDKGRD

FATVRKVLSMPQVNIVKKTEVQTGGFSKESILPKRNSDKLIARKKDWDP

KKYGGFDSPTVAYSVLVVAKVEKGKSKKLKSVKELLGITIMERSSFEKN

PIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAF

KYFDTTIDRKRYTSTKEVLDATLIHQSITGLYETRIDLSQLGGD

S. py Cas9 amino acid sequence expressed from DNA codon optimized for expression in *E. coli* containing 3 NLS sequences and a purification His-tag (SEQ ID No. 408).

MGSSAPKKKRKVGIHGVPAAMDKKYSIGLDIGINSVGWAVITDEYKVPS

KKEKVLGNTDRHSIKKNLIGALLEDSGETAEATRLKRTARRRYTRRKNR

ICYLQEIFSNEMAKVDDSFFHRLEESFLVEEDKKHERHPIFGNIVDEVA

YHEKYPTIYHLRKKLVDSTDKADLRLIYLALAHMIKFRGHFLIEGDLNP

DNSDVDKLFIQLVQTYNQLFEENPINASGVDAKAILSARLSKSRRLENL

IAQLPGEKKNGLFGNLIALSLGLTPNEKSNEDLAEDAKLQLSKDTYDDD

LDNLLAQIGDQYADLFLAAKNLSDAILLSDILRVNTEITKAPLSASMIK

RYDEHHQDLTLLKALVRQQLPEKYKEIFFDQSKNGYAGYIDGGASQEEF

YKFIKPILEKMDGTEELLVKLNREDLLRKQRTFDNGSIPHQIHLGELHA

ILRRQEDFYPFLKDNREKIEKILTFRIPYYVGPLARGNSRFAWMTRKSE

ETITPWNFEEVVDKGASAQSFIERMINEDKNLPNEKVLPKHSLLYEYFT

VYNELTKVKYVTEGMRKPAELSGEQKKAIVDLLEKTNRKVIVKQLKEDY

FKKIECFDSVEISGVEDRFNASLGTYHDLLKIIKDKDFLDNEENEDILE

DIVLTLTLFEDREMIEERLKTYAHLFDDKVMKQLKRRRYTGWGRLSRKL

INGIRDKQSGKTILDFLKSDGFANRNFMQLIHDDSLTFKEDIQKAQVSG

QGDSLHEHIANLAGSPAIKKGILQTVKVVDELVKVMGRHKPENIVIEMA

RENQTTQKGQKNSRERMKRIEEGIKELGSQILKEHPVENTQLQNEKLYL

YYLQNGRDMYVDQELDINRLSDYDVDHIVPQSFLKDDSIDNKVLTRSDK

NRGKSDNVPSEEVVKKMKNYWRQLLNAKLITQRKEDNLIKAERGGLSEL

DKAGFIKRQLVETRQITKHVAQILDSRMNTKYDENDKLIREVKVITLKS

KLVSDERKDFQFYKVREINNYHHAHDAYLNAVVGTALIKKYPKLESEFV

YGDYKVYDVRKMIAKSEQEIGKATAKYFFYSNIMNFFKTEITLANGEIR

KRPLIETNGETGEIVWDKGRDFATVRKVLSMPQVNIVKKTEVQTGGFSK

ESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFE

LENGRKRMLASAGELQKGNELALPSKYVNFLYLASHYEKLKGSPEDNEQ

KQLFVEQHKHYLDEIIEQISEFSKRVILADANLDKVLSAYNKHRDKPIR

EQAENIIHLFTLINLGAPAAFKYFDTTIDRKRYTSTKEVLDATLIHQSI

TGLYETRIDLSQLGGDAAPKKKRKVDPKKKRKVAAALEHHHHHH

S. py Cas9 DNA sequence codon optimized for expression in *E. coli* containing 3 NLS sequences and a purification His-tag (SEQ ID No. 409).

ATGGGCAGCAGCGCCCCAAAGAAGAAGCGGAAGGTCGGTATCCACGGAGT

CCCAGCAGCCATGGACAAAAAGTACTCTATTGGCCTGGATATCGGGACCA

ACAGCGTCGGGTGGGCTGTTATCACCGACGAGTATAAAGTACCTTCGAAA

AAGTTCAAAGTGCTGGGCAACACCGATCGCCATTCAATCAAAAAGAACTT

GATTGGTGCGCTGTTGTTTGACTCCGGGGAAACCGCCGAGGCGACTCGCC

TTAAACGTACAGCACGTCGCCGGTACACTCGGCGTAAGAATCGCATTTGC

TATTTGCAGGAAATCTTTAGCAACGAGATGGCAAAAGTCGATGACTCGTT

TTTCCACCGCCTCGAGGAAAGCTTTCTGGTGGAGGAAGACAAAAAGCATG

AGCGTCACCCGATCTTCGGCAACATTGTCGATGAAGTAGCGTATCATGAA

AAATACCCAACCATTTACCACTTACGCAAAAAGCTGGTGGACAGCACTGA

CAAAGCTGATTTGCGCCTTATCTATTTAGCCCTGGCACATATGATTAAGT

TTCGTGGTCACTTCCTGATCGAAGGAGACTTAAATCCCGACAACAGTGAT

GTTGATAAATTGTTTATTCAGCTTGTCCAAACTTACAATCAACTGTTCGA

GGAAAACCCGATCAATGCCTCCGGTGTGGATGCAAAAGCCATTTTAAGTG

CACGCCTTAGCAAGTCCCGTCGCTTAGAAAACCTTATCGCGCAGCTGCCC

GGCGAGAAAAAGAATGGTTTGTTTGGGAACCTTATTGCCTTGAGCTTAGG

CCTCACCCCGAATTTCAAAAGTAATTTCGATCTTGCAGAAGACGCCAAAT

TACAACTGTCGAAGGATACTTATGATGACGATCTCGATAATCTGTTAGCG

CAGATTGGTGACCAATACGCCGATCTTTTTCTGGCGGCTAAAAATCTGAG

CGACGCCATCTTGCTTTCGGATATTCTCCGCGTTAACACCGAAATCACGA

AAGCGCCTCTTAGTGCCAGCATGATTAAACGTTATGATGAACACCACCAG

GACCTGACCTTACTCAAAGCGTTGGTTCGCCAGCAACTGCCAGAGAAGTA

CAAAGAAATCTTCTTTGATCAGTCAAAGAATGGTTATGCCGGCTATATTG

ACGGGGGTGCAAGCCAAGAGGAATTCTACAAATTTATCAAGCCTATTCTG

GAGAAAATGGATGGCACCGAAGAGTTATTGGTGAAGCTTAACCGTGAAGA

CCTCCTGCGGAAACAGCGCACATTCGATAATGGTTCGATCCCACACCAAA

TCCATTTGGGGGAGTTACACGCTATTTTGCGTCGCCAGGAAGACTTTTAC

CCTTTCCTGAAGGATAACCGGGAGAAAATTGAGAAGATCCTTACCTTTCG

TATTCCGTATTACGTAGGCCCCTTAGCACGGGGTAATAGCCGTTTCGCGT
GGATGACACGGAAGTCGGAAGAGACGATCACCCCGTGGAACTTCGAAGAG
GTAGTCGACAAGGGCGCATCAGCGCAGTCTTTTATTGAACGTATGACGAA
TTTCGATAAAAACTTGCCCAATGAGAAGGTGCTTCCGAAACATTCCTTGT
TATATGAATATTTTACAGTTTACAACGAGCTGACCAAGGTTAAATACGTG
ACGGAAGGAATGCGCAAGCCCGCTTTTCTTAGCGGTGAGCAAAAAAGGC
GATCGTCGACCTGTTATTCAAAACGAATCGTAAGGTGACTGTAAAGCAAC
TCAAAGAAGATTACTTCAAAAAGATTGAGTGCTTCGACAGCGTCGAAATC
TCTGGGGTAGAGGATCGGTTTAACGCAAGTTTAGGTACCTACCATGACCT
GCTTAAAATCATTAAGGATAAAGACTTCTTAGATAATGAAGAGAACGAAG
ATATTCTCGAGGACATCGTCTTGACGTTAACCTTATTTGAGGATCGTGAA
ATGATTGAGGAACGCCTCAAAACTTATGCCCACCTGTTCGACGATAAGGT
GATGAAGCAGCTGAAACGTCGGCGCTACACAGGATGGGGCCGCTTGAGTC
GCAAACTTATTAACGGAATCCGTGACAAGCAATCCGGCAAAACGATTCTG
GATTTCTTGAAGTCGGACGGATTTGCTAATCGCAACTTCATGCAGTTGAT
CCATGATGACTCCCTGACTTTTAAAGAGGATATTCAAAAGGCGCAGGTTA
GTGGTCAAGGCGACAGCTTACACGAACACATCGCAAATTTGGCTGGTTCG
CCGGCCATTAAAAAGGGGATCCTCCAGACCGTGAAAGTTGTAGATGAGCT
TGTTAAGGTCATGGGTCGTCATAAGCCCGAAAACATCGTGATTGAAATGG
CGCGGGAGAATCAAACGACCCAGAAAGGACAAAAGAATAGCCGTGAACGG
ATGAAGCGGATCGAGGAAGGCATTAAAGAGCTGGGGTCTCAAATCTTGAA
GGAACACCCTGTGGAGAACACTCAGCTCCAAAATGAAAAACTTTACCTGT
ACTATTTGCAGAACGGACGCGATATGTACGTGGACCAAGAGTTGGATATT
AATCGGCTGAGTGACTACGACGTTGATCATATCGTCCCGCAGAGCTTCCT
CAAAGACGATTCTATTGACAATAAGGTACTGACGCGCTCTGATAAAAACC
GTGGTAAGTCGGACAACGTGCCCTCCGAAGAGGTTGTGAAAAAGATGAAA
AATTATTGGCGCCAGCTTTTAAACGCGAAGCTGATCACACAACGTAAATT
CGATAATTTGACCAAGGCTGAACGGGGTGGCCTGAGCGAGTTAGATAAGG
CAGGATTTATTAAACGCCAGTTAGTGGAGACTCGTCAAATCACCAAACAT
GTCGCGCAGATTTTGGACAGCCGGATGAACACCAAGTACGATGAAAATGA
CAAACTGATCCGTGAGGTGAAAGTCATTACTCTGAAGTCCAAATTAGTTA
GTGATTTCCGGAAGGACTTTCAATTCTACAAAGTCCGTGAAATTAATAAC
TATCATCACGCACATGACGCGTACCTGAATGCAGTGGTTGGGACCGCCCT
TATCAAGAAATATCCTAAGCTGGAGTCGGAGTTTGTCTATGGCGACTATA
AGGTATACGATGTTCGCAAAATGATTGCGAAATCTGAGCAGGAGATCGGT
AAGGCAACCGCAAAATATTTCTTTTACTCAAACATTATGAATTTCTTTAA
GACAGAAATCACTCTGGCCAACGGGGAGATTCGCAAACGTCCGTTGATCG
AAACAAACGGCGAGACTGGCGAAATTGTTTGGGACAAAGGGCGTGATTTC
GCGACGGTGCGCAAGGTACTGAGCATGCCTCAAGTCAATATTGTTAAGAA
AACCGAAGTGCAGACGGGCGGGTTTTCCAAGGAAAGCATCTTACCCAAAC
GTAATTCAGATAAACTTATTGCACGCAAAAAGGACTGGGATCCGAAAAAG
TATGGAGGCTTCGACAGTCCAACCGTAGCCTACTCTGTTCTCGTTGTAGC
GAAAGTAGAAAAGGGTAAATCCAAGAAACTGAAATCTGTCAAGGAGTTGC
TTGGAATCACCATTATGGAGCGTAGCTCCTTCGAGAAGAACCCGATTGAC
TTTCTGGAAGCCAAAGGATATAAAGAGGTCAAGAAAGATCTTATCATTAA
GCTGCCTAAGTATTCACTCTTCGAGCTGGAAAATGGTCGTAAACGCATGC
TCGCTTCTGCCGGCGAGTTGCAGAAGGGCAATGAATTAGCACTTCCATCA
AAGTACGTTAACTTCCTGTATTTGGCCAGCCATTACGAGAAACTGAAGGG
GTCTCCAGAGGACAACGAACAGAAACAATTATTTGTAGAGCAGCACAAGC
ATTATCTTGATGAAATCATTGAGCAAATTTCCGAATTCAGTAAACGCGTA
ATCCTGGCCGATGCAAACCTCGACAAGGTGCTGAGCGCTTACAATAAGCA
TCGCGACAAACCTATCCGTGAGCAGGCTGAAAATATCATTCACCTGTTCA
CATTAACGAACCTGGGCGCTCCGGCCGCTTTTAAATATTTCGACACGACA
ATCGACCGTAAGCGCTATACCAGTACGAAAGAAGTGTTGGATGCGACCCT
TATTCACCAGTCAATTACAGGATTATATGAGACCCGTATCGACCTTAGCC
AATTAGGTGGGGATGCGGCCCCGAAGAAAAAACGCAAAGTGGATCCGAAG
AAAAAACGCAAAGTGGCGGCCGCACTCGAGCACCACCACCACCACCACTG
A

S. py Cas9 amino acid sequence expressed from DNA codon optimized for expression in human cells containing a V5 epitope tag and 2 NLS sequences (SEQ ID No. 410).

MGKPIPNPLLGLDSTAPKKKRKVGIHGVPAADKKYSIGLDIGTNSVGWA
VITDEYKVPSKKFKVLGNTDRHSIKKNLIGALLFDSGETAEATRLKRTA
RRRYTRRKNRICYLQEIFSNEMAKVDDSFFHRLEESFLVEEDKKHERHP
IFGNIVDEVAYHEKYPTIYHLRKKLVDSTDKADLRLIYLALAHMIKFRG
HFLIEGDLNPDNSDVDKLFIQLVQTYNQLFEENPINASGVDAKAILSAR
LSKSRRLENLIAQLPGEKKNGLFGNLIALSLGLTPNFKSNFDLAEDAKL
QLSKDTYDDDLDNLLAQIGDQYADLFLAAKNLSDAILLSDILRVNTEIT
KAPLSASMIKRYDEHHQDLTLLKALVRQQLPEKYKEIFFDQSKNGYAGY
IDGGASQEEFYKFIKPILEKMDGTEELLVKLNREDLLRKQRTFDNGSIP
HQIHLGELHAILRRQEDFYPFLKDNREKIEKILTFRIPYYVGPLARGNS
RFAWMTRKSEETITPWNFEEVVDKGASAQSFIERMTNFDKNLPNEKVLP
KHSLLYEYFTVYNELTKVKYVTEGMRKPAFLSGEQKKAIVDLLFKTNRK
VTVKQLKEDYFKKIECFDSVEISGVEDRFNASLGTYHDLLKIIKDKDFL
DNEENEDILEDIVLTLTLFEDREMIEERLKTYAHLFDDKVMKQLKRRRY
TGWGRLSRKLINGIRDKQSGKTILDFLKSDGFANRNFMQLIHDDSLTFK
EDIQKAQVSGQGDSLHEHIANLAGSPAIKKGILQTVKVVDELVKVMGRH
KPENIVIEMARENQTTQKGQKNSRERMKRIEEGIKELGSQILKEHPVEN
TQLQNEKLYLYYLQNGRDMYVDQELDINRLSDYDVDHIVPQSFLKDDSI
DNKVLTRSDKNRGKSDNVPSEEVVKKMKNYWRQLLNAKLITQRKFDNLT
KAERGGLSELDKAGFIKRQLVETRQITKHVAQILDSRMNTKYDENDKLI

-continued

REVKVITLKSKLVSDFRKDFQFYKVREINNYHHAHDAYLNAVVGTALIK

KYPKLESEFVYGDYKVYDVRKMIAKSEQEIGKATAKYFFYSNIMNFFKT

EITLANGEIRKRPLIETNGETGEIVWDKGRDFATVRKVLSMPQVNIVKK

TEVQTGGFSKESILPKRNSDKLIARKKDWDPKKYGGFDSPTVAYSVLVV

AKVEKGKSKKLKSVKELLGITIMERSSFEKNPIDFLEAKGYKEVKKDLI

IKLPKYSLFELENGRKRMLASAGELQKGNELALPSKYVNFLYLASHYEK

LKGSPEDNEQKQLFVEQHKHYLDEIIEQISEFSKRVILADANLDKVLSA

YNKHRDKPIREQAENIIHLFTLTNLGAPAAFKYFDTTIDRKRYTSTKEV

LDATLIHQSITGLYETRIDLSQLGGDSRADPKKKRKVEFHHTGLVDPSS

VPSLSLNR

S. py Cas9 DNA sequence codon optimized for expression in human cells containing a V5 epitope tag and 2 NLS sequences (SEQ ID No. 411).

ATGGGCAAGCCCATCCCTAACCCCCTGTTGGGGCTGGACAGCACCGCTCC

CAAAAAGAAAAGGAAGGTGGGCATTCACGGCGTGCCTGCGGCCGACAAA

AGTACAGCATCGGCCTTGATATCGGCACCAATAGCGTGGGCTGGGCCGTT

ATCACAGACGAATACAAGGTACCCAGCAAGAAGTTCAAGGTGCTGGGGAA

TACAGACAGGCACTCTATCAAGAAAAACCTTATCGGGGCTCTGCTGTTTG

ACTCAGGCGAGACCGCCGAGGCCACCAGGTTGAAGAGGACCGCAAGGCGA

AGGTACACCCGGAGGAAGAACAGGATCTGCTATCTGCAGGAGATCTTCAG

CAACGAGATGGCCAAGGTGGACGACAGCTTCTTCCACAGGCTGGAGGAGA

GCTTCCTTGTCGAGGAGGATAAGAAGCACGAACGACACCCCATCTTCGGC

AACATAGTCGACGAGGTCGCTTATCACGAGAAGTACCCCACCATCTACCA

CCTGCGAAAGAAATTGGTGGATAGCACCGATAAAGCCGACTTGCGACTTA

TCTACTTGGCTCTGGCCACATGATTAAGTTCAGGGGCCACTTCCTGATC

GAGGGCGACCTTAACCCCGACAACAGTGACGTAGACAAATTGTTCATCCA

GCTTGTACAGACCTATAACCAGCTGTTCGAGGAAAACCCTATTAACGCCA

GCGGGGTGGATGCGAAGGCCATACTTAGCGCCAGGCTGAGCAAAAGCAGG

CGCTTGGAGAACCTGATAGCCCAGCTGCCCGGTGAAAAGAAGAACGGCCT

CTTCGGTAATCTGATTGCCCTGAGCCTGGGCCTGACCCCCAACTTCAAGA

GCAACTTCGACCTGGCAGAAGATGCCAAGCTGCAGTTGAGTAAGGACACC

TATGACGACGACTTGGACAATCTGCTCGCCCAAATCGGCGACCAGTACGC

TGACCTGTTCCTCGCCGCCAAGAACCTTTCTGACGCAATCCTGCTTAGCG

ATATCCTTAGGGTGAACACAGAGATCACCAAGGCCCCCCTGAGCGCCAGC

ATGATCAAGAGGTACGACGAGCACCATCAGGACCTGACCCTTCTGAAGGC

CCTGGTGAGGCAGCAACTGCCCGAGAAGTACAAGGAGATCTTTTTCGACC

AGAGCAAGAACGGCTACGCCGGCTACATCGACGGCGGAGCCAGCCAAGAG

GAGTTCTACAAGTTCATCAAGCCCATCCTGGAGAAGATGGATGGCACCGA

GGAGCTGCTGGTGAAGCTGAACAGGGAAGATTTGCTCCGGAAGCAGAGGA

CCTTTGACAACGGTAGCATCCCCCACCAGATCCACCTGGGCGAGCTGCAC

GCAATACTGAGGCGACAGGAGGATTTCTACCCCTTCCTCAAGGACAATAG

GGAGAAAATCGAAAAGATTCTGACCTTCAGGATCCCCTACTACGTGGGCC

CTCTTGCCAGGGGCAACAGCCGATTCGCTTGGATGACAAGAAAGAGCGAG

GAGACCATCACCCCCTGGAACTTCGAGGAAGTGGTGGACAAAGGAGCAAG

CGCGCAGTCTTTCATCGAACGGATGACCAATTTCGACAAAAACCTGCCTA

ACGAGAAGGTGCTGCCCAAGCACAGCCTGCTTTACGAGTACTTCACCGTG

TACAACGAGCTCACCAAGGTGAAATATGTGACCGAGGGCATGCGAAAACC

CGCTTTCCTGAGCGGCGAGCAGAAGAAGGCCATCGTGGACCTGCTGTTCA

AGACCAACAGGAAGGTGACCGTGAAGCAGCTGAAGGAGGACTACTTCAAG

AAGATCGAGTGCTTTGATAGCGTGGAAATAAGCGGCGTGGAGGACAGGTT

CAACGCCAGCCTGGGCACCTACCACGACTTGTTGAAGATAATCAAAGACA

AGGATTTCCTGGATAATGAGGAGAACGAGGATATACTCGAGGACATCGTG

CTGACTTTGACCCTGTTTGAGGACCGAGAGATGATTGAAGAAAGGCTCAA

AACCTACGCCCACCTGTTCGACGACAAAGTGATGAAACAACTGAAGAGAC

GAAGATACACCGGCTGGGGCAGACTGTCCAGGAAGCTCATCAACGGCATT

AGGGACAAGCAGAGCGGCAAGACCATCCTGGATTTCCTGAAGTCCGACGG

CTTCGCCAACCGAAACTTCATGCAGCTGATTCACGATGACAGCTTGACCT

TCAAGGAGGACATCCAGAAGGCCCAGGTTAGCGGCCAGGGCGACTCCCTG

CACGAACATATTGCAAACCTGGCAGGCTCCCCTGCGATCAAGAAGGGCAT

ACTGCAGACCGTTAAGGTTGTGGACGAATTGGTCAAGGTCATGGGCAGGC

ACAAGCCCGAAAACATAGTTATAGAGATGGCCAGAGAGAACCAGACCACC

CAAAAGGGCCAGAAGAACAGCCGGGAGCGCATGAAAAGGATCGAGGAGGG

TATCAAGGAACTCGGAAGCCAGATCCTCAAAGAGCACCCCGTGGAGAATA

CCCAGCTCCAGAACGAGAAGCTGTACCTGTACTACCTGCAGAACGGCAGG

GACATGTACGTTGACCAGGAGTTGGACATCAACAGGCTTTCAGACTATGA

CGTGGATCACATAGTGCCCCAGAGCTTTCTTAAAGACGATAGCATCGACA

ACAAGGTCCTGACCCGCTCCGACAAAAACAGGGGCAAAAGCGACAACGTG

CCAAGCGAAGAGGTGGTTAAAAAGATGAAGAACTACTGGAGGCAACTGCT

CAACGCGAAATTGATCACCCAGAGAAAGTTCGATAACCTGACCAAGGCCG

AGAGGGGCGGACTCTCCGAACTTGACAAAGCGGGCTTCATAAAGAGGCAG

CTGGTCGAGACCCGACAGATCACGAAGCACGTGCCCAAATCCTCGACAG

CAGAATGAATACCAAGTACGATGAGAATGACAAACTCATCAGGGAAGTGA

AAGTGATTACCCTGAAGAGCAAGTTGGTGTCCGACTTTCGCAAAGATTTC

CAGTTCTACAAGGTGAGGGAGATCAACAACTACCACCATGCCCACGACGC

ATACCTGAACGCCGTGGTCGGCACCGCCCTGATTAAGAAGTATCCAAAGC

TGGAGTCCGAATTTGTCTACGGCGACTACAAAGTTTACGATGTGAGGAAG

ATGATCGCTAAGAGCGAACAGGAGATCGGCAAGGCCACCGCTAAGTATTT

CTTCTACAGCAACATCATGAACTTTTTCAAGACCGAGATCACACTTGCCA

ACGGCGAAATCAGGAAGAGGCCGCTTATCGAGACCAACGGTGAGACCGGC

GAGATCGTGTGGGACAAGGGCAGGGACTTCGCCACCGTGAGGAAAGTCCT

GAGCATGCCCCAGGTGAATATTGTGAAAAAAACTGAGGTGCAGACAGGCG

GCTTTAGCAAGGAATCCATCCTGCCCAAGAGGAACAGCGACAAGCTGATC

GCCCGGAAGAAGGACTGGGACCCTAAGAAGTATGGAGGCTTCGACAGCCC

CACCGTAGCCTACAGCGTGCTGGTGGTCGCGAAGGTAGAGAAGGGGAAGA

GCAAGAAACTGAAGAGCGTGAAGGAGCTGCTCGGCATAACCATCATGGAG

AGGTCCAGCTTTGAGAAGAACCCCATTGACTTTTTGGAAGCCAAGGGCTA

CAAAGAGGTCAAAAAGGACCTGATCATCAAACTCCCCAAGTACTCCCTGT

TTGAATTGGAGAACGGCAGAAAGAGGATGCTGGCGAGCGCTGGGGAACTG

CAAAAGGGCAACGAACTGGCGCTGCCCAGCAAGTACGTGAATTTTCTGTA

CCTGGCGTCCCACTACGAAAAGCTGAAAGGCAGCCCCGAGGACAACGAGC

AGAAGCAGCTGTTCGTGGAGCAGCACAAGCATTACCTGGACGAGATAATC

GAGCAAATCAGCGAGTTCAGCAAGAGGGTGATTCTGGCCGACGCGAACCT

GGATAAGGTCCTCAGCGCCTACAACAAGCACCGAGACAAACCCATCAGGG

AGCAGGCCGAGAATATCATACACCTGTTCACCCTGACAAATCTGGGCGCA

CCTGCGGCATTCAAATACTTCGATACCACCATCGACAGGAAAAGGTACAC

TAGCACTAAGGAGGTGCTGGATGCCACCTTGATCCACCAGTCCATTACCG

GCCTGTATGAGACCAGGATCGACCTGAGCCAGCTTGGAGGCGACTCTAGG

GCGGACCCAAAAAAGAAAAGGAAGGTGGAATTCCACCACACTGGACTAGT

GGATCCGAGCTCGGTACCAAGCTTAAGTTTAAACCGCTGA

S. py Cas9 DNA sequence codon optimized for expression in human cells as a T7 RNA polymerase expression cassette (SEQ ID No. 412). The sequence contains a T7 RNA polymerase promoter, a V5 epitope tag, a nuclear localization signal, the codon optimized Cas9 sequence, a second nuclear localization signal, and the BGH (bovine growth hormone) gene 3'-UTR element with a polyadenylation signal.

TAATACGACTCACTATAGGGAGACCCAAGCTGGCTAGCGTTTAAACGGGC

CCTCTAGACTCGAGCGGCCGCCACCATGGGCAAGCCCATCCCTAACCCCC

TGTTGGGGCTGGACAGCACCGCTCCCAAAAAGAAAAGGAAGGTGGGCATT

CACGGCGTGCCTGCGGCCGACAAAAAGTACAGCATCGGCCTTGATATCGG

CACCAATAGCGTGGGCTGGGCCGTTATCACAGACGAATACAAGGTACCCA

GCAAGAAGTTCAAGGTGCTGGGGAATACAGACAGGCACTCTATCAAGAAA

AACCTTATCGGGCTCTGCTGTTTGACTCAGGCGAGACCGCCGAGGCCAC

CAGGTTGAAGAGGACCGCAAGGCGAAGGTACACCCGGAGGAAGAACAGGA

TCTGCTATCTGCAGGAGATCTTCAGCAACGAGATGGCCAAGGTGGACGAC

AGCTTCTTCCACAGGCTGGAGGAGAGCTTCCTTGTCGAGGAGGATAAGAA

GCACGAACGACACCCCATCTTCGGCAACATAGTCGACGAGGTCGCTTATC

ACGAGAAGTACCCCACCATCTACCACCTGCGAAAGAAATTGGTGGATAGC

ACCGATAAAGCCGACTTGCGACTTATCTACTTGGCTCTGGCGCACATGAT

TAAGTTCAGGGGCCACTTCCTGATCGAGGGCGACCTTAACCCCGACAACA

GTGACGTAGACAAATTGTTCATCCAGCTTGTACAGACCTATAACCAGCTG

TTCGAGGAAAACCCTATTAACGCCAGCGGGGTGGATGCGAAGGCCATACT

TAGCGCCAGGCTGAGCAAAAGCAGGCGCTTGGAGAACCTGATAGCCCAGC

TGCCCGGTGAAAAGAAGAACGGCCTCTTCGGTAATCTGATTGCCCTGAGC

CTGGGCCTGACCCCCAACTTCAAGAGCAACTTCGACCTGGCAGAAGATGC

CAAGCTGCAGTTGAGTAAGGACACCCTATGACGACGACTTGGACAATCTGC

TCGCCCAAATCGGCGACCAGTACGCTGACCTGTTCCTCGCCGCCAAGAAC

CTTTCTGACGCAATCCTGCTTAGCGATATCCTTAGGGTGAACACAGAGAT

CACCAAGGCCCCCCTGAGCGCCAGCATGATCAAGAGGTACGACGAGCACC

ATCAGGACCTGACCCTTCTGAAGGCCCTGGTGAGGCAGCAACTGCCCGAG

AAGTACAAGGAGATCTTTTTCGACCAGAGCAAGAACGGCTACGCCGGCTA

CATCGACGGCGGAGCCAGCCAAGAGGAGTTCTACAAGTTCATCAAGCCCA

TCCTGGAGAAGATGGATGGCACCGAGGAGCTGCTGGTGAAGCTGAACAGG

GAAGATTTGCTCCGGAAGCAGAGGACCTTTGACAACGGTAGCATCCCCCA

CCAGATCCACCTGGGCGAGCTGCACGCAATACTGAGGCGACAGGAGGATT

TCTACCCCTTCCTCAAGGACAATAGGGAGAAAATCGAAAAGATTCTGACC

TTCAGGATCCCCTACTACGTGGGCCCTCTTGCCAGGGGCAACAGCCGATT

CGCTTGGATGACAAGAAAGAGCGAGGAGACCATCACCCCCTGGAACTTCG

AGGAAGTGGTGGACAAAGGAGCAAGCGCGCAGTCTTTCATCGAACGGATG

ACCAATTTCGACAAAAACCTGCCTAACGAGAAGGTGCTGCCCAAGCACAG

CCTGCTTTACGAGTACTTCACCGTGTACAACGAGCTCACCAAGGTGAAAT

ATGTGACCGAGGGCATGCGAAAACCCGCTTTCCTGAGCGGCGAGCAGAAG

AAGGCCATCGTGGACCTGCTGTTCAAGACCAACAGGAAGGTGACCGTGAA

GCAGCTGAAGGAGGACTACTTCAAGAAGATCGAGTGCTTTGATAGCGTGG

AAATAAGCGGCGTGGAGGACAGGTTCAACGCCAGCCTGGGCACCTACCAC

GACTTGTTGAAGATAATCAAAGACAAGGATTTCCTGGATAATGAGGAGAA

CGAGGATATACTCGAGGACATCGTGCTGACTTTGACCCTGTTTGAGGACC

GAGAGATGATTGAAGAAAGGCTCAAAACCTACGCCCACCTGTTCGACGAC

AAAGTGATGAAACAACTGAAGAGACGAAGATACACCGGCTGGGGCAGACT

GTCCAGGAAGCTCATCAACGGCATTAGGGACAAGCAGAGCGGCAAGACCA

TCCTGGATTTCCTGAAGTCCGACGGCTTCGCCAACCGAAACTTCATGCAG

CTGATTCACGATGACAGCTTGACCTTCAAGGAGGACATCCAGAAGGCCCA

GGTTAGCGGCCAGGGCGACTCCCTGCACGAACATATTGCAAACCTGGCAG

GCTCCCCTGCGATCAAGAAGGGCATACTGCAGACCGTTAAGGTTGTGGAC

GAATTGGTCAAGGTCATGGGCAGGCACAAGCCCGAAAACATAGTTATAGA

GATGGCCAGAGAGAACCAGACCACCCAAAAGGGCCAGAAGAACAGCCGGG

AGCGCATGAAAAGGATCGAGGAGGGTATCAAGGAACTCGGAAGCCAGATC

CTCAAAGAGCACCCCGTGGAGAATACCCAGCTCCAGAACGAGAAGCTGTA

CCTGTACTACCTGCAGAACGGCAGGGACATGTACGTTGACCAGGAGTTGG

ACATCAACAGGCTTTCAGACTATGACGTGGATCACATAGTGCCCCAGAGC

TTTCTTAAAGACGATAGCATCGACAACAAGGTCCTGACCCGCTCCGACAA

AAACAGGGGCAAAAGCGACAACGTGCCAAGCGAAGAGGTGGTTAAAAAGA

TGAAGAACTACTGGAGGCAACTGCTCAACGCGAAATTGATCACCCAGAGA

```
AAGTTCGATAACCTGACCAAGGCCGAGAGGGGCGGACTCTCCGAACTTGA
CAAAGCGGGCTTCATAAAGAGGCAGCTGGTCGAGACCCGACAGATCACGA
AGCACGTGGCCCAAATCCTCGACAGCAGAATGAATACCAAGTACGATGAG
AATGACAAACTCATCAGGGAAGTGAAAGTGATTACCCTGAAGAGCAAGTT
GGTGTCCGACTTTCGCAAAGATTTCCAGTTCTACAAGGTGAGGGAGATCA
ACAACTACCACCATGCCCACGACGCATACCTGAACGCCGTGGTCGGCACC
GCCCTGATTAAGAAGTATCCAAAGCTGGAGTCCGAATTTGTCTACGGCGA
CTACAAAGTTTACGATGTGAGGAAGATGATCGCTAAGAGCGAACAGGAGA
TCGGCAAGGCCACCGCTAAGTATTTCTTCTACAGCAACATCATGAACTTT
TTCAAGACCGAGATCACACTTGCCAACGGCGAAATCAGGAAGAGGCCGCT
TATCGAGACCAACGGTGAGACCGGCGAGATCGTGTGGGACAAGGGCAGGG
ACTTCGCCACCGTGAGGAAAGTCCTGAGCATGCCCCAGGTGAATATTGTG
AAAAAAACTGAGGTGCAGACAGGCGGCTTTAGCAAGGAATCCATCCTGCC
CAAGAGGAACAGCGACAAGCTGATCGCCCGGAAGAAGGACTGGGACCCTA
AGAAGTATGGAGGCTTCGACAGCCCCACCGTAGCCTACAGCGTGCTGGTG
GTCGCGAAGGTAGAGAAGGGGAAGAGCAAGAAACTGAAGAGCGTGAAGGA
GCTGCTCGGCATAACCATCATGGAGAGGTCCAGCTTTGAAGAACCCCA
TTGACTTTTTGGAAGCCAAGGGCTACAAAGAGGTCAAAAAGGACCTGATC
ATCAAACTCCCCAAGTACTCCCTGTTTGAATTGGAGAACGGCAGAAAGAG
GATGCTGGCGAGCGCTGGGGAACTGCAAAAGGGCAACGAACTGGCGCTGC
CCAGCAAGTACGTGAATTTTCTGTACCTGGCGTCCCACTACGAAAAGCTG
AAAGGCAGCCCCGAGGACAACGAGCAGAAGCAGCTGTTCGTGGAGCAGCA
CAAGCATTACCTGGACGAGATAATCGAGCAAATCAGCGAGTTCAGCAAGA
GGGTGATTCTGGCCGACGCGAACCTGGATAAGGTCCTCAGCGCCTACAAC
AAGCACCGAGACAAACCCATCAGGGAGCAGGCCGAGAATATCATACACCT
GTTCACCCTGACAAATCTGGGCGCACCTGCGGCATTCAAATACTTCGATA
CCACCATCGACAGGAAAGGTACACTAGCACTAAGGAGGTGCTGGATGCC
ACCTTGATCCACCAGTCCATTACCGGCCTGTATGAGACCAGGATCGACCT
GAGCCAGCTTGGAGGCGACTCTAGGGCGGACCCAAAAAAGAAAGGAAGG
TGGAATTCCACCACACTGGACTAGTGGATCCGAGCTCGGTACCAAGCTTA
AGTTTAAACCGCTGATCAGCCTCGACTGTGCCTTCTAGTTGCCAGCCATC
TGTTGTTTGCCCCTCCCCCGTGCCTTCCTTGACCCTGGAAGGTGCCACTC
CCACTGTCCTTTCCTAATAAAATGAGGAAATTGCATCGCATTGTCTGAGT
AGGTGTCATTCTATTCTGGGGGGTGGGTGGGGCAGGACAGCAAGGGGGA
GGATTGGGAAGACAATAGCAGGCATGCTGGGGATGCGGTGGGCTCTATGG
C
```

S. py Cas9 mRNA (SEQ ID No. 413) as made from the expression cassette (SEQ ID No. 412). The sequence contains a V5 epitope tag, a nuclear localization signal, the codon optimized Cas9 sequence, a second nuclear localization signal, and the BGH (bovine growth hormone) gene 3'-UTR element and poly-A tail.

```
GGGAGACCCAAGCUGGCUAGCGUUUAAACGGGCCCUCUAGACUCGAGCGG
CCGCCACCAUGGGCAAGCCCAUCCCUAACCCCCUGUUGGGGCUGGACAGC
ACCGCUCCCAAAAAGAAAAGGAAGGUGGGCAUUCACGGCGUGCCUGCGGC
CGACAAAAAGUACAGCAUCGGCCUUGAUAUCGGCACCAAUAGCGUGGGCU
GGGCCGUUAUCACAGACGAAUACAAGGUACCCAGCAAGAAGUUCAAGGUG
CUGGGGAAUACAGACAGGCACUCUAUCAAGAAAAACCUUAUCGGGGCUCU
GCUGUUUGACUCAGGCGAGACCGCCGAGGCCACCAGGUUGAAGAGGACCG
CAAGGCGAAGGUACACCCGGAGGAAGAACAGGAUCUGCUAUCUGCAGGAG
AUCUUCAGCAACGAGAUGGCCAAGGUGGACGACAGCUUCUUCCACAGGCU
GGAGGAGAGCUUCCUUGUCGAGGAGGAUAAGAAGCACGAACGACACCCCA
UCUUCGGCAACAUAGUCGACGAGGUCGCUUAUCACGAGAAGUACCCCACC
AUCUACCACCUGCGAAAGAAAUUGGUGGAUAGCACCGAUAAAGCCGACUU
GCGACUUAUCUACUUGGCUCUGGCGCACAUGAUUAAGUUCAGGGGCCACU
UCCUGAUCGAGGGCGACCUUAACCCCGACAACAGUGACGUAGACAAAUUG
UUCAUCCAGCUUGUACAGACCUAUAACCAGCUGUUCGAGGAAAACCCUAU
UAACGCCAGCGGGGUGGAUGCGAAGGCCAUACUUAGCGCCAGGCUGAGCA
AAAGCAGGCGCUUGGAGAACCUGAUAGCCCAGCUGCCCGGUGAAAGAAG
AACGGCCUCUUCGGUAAUCUGAUUGCCCUGAGCCUGGGCCUGACCCCCAA
CUUCAAGAGCAACUUCGACCUGGCAGAAGAUGCCAAGCUGCAGUUGAGUA
AGGACACCUAUGACGACGACUUGGACAAUCUGCUCGCCCAAAUCGGCGAC
CAGUACGCUGACCUGUUCCUCGCCGCCAAGAACCUUUCUGACGCAAUCCU
GCUUAGCGAUAUCCUUAGGGUGAACACAGAGAUCACCAAGGCCCCCCUGA
GCGCCAGCAUGAUCAAGAGGUACGACGAGCACCAUCAGGACCUGACCCUU
CUGAAGGCCCUGGUGAGGCAGCAACUGCCCGAGAAGUACAAGGAGAUCUU
UUUCGACCAGAGCAAGAACGGCUACGCCGGCUACAUCGACGGCGGAGCCA
GCCAAGAGGAGUUCUACAAGUUCAUCAAGCCCAUCCUGGAGAAGAUGGAU
GGCACCGAGGAGCUGCUGGUGAAGCUGAACAGGGAAGAUUUGCUCCGGAA
GCAGAGGACCUUUGACAACGGUAGCAUCCCCCACCAGAUCCACCUGGGCG
AGCUGCACGCAAUACUGAGGCGACAGGAGGAUUUCUACCCCUUCCUCAAG
GACAAUAGGGAGAAAAUCGAAAAGAUUCUGACCUUCAGGAUCCCCUACUA
CGUGGGCCCUCUUGCCAGGGGCAACAGCCGAUUCGCUUGGAUGACAAGAA
AGAGCGAGGAGACCAUCACCCCCUGGAACUUCGAGGAAGUGGUGGACAAA
GGAGCAAGCGCGCAGUCUUUCAUCGAACGGAUGACCAAUUUCGACAAAAA
CCUGCCUAACGAGAAGGUGCUGCCCAAGCACAGCCUGCUUUACGAGUACU
UCACCGUGUACAACGAGCUCACCAAGGUGAAAUAUGUGACCGAGGGCAUG
CGAAAACCCGCUUUCCUGAGCGGCGAGCAGAAGAAGGCCAUCGUGGACCU
GCUGUUCAAGACCAACAGGAAGGUGACCGUGAAGCAGCUGAAGGAGGACU
ACUUCAAGAAGAUCGAGUGCUUUGAUAGCGUGGAAAUAAGCGGCGUGGAG
GACAGGUUCAACGCCAGCCUGGGCACCUACCACGACUUGUUGAAGAUAAU
CAAAGACAAGGAUUUCCUGGAUAAUGAGGAGAACGAGGAUAUACUCGAGG
ACAUCGUGCUGACUUUGACCCUGUUUGAGGACCGAGAGAUGAUUGAAGAA
```

-continued

AGGCUCAAAACCUACGCCCACCUGUUCGACGACAAAGUGAUGAAACAACU

GAAGAGACGAAGAUACACCGGCUGGGGCAGACUGUCCAGGAAGCUCAUCA

ACGGCAUUAGGGACAAGCAGAGCGGCAAGACCAUCCUGGAUUUCCUGAAG

UCCGACGGCUUCGCCAACCGAAACUUCAUGCAGCUGAUUCACGAUGACAG

CUUGACCUUCAAGGAGGACAUCCAGAAGGCCCAGGUUAGCGGCCAGGGCG

ACUCCCUGCACGAACAUAUUGCAAACCUGGCAGGCUCCCCUGCGAUCAAG

AAGGGCAUACUGCAGACCGUUAAGGUUGUGGACGAAUUGGUCAAGGUCAU

GGGCAGGCACAAGCCCGAAAACAUAGUUAUAGAGAUGGCCAGAGAGAACC

AGACCACCCAAAAGGGCCAGAAGAACAGCCGGGAGCGCAUGAAAAGGAUC

GAGGAGGGUAUCAAGGAACUCGGAAGCCAGAUCCUCAAAGAGCACCCCGU

GGAGAAUACCCAGCUCCAGAACGAGAAGCUGUACCUGUACUACCUGCAGA

ACGGCAGGGACAUGUACGUUGACCAGGAGUUGGACAUCAACAGGCUUUCA

GACUAUGACGUGGAUCACAUAGUGCCCCAGAGCUUUCUUAAAGACGAUAG

CAUCGACAACAAGGUCCUGACCCGCUCCGACAAAAACAGGGGCAAAAGCG

ACAACGUGCCAAGCGAAGAGGUGGUUAAAAAGAUGAAGAACUACUGGAGG

CAACUGCUCAACGCGAAAUUGAUCACCCAGAGAAAGUUCGAUAACCUGAC

CAAGGCCGAGAGGGGCGGACUCUCCGAACUUGACAAAGCGGGCUUCAUAA

AGAGGCAGCUGGUCGAGACCCGACAGAUCACGAAGCACGUGGCCCAAAUC

CUCGACAGCAGAAUGAAUACCAAGUACGAUGAGAAUGACAAACUCAUCAG

GGAAGUGAAAGUGAUUACCCUGAAGAGCAAGUUGGUGUCCGACUUUCGCA

AAGAUUUCCAGUUCUACAAGGUGAGGGAGAUCAACAACUACCACCAUGCC

CACGACGCAUACCUGAACGCCGUGGUCGGCACCGCCCUGAUUAAGAAGUA

UCCAAAGCUGGAGUCCGAAUUUGUCUACGGCGACUACAAAGUUUACGAUG

UGAGGAAGAUGAUCGCUAAGAGCGAACAGGAGAUCGGCAAGGCCACCGCU

AAGUAUUUCUUCUACAGCAACAUCAUGAACUUUUUCAAGACCGAGAUCAC

ACUUGCCAACGGCGAAAUCAGGAAGAGAGGCCGCUUAUCGAGACCAACGGUG

AGACCGGCGAGAUCGUGUGGGACAAGGGCAGGGACUUCGCCACCGUGAGG

AAAGUCCUGAGCAUGCCCCAGGUGAAUAUUGUGAAAAAACUGAGGUGCA

GACAGGCGGCUUUAGCAAGGAAUCCAUCCUGCCCAAGAGGAACAGCGACA

AGCUGAUCGCCCGGAAGAAGGACUGGGACCCUAAGAAGUAUGGAGGCUUC

GACAGCCCCACCGUAGCCUACAGCGUGCUGGUGGUCGCGAAGGUAGAGAA

GGGGAAGAGCAAGAAACUGAAGAGCGUGAAGGAGCUGCUCGGCAUAACCA

UCAUGGAGAGGUCCAGCUUUGAGAAGAACCCCAUUGACUUUUUGGAAGCC

AAGGGCUACAAAGAGGUCAAAAAGGACCUGAUCAUCAAACUCCCCAAGUA

CUCCCUGUUUGAAUUGGAGAACGGCAGAAAGAGGAUGCUGGCGAGCGCUG

GGGAACUGCAAAAGGGCAACGAACUGGCGCUGCCCAGCAAGUACGUGAAU

UUUCUGUACCUGGCGUCCCACUACGAAAAGCUGAAAGGCAGCCCCGAGGA

CAACGAGCAGAAGCAGCUGUUCGUGGAGCAGCACAAGCAUUACCUGGACG

AGAUAAUCGAGCAAAUCAGCGAGUUCAGCAAGAGGGUGAUUCUGGCCGAC

GCGAACCUGGAUAAGGUCCUCAGCGCCUACAACAAGCACCGAGACAAACC

CAUCAGGGAGCAGGCCGAGAAUAUCAUACACCUGUUCACCCUGACAAAUC

UGGGCGCACCUGCGGCAUUCAAAUACUUCGAUACCACCAUCGACAGGAAA

AGGUACACUAGCACUAAGGAGGUGCUGGAUGCCACCUUGAUCCACCAGUC

CAUUACCGGCCUGUAUGAGACCAGGAUCGACCUGAGCCAGCUUGGAGGCG

ACUCUAGGGCGGACCCAAAAAAGAAAAGGAAGGUGGAAUUCCACCACACU

GGACUAGUGGAUCCGAGCUCGGUACCAAGCUUAAGUUUAAACCGCUGAUC

AGCCUCGACUGUGCCUUCUAGUUGCCAGCCAUCUGUUGUUUGCCCCUCCC

CCGUGCCUUCCUUGACCCUGGAAGGUGCCACUCCCACUGUCCUUUCCUAA

UAAAAUGAGGAAAUUGCAUCGCAUUGUCUGAGUAGGUGUCAUUCUAUUCU

GGGGGGUGGGGUGGGGCAGGACAGCAAGGGGGAGGAUUGGGAAGACAAUA

GCAGGCAUGCUGGGGAUGCGGUGGGCUCUAUGGC-polyA

EXAMPLE 12

The following example demonstrates reduced stimulation of the innate immune system in mammalian cells by the truncated chemically modified crRNA:tracrRNA complexes of the present invention when compared with unmodified IVT sgRNAs.

Mammalian cells possess a variety of receptors intended to identify and respond to foreign RNAs as part of anti-viral immunity. This includes receptors such as TLR-3, TLR-7, TLR8, RIG-I, MDA5, OAS, PKR, and others. In broad terms, RNAs that are short or contain chemical modifications present in mammalian cells (such as 2'OMe RNA) evade detection or are less stimulatory than are long, unmodified RNAs. The present example compares the level of stimulation of 2 immune response associated genes (IFIT1 and IFITM1) when mammalian HEK293 cells are transfected with truncated unmodified or truncated modified crRNA:tracrRNA complexes of the present invention with a commercial IVT sgRNA (Thermo Fisher Scientific, Waltham, Mass.).

CRISPR guide RNAs specific to human HPRT1 site 38285 were employed. Sequences are shown in Table 11 below. The unmodified crRNA:tracrRNA complexes (SEQ ID Nos. 48 and 2), the modified crRNA:tracrRNA complexes (SEQ ID Nos. 178 and 100) and the sgRNA (SEQ ID No. 414) were transfected into HEK-Cas9 cells at 30 nM concentration as outlined in Example 2 above. RNA was prepared 24 hours after transfection using the SV96 Total RNA Isolation Kit (Promega, Madison, Wis.). cDNA was synthesized using 150 ng total RNA with SuperScript™-II Reverse Transcriptase (Invitrogen, Carlsbad, Calif.) per the manufacturer's instructions using both random hexamer and oligo-dT priming. Transfection experiments were all performed a minimum of three times.

Figure 13:
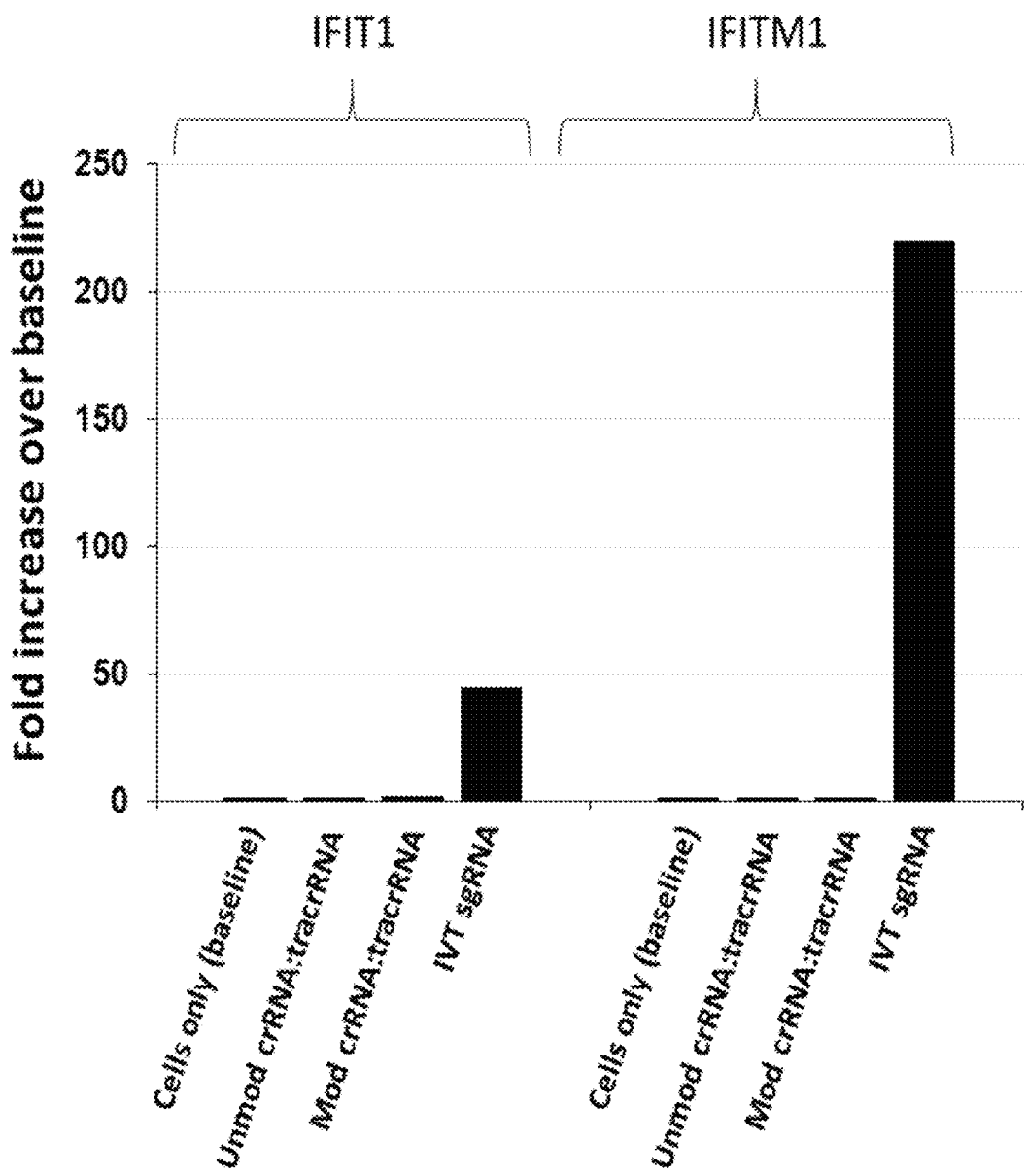
FIG. 13 shows a plot of RT-qPCR data from HEK-Cas9 cells transfected with different CRISPR gRNAs showing relative expression levels of IFIT1 and IFITM1, 2 genes involved in interferon signaling pathways.

Quantitative real-time PCR was performed using 10 ng cDNA per 10 μL reaction with Immolase™ DNA Polymerase (Bioline, Randolph, Mass.), 200 nM primers, and 200 nM probe. Cycling conditions employed were: 95° C. for 10 minutes followed by 40 cycles of 2-step PCR with 95° C. for 15 seconds and 60° C. for 1 minute. PCR and fluorescence measurements were done using an ABI Prism™ 7900 Sequence Detector (Applied Biosystems Inc., Foster City, Calif.). All reactions were performed in triplicate using 2-color multiplexing. Expression data were normalized against an average of two internal control genes. Copy number standards were linearized cloned amplicons for all assays. Unknowns were extrapolated against standards to establish absolute quantitative measurements. Housekeeping internal control normalization assays were HPRT1 (primers and probe SEQ ID Nos. 415-417) and SFRS9 (primers and probe SEQ ID Nos. 418-420). Immune activation pathway assays were IFITM1 (primers and probe SEQ ID Nos. 421-423) and IFIT1 (primers and probe SEQ ID Nos. 424-426). The results were normalized using non-transfected cells as baseline and are shown in FIG. 13.

TABLE 11

Nucleic acid reagents employed in immune activation experiments in Example 12.

| SEQ ID No. | Reagent | Sequence |
|---|---|---|
| 48 | Unmodified crRNA | cuuauauccaacacuucgugguuuuagagcuaugcu |
| 2 | Unmodified tracrRNA | agcauagcaaguuaaaauaaggcuaguccguuaucaacuugaaaaaguggcaccgagucggugcuuu |
| 178 | Modified crRNA | c*u*u*auauccaacacuucgugguuuuagagcuau*g*c*u |
| 100 | Modified tracrRNA | a*g*cauagcaaguuaaaauaaggcuaguccguuaucaacuugaaaaaguggcaccgagucggugcu*u*u |
| 414 | IVTsgRNA | ppp-gcuauauccaacacuucgugguuuuagagcuagaaauagcaaguuaaaauaaggcuaguccguuaucaacuugaaaaaguggcaccgagucggugcuuuuuuu |
| 415 | Hs HPRT F517 | GACTTTGCTTTCCTTGGTCAG |
| 416 | Hs HPRT R591 | GGCTTATATCCAACACTTCGTGGG |
| I[1] | Hs HPRT P554 | FAM-ATGGTCAAG(ZEN)GTCGCAAGCTTGCTGGT-ZEN |
| 418 | Hs SFRS9 F569 | TGTGCAGAAGGATGGAGT |
| 419 | Hs SFRS9 R712 | CTGGTGCTTCTCTCAGGATA |
| II[2] | Hs SFRS9 P644 | HEX-TGGAATATG(ZEN)CCCTGCGTAAACTGGA-ZEN |
| 421 | Hs IFITM1 For | CTCTTCTTGAACTGGTGCTGTCTG |
| 422 | Hs IFITM1 Rev | CAGGATGAATCCAATGGTCATGAGG |
| III[3] | Hs IFITM1 Probe FAM | FAM-AAGTGCCTG(ZEN)AACATCTGGGCCCTGATT-ZEN |
| 424 | Hs IFIT1 For | CCATTGTCTGGATTTAAGCGG |
| 425 | Hs IFIT1 Rev | GCCACAAAAAATCACAAGCCA |
| IV[4] | Hs IFIT1 Probe HEX | HEX-TTTCTTTGC(ZEN)TTCCCCTAAGGCAGGCTG-ZEN |

[1]Compound I is an oligonuceotide having the formula SEQ ID NO: 417-(ZEN)-SEQ ID NO: 441.
[2]Compound II is an oligonucleotide having the formula SEQ ID NO: 420-(ZEN)-SEQ ID NO: 442.
[3]Compound III is an oligonucleotide having the formula SEQ ID NO: 423-(ZEN)-SEQ ID NO: 443.
[4]Compound IV is an oligonucleotide having the formula SEQ ID NO: 426-(ZEN)-SEQ ID NO: 444.
Oligonucleotide sequences are shown 5'-3'.
Uppercase = DNA;
Lowercase = RNA;
Underlined = 2'-O-methyl RNA;
*= phosphorothioate internucleotide linkage;
ppp = triphosphate;
ZEN = napthyl-azo modifier, dark quencher;
FAM = 6-carboxyfluorescein;
HEX = hexachlorofluorescein.

Treatment with the unmodified or chemically modified truncated crRNA:tracrRNA complex did not lead to detectable increases in IFIT1 or IFITM1 expression over baseline. In contrast, treatment with the longer IVT sgRNA led to a 45-fold induction of IFITM1 and a 220-fold induction of IFIT1. Thus, significant stimulation of the innate immune system occurred using the sgRNA that was absent using the short crRNA:tracrRNA complexes of the present invention.

EXAMPLE 13

The following example combines modification patterns identified in Examples 6 and 7 as being particularly efficacious to demonstrate new highly modified crRNA and tracrRNA compositions that perform with high efficiency in mammalian CRISPR genome editing applications.

A series of crRNAs and tracrRNAs (Table 12) were synthesized having chemical modifications as indicated. The crRNAs employed a 20 base protospacer domain targeting the same site in the human HPRT1 gene (38285) at the 5'-end with a 16 base tracrRNA binding domain at the 3'-end. The tracrRNAs were synthesized having chemical modifications as indicated, using the 67 nucleotide or 62 nucleotide truncated versions of the tracrRNA sequence. The crRNAs and tracrRNAs listed in Table 12 were paired as indicated and transfected into the HEK-Cas9 cells at 30 nM concentration and processed as described in previous Examples. Relative gene editing activities were assessed by comparing cleavage rates in the HPRT1 gene using the T7EI mismatch endonuclease cleavage assay, with quantitative measurement of products done using the Fragment Analyzer.

compositions having moderate (SEQ ID No. 450, with 19/67 residues modified, or 28%) or high (SEQ ID No. 449, with 46/67 residues modified, or 69%) levels of 2'F RNA modification are highly functional. Information derived from Example 6 (in particular, the 2'OMe "walk", SEQ ID Nos. 144-162) was used to identify specific residues that can be modified within the internal domain of the tracrRNA (see FIG. 6). The crRNA:tracrRNA pair #5 demonstrates that an extremely highly modified tracrRNA, which in this case was a truncated 62 nucleotide design (SEQ ID No. 451, having 51/62 residues modified with 2'OMe RNA, or 82%), has high potency in triggering CRISPR genome editing in mammalian cells. Therefore, the original 89 RNA nucleotide wild-type tracrRNA has been optimized herein to a form that has as little as 11 RNA residues remaining (11/62), thereby significantly reducing risk of RNA-based activation of the mammalian innate immune system and reducing the nuclease-susceptible RNA content of the tracrRNA to a minimal level.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and

TABLE 12

Activity of highly modified crRNA: tracrRNA complexes to direct Cas9-mediated gene editing in mammalian cells.

| cr/tracr RNA pair | SEQ ID No. | crRNA Sequence tracrRNA Sequence | Cleavage % |
|---|---|---|---|
| 1 | 448 | c*u*u*auauccaacacuucgugguuuuagagcuau*g*c*u | 57 |
|   | 2   | agcauagcaaguuaaaauaaggcuaguccguuaucaacuuga aaaaguggcaccgagucggugcuuu | |
| 2 | 448 | c*u*u*auauccaacacuucgugguuuuagagcuau*g*c*u | 58 |
|   | 100 | a*g*cauagcaaguuaaaauaaggcuaguccguuaucaacuu gaaaaaguggcaccgagucggugcu*u*u | |
| 3 | 48  | cuuauauccaacacuucgugguuuuagagcuaugcu | 58 |
|   | 449 | a*g*cauagcaaguuaaaauaaggcuaguccguuaucaacuu gaaaaaguggcaccgagucggugcu*u*u | |
| 4 | 48  | cuuauauccaacacuucgugguuuuagagcuaugcu | 57 |
|   | 450 | a*g*cauagcaaguuaaaauaaggcuaguccguuaucaacuu gaaaaaguggcaccgagucggugcu*u*u | |
| 5 | 48  | cuuauauccaacacuucgugguuuuagagcuaugcu | 65 |
|   | 451 | a*g*cauagcaaguuaaaauaaggcuaguccguuaucaacuu gaaaaaguggcaccgagucg*g*u | |

Oligonucleotide sequences are shown 5'-3'.
Lowercase = RNA;
Underlined = 2'-O-methyl RNA;
Lowercase italic = 2'F RNA;
* = phosphorothioate internucleotide linkage.
The relative functional activity of each complex is indicated by the % cleavage in a T7EI heteroduplex assay for each dose studied.

The crRNA:tracrRNA pairs #1 and #2 show that a highly 2'F RNA modified crRNA (SEQ ID No. 448, which has 22/36 residues modified, or 61%) is highly functional when paired with either an unmodified tracrRNA (SEQ ID No. 2) or a highly 2'OMe modified tracrRNA (SEQ ID No. 100). The crRNA:tracrRNA pairs #3 and #4 show that tracrRNA "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated tracrRNA selected from the group consisting of SEQ ID NOs.: 11-13, 17, 87-107, 109-118, 120-122, 126, 129, 131, 132, 134-137, 142, 144, 145, and 147-162, wherein the isolated tracrRNA is active in a Clustered Regularly Interspaced Short Palindromic Repeats (CRISPR)/CRISPR-associated protein endonuclease system.

* * * * *